US011242385B2

(12) United States Patent
Xiao et al.

(10) Patent No.: US 11,242,385 B2
(45) Date of Patent: Feb. 8, 2022

(54) ANTI-CD137 ANTIBODIES AND METHODS OF USE THEREOF

(71) Applicant: Agenus Inc., Lexington, MA (US)

(72) Inventors: Yanping Xiao, Brookline, MA (US); Nicholas Stuart Wilson, San Carlos, CA (US); Benjamin Maxime Morin, Somerville, MA (US); Mark Arthur Findeis, Belmont, MA (US); Cornelia Anne Mundt, Lörrach (DE); Marc van Dijk, Bosch en Duin (NL); Dhan Sidhartha Chand, Woburn, MA (US); David Adam Savitsky, Boxford, MA (US); Dennis John Underwood, Jamaica Plain, MA (US); Olga Ignatovich, Cambridge (GB)

(73) Assignee: AGENUS INC., Lexington, MA (US)

( * ) Notice: Subject to any disclaimer, the term of this patent is extended or adjusted under 35 U.S.C. 154(b) by 587 days.

(21) Appl. No.: 15/951,950

(22) Filed: Apr. 12, 2018

(65) Prior Publication Data

US 2018/0344870 A1    Dec. 6, 2018

Related U.S. Application Data

(60) Provisional application No. 62/485,365, filed on Apr. 13, 2017.

(51) Int. Cl.
| | | |
|---|---|---|
| *C12N 15/13* | (2006.01) | |
| *C07K 16/28* | (2006.01) | |
| *C12N 15/09* | (2006.01) | |
| *A61K 47/68* | (2017.01) | |
| *A61K 39/395* | (2006.01) | |
| *A61K 45/06* | (2006.01) | |
| *A61K 51/10* | (2006.01) | |
| *C07K 16/46* | (2006.01) | |
| *A61K 39/00* | (2006.01) | |

(52) U.S. Cl.
CPC ........ *C07K 16/28* (2013.01); *A61K 39/39558* (2013.01); *A61K 45/06* (2013.01); *A61K 47/6883* (2017.08); *A61K 51/10* (2013.01); *C07K 16/2818* (2013.01); *C07K 16/2875* (2013.01); *C07K 16/2878* (2013.01); *C07K 16/468* (2013.01); *C12N 15/09* (2013.01); *A61K 2039/572* (2013.01); *A61K 2039/577* (2013.01); *C07K 2317/33* (2013.01); *C07K 2317/34* (2013.01); *C07K 2317/72* (2013.01); *C07K 2317/75* (2013.01)

(58) Field of Classification Search
None
See application file for complete search history.

(56) References Cited

U.S. PATENT DOCUMENTS

| 6,210,669 B1 | 4/2001 | Aruffo |
|---|---|---|
| 7,214,493 B2 | 5/2007 | Kunkel |
| 7,659,384 B2 | 2/2010 | Kunkel |
| 7,829,088 B2 | 11/2010 | Kwon |
| 8,329,197 B2 | 12/2012 | Noelle |
| 8,475,790 B2 | 7/2013 | Jure-Kunkel |
| 8,772,026 B2 | 7/2014 | Chen |
| 8,821,867 B2 | 9/2014 | Ahrens |
| 9,132,281 B2 | 9/2015 | Zeng |
| 9,758,589 B2 | 9/2017 | Kohrt et al. |
| 10,144,778 B2 | 12/2018 | Eisenbach-Schwartz et al. |
| 10,174,122 B2 | 1/2019 | Kwon et al. |
| 10,233,251 B2 | 3/2019 | Gray et al. |
| 2014/0234320 A1 | 8/2014 | Croft |
| 2015/0037346 A1 | 2/2015 | Lesokhin et al. |
| 2015/0307620 A1 | 10/2015 | Vella et al. |
| 2015/0374731 A1 | 12/2015 | Coral |
| 2016/0244528 A1 | 8/2016 | Gray et al. |
| 2017/0174773 A1 | 6/2017 | Davis et al. |
| 2018/0118841 A1 | 5/2018 | Ellmark et al. |
| 2018/0282422 A1 | 10/2018 | Xu et al. |
| 2019/0031765 A1 | 1/2019 | Long et al. |
| 2019/0169308 A1 | 6/2019 | Dahlen et al. |
| 2019/0194329 A1 | 6/2019 | Akamatsu et al. |
| 2019/0284292 A1 | 9/2019 | Wang |
| 2019/0338040 A1 | 11/2019 | Keyt et al. |
| 2019/0352414 A1 | 11/2019 | Ellmark et al. |
| 2019/0382491 A1 | 12/2019 | Jure-Kunkel et al. |
| 2020/0010557 A1 | 1/2020 | Gajewski et al. |
| 2020/0017594 A9 | 1/2020 | Al-Shamkhani et al. |
| 2020/0017595 A1 | 1/2020 | Geuijen et al. |
| 2020/0062854 A1 | 2/2020 | Liu et al. |

FOREIGN PATENT DOCUMENTS

| EP | 3192805 A1 | 7/2017 |
|---|---|---|
| WO | WO 2000024896 A2 | 5/2000 |
| WO | WO 2005035584 A1 | 4/2005 |

(Continued)

OTHER PUBLICATIONS

Agenus—Non-Confidential Overview—Oct. 2017.
Agenus—Non-Confidential Overview—Nov. 2017.
Immunomodul Abs deck-Blair Maidstone 2017 Final—Mar. 29-30, 2017.
Akhmetzyanova, I., et al., (2016) "CD137 Agonist Therapy Can Reprogram Regulatory T Cells into Cytotoxic CD4 + T Cells with Antitumor Activity" J. Immunol. 196:484-492.
Alfaro, C., et al., (2015) "Functional expression of CD137 (4-1BB) on T helper follicular cells" OncoImmunology 4(12): e1054597.

(Continued)

*Primary Examiner* — Michael D Pak
(74) *Attorney, Agent, or Firm* — Andrew T. Wilkins; Kayla L. Metzger; Dechert LLP

(57) ABSTRACT

The instant disclosure provides antibodies that specifically bind to CD137 (e.g., human CD137) and increases CD137 function. Also provided are pharmaceutical compositions comprising these antibodies, nucleic acids encoding these antibodies, expression vectors and host cells for making these antibodies, and methods of treating a subject using these antibodies.

24 Claims, 21 Drawing Sheets

Specification includes a Sequence Listing.

(56) References Cited

FOREIGN PATENT DOCUMENTS

| | | |
|---|---|---|
| WO | WO 2007134384 A2 | 11/2007 |
| WO | WO 2012145183 A2 | 10/2012 |
| WO | WO 2014143909 A1 | 9/2014 |
| WO | WO 2016154544 A1 | 9/2016 |
| WO | WO 2017040790 A1 | 3/2017 |
| WO | WO 2017055398 A2 | 4/2017 |
| WO | WO 2017123650 A2 | 7/2017 |
| WO | WO 2017123673 A2 | 7/2017 |
| WO | WO 2017181034 A1 | 10/2017 |
| WO | WO 2017193094 A1 | 11/2017 |
| WO | WO 2017218970 A1 | 12/2017 |
| WO | WO 2018020273 A1 | 2/2018 |
| WO | WO 2018045110 A1 | 3/2018 |
| WO | WO 2018115003 A2 | 6/2018 |
| WO | WO 2018127473 A1 | 7/2018 |

OTHER PUBLICATIONS

Bartkowiak, T. and Curran, M.A., (2015) "4-1BB Agonists: Multi-Potent Potentiators of Tumor Immunity" Front Oncol. 8(5):117.
Bartkowiak, T. et al., (2018) "Activation of 4-1BB on Liver Myeloid Cells Triggers Hepatitis via an Interleukin-27-Dependent Pathway" Clin. Cancer Res. 24(5):1138-1151.
Belcaid Z., et al., (2014) "Focal radiation therapy combined with 4-1BB activation and CTLA-4 blockade yields long-term survival and a protective antigen-specific memory response in a murine glioma model" PloS One 9(7):e101764.
Bitra, A., et al., (2017) "Crystal structure of murine 4-1BB and its interaction with 4-1BBL support a role for galectin-9 in 4-1BB signaling" J. Biol. Chem. 293(4):1317-1329.
Bournazos, S. and Ravetch, J., (2015) "Fγ receptor pathways during active and passive immunization" Immunological Reviews 268:88-103.
Bulliard, Y, et al., (2013) "Activating Fcγ receptors contribute to the antitumor activities of immunoregulatory receptor-targeting antibodies" J. Exp. Med. 210(9):1685-93.
Bulliard, Y, et al., (2014) "OX40 engagement depletes intratumoral Tregs via activating FcγRs, leading to antitumor efficacy" Immunology and Cell Biology 92:475-480.
Chaco, J.A., et al., (2013) "Co-Stimulation through 4-1BB/CD137 Improves the Expansion and Function of CD8+ Melanoma Tumor-Infiltrating Lymphocytes for Adoptive T-Cell Therapy" PLoS One 8(4):e60031.
Chan, Siaw-Lin et al., (2009) "Epitope Mapping of a Chimeric Cd137 Mab: A Necessary Step for Assessing the Biologic Relevance of Non-Human Primate Models", Journal of Molecular Recognition, vol. 22, No. 3, pp. 242-249.
Chester, C., et al., (2018) "Immunotherapy targeting 4-1BB: mechanistic rationale, clinical results, and future strategies" Blood 131(1):49-57.
Chin, S.M., et al., (2018) "Structure of the 4-1BB/4-1BBL complex and distinct binding and functional properties of utomilumab and urelumab" Nature Communication 9:4679.
Collins, A.V., et al., (2002) "The Interaction Properties of Costimulatory Molecules Revisited" Immunity, 17:201-210.
Compte, M., et al., (2018) "A tumor-targeted trimeric 4-1BB-agonistic antibody induces potent anti-tumor immunity without systemic toxicity" Nature Communications 9:4809.
Croft, M., (2009) "The role of TNF superfamily members in T-cell function and diseases" Nature Reviews 9:271-285.
Curran, M.A., et al., (2011) "Combination CTLA-4 blockage and 4-1BB activation enhances tumor rejection by increasing t-cell infiltration, proliferation, and cytokine production" PLoS ONE 6(4):1-11.
De Mol, N.J., et al., (2005) "Surface Plasmon Resonance Thermodynamic and Kinetic Analysis as a Strategic Tool in Drug Design. Distinct Ways for Phosphopeptides to Plug into Src- and Grb2 SH2 Domains" J. Med. Chem. 48:753-763.

Dharmadhikaria, B., et al., (2016) "CD137 and CD137L signals are main drivers of type 1, cell-mediated immune responses" Oncoimmunology 5(4):e1113367.
Finco, D., et al., (2014) "Cytokine release assays: Current practices and future directions" Cytokine 66:143-155.
Fisher, T.S., et al., (2012) "Targeting of 4-1BB by monoclonal antibody PF-05082566 enhances T-cell function and promotes anti-tumor activity" Cancer Immunol Immunother. 61(10):1721-33.
Gopal, A., et al., (2015) "A phase I study of PF-05082566 (anti-4-1BB) + rituximab in patients with CD20+ NHL" J. Clin. Oncol. 33 (suppl; abstr 3004).
Gruss, H., and Dower, S.K., (1995) "Tumor Necrosis Factor Ligand Superfamily: Involvement in the Pathology of Malignant Lymphomas" Blood 85:12:3378-3404.
Guo, Z., et al., (2013) "Combined TIM-3 blockade and CD137 activation affords the long-term protection in a murine model of ovarian cancer" J. Translational Med. 11(215):1-11.
Houot, R., and Kohrt, L., (2014) "CD137 stimulation enhances the vaccinal effect of anti-tumor antibodies" OncoImmunology 3(7):e941740.
Ito, F., et al., (2004) "Anti-CD137 Monoclonal Antibody Administration Augments the Antitumor Efficacy of Dendritic Cell-Based Vaccines" Cander Res. 64:8411-8419.
Kim, Y.H., et al., (2008) "Combination Therapy with Cisplatin and Anti-4-1BB: Synergistic Anti-cancer Effects and Amelioration of Cisplatin-induced Nephrotoxicity" Cancer Res. 68(18):7264-7269.
Kim, Y.H., et al., (2009) "Mechanisms involved in synergistic anticancer effects of anti-4-1BB and cyclophosphamide therapy" Mol. Cancer Ther. 8(2):469-78.
Kocak, E., et al., (2006) "Combination Therapy with Anti-CTL Antigen-4 and Anti-4-1BB Antibodies Enhances Cancer Immunity and Reduces Autoimmunity" Cancer Res. 66(14):7276-7284.
Korhrt, H.E., et al., (2011) "CD137 stimulation enhances the antilymphoma activity of anti-CD20 antibodies" Blood 117(8):2423-2432.
Korhrt, H.E., et al., (2014) "Targeting CD137 enhances the efficacy of cetuximab" J. Clin. Invest. 124(6):2668-2682.
Kwon, B., et al., (2002) "Immune Responses in 4-1BB (CD137)-Deficient Mice" J. Immunol. 168:5483-5490.
Kwon, B., et al., (2018) "Anti-CD137 Cancer Immunotherapy Suppresses Tumor Growth—Response" Cancer Res. 78:1572-1573.
Langstein, J. et al., (1999) "CD137 Induces Proliferation and Endomitosis in Monocytes" Blood 94(9):3161-3168.
Lee, H., et al., (2002) "4-1BB Promotes the Survival of CD8+T Lymphocytes by Increasing Expression of Bcl-$x_L$ and Bfl-1 " J. Immunol. 169:4882-4888.
Lin, G.H.Y., et al., (2013) "GITR-Dependent Regulation of 4-1BB Expression: Implications for T Cell Memory and Anti-4-1BB-Induced Pathology" J. of Immunol. 190:4627-4639.
Lin, W. et al., (2008) "Fc-Dependent Expression of CD137 On Human NK Cells: Insights Into "Antagonistic" effects of anti-CD137 monoclonal antibodies", Blood, vol. 112, No. 3, pp. 699-707.
Lynch, D.H., et al., (2008) "The promise of 4-1BB (CD137)-mediated immunomodulation and the immunotherapy of cancer" Immunological Reviews 222:277-286.
Melero, I., et al., (1997) "Monoclonal antibodies against the 4-IBB T-cell activation molecule eradicate established tumors" Nature Medicine 3(6):682-685.
Melero, I., et al., (1998) "Amplification of tumor immunity by gene transfer of the co-stimulatory 4-1BB ligand: synergy with the CD28 co-stimulatory pathway" Eur. J. Immunol. 28:1116-1121.
Melero, I., et al., (2008) "Multi-layered action mechanisms of CD137 (4-1BB)-targeted immunotherapies" Trends in Pharmacological Sciences 29(8):383-390.
Navabi, S.S., et al., (2015) "Natural Killer Cell Functional Activity After 4-1BB Costimulation" Inflammation 38(3):1181-1190.
Nimmerjahn, F. and Ravetach, J.V. (2008) "Fcγ receptors as regulators of immune responses" Nature Reviews 8:34-47.
Nishikawa, H., et al., ( ) "Regulatory T cells in tumor immunity" Int. J. Cancer: 127:759-767.

(56) References Cited

OTHER PUBLICATIONS

Petersson, K., et al., (2002) "Crystal structure of a SEA variant in complex with MHC class II reveals the ability of SEA to crosslink MHC molecules" Structure 10:1619-1626.
Pollok, E.P., et al., (1994) "4-1BB T-cell antigen binds to mature B cells and macrophages, and costimulates anti-μ-primed splenic B cells" Eur. J. Immunol. 24:367-374.
Sánchez-Paulete, A.F., et al., (2015) "Cancer Immunotherapy with Immunomodulatory Anti-CD137 and Anti-PD-1 Monoclonal Antibodies Requires BATF3-Dependent Dendritic Cells" Cancer Discov. 6(1):71-9.
Segal N.H., et al., (2017) "Results from an Integrated Safety Analysis of Urelumab, an Agonist Anti-CD137 Monoclonal Antibody" Clin. Cancer Res. 23(8):1929-1936.
Segal N.H., et al., (2018) "Phase I Study of Single-Agent Utomilumab (PF05082566), a 4-1BB/CD137 Agonist, in Patients with Advanced Cancer" Clin Cancer Res. 24(8):1816-1823.
Seth, A., et al., (1994) "Binary and ternary complexes between T-cell receptor class II MC and superantigen in vitro" Nature 369:324-327.
Srivastava R.M., et al., (2017) "CD137 Stimulation Enhances Cetuximab-Induced Natural Killer: Dendritic Cell Priming of Antitumor T-Cell Immunity in Patients with Head and Neck Cancer" Clin. Cancer Res. 23(3):707-716.
Starck, L., et al., (2005) "Costimulation by CD137/4-1BB inhibits T cell apoptosis and induces Bcl-$x_L$ and c-FLIP*short* via phosphatidylinositol 3-kinase and AKT/protein kinase B" Eur. J. Immunol. 35:1257-1266.
Stebbings, R., et al., (2007) ""Cytokine Storm" in the Phase I Trial of Monoclonal Antibody TGN1412: Better Understanding the Causes to Improve PreClinical Testing of Immunotherapeutics" J. Immunol. 179:3325-3331.
Vidal, J., et al., "In vitro cytokine release assays for predicting cytokine release syndrome: The current state-of-the-science. Report of a European Medicines Agency Workshop" Cytokine 51:213-215.
Vidarsson, G., et al., (2014) "IgG subclasses and allotypes: from structure to effector functions" Frontiers in Immunol. 5(520):1-17.
Wei H., et al., (2013) "Combinatorial PD-1 blockade and CD137 activation has therapeutic efficacy in murine cancer models and synergizes with cisplatin" PLoS One. 8(12):1-11.
Wei H., et al., (2014) "Dual targeting of CD137 co-stimulatory and PD-1 co-inhibitory molecules for ovarian cancer immunotherapy" OncoImmunology 3:e28248.
Weigelin, B., et al., (2015) "Focusing and sustaining the antitumor CTL effector killer response by agonist anti-CD137 mAb" PNA 112(24):7551-7556.
Weigelin, B., et al., (2016) "Anti-CD137 monoclonal antibodies and adoptive T cell therapy: a perfect marriage?" Cancer Immunol. Immunother. 65:493-497.
Wen, T., et al., (2002) "4-1BB Ligand-Mediated Costimulation of Human T Cells Induces CD4 and CD8 T Cell Expansion, Cytokine Production, and the Development of Cytolytic Effector Function" J. of Immnol. 168:4897-4906.
Westwood J.A., et al., (2014) "Routes of delivery for CpG and anti-CD137 for the treatment of orthotopic kidney tumors in mice" PLoS One 9(5):1-10.
Wilcox, R.A., et al., (2002) "Cutting Edge: Expression of Functional CD137 Receptor by Dendritic Cells" J. Immunol.168:4262-4267.
Williams, J.B., et al., (2017) "The EGR2 targets LAG-3 and 4-1BB describe and regulate dysfunctional antigen-specific CD8+ T cells in the tumor microenvironment" J. Exp. Med. 214(2):381-400.
Wilson, N.S., et al., (2011) "An Fcγ Receptor-Dependent Mechanism Drives Antibody-Mediated Target-Receptor Signaling in Cancer Cells" Cancer Cell 19:101-113.
Wolfl, M., et al., (2007) "Activation-induced expression of CD137 permits detection, isolation, and expansion of the full repertoire of CD8+ T cells responding to antigen without requiring knowledge of epitope specificities" Blood 110(1):201-210.
Won, E., et al., (2009) "The Structure of the Timer of Human 4-1BB Ligand is Unique among Members of the Tumor Necrosis Factor Superfamily" J. of Biol. Chem. 285(12):9202-9210.
Wu, J., and Lanier L.L.., (2003) "Natural Killer Cells and Cancer" Cancer Res. 90:127-156.
Xiao, Y., et al., (2014) "RGMb is a novel binding partner for PD-L2 and its engagement with PD-L2 promotes respiratory tolerance" J. Exp. Med. 211(5):943-959.
Yi, L., et al., (2014) "Human and Mouse CD137 Have Predominantly Different Binding CRDs to Their Respective Ligands" PLoS One 9(1):e86337.
Yonezawa, A., et al., (2015) "Boosting Cancer Immunotherapy with Anti-CD137 Antibody Therapy" Clin. Cancer Res. 21:3113-3120.
Zhang, X., et al., (2009) "CD137 Promotes Proliferation and Survival of Human B Cells" J. Immunol. 184:787-795.
Zhang, X., et al., (2010) "CD137 Promotes Proliferation and Survival of Human B Cells" J. Immunol. 184:787-795.
Zhang, D., et al., (2016) "Fc engineering approaches to enhance the agonism and effector functions of an anti-OX40 antibody" J. Biol. Chem. 291(53):27134-27146.
Zheng, G., et al., (2004) "The 4-1BB Costimulation Augments the Proliferation of CD4$^+$CD25$^+$Regulatory T Cells" J. Immunol. 173:2428-2434.
Zhu, Y., et al., (2007) "CD137 stimulation delivers an antigen-independent growth signal for T lymphocytes with memory phenotype" Blood 109:4882-4889.
International Search Report and Written Opinion for PCT International Application No. PCT/US2018/027310, dated Oct. 15, 2018.

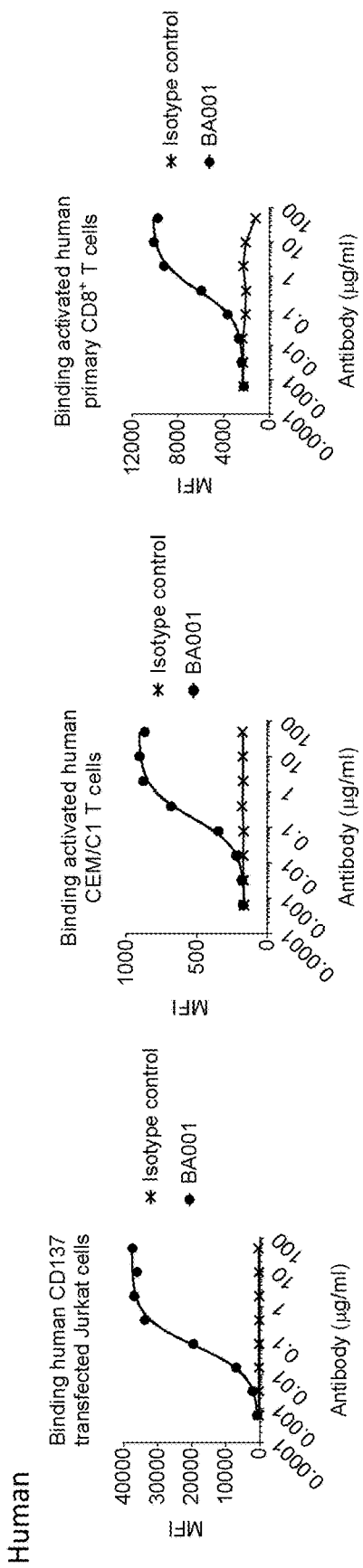

FIG. 13

```
NP_001552.2_CD137_HUMAN      MGNSCYNIVATLLLVLNFERTRSLQDPCSNCPAGTFCDNNRSQICSPCPPNSFSSAGGQRTCDIRCRQCKGVFRTRKECSS    80
XP_005544946.1_CD137_MACFA   MGNSCYNIVATLLLVLNFERTRSLQDLCSNCPAGTFCDNNRSQICSPCPPNSFSSAGGQRTCDIRCRQCKGVFRTRKECSS    80
                             ************************ :***************************************************

NP_001552.2_CD137_HUMAN      TSNAECDCTPGFHCLGAGCSMCEQDCKQGQELTKKGCKDCCFGTFNDQKRGICRPWTNCSLDGKSVLVNGTKERDVVCGP   160
XP_005544946.1_CD137_MACFA   TSNAECDCISGYHCLGAECSMCEQDCKQGQELTKKGCKDCCFGTFNDQKRGICRPWTNCSLDGKSVLVNGTKERDVVCGP   160
                             ******* .*:****.*****************************************************************

NP_001552.2_CD137_HUMAN      SPADLSPGASSVTPPAPAREPGHSPQIISFFLALTSTALLFLLFFLTLRFSVVKRGRKKLLYIFKQPFMRPVQTTQEEDG   240
XP_005544946.1_CD137_MACFA   SPADLSPGASSATPPAPAREPGHSPQII-FFLALTSTVLLFLLFFLTLRFSVVKRSRKKLLYIFKQPFMRPVQTTQEEDG   239
                             ***********:*************** *********:**************:*************************

NP_001552.2_CD137_HUMAN      CSCRFPEEEEGGCEL    (SEQ ID NO: 25)   255
XP_005544946.1_CD137_MACFA   CSCRFPEEEEGGCEL    (SEQ ID NO: 88)   254
                             ***************
```

FIG. 15A (SEQ ID NO: 25)
(SEQ ID NO: 89)

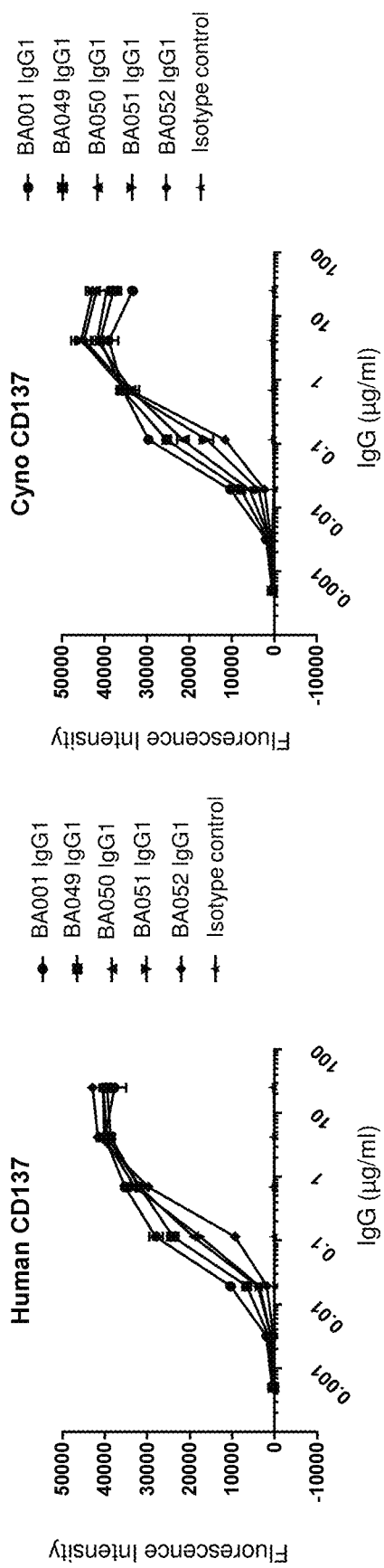
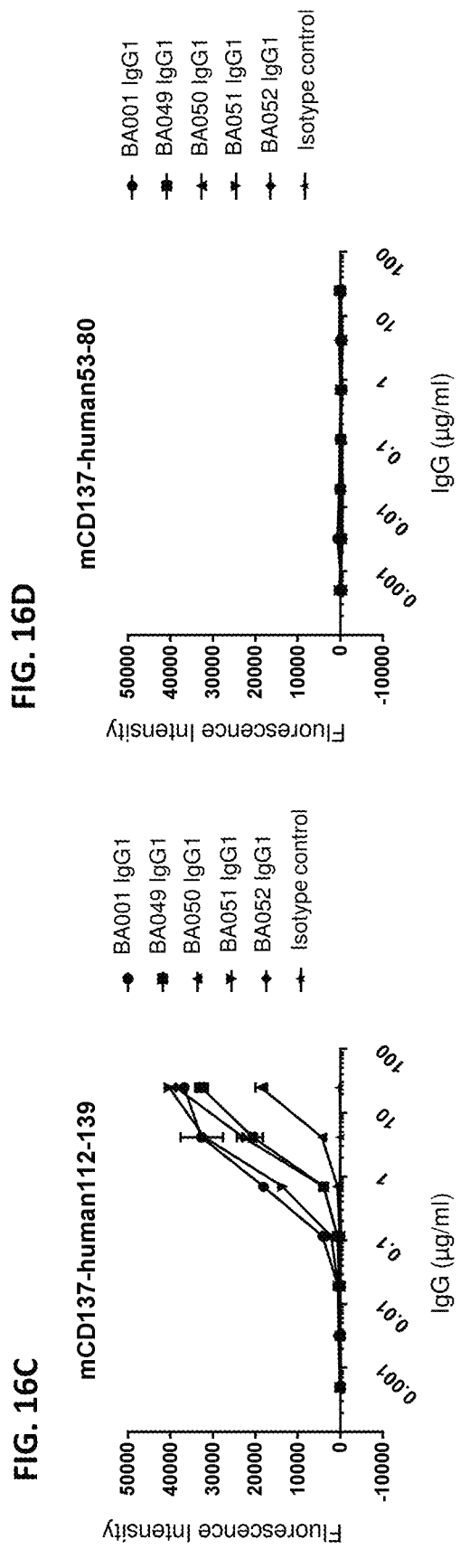

SEQUENCE LISTING

```
<160> NUMBER OF SEQ ID NOS: 89

<210> SEQ ID NO 1
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 1

Gly Tyr Tyr Met His
1               5

<210> SEQ ID NO 2
<211> LENGTH: 17
```

```
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 2

Trp Ile Asn Pro Asn Ser Gly Gly Thr Asn Tyr Ala Gln Lys Phe Gln
1               5                   10                  15

Gly

<210> SEQ ID NO 3
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 3

Glu Pro Gly Tyr Tyr Gly Ser Gly Leu Asp Tyr
1               5                   10

<210> SEQ ID NO 4
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 4

Gly Gly Asp Asp Ile Gly Asp Lys Arg Val His
1               5                   10

<210> SEQ ID NO 5
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 5

Glu Asp Arg Tyr Arg Pro Ser
1               5

<210> SEQ ID NO 6
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 6

Gln Val Trp Asp Ser Ser Ser Asp His Pro Gly Val
1               5                   10

<210> SEQ ID NO 7
<211> LENGTH: 120
<212> TYPE: PRT
<213> ORGANISM: Artificial Sequence
```

```
<220> FEATURE:
<221> NAME/KEY: source
<223> OTHER INFORMATION: /note="Description of Artificial Sequence:
      Synthetic polypeptide"
<220> FEATURE:
<221> NAME/KEY: VARIANT
<222> LOCATION: (1)..(1)
<223> OTHER INFORMATION: /replace="Pyroglutamate"
<220> FEATURE:
<221> NAME/KEY: MISC_FEATURE
<222> LOCATION: (1)..(120)
<223> OTHER INFORMATION: /note="Variant residues given in the sequence
      have no preference with respect to those in the annotations
      for variant positions"

<400> SEQUENCE: 7

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Glu Pro Gly Tyr Tyr Gly Ser Gly Leu Asp Tyr Trp Gly Gln
            100                 105                 110

Gly Thr Leu Val Thr Val Ser Ser
        115                 120

<210> SEQ ID NO 8
<211> LENGTH: 109
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 8

Ser Tyr Val Leu Thr Gln Pro Pro Ser Val Ser Val Ala Pro Gly Glu
1               5                   10                  15

Thr Ala Arg Ile Thr Cys Gly Gly Asp Asp Ile Gly Asp Lys Arg Val
            20                  25                  30

His Trp Tyr Gln Lys Lys Pro Asp Gln Ala Pro Val Leu Val Val Tyr
        35                  40                  45

Glu Asp Arg Tyr Arg Pro Ser Gly Ile Pro Glu Arg Ile Ser Gly Ser
    50                  55                  60

Asn Ser Gly Asn Thr Ala Thr Leu Thr Leu Ser Arg Val Glu Ala Gly
65                  70                  75                  80

Asp Glu Ala Asp Tyr Tyr Cys Gln Val Trp Asp Ser Ser Ser Asp His
                85                  90                  95

Pro Gly Val Phe Gly Gly Gly Thr Gln Leu Ile Ile Leu
            100                 105

<210> SEQ ID NO 9
<211> LENGTH: 449
<212> TYPE: PRT
<213> ORGANISM: Artificial Sequence
```

```
<220> FEATURE:
<221> NAME/KEY: source
<223> OTHER INFORMATION: /note="Description of Artificial Sequence:
      Synthetic polypeptide"
<220> FEATURE:
<221> NAME/KEY: VARIANT
<222> LOCATION: (1)..(1)
<223> OTHER INFORMATION: /replace="Pyroglutamate"
<220> FEATURE:
<221> NAME/KEY: MISC_FEATURE
<222> LOCATION: (1)..(449)
<223> OTHER INFORMATION: /note="Variant residues given in the sequence
      have no preference with respect to those in the annotations
      for variant positions"

<400> SEQUENCE: 9

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Glu Pro Gly Tyr Tyr Gly Ser Gly Leu Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Arg Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335
```

```
Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
            355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385             390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
            435                 440                 445

Gly

<210> SEQ ID NO 10
<211> LENGTH: 449
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: VARIANT
<222> LOCATION: (1)..(1)
<223> OTHER INFORMATION: /replace="Pyroglutamate"
<220> FEATURE:
<221> NAME/KEY: MISC_FEATURE
<222> LOCATION: (1)..(449)
<223> OTHER INFORMATION: /note="Variant residues given in the sequence
      have no preference with respect to those in the annotations
      for variant positions"

<400> SEQUENCE: 10

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Glu Pro Gly Tyr Tyr Gly Ser Gly Leu Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175
```

```
Leu Gln Ser Ser Gly Leu Tyr Ser Leu Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Arg Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
            245                 250                 255

Ser Arg Thr Pro Glu Val Thr Cys Val Val Val Asp Val Ser His Glu
        260                 265                 270

Asp Pro Glu Val Lys Phe Asn Trp Tyr Val Asp Gly Val Glu Val His
    275                 280                 285

Asn Ala Lys Thr Lys Pro Arg Glu Glu Gln Tyr Ala Ser Thr Tyr Arg
290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
            325                 330                 335

Lys Thr Ile Ser Lys Ala Lys Gly Gln Pro Arg Glu Pro Gln Val Tyr
        340                 345                 350

Thr Leu Pro Pro Ser Arg Glu Glu Met Thr Lys Asn Gln Val Ser Leu
    355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
            405                 410                 415

Lys Ser Arg Trp Gln Gln Gly Asn Val Phe Ser Cys Ser Val Met His
        420                 425                 430

Glu Ala Leu His Asn His Tyr Thr Gln Lys Ser Leu Ser Leu Ser Pro
    435                 440                 445

Gly

<210> SEQ ID NO 11
<211> LENGTH: 449
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: VARIANT
<222> LOCATION: (1)..(1)
<223> OTHER INFORMATION: /replace="Pyroglutamate"
<220> FEATURE:
<221> NAME/KEY: MISC_FEATURE
<222> LOCATION: (1)..(449)
<223> OTHER INFORMATION: /note="Variant residues given in the sequence
      have no preference with respect to those in the annotations
      for variant positions"

<400> SEQUENCE: 11

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
```

```
            20                  25                  30
Tyr Met His Trp Val Arg Gln Ala Pro Gly Gln Gly Leu Glu Trp Met
            35                  40                  45
Gly Trp Ile Asn Pro Asn Ser Gly Gly Thr Asn Tyr Ala Gln Lys Phe
 50                  55                  60
Gln Gly Arg Val Thr Met Thr Arg Asp Thr Ser Ile Ser Thr Ala Tyr
 65                  70                  75                  80
Met Glu Leu Ser Arg Leu Arg Ser Asp Asp Thr Ala Val Tyr Tyr Cys
                85                  90                  95
Ala Arg Glu Pro Gly Tyr Tyr Gly Ser Gly Leu Asp Tyr Trp Gly Gln
                100                 105                 110
Gly Thr Leu Val Thr Val Ser Ser Ala Ser Thr Lys Gly Pro Ser Val
                115                 120                 125
Phe Pro Leu Ala Pro Ser Ser Lys Ser Thr Ser Gly Gly Thr Ala Ala
            130                 135                 140
Leu Gly Cys Leu Val Lys Asp Tyr Phe Pro Glu Pro Val Thr Val Ser
145                 150                 155                 160
Trp Asn Ser Gly Ala Leu Thr Ser Gly Val His Thr Phe Pro Ala Val
                165                 170                 175
Leu Gln Ser Ser Gly Leu Tyr Ser Leu Ser Ser Val Val Thr Val Pro
                180                 185                 190
Ser Ser Ser Leu Gly Thr Gln Thr Tyr Ile Cys Asn Val Asn His Lys
                195                 200                 205
Pro Ser Asn Thr Lys Val Asp Lys Arg Val Glu Pro Lys Ser Cys Asp
            210                 215                 220
Lys Thr His Thr Cys Pro Pro Cys Pro Ala Pro Glu Leu Leu Gly Gly
225                 230                 235                 240
Pro Ser Val Phe Leu Phe Pro Pro Lys Pro Lys Asp Thr Leu Met Ile
                245                 250                 255
Ser Arg Thr Pro Glu Val Thr Cys Val Val Val Asp Val Ser His Glu
                260                 265                 270
Asp Pro Glu Val Lys Phe Asn Trp Tyr Val Asp Gly Val Glu Val His
            275                 280                 285
Asn Ala Lys Thr Lys Pro Arg Glu Glu Gln Tyr Asn Ser Thr Tyr Arg
            290                 295                 300
Val Val Ser Val Leu Thr Val Leu His Gln Asp Trp Leu Asn Gly Lys
305                 310                 315                 320
Glu Tyr Lys Cys Lys Val Ser Asn Lys Ala Phe Pro Ala Pro Ile Glu
                325                 330                 335
Lys Thr Ile Ser Lys Ala Lys Gly Gln Pro Arg Glu Pro Gln Val Tyr
            340                 345                 350
Thr Leu Pro Pro Ser Arg Glu Glu Met Thr Lys Asn Gln Val Ser Leu
            355                 360                 365
Thr Cys Leu Val Lys Gly Phe Tyr Pro Ser Asp Ile Ala Val Glu Trp
            370                 375                 380
Glu Ser Asn Gly Gln Pro Glu Asn Asn Tyr Lys Thr Thr Pro Pro Val
385                 390                 395                 400
Leu Asp Ser Asp Gly Ser Phe Phe Leu Tyr Ser Lys Leu Thr Val Asp
                405                 410                 415
Lys Ser Arg Trp Gln Gln Gly Asn Val Phe Ser Cys Ser Val Met His
                420                 425                 430
Glu Ala Leu His Asn His Tyr Thr Gln Lys Ser Leu Ser Leu Ser Pro
            435                 440                 445
```

Gly

<210> SEQ ID NO 12
<211> LENGTH: 445
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: VARIANT
<222> LOCATION: (1)..(1)
<223> OTHER INFORMATION: /replace="Pyroglutamate"
<220> FEATURE:
<221> NAME/KEY: MISC_FEATURE
<222> LOCATION: (1)..(445)
<223> OTHER INFORMATION: /note="Variant residues given in the sequence
      have no preference with respect to those in the annotations
      for variant positions"

<400> SEQUENCE: 12

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Glu Pro Gly Tyr Tyr Gly Ser Gly Leu Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Cys Ser Arg Ser Thr Ser Glu Ser Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Asn Phe Gly Thr Gln Thr Tyr Thr Cys Asn Val Asp His Lys
        195                 200                 205

Pro Ser Asn Thr Lys Val Asp Lys Thr Val Glu Arg Lys Cys Cys Val
    210                 215                 220

Glu Cys Pro Pro Cys Pro Ala Pro Pro Val Ala Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Gln Phe Asn Trp Tyr Val Asp Gly Val Glu Val His Asn Ala Lys Thr
        275                 280                 285

```
Lys Pro Arg Glu Glu Gln Phe Asn Ser Thr Phe Arg Val Val Ser Val
    290                 295                 300
Leu Thr Val Val His Gln Asp Trp Leu Asn Gly Lys Glu Tyr Lys Cys
305                 310                 315                 320
Lys Val Ser Asn Lys Gly Leu Pro Ala Pro Ile Glu Lys Thr Ile Ser
                325                 330                 335
Lys Thr Lys Gly Gln Pro Arg Glu Pro Gln Val Tyr Thr Leu Pro Pro
            340                 345                 350
Ser Arg Glu Glu Met Thr Lys Asn Gln Val Ser Leu Thr Cys Leu Val
        355                 360                 365
Lys Gly Phe Tyr Pro Ser Asp Ile Ala Val Glu Trp Glu Ser Asn Gly
370                 375                 380
Gln Pro Glu Asn Asn Tyr Lys Thr Thr Pro Pro Met Leu Asp Ser Asp
385                 390                 395                 400
Gly Ser Phe Phe Leu Tyr Ser Lys Leu Thr Val Asp Lys Ser Arg Trp
                405                 410                 415
Gln Gln Gly Asn Val Phe Ser Cys Ser Val Met His Glu Ala Leu His
            420                 425                 430
Asn His Tyr Thr Gln Lys Ser Leu Ser Leu Ser Pro Gly
        435                 440                 445

<210> SEQ ID NO 13
<211> LENGTH: 445
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: VARIANT
<222> LOCATION: (1)..(1)
<223> OTHER INFORMATION: /replace="Pyroglutamate"
<220> FEATURE:
<221> NAME/KEY: MISC_FEATURE
<222> LOCATION: (1)..(445)
<223> OTHER INFORMATION: /note="Variant residues given in the sequence
      have no preference with respect to those in the annotations
      for variant positions"

<400> SEQUENCE: 13

Gln Val Gln Leu Val Gln Ser Gly Ala Glu Val Lys Lys Pro Gly Ala
1               5                   10                  15
Ser Val Lys Val Ser Cys Lys Ala Ser Gly Tyr Thr Phe Thr Gly Tyr
            20                  25                  30
Tyr Met His Trp Val Arg Gln Ala Pro Gly Gln Gly Leu Glu Trp Met
        35                  40                  45
Gly Trp Ile Asn Pro Asn Ser Gly Gly Thr Asn Tyr Ala Gln Lys Phe
    50                  55                  60
Gln Gly Arg Val Thr Met Thr Arg Asp Thr Ser Ile Ser Thr Ala Tyr
65                  70                  75                  80
Met Glu Leu Ser Arg Leu Arg Ser Asp Asp Thr Ala Val Tyr Tyr Cys
                85                  90                  95
Ala Arg Glu Pro Gly Tyr Tyr Gly Ser Gly Leu Asp Tyr Trp Gly Gln
            100                 105                 110
Gly Thr Leu Val Thr Val Ser Ser Ala Ser Thr Lys Gly Pro Ser Val
        115                 120                 125
Phe Pro Leu Ala Pro Cys Ser Arg Ser Thr Ser Glu Ser Thr Ala Ala
    130                 135                 140
```

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
            165                 170                 175

Leu Gln Ser Ser Gly Leu Tyr Ser Leu Ser Ser Val Val Thr Val Pro
            180                 185                 190

Ser Ser Asn Phe Gly Thr Gln Thr Tyr Thr Cys Asn Val Asp His Lys
            195                 200                 205

Pro Ser Asn Thr Lys Val Asp Lys Thr Val Glu Arg Lys Cys Cys Val
            210                 215                 220

Glu Cys Pro Pro Cys Pro Ala Pro Pro Val Ala Gly Pro Ser Val Phe
225                 230                 235                 240

Leu Phe Pro Pro Lys Pro Lys Asp Thr Leu Met Ile Ser Arg Thr Pro
            245                 250                 255

Glu Val Thr Cys Val Val Val Asp Val Ser His Glu Asp Pro Glu Val
            260                 265                 270

Gln Phe Asn Trp Tyr Val Asp Gly Val Glu Val His Asn Ala Lys Thr
            275                 280                 285

Lys Pro Arg Glu Glu Gln Phe Ala Ser Thr Phe Arg Val Val Ser Val
290                 295                 300

Leu Thr Val Val His Gln Asp Trp Leu Asn Gly Lys Glu Tyr Lys Cys
305                 310                 315                 320

Lys Val Ser Asn Lys Gly Leu Pro Ala Pro Ile Glu Lys Thr Ile Ser
            325                 330                 335

Lys Thr Lys Gly Gln Pro Arg Glu Pro Gln Val Tyr Thr Leu Pro Pro
            340                 345                 350

Ser Arg Glu Glu Met Thr Lys Asn Gln Val Ser Leu Thr Cys Leu Val
            355                 360                 365

Lys Gly Phe Tyr Pro Ser Asp Ile Asn Val Glu Trp Glu Ser Asn Gly
            370                 375                 380

Gln Pro Glu Asn Asn Tyr Lys Thr Thr Pro Pro Met Leu Asp Ser Asp
385                 390                 395                 400

Gly Ser Phe Phe Leu Tyr Ser Lys Leu Thr Val Asp Lys Ser Arg Trp
            405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly
            435                 440                 445

<210> SEQ ID NO 14
<211> LENGTH: 446
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: VARIANT
<222> LOCATION: (1)..(1)
<223> OTHER INFORMATION: /replace="Pyroglutamate"
<220> FEATURE:
<221> NAME/KEY: MISC_FEATURE
<222> LOCATION: (1)..(446)
<223> OTHER INFORMATION: /note="Variant residues given in the sequence
      have no preference with respect to those in the annotations
      for variant positions"

<400> SEQUENCE: 14

-continued

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
            35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Glu Pro Gly Tyr Tyr Gly Ser Gly Leu Asp Tyr Trp Gly Gln
            100                 105                 110

Gly Thr Leu Val Thr Val Ser Ser Ala Ser Thr Lys Gly Pro Ser Val
            115                 120                 125

Phe Pro Leu Ala Pro Cys Ser Arg Ser Thr Ser Glu Ser Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
            165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
            195                 200                 205

Pro Ser Asn Thr Lys Val Asp Lys Arg Val Glu Ser Lys Tyr Gly Pro
    210                 215                 220

Pro Cys Pro Pro Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
            245                 250                 255

Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
    275                 280                 285

Thr Lys Pro Arg Glu Glu Gln Phe Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
            325                 330                 335

Ser Lys Ala Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
    355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
            405                 410                 415

Trp Gln Glu Gly Asn Val Phe Ser Cys Ser Val Met His Glu Ala Leu

```
                420           425           430
His Asn His Tyr Thr Gln Lys Ser Leu Ser Leu Ser Leu Gly
            435                 440                 445

<210> SEQ ID NO 15
<211> LENGTH: 329
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 15

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly
                325
```

<210> SEQ ID NO 16
<211> LENGTH: 329
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 16

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Ala Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly
                325
```

<210> SEQ ID NO 17
<211> LENGTH: 329

```
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 17
```

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65              70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Glu His Glu Asp Pro Glu Val Lys Phe Asn Trp
145             150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Phe Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225             230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305             310                 315                 320

Gln Lys Ser Leu Ser Leu Ser Pro Gly
                325

```
<210> SEQ ID NO 18
<211> LENGTH: 325
<212> TYPE: PRT
<213> ORGANISM: Artificial Sequence
<220> FEATURE:
<221> NAME/KEY: source
```

<223> OTHER INFORMATION: /note="Description of Artificial Sequence:
      Synthetic polypeptide"

<400> SEQUENCE: 18

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu
    210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
    290                 295                 300

Ser Val Met His Glu Ala Leu His Asn His Tyr Thr Gln Lys Ser Leu
305                 310                 315                 320

Ser Leu Ser Pro Gly
                325

<210> SEQ ID NO 19
<211> LENGTH: 325
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 19

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
                100                 105                 110

Pro Val Ala Gly Pro Ser Val Phe Leu Phe Pro Pro Lys Pro Lys Asp
            115                 120                 125

Thr Leu Met Ile Ser Arg Thr Pro Glu Val Thr Cys Val Val Val Asp
        130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Ala
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu
        210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Asn Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
        290                 295                 300

Ser Val Met His Glu Ala Leu His Asn His Tyr Thr Gln Lys Ser Leu
305                 310                 315                 320

Ser Leu Ser Pro Gly
                325

<210> SEQ ID NO 20
<211> LENGTH: 326
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 20

Ala Ser Thr Lys Gly Pro Ser Val Phe Pro Leu Ala Pro Cys Ser Arg
1               5                   10                  15

```
Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly
                325

<210> SEQ ID NO 21
<211> LENGTH: 215
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 21

Ser Tyr Val Leu Thr Gln Pro Pro Ser Val Ser Val Ala Pro Gly Glu
1               5                   10                  15

Thr Ala Arg Ile Thr Cys Gly Gly Asp Asp Ile Gly Asp Lys Arg Val
            20                  25                  30

His Trp Tyr Gln Lys Lys Pro Asp Gln Ala Pro Val Leu Val Val Tyr
```

```
                    35                  40                  45
Glu Asp Arg Tyr Arg Pro Ser Gly Ile Pro Glu Arg Ile Ser Gly Ser
 50                  55                  60

Asn Ser Gly Asn Thr Ala Thr Leu Thr Leu Ser Arg Val Glu Ala Gly
 65                  70                  75                  80

Asp Glu Ala Asp Tyr Tyr Cys Gln Val Trp Asp Ser Ser Asp His
                 85                  90                  95

Pro Gly Val Phe Gly Gly Gly Thr Gln Leu Ile Ile Leu Gly Gln Pro
                100                 105                 110

Lys Ala Ala Pro Ser Val Thr Leu Phe Pro Pro Ser Ser Glu Glu Leu
            115                 120                 125

Gln Ala Asn Lys Ala Thr Leu Val Cys Leu Ile Ser Asp Phe Tyr Pro
130                 135                 140

Gly Ala Val Thr Val Ala Trp Lys Ala Asp Ser Ser Pro Val Lys Ala
145                 150                 155                 160

Gly Val Glu Thr Thr Thr Pro Ser Lys Gln Ser Asn Asn Lys Tyr Ala
                165                 170                 175

Ala Ser Ser Tyr Leu Ser Leu Thr Pro Glu Gln Trp Lys Ser His Arg
            180                 185                 190

Ser Tyr Ser Cys Gln Val Thr His Glu Gly Ser Thr Val Glu Lys Thr
        195                 200                 205

Val Ala Pro Thr Glu Cys Ser
    210                 215

<210> SEQ ID NO 22
<211> LENGTH: 106
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 22

Gly Gln Pro Lys Ala Ala Pro Ser Val Thr Leu Phe Pro Pro Ser Ser
 1                   5                  10                  15

Glu Glu Leu Gln Ala Asn Lys Ala Thr Leu Val Cys Leu Ile Ser Asp
                 20                  25                  30

Phe Tyr Pro Gly Ala Val Thr Val Ala Trp Lys Ala Asp Ser Ser Pro
             35                  40                  45

Val Lys Ala Gly Val Glu Thr Thr Thr Pro Ser Lys Gln Ser Asn Asn
 50                  55                  60

Lys Tyr Ala Ala Ser Ser Tyr Leu Ser Leu Thr Pro Glu Gln Trp Lys
 65                  70                  75                  80

Ser His Arg Ser Tyr Ser Cys Gln Val Thr His Glu Gly Ser Thr Val
                 85                  90                  95

Glu Lys Thr Val Ala Pro Thr Glu Cys Ser
                100                 105

<210> SEQ ID NO 23
<211> LENGTH: 23
<212> TYPE: PRT
<213> ORGANISM: Homo sapiens

<400> SEQUENCE: 23

Met Gly Asn Ser Cys Tyr Asn Ile Val Ala Thr Leu Leu Leu Val Leu
 1                   5                  10                  15
```

Asn Phe Glu Arg Thr Arg Ser
            20

<210> SEQ ID NO 24
<211> LENGTH: 163
<212> TYPE: PRT
<213> ORGANISM: Homo sapiens

<400> SEQUENCE: 24

Leu Gln Asp Pro Cys Ser Asn Cys Pro Ala Gly Thr Phe Cys Asp Asn
1               5                   10                  15

Asn Arg Asn Gln Ile Cys Ser Pro Cys Pro Pro Asn Ser Phe Ser Ser
            20                  25                  30

Ala Gly Gly Gln Arg Thr Cys Asp Ile Cys Arg Gln Cys Lys Gly Val
        35                  40                  45

Phe Arg Thr Arg Lys Glu Cys Ser Ser Thr Ser Asn Ala Glu Cys Asp
    50                  55                  60

Cys Thr Pro Gly Phe His Cys Leu Gly Ala Gly Cys Ser Met Cys Glu
65                  70                  75                  80

Gln Asp Cys Lys Gln Gly Gln Glu Leu Thr Lys Lys Gly Cys Lys Asp
                85                  90                  95

Cys Cys Phe Gly Thr Phe Asn Asp Gln Lys Arg Gly Ile Cys Arg Pro
            100                 105                 110

Trp Thr Asn Cys Ser Leu Asp Gly Lys Ser Val Leu Val Asn Gly Thr
        115                 120                 125

Lys Glu Arg Asp Val Val Cys Gly Pro Ser Pro Ala Asp Leu Ser Pro
    130                 135                 140

Gly Ala Ser Ser Val Thr Pro Pro Ala Pro Ala Arg Glu Pro Gly His
145                 150                 155                 160

Ser Pro Gln

<210> SEQ ID NO 25
<211> LENGTH: 255
<212> TYPE: PRT
<213> ORGANISM: Homo sapiens

<400> SEQUENCE: 25

Met Gly Asn Ser Cys Tyr Asn Ile Val Ala Thr Leu Leu Leu Val Leu
1               5                   10                  15

Asn Phe Glu Arg Thr Arg Ser Leu Gln Asp Pro Cys Ser Asn Cys Pro
            20                  25                  30

Ala Gly Thr Phe Cys Asp Asn Asn Arg Asn Gln Ile Cys Ser Pro Cys
        35                  40                  45

Pro Pro Asn Ser Phe Ser Ser Ala Gly Gly Gln Arg Thr Cys Asp Ile
    50                  55                  60

Cys Arg Gln Cys Lys Gly Val Phe Arg Thr Arg Lys Glu Cys Ser Ser
65                  70                  75                  80

Thr Ser Asn Ala Glu Cys Asp Cys Thr Pro Gly Phe His Cys Leu Gly
                85                  90                  95

Ala Gly Cys Ser Met Cys Glu Gln Asp Cys Lys Gln Gly Gln Glu Leu
            100                 105                 110

Thr Lys Lys Gly Cys Lys Asp Cys Cys Phe Gly Thr Phe Asn Asp Gln
        115                 120                 125

Lys Arg Gly Ile Cys Arg Pro Trp Thr Asn Cys Ser Leu Asp Gly Lys
    130                 135                 140

Ser Val Leu Val Asn Gly Thr Lys Glu Arg Asp Val Val Cys Gly Pro

```
            145                 150                 155                 160
    Ser Pro Ala Asp Leu Ser Pro Gly Ala Ser Ser Val Thr Pro Pro Ala
                    165                 170                 175

Pro Ala Arg Glu Pro Gly His Ser Pro Gln Ile Ile Ser Phe Phe Leu
                    180                 185                 190

Ala Leu Thr Ser Thr Ala Leu Leu Phe Leu Leu Phe Phe Leu Thr Leu
                    195                 200                 205

Arg Phe Ser Val Val Lys Arg Gly Arg Lys Lys Leu Leu Tyr Ile Phe
                    210                 215                 220

Lys Gln Pro Phe Met Arg Pro Val Gln Thr Thr Gln Glu Glu Asp Gly
    225                 230                 235                 240

Cys Ser Cys Arg Phe Pro Glu Glu Glu Glu Gly Gly Cys Glu Leu
                    245                 250                 255

<210> SEQ ID NO 26
<211> LENGTH: 17
<212> TYPE: PRT
<213> ORGANISM: Homo sapiens

<400> SEQUENCE: 26

Phe Asn Asp Gln Lys Arg Gly Ile Cys Arg Pro Trp Thr Asn Cys Ser
1               5                   10                  15

Leu

<210> SEQ ID NO 27
<211> LENGTH: 31
<212> TYPE: PRT
<213> ORGANISM: Homo sapiens

<400> SEQUENCE: 27

Phe Asn Asp Gln Lys Arg Gly Ile Cys Arg Pro Trp Thr Asn Cys Ser
1               5                   10                  15

Leu Asp Gly Lys Ser Val Leu Val Asn Gly Thr Lys Glu Arg Asp
                20                  25                  30

<210> SEQ ID NO 28
<211> LENGTH: 10
<212> TYPE: PRT
<213> ORGANISM: Homo sapiens

<400> SEQUENCE: 28

Thr Pro Gly Phe His Cys Leu Gly Ala Gly
1               5                   10

<210> SEQ ID NO 29
<211> LENGTH: 6
<212> TYPE: PRT
<213> ORGANISM: Homo sapiens

<400> SEQUENCE: 29

Lys Gln Gly Gln Glu Leu
1               5

<210> SEQ ID NO 30
<211> LENGTH: 28
<212> TYPE: PRT
<213> ORGANISM: Homo sapiens

<400> SEQUENCE: 30

Leu Thr Lys Lys Gly Cys Lys Asp Cys Cys Phe Gly Thr Phe Asn Asp
1               5                   10                  15
```

```
Gln Lys Arg Gly Ile Cys Arg Pro Trp Thr Asn Cys
            20                  25

<210> SEQ ID NO 31
<211> LENGTH: 15
<212> TYPE: PRT
<213> ORGANISM: Homo sapiens

<400> SEQUENCE: 31

Phe Asn Asp Gln Lys Arg Gly Ile Cys Arg Pro Trp Thr Asn Cys
1               5                   10                  15

<210> SEQ ID NO 32

<400> SEQUENCE: 32

000

<210> SEQ ID NO 33
<211> LENGTH: 232
<212> TYPE: PRT
<213> ORGANISM: Homo sapiens

<400> SEQUENCE: 33

Leu Gln Asp Pro Cys Ser Asn Cys Pro Ala Gly Thr Phe Cys Asp Asn
1               5                   10                  15

Asn Arg Asn Gln Ile Cys Ser Pro Cys Pro Pro Asn Ser Phe Ser Ser
            20                  25                  30

Ala Gly Gly Gln Arg Thr Cys Asp Ile Cys Arg Gln Cys Lys Gly Val
        35                  40                  45

Phe Arg Thr Arg Lys Glu Cys Ser Ser Thr Ser Asn Ala Glu Cys Asp
    50                  55                  60

Cys Thr Pro Gly Phe His Cys Leu Gly Ala Gly Cys Ser Met Cys Glu
65                  70                  75                  80

Gln Asp Cys Lys Gln Gly Gln Glu Leu Thr Lys Lys Gly Cys Lys Asp
                85                  90                  95

Cys Cys Phe Gly Thr Phe Asn Asp Gln Lys Arg Gly Ile Cys Arg Pro
            100                 105                 110

Trp Thr Asn Cys Ser Leu Asp Gly Lys Ser Val Leu Val Asn Gly Thr
        115                 120                 125

Lys Glu Arg Asp Val Val Cys Gly Pro Ser Pro Ala Asp Leu Ser Pro
    130                 135                 140

Gly Ala Ser Ser Val Thr Pro Pro Ala Pro Ala Arg Glu Pro Gly His
145                 150                 155                 160

Ser Pro Gln Ile Ile Ser Phe Phe Leu Ala Leu Thr Ser Thr Ala Leu
                165                 170                 175

Leu Phe Leu Leu Phe Phe Leu Thr Leu Arg Phe Ser Val Val Lys Arg
            180                 185                 190

Gly Arg Lys Lys Leu Leu Tyr Ile Phe Lys Gln Pro Phe Met Arg Pro
        195                 200                 205

Val Gln Thr Thr Gln Glu Glu Asp Gly Cys Ser Cys Arg Phe Pro Glu
    210                 215                 220

Glu Glu Glu Gly Gly Cys Glu Leu
225                 230

<210> SEQ ID NO 34
<211> LENGTH: 38
<212> TYPE: PRT
```

<213> ORGANISM: Homo sapiens

<400> SEQUENCE: 34

```
Asp Pro Cys Ser Asn Cys Pro Ala Gly Thr Phe Cys Asp Asn Asn Arg
1               5                   10                  15

Asn Gln Ile Cys Ser Pro Cys Pro Pro Asn Ser Phe Ser Ser Ala Gly
            20                  25                  30

Gly Gln Arg Thr Cys Asp
            35
```

<210> SEQ ID NO 35
<211> LENGTH: 161
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 35

```
Leu Gln Asp Pro Cys Ser Asn Cys Pro Ala Gly Thr Phe Cys Arg Lys
1               5                   10                  15

Tyr Asn Pro Val Cys Lys Ser Cys Pro Pro Ser Thr Phe Ser Ser Ala
            20                  25                  30

Gly Gly Gln Arg Thr Cys Asp Ile Cys Arg Gln Cys Lys Gly Val Phe
        35                  40                  45

Arg Thr Arg Lys Glu Cys Ser Ser Thr Ser Asn Ala Glu Cys Asp Cys
    50                  55                  60

Thr Pro Gly Phe His Cys Leu Gly Ala Gly Cys Ser Met Cys Glu Gln
65                  70                  75                  80

Asp Cys Lys Gln Gly Gln Glu Leu Thr Lys Lys Gly Cys Lys Asp Cys
                85                  90                  95

Cys Phe Gly Thr Phe Asn Asp Gln Lys Arg Gly Ile Cys Arg Pro Trp
            100                 105                 110

Thr Asn Cys Ser Leu Asp Gly Lys Ser Val Leu Val Asn Gly Thr Lys
        115                 120                 125

Glu Arg Asp Val Val Cys Gly Pro Ser Pro Ala Asp Leu Ser Pro Gly
    130                 135                 140

Ala Ser Ser Val Thr Pro Pro Ala Pro Ala Arg Pro Gly His Ser Pro
145                 150                 155                 160

Gln
```

<210> SEQ ID NO 36
<211> LENGTH: 163
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 36

```
Leu Gln Asp Pro Cys Ser Asn Cys Pro Ala Gly Thr Phe Cys Asp Asn
1               5                   10                  15

Asn Arg Asn Gln Ile Cys Ser Pro Cys Pro Pro Asn Ser Phe Ser Ser
            20                  25                  30

Ile Gly Gly Gln Pro Asn Cys Asn Ile Cys Arg Val Cys Ala Gly Tyr
        35                  40                  45

Phe Arg Phe Lys Lys Phe Cys Ser Ser Thr Ser Asn Ala Glu Cys Asp
```

```
                50                  55                  60
Cys Thr Pro Gly Phe His Cys Leu Gly Ala Gly Cys Ser Met Cys Glu
 65                  70                  75                  80

Gln Asp Cys Lys Gln Gly Gln Glu Leu Thr Lys Lys Gly Cys Lys Asp
                 85                  90                  95

Cys Cys Phe Gly Thr Phe Asn Asp Gln Lys Arg Gly Ile Cys Arg Pro
                100                 105                 110

Trp Thr Asn Cys Ser Leu Asp Gly Lys Ser Val Leu Val Asn Gly Thr
            115                 120                 125

Lys Glu Arg Asp Val Val Cys Gly Pro Ser Pro Ala Asp Leu Ser Pro
        130                 135                 140

Gly Ala Ser Ser Val Thr Pro Pro Ala Pro Ala Arg Glu Pro Gly His
145                 150                 155                 160

Ser Pro Gln
```

<210> SEQ ID NO 37
<211> LENGTH: 163
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 37

```
Leu Gln Asp Pro Cys Ser Asn Cys Pro Ala Gly Thr Phe Cys Asp Asn
 1               5                  10                  15

Asn Arg Asn Gln Ile Cys Ser Pro Cys Pro Pro Asn Ser Phe Ser Ser
                 20                  25                  30

Ala Gly Gly Gln Arg Thr Cys Asp Ile Cys Arg Gln Cys Lys Gly Val
            35                  40                  45

Phe Arg Thr Arg Lys Glu Cys Ser Ser Thr His Asn Ala Glu Cys Glu
 50                  55                  60

Cys Ile Glu Gly Phe His Cys Leu Gly Pro Gln Cys Thr Arg Cys Glu
 65                  70                  75                  80

Lys Asp Cys Arg Pro Gly Gln Glu Leu Thr Lys Lys Gly Cys Lys Asp
                 85                  90                  95

Cys Cys Phe Gly Thr Phe Asn Asp Gln Lys Arg Gly Ile Cys Arg Pro
                100                 105                 110

Trp Thr Asn Cys Ser Leu Asp Gly Lys Ser Val Leu Val Asn Gly Thr
            115                 120                 125

Lys Glu Arg Asp Val Val Cys Gly Pro Ser Pro Ala Asp Leu Ser Pro
        130                 135                 140

Gly Ala Ser Ser Val Thr Pro Pro Ala Pro Ala Arg Glu Pro Gly His
145                 150                 155                 160

Ser Pro Gln
```

<210> SEQ ID NO 38
<211> LENGTH: 164
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 38

```
Leu Gln Asp Pro Cys Ser Asn Cys Pro Ala Gly Thr Phe Cys Asp Asn
```

```
  1               5                  10                 15
Asn Arg Asn Gln Ile Cys Ser Pro Cys Pro Asn Ser Phe Ser Ser
            20                  25                 30

Ala Gly Gly Gln Arg Thr Cys Asp Ile Cys Arg Gln Cys Lys Gly Val
            35                  40                 45

Phe Arg Thr Arg Lys Glu Cys Ser Ser Thr Ser Asn Ala Glu Cys Asp
            50                  55                 60

Cys Thr Pro Gly Phe His Cys Leu Gly Ala Gly Cys Ser Met Cys Glu
65                  70                 75                 80

Gln Asp Cys Lys Gln Gly Gln Glu Leu Thr Lys Gln Gly Cys Lys Thr
                85                  90                 95

Cys Ser Leu Gly Thr Phe Asn Asp Gln Asn Gly Thr Gly Val Cys Arg
                100                 105                110

Pro Trp Thr Asn Cys Ser Leu Asp Gly Lys Ser Val Leu Val Asn Gly
                115                 120                125

Thr Lys Glu Arg Asp Val Val Cys Gly Pro Ser Pro Ala Asp Leu Ser
                130                 135                140

Pro Gly Ala Ser Ser Val Thr Pro Pro Ala Pro Ala Arg Glu Pro Gly
145                 150                 155                160

His Ser Pro Gln
```

<210> SEQ ID NO 39
<211> LENGTH: 163
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 39

```
Leu Gln Asp Pro Cys Ser Asn Cys Pro Ala Gly Thr Phe Cys Asp Asn
1               5                  10                 15

Asn Arg Asn Gln Ile Cys Ser Pro Cys Pro Asn Ser Phe Ser Ser
            20                  25                 30

Ala Gly Gly Gln Arg Thr Cys Asp Ile Cys Arg Gln Cys Lys Gly Val
            35                  40                 45

Phe Arg Thr Arg Lys Glu Cys Ser Ser Thr Ser Asn Ala Glu Cys Asp
            50                  55                 60

Cys Thr Pro Gly Phe His Cys Leu Gly Ala Gly Cys Ser Met Cys Glu
65                  70                 75                 80

Gln Asp Cys Lys Gln Gly Gln Glu Leu Thr Lys Lys Gly Cys Lys Asp
                85                  90                 95

Cys Cys Phe Gly Thr Phe Asn Asp Gln Lys Arg Gly Ile Cys Arg Pro
                100                 105                110

Trp Thr Asn Cys Ser Leu Asp Gly Arg Ser Val Leu Lys Thr Gly Thr
                115                 120                125

Thr Glu Lys Asp Val Val Cys Gly Pro Ser Pro Ala Asp Leu Ser Pro
                130                 135                140

Gly Ala Ser Ser Val Thr Pro Pro Ala Pro Ala Arg Glu Pro Gly His
145                 150                 155                160

Ser Pro Gln
```

<210> SEQ ID NO 40
<211> LENGTH: 98
<212> TYPE: PRT

```
<213> ORGANISM: Homo sapiens

<400> SEQUENCE: 40

Gln Val Gln Leu Val Gln Ser Gly Ala Glu Val Lys Lys Pro Gly Ala
1               5                   10                  15
Ser Val Lys Val Ser Cys Lys Ala Ser Gly Tyr Thr Phe Thr Gly Tyr
                20                  25                  30
Tyr Met His Trp Val Arg Gln Ala Pro Gly Gln Gly Leu Glu Trp Met
            35                  40                  45
Gly Trp Ile Asn Pro Asn Ser Gly Gly Thr Asn Tyr Ala Gln Lys Phe
        50                  55                  60
Gln Gly Arg Val Thr Met Thr Arg Asp Thr Ser Ile Ser Thr Ala Tyr
65                  70                  75                  80
Met Glu Leu Ser Arg Leu Arg Ser Asp Asp Thr Ala Val Tyr Tyr Cys
                85                  90                  95
Ala Arg

<210> SEQ ID NO 41
<211> LENGTH: 96
<212> TYPE: PRT
<213> ORGANISM: Homo sapiens

<400> SEQUENCE: 41

Ser Tyr Val Leu Thr Gln Pro Pro Ser Val Ser Val Ala Pro Gly Gln
1               5                   10                  15
Thr Ala Arg Ile Thr Cys Gly Gly Asn Asn Ile Gly Ser Lys Ser Val
                20                  25                  30
His Trp Tyr Gln Gln Lys Pro Gly Gln Ala Pro Val Leu Val Val Tyr
            35                  40                  45
Asp Asp Ser Asp Arg Pro Ser Gly Ile Pro Glu Arg Phe Ser Gly Ser
        50                  55                  60
Asn Ser Gly Asn Thr Ala Thr Leu Thr Ile Ser Arg Val Glu Ala Gly
65                  70                  75                  80
Asp Glu Ala Asp Tyr Tyr Cys Gln Val Trp Asp Ser Ser Ser Asp His
                85                  90                  95

<210> SEQ ID NO 42
<211> LENGTH: 39
<212> TYPE: PRT
<213> ORGANISM: Homo sapiens

<400> SEQUENCE: 42

Cys Cys Phe Gly Thr Phe Asn Asp Gln Lys Arg Gly Ile Cys Arg Pro
1               5                   10                  15
Trp Thr Asn Cys Ser Leu Asp Gly Lys Ser Val Leu Val Asn Gly Thr
                20                  25                  30
Lys Glu Arg Asp Val Val Cys
            35

<210> SEQ ID NO 43
<211> LENGTH: 4
<212> TYPE: PRT
<213> ORGANISM: Homo sapiens

<400> SEQUENCE: 43

Lys Arg Gly Ile
1
```

-continued

```
<210> SEQ ID NO 44
<211> LENGTH: 5
<212> TYPE: PRT
<213> ORGANISM: Mus musculus

<400> SEQUENCE: 44

Asn Gly Thr Gly Val
1               5

<210> SEQ ID NO 45
<211> LENGTH: 164
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 45

Leu Gln Asp Pro Cys Ser Asn Cys Pro Ala Gly Thr Phe Cys Asp Asn
1               5                   10                  15

Asn Arg Asn Gln Ile Cys Ser Pro Cys Pro Pro Asn Ser Phe Ser Ser
                20                  25                  30

Ala Gly Gly Gln Arg Thr Cys Asp Ile Cys Arg Gln Cys Lys Gly Val
            35                  40                  45

Phe Arg Thr Arg Lys Glu Cys Ser Ser Thr Ser Asn Ala Glu Cys Asp
50                  55                  60

Cys Thr Pro Gly Phe His Cys Leu Gly Ala Gly Cys Ser Met Cys Glu
65                  70                  75                  80

Gln Asp Cys Lys Gln Gly Gln Glu Leu Thr Lys Lys Gly Cys Lys Asp
                85                  90                  95

Cys Cys Phe Gly Thr Phe Asn Asp Gln Asn Gly Thr Gly Val Cys Arg
            100                 105                 110

Pro Trp Thr Asn Cys Ser Leu Asp Gly Lys Ser Val Leu Val Asn Gly
        115                 120                 125

Thr Lys Glu Arg Asp Val Val Cys Gly Pro Ser Pro Ala Asp Leu Ser
    130                 135                 140

Pro Gly Ala Ser Ser Val Thr Pro Pro Ala Pro Ala Arg Glu Pro Gly
145                 150                 155                 160

His Ser Pro Gln

<210> SEQ ID NO 46
<211> LENGTH: 163
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 46

Val Gln Asn Ser Cys Asp Asn Cys Gln Pro Gly Thr Phe Cys Arg Lys
1               5                   10                  15

Tyr Asn Pro Val Cys Lys Ser Cys Pro Pro Ser Thr Phe Ser Ser Ile
                20                  25                  30

Gly Gly Gln Pro Asn Cys Asn Ile Cys Arg Val Cys Ala Gly Tyr Phe
            35                  40                  45

Arg Phe Lys Lys Phe Cys Ser Ser Thr His Asn Ala Glu Cys Glu Cys
        50                  55                  60

Ile Glu Gly Phe His Cys Leu Gly Pro Gln Cys Thr Arg Cys Glu Lys
```

```
                65                  70                  75                  80
Asp Cys Arg Pro Gly Gln Glu Leu Thr Lys Gln Gly Cys Lys Thr Cys
                    85                  90                  95

Ser Leu Gly Thr Phe Asn Asp Gln Lys Arg Gly Ile Cys Arg Pro Trp
                   100                 105                 110

Thr Asn Cys Ser Leu Asp Gly Arg Ser Val Leu Lys Thr Gly Thr Thr
                115                 120                 125

Glu Lys Asp Val Val Cys Gly Pro Pro Val Val Ser Phe Ser Pro Ser
130                 135                 140

Thr Thr Ile Ser Val Thr Pro Glu Gly Gly Pro Gly Gly His Ser Leu
145                 150                 155                 160

Gln Val Leu

<210> SEQ ID NO 47
<211> LENGTH: 164
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 47

Val Gln Asn Ser Cys Asp Asn Cys Gln Pro Gly Thr Phe Cys Arg Lys
1               5                  10                  15

Tyr Asn Pro Val Cys Lys Ser Cys Pro Pro Ser Thr Phe Ser Ser Ala
                20                  25                  30

Gly Gly Gln Arg Thr Cys Asp Ile Cys Arg Gln Cys Lys Gly Val Phe
            35                  40                  45

Arg Thr Arg Lys Glu Cys Ser Ser Thr His Asn Ala Glu Cys Glu Cys
50                  55                  60

Ile Glu Gly Phe His Cys Leu Gly Pro Gln Cys Thr Arg Cys Glu Lys
65                  70                  75                  80

Asp Cys Arg Pro Gly Gln Glu Leu Thr Lys Gln Gly Cys Lys Thr Cys
                    85                  90                  95

Ser Leu Gly Thr Phe Asn Asp Gln Asn Gly Thr Gly Val Cys Arg Pro
                   100                 105                 110

Trp Thr Asn Cys Ser Leu Asp Gly Arg Ser Val Leu Lys Thr Gly Thr
                115                 120                 125

Thr Glu Lys Asp Val Val Cys Gly Pro Pro Val Val Ser Phe Ser Pro
130                 135                 140

Ser Thr Thr Ile Ser Val Thr Pro Glu Gly Gly Pro Gly Gly His Ser
145                 150                 155                 160

Leu Gln Val Leu

<210> SEQ ID NO 48
<211> LENGTH: 163
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 48

Val Gln Asn Ser Cys Asp Asn Cys Gln Pro Gly Thr Phe Cys Arg Lys
1               5                  10                  15

Tyr Asn Pro Val Cys Lys Ser Cys Pro Pro Ser Thr Phe Ser Ser Ile
```

```
                20                  25                  30
Gly Gly Gln Pro Asn Cys Asn Ile Cys Arg Val Cys Ala Gly Tyr Phe
            35                  40                  45

Arg Phe Lys Lys Phe Cys Ser Ser Thr His Asn Ala Glu Cys Glu Cys
        50                  55                  60

Ile Glu Gly Phe His Cys Leu Gly Pro Gln Cys Thr Arg Cys Glu Lys
65                  70                  75                  80

Asp Cys Arg Pro Gly Gln Glu Leu Thr Lys Lys Gly Cys Lys Asp Cys
                85                  90                  95

Cys Phe Gly Thr Phe Asn Asp Gln Lys Arg Gly Ile Cys Arg Pro Trp
            100                 105                 110

Thr Asn Cys Ser Leu Asp Gly Arg Ser Val Leu Lys Thr Gly Thr Thr
        115                 120                 125

Glu Lys Asp Val Val Cys Gly Pro Pro Val Val Ser Phe Ser Pro Ser
    130                 135                 140

Thr Thr Ile Ser Val Thr Pro Glu Gly Gly Pro Gly Gly His Ser Leu
145                 150                 155                 160

Gln Val Leu
```

<210> SEQ ID NO 49
<211> LENGTH: 450
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: VARIANT
<222> LOCATION: (1)..(1)
<223> OTHER INFORMATION: /replace="Pyroglutamate"
<220> FEATURE:
<221> NAME/KEY: MISC_FEATURE
<222> LOCATION: (1)..(450)
<223> OTHER INFORMATION: /note="Variant residues given in the sequence
      have no preference with respect to those in the annotations
      for variant positions"

<400> SEQUENCE: 49

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
            85                  90                  95

Ala Arg Glu Pro Gly Tyr Tyr Gly Ser Gly Leu Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160
```

```
Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Arg Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 50
<211> LENGTH: 450
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: VARIANT
<222> LOCATION: (1)..(1)
<223> OTHER INFORMATION: /replace="Pyroglutamate"
<220> FEATURE:
<221> NAME/KEY: MISC_FEATURE
<222> LOCATION: (1)..(450)
<223> OTHER INFORMATION: /note="Variant residues given in the sequence
      have no preference with respect to those in the annotations
      for variant positions"

<400> SEQUENCE: 50
```

```
Gln Val Gln Leu Val Gln Ser Gly Ala Glu Val Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
            35                  40                  45

Gly Trp Ile Asn Pro Asn Ser Gly Thr Asn Tyr Ala Gln Lys Phe
50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Glu Pro Gly Tyr Tyr Gly Ser Gly Leu Asp Tyr Trp Gly Gln
                100                 105                 110

Gly Thr Leu Val Thr Val Ser Ser Ala Ser Thr Lys Gly Pro Ser Val
            115                 120                 125

Phe Pro Leu Ala Pro Ser Ser Lys Ser Thr Ser Gly Gly Thr Ala Ala
130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
                180                 185                 190

Ser Ser Ser Leu Gly Thr Gln Thr Tyr Ile Cys Asn Val Asn His Lys
            195                 200                 205

Pro Ser Asn Thr Lys Val Asp Lys Arg Val Glu Pro Lys Ser Cys Asp
210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
                260                 265                 270

Asp Pro Glu Val Lys Phe Asn Trp Tyr Val Asp Gly Val Glu Val His
            275                 280                 285

Asn Ala Lys Thr Lys Pro Arg Glu Glu Gln Tyr Ala Ser Thr Tyr Arg
290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
                340                 345                 350

Thr Leu Pro Pro Ser Arg Glu Glu Met Thr Lys Asn Gln Val Ser Leu
            355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415
```

```
Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
            435                 440                 445

Gly Lys
    450

<210> SEQ ID NO 51
<211> LENGTH: 450
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: VARIANT
<222> LOCATION: (1)..(1)
<223> OTHER INFORMATION: /replace="Pyroglutamate"
<220> FEATURE:
<221> NAME/KEY: MISC_FEATURE
<222> LOCATION: (1)..(450)
<223> OTHER INFORMATION: /note="Variant residues given in the sequence
      have no preference with respect to those in the annotations
      for variant positions"

<400> SEQUENCE: 51

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Glu Pro Gly Tyr Tyr Gly Ser Gly Leu Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Arg Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255
```

```
Ser Arg Thr Pro Glu Val Thr Cys Val Val Asp Val Glu His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Phe Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 52
<211> LENGTH: 446
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: VARIANT
<222> LOCATION: (1)..(1)
<223> OTHER INFORMATION: /replace="Pyroglutamate"
<220> FEATURE:
<221> NAME/KEY: MISC_FEATURE
<222> LOCATION: (1)..(446)
<223> OTHER INFORMATION: /note="Variant residues given in the sequence
      have no preference with respect to those in the annotations
      for variant positions"

<400> SEQUENCE: 52

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95
```

```
Ala Arg Glu Pro Gly Tyr Tyr Gly Ser Gly Leu Asp Tyr Trp Gly Gln
                100                 105                 110
Gly Thr Leu Val Thr Val Ser Ser Ala Ser Thr Lys Gly Pro Ser Val
        115                 120                 125
Phe Pro Leu Ala Pro Cys Ser Arg Ser Thr Ser Glu Ser Thr Ala Ala
    130                 135                 140
Leu Gly Cys Leu Val Lys Asp Tyr Phe Pro Glu Pro Val Thr Val Ser
145                 150                 155                 160
Trp Asn Ser Gly Ala Leu Thr Ser Gly Val His Thr Phe Pro Ala Val
                165                 170                 175
Leu Gln Ser Ser Gly Leu Tyr Ser Leu Ser Ser Val Val Thr Val Pro
            180                 185                 190
Ser Ser Asn Phe Gly Thr Gln Thr Tyr Thr Cys Asn Val Asp His Lys
        195                 200                 205
Pro Ser Asn Thr Lys Val Asp Lys Thr Val Glu Arg Lys Cys Cys Val
    210                 215                 220
Glu Cys Pro Pro Cys Pro Ala Pro Pro Val Ala Gly Pro Ser Val Phe
225                 230                 235                 240
Leu Phe Pro Pro Lys Pro Lys Asp Thr Leu Met Ile Ser Arg Thr Pro
                245                 250                 255
Glu Val Thr Cys Val Val Val Asp Val Ser His Glu Asp Pro Glu Val
            260                 265                 270
Gln Phe Asn Trp Tyr Val Asp Gly Val Glu Val His Asn Ala Lys Thr
        275                 280                 285
Lys Pro Arg Glu Glu Gln Phe Asn Ser Thr Phe Arg Val Val Ser Val
    290                 295                 300
Leu Thr Val Val His Gln Asp Trp Leu Asn Gly Lys Glu Tyr Lys Cys
305                 310                 315                 320
Lys Val Ser Asn Lys Gly Leu Pro Ala Pro Ile Glu Lys Thr Ile Ser
                325                 330                 335
Lys Thr Lys Gly Gln Pro Arg Glu Pro Gln Val Tyr Thr Leu Pro Pro
            340                 345                 350
Ser Arg Glu Glu Met Thr Lys Asn Gln Val Ser Leu Thr Cys Leu Val
        355                 360                 365
Lys Gly Phe Tyr Pro Ser Asp Ile Ala Val Glu Trp Glu Ser Asn Gly
    370                 375                 380
Gln Pro Glu Asn Asn Tyr Lys Thr Thr Pro Pro Met Leu Asp Ser Asp
385                 390                 395                 400
Gly Ser Phe Phe Leu Tyr Ser Lys Leu Thr Val Asp Lys Ser Arg Trp
                405                 410                 415
Gln Gln Gly Asn Val Phe Ser Cys Ser Val Met His Glu Ala Leu His
            420                 425                 430
Asn His Tyr Thr Gln Lys Ser Leu Ser Leu Ser Pro Gly Lys
        435                 440                 445

<210> SEQ ID NO 53
<211> LENGTH: 446
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: VARIANT
<222> LOCATION: (1)..(1)
<223> OTHER INFORMATION: /replace="Pyroglutamate"
```

```
<220> FEATURE:
<221> NAME/KEY: MISC_FEATURE
<222> LOCATION: (1)..(446)
<223> OTHER INFORMATION: /note="Variant residues given in the sequence
      have no preference with respect to those in the annotations
      for variant positions"

<400> SEQUENCE: 53

Gln Val Gln Leu Val Gln Ser Gly Ala Glu Val Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Glu Pro Gly Tyr Tyr Gly Ser Gly Leu Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Cys Ser Arg Ser Thr Ser Glu Ser Thr Ala Ala
130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Asn Phe Gly Thr Gln Thr Tyr Thr Cys Asn Val Asp His Lys
        195                 200                 205

Pro Ser Asn Thr Lys Val Asp Lys Thr Val Glu Arg Lys Cys Cys Val
210                 215                 220

Glu Cys Pro Pro Cys Pro Ala Pro Pro Val Ala Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Gln Phe Asn Trp Tyr Val Asp Gly Val Glu Val His Asn Ala Lys Thr
        275                 280                 285

Lys Pro Arg Glu Glu Gln Phe Ala Ser Thr Phe Arg Val Val Ser Val
290                 295                 300

Leu Thr Val Val His Gln Asp Trp Leu Asn Gly Lys Glu Tyr Lys Cys
305                 310                 315                 320

Lys Val Ser Asn Lys Gly Leu Pro Ala Pro Ile Glu Lys Thr Ile Ser
                325                 330                 335

Lys Thr Lys Gly Gln Pro Arg Glu Pro Gln Val Tyr Thr Leu Pro Pro
            340                 345                 350

Ser Arg Glu Glu Met Thr Lys Asn Gln Val Ser Leu Thr Cys Leu Val
        355                 360                 365

Lys Gly Phe Tyr Pro Ser Asp Ile Asn Val Glu Trp Glu Ser Asn Gly
```

-continued

```
                370                 375                 380
Gln Pro Glu Asn Asn Tyr Lys Thr Thr Pro Pro Met Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
                420                 425                 430

Asn His Tyr Thr Gln Lys Ser Leu Ser Leu Ser Pro Gly Lys
                435                 440                 445

<210> SEQ ID NO 54
<211> LENGTH: 447
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: VARIANT
<222> LOCATION: (1)..(1)
<223> OTHER INFORMATION: /replace="Pyroglutamate"
<220> FEATURE:
<221> NAME/KEY: MISC_FEATURE
<222> LOCATION: (1)..(447)
<223> OTHER INFORMATION: /note="Variant residues given in the sequence
      have no preference with respect to those in the annotations
      for variant positions"

<400> SEQUENCE: 54

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
                20                  25                  30

Tyr Met His Trp Val Arg Gln Ala Pro Gly Gln Gly Leu Glu Trp Met
            35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Glu Pro Gly Tyr Tyr Gly Ser Gly Leu Asp Tyr Trp Gly Gln
                100                 105                 110

Gly Thr Leu Val Thr Val Ser Ser Ala Ser Thr Lys Gly Pro Ser Val
            115                 120                 125

Phe Pro Leu Ala Pro Cys Ser Arg Ser Thr Ser Glu Ser Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
                180                 185                 190

Ser Ser Ser Leu Gly Thr Lys Thr Tyr Thr Cys Asn Val Asp His Lys
            195                 200                 205

Pro Ser Asn Thr Lys Val Asp Lys Arg Val Glu Ser Lys Tyr Gly Pro
    210                 215                 220

Pro Cys Pro Pro Cys Pro Ala Pro Glu Phe Leu Gly Gly Pro Ser Val
```

-continued

```
            225                 230                 235                 240
        Phe Leu Phe Pro Pro Lys Pro Lys Asp Thr Leu Met Ile Ser Arg Thr
                        245                 250                 255

Pro Glu Val Thr Cys Val Val Val Asp Val Ser Gln Glu Asp Pro Glu
                        260                 265                 270

Val Gln Phe Asn Trp Tyr Val Asp Gly Val Glu Val His Asn Ala Lys
                        275                 280                 285

Thr Lys Pro Arg Glu Glu Gln Phe Asn Ser Thr Tyr Arg Val Val Ser
                        290                 295                 300

Val Leu Thr Val Leu His Gln Asp Trp Leu Asn Gly Lys Glu Tyr Lys
        305                 310                 315                 320

Cys Lys Val Ser Asn Lys Gly Leu Pro Ser Ser Ile Glu Lys Thr Ile
                        325                 330                 335

Ser Lys Ala Lys Gly Gln Pro Arg Glu Pro Gln Val Tyr Thr Leu Pro
                        340                 345                 350

Pro Ser Gln Glu Glu Met Thr Lys Asn Gln Val Ser Leu Thr Cys Leu
                        355                 360                 365

Val Lys Gly Phe Tyr Pro Ser Asp Ile Ala Val Glu Trp Glu Ser Asn
        370                 375                 380

Gly Gln Pro Glu Asn Asn Tyr Lys Thr Thr Pro Pro Val Leu Asp Ser
        385                 390                 395                 400

Asp Gly Ser Phe Phe Leu Tyr Ser Arg Leu Thr Val Asp Lys Ser Arg
                        405                 410                 415

Trp Gln Glu Gly Asn Val Phe Ser Cys Ser Val Met His Glu Ala Leu
                        420                 425                 430

His Asn His Tyr Thr Gln Lys Ser Leu Ser Leu Ser Leu Gly Lys
                    435                 440                 445

<210> SEQ ID NO 55
<211> LENGTH: 245
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 55

Gln Val Gln Leu Val Gln Ser Gly Ala Glu Val Lys Lys Pro Gly Ala
        1               5                   10                  15

Ser Val Lys Val Ser Cys Lys Ala Ser Gly Tyr Thr Phe Thr Gly Tyr
                        20                  25                  30

Tyr Met His Trp Val Arg Gln Ala Pro Gly Gln Gly Leu Glu Trp Met
                    35                  40                  45

Gly Trp Ile Asn Pro Asn Ser Gly Gly Thr Asn Tyr Ala Gln Lys Phe
            50                  55                  60

Gln Gly Arg Val Thr Met Thr Arg Asp Thr Ser Ile Ser Thr Ala Tyr
        65                  70                  75                  80

Met Glu Leu Ser Arg Leu Arg Ser Asp Asp Thr Ala Val Tyr Tyr Cys
                        85                  90                  95

Ala Arg Glu Pro Gly Tyr Tyr Gly Ser Gly Leu Asp Tyr Trp Gly Gln
                        100                 105                 110

Gly Thr Leu Val Thr Val Ser Ser Gly Gly Gly Gly Ser Gly Gly Gly
                    115                 120                 125

Gly Ser Gly Gly Gly Gly Ala Ser Ser Tyr Val Leu Thr Gln Pro Pro
        130                 135                 140
```

```
Ser Val Ser Val Ala Pro Gly Glu Thr Ala Arg Ile Thr Cys Gly Gly
145                 150                 155                 160

Asp Asp Ile Gly Asp Lys Arg Val His Trp Tyr Gln Lys Lys Pro Asp
            165                 170                 175

Gln Ala Pro Val Leu Val Val Tyr Glu Asp Arg Tyr Arg Pro Ser Gly
        180                 185                 190

Ile Pro Glu Arg Ile Ser Gly Ser Asn Ser Gly Asn Thr Ala Thr Leu
            195                 200                 205

Thr Leu Ser Arg Val Glu Ala Gly Asp Glu Ala Asp Tyr Tyr Cys Gln
        210                 215                 220

Val Trp Asp Ser Ser Ser Asp His Pro Gly Val Phe Gly Gly Gly Thr
225                 230                 235                 240

Gln Leu Ile Ile Leu
            245
```

<210> SEQ ID NO 56
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 56

```
Thr Phe Thr Gly Tyr Tyr Met His
1               5
```

<210> SEQ ID NO 57
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 57

```
Ser Phe Thr Gly Tyr Tyr Met His
1               5
```

<210> SEQ ID NO 58
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 58

```
Asn Phe Ser Gly Tyr Tyr Met His
1               5
```

<210> SEQ ID NO 59
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 59

```
Glu Pro Gly Tyr Tyr Gly Thr Gly Leu Asp Tyr
1               5                   10
```

<210> SEQ ID NO 60
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 60

```
Gln Val Trp Asn Ser Ser Ser Asp His Pro Gly Val
1               5                   10
```

<210> SEQ ID NO 61
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 61

```
Gln Val Trp Asp Ser Ser Ser Asp Tyr Pro Gly Val
1               5                   10
```

<210> SEQ ID NO 62
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 62

```
Gln Val Trp Tyr Ser Ser Pro Asp His Pro Gly Val
1               5                   10
```

<210> SEQ ID NO 63
<211> LENGTH: 120
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: VARIANT
<222> LOCATION: (1)..(1)
<223> OTHER INFORMATION: /replace="Pyroglutamate"
<220> FEATURE:
<221> NAME/KEY: MISC_FEATURE
<222> LOCATION: (1)..(120)
<223> OTHER INFORMATION: /note="Variant residues given in the sequence
      have no preference with respect to those in the annotations
      for variant positions"

<400> SEQUENCE: 63

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45
```

```
Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Glu Pro Gly Tyr Tyr Gly Thr Gly Leu Asp Tyr Trp Gly Gln
                100                 105                 110

Gly Thr Leu Val Thr Val Ser Ser
            115                 120

<210> SEQ ID NO 64
<211> LENGTH: 120
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: VARIANT
<222> LOCATION: (1)..(1)
<223> OTHER INFORMATION: /replace="Pyroglutamate"
<220> FEATURE:
<221> NAME/KEY: MISC_FEATURE
<222> LOCATION: (1)..(120)
<223> OTHER INFORMATION: /note="Variant residues given in the sequence
      have no preference with respect to those in the annotations
      for variant positions"

<400> SEQUENCE: 64

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Gly Tyr
                20                  25                  30

Tyr Met His Trp Val Arg Gln Ala Pro Gly Gln Gly Leu Glu Trp Met
            35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Glu Pro Gly Tyr Tyr Gly Ser Gly Leu Asp Tyr Trp Gly Gln
                100                 105                 110

Gly Thr Leu Val Thr Val Ser Ser
            115                 120

<210> SEQ ID NO 65
<211> LENGTH: 120
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: VARIANT
<222> LOCATION: (1)..(1)
<223> OTHER INFORMATION: /replace="Pyroglutamate"
<220> FEATURE:
<221> NAME/KEY: MISC_FEATURE
<222> LOCATION: (1)..(120)
<223> OTHER INFORMATION: /note="Variant residues given in the sequence
      have no preference with respect to those in the annotations
``` for variant positions"

<400> SEQUENCE: 65

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Asn Phe Ser Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Ile Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Glu Pro Gly Tyr Tyr Gly Ser Gly Leu Asp Tyr Trp Gly Gln
            100                 105                 110

Gly Thr Leu Val Thr Val Ser Ser
        115                 120

<210> SEQ ID NO 66
<211> LENGTH: 109
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 66

Ser Tyr Val Leu Thr Gln Pro Pro Ser Val Ser Val Ala Pro Gly Glu
1               5                   10                  15

Thr Ala Arg Ile Thr Cys Gly Gly Asp Asp Ile Gly Asp Lys Arg Val
            20                  25                  30

His Trp Tyr Gln Lys Lys Pro Asp Gln Ala Pro Val Leu Val Val Tyr
        35                  40                  45

Glu Asp Arg Tyr Arg Pro Ser Gly Ile Pro Glu Arg Ile Ser Gly Ser
    50                  55                  60

Asn Ser Gly Asn Thr Ala Thr Leu Thr Leu Ser Arg Val Glu Ala Gly
65                  70                  75                  80

Asp Glu Ala Asp Tyr Tyr Cys Gln Val Trp Asn Ser Ser Ser Asp His
                85                  90                  95

Pro Gly Val Phe Gly Gly Gly Thr Gln Leu Ile Ile Leu
            100                 105

<210> SEQ ID NO 67
<211> LENGTH: 109
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 67

Ser Tyr Val Leu Thr Gln Pro Pro Ser Val Ser Val Ala Pro Gly Glu
1               5                   10                  15

Thr Ala Arg Ile Thr Cys Gly Gly Asp Asp Ile Gly Asp Lys Arg Val
            20                  25                  30

His Trp Tyr Gln Lys Lys Pro Asp Gln Ala Pro Val Leu Val Val Tyr
            35                  40                  45

Glu Asp Arg Tyr Arg Pro Ser Gly Ile Pro Glu Arg Ile Ser Gly Ser
 50                  55                  60

Asn Ser Gly Asn Thr Ala Thr Leu Thr Leu Ser Arg Val Glu Ala Gly
 65                  70                  75                  80

Asp Glu Ala Asp Tyr Tyr Cys Gln Val Trp Asp Ser Ser Asp Tyr
                 85                  90                  95

Pro Gly Val Phe Gly Gly Gly Thr Gln Leu Ile Ile Leu
            100                 105

<210> SEQ ID NO 68
<211> LENGTH: 109
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 68

Ser Tyr Val Leu Thr Gln Pro Pro Ser Val Ser Val Ala Pro Gly Glu
 1               5                  10                  15

Thr Ala Arg Ile Thr Cys Gly Gly Asp Asp Ile Gly Asp Lys Arg Val
                 20                  25                  30

His Trp Tyr Gln Lys Lys Pro Asp Gln Ala Pro Val Leu Val Val Tyr
            35                  40                  45

Glu Asp Arg Tyr Arg Pro Ser Gly Ile Pro Glu Arg Ile Ser Gly Ser
 50                  55                  60

Asn Ser Gly Asn Thr Ala Thr Leu Thr Leu Ser Arg Val Glu Ala Gly
 65                  70                  75                  80

Asp Glu Ala Asp Tyr Tyr Cys Gln Val Trp Tyr Ser Ser Pro Asp His
                 85                  90                  95

Pro Gly Val Phe Gly Gly Gly Thr Gln Leu Ile Ile Leu
            100                 105

<210> SEQ ID NO 69
<211> LENGTH: 245
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: VARIANT
<222> LOCATION: (1)..(1)
<223> OTHER INFORMATION: /replace="Pyroglutamate"
<220> FEATURE:
<221> NAME/KEY: MISC_FEATURE
<222> LOCATION: (1)..(245)
<223> OTHER INFORMATION: /note="Variant residues given in the sequence
      have no preference with respect to those in the annotations
      for variant positions"

<400> SEQUENCE: 69

Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Gly Tyr
                 20                  25                  30

Tyr Met His Trp Val Arg Gln Ala Pro Gly Gln Gly Leu Glu Trp Met
            35                  40                  45

-continued

```
Gly Trp Ile Asn Pro Asn Ser Gly Gly Thr Asn Tyr Ala Gln Lys Phe
 50                  55                  60

Gln Gly Arg Val Thr Met Thr Arg Asp Thr Ser Ile Ser Thr Ala Tyr
 65                  70                  75                  80

Met Glu Leu Ser Arg Leu Arg Ser Asp Asp Thr Ala Val Tyr Tyr Cys
                 85                  90                  95

Ala Arg Glu Pro Gly Tyr Tyr Gly Thr Gly Leu Asp Tyr Trp Gly Gln
                100                 105                 110

Gly Thr Leu Val Thr Val Ser Ser Gly Gly Gly Ser Gly Gly Gly
                115                 120                 125

Gly Ser Gly Gly Gly Ala Ser Ser Tyr Val Leu Thr Gln Pro Pro
130                 135                 140

Ser Val Ser Val Ala Pro Gly Glu Thr Ala Arg Ile Thr Cys Gly Gly
145                 150                 155                 160

Asp Asp Ile Gly Asp Lys Arg Val His Trp Tyr Gln Lys Lys Pro Asp
                165                 170                 175

Gln Ala Pro Val Leu Val Val Tyr Glu Asp Arg Tyr Arg Pro Ser Gly
                180                 185                 190

Ile Pro Glu Arg Ile Ser Gly Ser Asn Ser Gly Asn Thr Ala Thr Leu
                195                 200                 205

Thr Leu Ser Arg Val Glu Ala Gly Asp Glu Ala Asp Tyr Tyr Cys Gln
                210                 215                 220

Val Trp Asp Ser Ser Ser Asp His Pro Gly Val Phe Gly Gly Gly Thr
225                 230                 235                 240

Gln Leu Ile Ile Leu
                245
```

<210> SEQ ID NO 70
<211> LENGTH: 245
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: VARIANT
<222> LOCATION: (1)..(1)
<223> OTHER INFORMATION: /replace="Pyroglutamate"
<220> FEATURE:
<221> NAME/KEY: MISC_FEATURE
<222> LOCATION: (1)..(245)
<223> OTHER INFORMATION: /note="Variant residues given in the sequence
      have no preference with respect to those in the annotations
      for variant positions"

<400> SEQUENCE: 70

```
Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Ser Phe Thr Gly Tyr
                 20                  25                  30

Tyr Met His Trp Val Arg Gln Ala Pro Gly Gln Gly Leu Glu Trp Met
                 35                  40                  45

Gly Trp Ile Asn Pro Asn Ser Gly Gly Thr Asn Tyr Ala Gln Lys Phe
 50                  55                  60

Gln Gly Arg Val Thr Met Thr Arg Asp Thr Ser Ile Ser Thr Ala Tyr
 65                  70                  75                  80

Met Glu Leu Ser Arg Leu Arg Ser Asp Asp Thr Ala Val Tyr Tyr Cys
                 85                  90                  95
```

```
Ala Arg Glu Pro Gly Tyr Tyr Gly Ser Gly Leu Asp Tyr Trp Gly Gln
            100                 105                 110

Gly Thr Leu Val Thr Val Ser Ser Gly Gly Gly Ser Gly Gly Gly
        115                 120                 125

Gly Ser Gly Gly Gly Ala Ser Ser Tyr Val Leu Thr Gln Pro Pro
    130                 135                 140

Ser Val Ser Val Ala Pro Gly Glu Thr Ala Arg Ile Thr Cys Gly Gly
145                 150                 155                 160

Asp Asp Ile Gly Asp Lys Arg Val His Trp Tyr Gln Lys Lys Pro Asp
                165                 170                 175

Gln Ala Pro Val Leu Val Val Tyr Glu Asp Arg Tyr Arg Pro Ser Gly
            180                 185                 190

Ile Pro Glu Arg Ile Ser Gly Ser Asn Ser Gly Asn Thr Ala Thr Leu
        195                 200                 205

Thr Leu Ser Arg Val Glu Ala Gly Asp Glu Ala Asp Tyr Tyr Cys Gln
    210                 215                 220

Val Trp Asn Ser Ser Asp His Pro Gly Val Phe Gly Gly Gly Thr
225                 230                 235                 240

Gln Leu Ile Ile Leu
            245

<210> SEQ ID NO 71
<211> LENGTH: 245
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: VARIANT
<222> LOCATION: (1)..(1)
<223> OTHER INFORMATION: /replace="Pyroglutamate"
<220> FEATURE:
<221> NAME/KEY: MISC_FEATURE
<222> LOCATION: (1)..(245)
<223> OTHER INFORMATION: /note="Variant residues given in the sequence
      have no preference with respect to those in the annotations
      for variant positions"

<400> SEQUENCE: 71

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Glu Pro Gly Tyr Tyr Gly Ser Gly Leu Asp Tyr Trp Gly Gln
            100                 105                 110

Gly Thr Leu Val Thr Val Ser Ser Gly Gly Gly Ser Gly Gly Gly
        115                 120                 125

Gly Ser Gly Gly Gly Ala Ser Ser Tyr Val Leu Thr Gln Pro Pro
    130                 135                 140
```

```
Ser Val Ser Val Ala Pro Gly Glu Thr Ala Arg Ile Thr Cys Gly Gly
145                 150                 155                 160

Asp Asp Ile Gly Asp Lys Arg Val His Trp Tyr Gln Lys Lys Pro Asp
                165                 170                 175

Gln Ala Pro Val Leu Val Val Tyr Glu Asp Arg Tyr Arg Pro Ser Gly
            180                 185                 190

Ile Pro Glu Arg Ile Ser Gly Ser Asn Ser Gly Asn Thr Ala Thr Leu
            195                 200                 205

Thr Leu Ser Arg Val Glu Ala Gly Asp Glu Ala Asp Tyr Tyr Cys Gln
        210                 215                 220

Val Trp Asp Ser Ser Ser Asp Tyr Pro Gly Val Phe Gly Gly Gly Thr
225                 230                 235                 240

Gln Leu Ile Ile Leu
                245

<210> SEQ ID NO 72
<211> LENGTH: 245
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: VARIANT
<222> LOCATION: (1)..(1)
<223> OTHER INFORMATION: /replace="Pyroglutamate"
<220> FEATURE:
<221> NAME/KEY: MISC_FEATURE
<222> LOCATION: (1)..(245)
<223> OTHER INFORMATION: /note="Variant residues given in the sequence
      have no preference with respect to those in the annotations
      for variant positions"

<400> SEQUENCE: 72

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Asn Phe Ser Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Ile Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Glu Pro Gly Tyr Tyr Gly Ser Gly Leu Asp Tyr Trp Gly Gln
            100                 105                 110

Gly Thr Leu Val Thr Val Ser Ser Gly Gly Gly Gly Ser Gly Gly Gly
        115                 120                 125

Gly Ser Gly Gly Gly Gly Ala Ser Ser Tyr Val Leu Thr Gln Pro Pro
    130                 135                 140

Ser Val Ser Val Ala Pro Gly Glu Thr Ala Arg Ile Thr Cys Gly Gly
145                 150                 155                 160

Asp Asp Ile Gly Asp Lys Arg Val His Trp Tyr Gln Lys Lys Pro Asp
                165                 170                 175

Gln Ala Pro Val Leu Val Val Tyr Glu Asp Arg Tyr Arg Pro Ser Gly
            180                 185                 190
```

```
Ile Pro Glu Arg Ile Ser Gly Ser Asn Ser Gly Asn Thr Ala Thr Leu
            195                 200                 205

Thr Leu Ser Arg Val Glu Ala Gly Asp Glu Ala Asp Tyr Tyr Cys Gln
        210                 215                 220

Val Trp Tyr Ser Ser Pro Asp His Pro Gly Val Phe Gly Gly Gly Thr
225                 230                 235                 240

Gln Leu Ile Ile Leu
                245

<210> SEQ ID NO 73
<211> LENGTH: 449
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: VARIANT
<222> LOCATION: (1)..(1)
<223> OTHER INFORMATION: /replace="Pyroglutamate"
<220> FEATURE:
<221> NAME/KEY: MISC_FEATURE
<222> LOCATION: (1)..(449)
<223> OTHER INFORMATION: /note="Variant residues given in the sequence
      have no preference with respect to those in the annotations
      for variant positions"

<400> SEQUENCE: 73

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Glu Pro Gly Tyr Tyr Gly Thr Gly Leu Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Arg Val Glu Pro Lys Ser Cys Asp
    210                 215                 220

Lys Thr His Thr Cys Pro Pro Cys Pro Ala Pro Glu Leu Leu Gly Gly
225                 230                 235                 240
```

```
Pro Ser Val Phe Leu Phe Pro Pro Lys Pro Lys Asp Thr Leu Met Ile
            245                 250                 255

Ser Arg Thr Pro Glu Val Thr Cys Val Val Asp Val Ser His Glu
        260                 265                 270

Asp Pro Glu Val Lys Phe Asn Trp Tyr Val Asp Gly Val Glu Val His
    275                 280                 285

Asn Ala Lys Thr Lys Pro Arg Glu Glu Gln Tyr Asn Ser Thr Tyr Arg
290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
            325                 330                 335

Lys Thr Ile Ser Lys Ala Lys Gly Gln Pro Arg Glu Pro Gln Val Tyr
        340                 345                 350

Thr Leu Pro Pro Ser Arg Glu Glu Met Thr Lys Asn Gln Val Ser Leu
    355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
            405                 410                 415

Lys Ser Arg Trp Gln Gln Gly Asn Val Phe Ser Cys Ser Val Met His
        420                 425                 430

Glu Ala Leu His Asn His Tyr Thr Gln Lys Ser Leu Ser Leu Ser Pro
    435                 440                 445

Gly

<210> SEQ ID NO 74
<211> LENGTH: 450
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: VARIANT
<222> LOCATION: (1)..(1)
<223> OTHER INFORMATION: /replace="Pyroglutamate"
<220> FEATURE:
<221> NAME/KEY: MISC_FEATURE
<222> LOCATION: (1)..(450)
<223> OTHER INFORMATION: /note="Variant residues given in the sequence
      have no preference with respect to those in the annotations
      for variant positions"

<400> SEQUENCE: 74

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
```

85                  90                  95
Ala Arg Glu Pro Gly Tyr Tyr Gly Thr Gly Leu Asp Tyr Trp Gly Gln
                100                 105                 110
Gly Thr Leu Val Thr Val Ser Ser Ala Ser Thr Lys Gly Pro Ser Val
                115                 120                 125
Phe Pro Leu Ala Pro Ser Ser Lys Ser Thr Ser Gly Gly Thr Ala Ala
            130                 135                 140
Leu Gly Cys Leu Val Lys Asp Tyr Phe Pro Glu Pro Val Thr Val Ser
145                 150                 155                 160
Trp Asn Ser Gly Ala Leu Thr Ser Gly Val His Thr Phe Pro Ala Val
                165                 170                 175
Leu Gln Ser Ser Gly Leu Tyr Ser Leu Ser Ser Val Val Thr Val Pro
                180                 185                 190
Ser Ser Ser Leu Gly Thr Gln Thr Tyr Ile Cys Asn Val Asn His Lys
                195                 200                 205
Pro Ser Asn Thr Lys Val Asp Lys Arg Val Glu Pro Lys Ser Cys Asp
            210                 215                 220
Lys Thr His Thr Cys Pro Pro Cys Pro Ala Pro Glu Leu Leu Gly Gly
225                 230                 235                 240
Pro Ser Val Phe Leu Phe Pro Pro Lys Pro Lys Asp Thr Leu Met Ile
                245                 250                 255
Ser Arg Thr Pro Glu Val Thr Cys Val Val Val Asp Val Ser His Glu
                260                 265                 270
Asp Pro Glu Val Lys Phe Asn Trp Tyr Val Asp Gly Val Glu Val His
                275                 280                 285
Asn Ala Lys Thr Lys Pro Arg Glu Glu Gln Tyr Asn Ser Thr Tyr Arg
            290                 295                 300
Val Val Ser Val Leu Thr Val Leu His Gln Asp Trp Leu Asn Gly Lys
305                 310                 315                 320
Glu Tyr Lys Cys Lys Val Ser Asn Lys Ala Leu Pro Ala Pro Ile Glu
                325                 330                 335
Lys Thr Ile Ser Lys Ala Lys Gly Gln Pro Arg Glu Pro Gln Val Tyr
                340                 345                 350
Thr Leu Pro Pro Ser Arg Glu Glu Met Thr Lys Asn Gln Val Ser Leu
            355                 360                 365
Thr Cys Leu Val Lys Gly Phe Tyr Pro Ser Asp Ile Ala Val Glu Trp
        370                 375                 380
Glu Ser Asn Gly Gln Pro Glu Asn Asn Tyr Lys Thr Thr Pro Pro Val
385                 390                 395                 400
Leu Asp Ser Asp Gly Ser Phe Phe Leu Tyr Ser Lys Leu Thr Val Asp
                405                 410                 415
Lys Ser Arg Trp Gln Gln Gly Asn Val Phe Ser Cys Ser Val Met His
                420                 425                 430
Glu Ala Leu His Asn His Tyr Thr Gln Lys Ser Leu Ser Leu Ser Pro
            435                 440                 445
Gly Lys
    450

<210> SEQ ID NO 75
<211> LENGTH: 449
<212> TYPE: PRT
<213> ORGANISM: Artificial Sequence
<220> FEATURE:
<221> NAME/KEY: source
<223> OTHER INFORMATION: /note="Description of Artificial Sequence:

```
      Synthetic polypeptide"
<220> FEATURE:
<221> NAME/KEY: VARIANT
<222> LOCATION: (1)..(1)
<223> OTHER INFORMATION: /replace="Pyroglutamate"
<220> FEATURE:
<221> NAME/KEY: MISC_FEATURE
<222> LOCATION: (1)..(449)
<223> OTHER INFORMATION: /note="Variant residues given in the sequence
      have no preference with respect to those in the annotations
      for variant positions"

<400> SEQUENCE: 75

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Glu Pro Gly Tyr Tyr Gly Ser Gly Leu Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Arg Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350
```

```
Thr Leu Pro Pro Ser Arg Glu Glu Met Thr Lys Asn Gln Val Ser Leu
            355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
                420                 425                 430

Glu Ala Leu His Asn His Tyr Thr Gln Lys Ser Leu Ser Leu Ser Pro
            435                 440                 445

Gly

<210> SEQ ID NO 76
<211> LENGTH: 450
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: VARIANT
<222> LOCATION: (1)..(1)
<223> OTHER INFORMATION: /replace="Pyroglutamate"
<220> FEATURE:
<221> NAME/KEY: MISC_FEATURE
<222> LOCATION: (1)..(450)
<223> OTHER INFORMATION: /note="Variant residues given in the sequence
      have no preference with respect to those in the annotations
      for variant positions"

<400> SEQUENCE: 76

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Glu Pro Gly Tyr Tyr Gly Ser Gly Leu Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190
```

```
Ser Ser Ser Leu Gly Thr Gln Thr Tyr Ile Cys Asn Val Asn His Lys
            195                 200                 205

Pro Ser Asn Thr Lys Val Asp Lys Arg Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
                260                 265                 270

Asp Pro Glu Val Lys Phe Asn Trp Tyr Val Asp Gly Val Glu Val His
            275                 280                 285

Asn Ala Lys Thr Lys Pro Arg Glu Glu Gln Tyr Asn Ser Thr Tyr Arg
        290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
                340                 345                 350

Thr Leu Pro Pro Ser Arg Glu Glu Met Thr Lys Asn Gln Val Ser Leu
            355                 360                 365

Thr Cys Leu Val Lys Gly Phe Tyr Pro Ser Asp Ile Ala Val Glu Trp
        370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
                420                 425                 430

Glu Ala Leu His Asn His Tyr Thr Gln Lys Ser Leu Ser Leu Ser Pro
            435                 440                 445

Gly Lys
    450

<210> SEQ ID NO 77
<211> LENGTH: 449
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: VARIANT
<222> LOCATION: (1)..(1)
<223> OTHER INFORMATION: /replace="Pyroglutamate"
<220> FEATURE:
<221> NAME/KEY: MISC_FEATURE
<222> LOCATION: (1)..(449)
<223> OTHER INFORMATION: /note="Variant residues given in the sequence
      have no preference with respect to those in the annotations
      for variant positions"

<400> SEQUENCE: 77

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Asn Phe Ser Gly Tyr
            20                  25                  30
```

```
Tyr Met His Trp Val Arg Gln Ala Pro Gly Gln Gly Leu Glu Trp Met
         35                  40                  45
Gly Trp Ile Asn Pro Asn Ser Gly Gly Thr Asn Tyr Ala Gln Lys Phe
 50                  55                  60
Gln Gly Arg Val Thr Ile Thr Arg Asp Thr Ser Ile Ser Thr Ala Tyr
 65                  70                  75                  80
Met Glu Leu Ser Arg Leu Arg Ser Asp Asp Thr Ala Val Tyr Tyr Cys
                 85                  90                  95
Ala Arg Glu Pro Gly Tyr Tyr Gly Ser Gly Leu Asp Tyr Trp Gly Gln
             100                 105                 110
Gly Thr Leu Val Thr Val Ser Ser Ala Ser Thr Lys Gly Pro Ser Val
         115                 120                 125
Phe Pro Leu Ala Pro Ser Ser Lys Ser Thr Ser Gly Gly Thr Ala Ala
130                 135                 140
Leu Gly Cys Leu Val Lys Asp Tyr Phe Pro Glu Pro Val Thr Val Ser
145                 150                 155                 160
Trp Asn Ser Gly Ala Leu Thr Ser Gly Val His Thr Phe Pro Ala Val
                 165                 170                 175
Leu Gln Ser Ser Gly Leu Tyr Ser Leu Ser Ser Val Val Thr Val Pro
             180                 185                 190
Ser Ser Ser Leu Gly Thr Gln Thr Tyr Ile Cys Asn Val Asn His Lys
         195                 200                 205
Pro Ser Asn Thr Lys Val Asp Lys Arg Val Glu Pro Lys Ser Cys Asp
210                 215                 220
Lys Thr His Thr Cys Pro Pro Cys Pro Ala Pro Glu Leu Leu Gly Gly
225                 230                 235                 240
Pro Ser Val Phe Leu Phe Pro Pro Lys Pro Lys Asp Thr Leu Met Ile
                 245                 250                 255
Ser Arg Thr Pro Glu Val Thr Cys Val Val Val Asp Val Ser His Glu
             260                 265                 270
Asp Pro Glu Val Lys Phe Asn Trp Tyr Val Asp Gly Val Glu Val His
         275                 280                 285
Asn Ala Lys Thr Lys Pro Arg Glu Glu Gln Tyr Asn Ser Thr Tyr Arg
290                 295                 300
Val Val Ser Val Leu Thr Val Leu His Gln Asp Trp Leu Asn Gly Lys
305                 310                 315                 320
Glu Tyr Lys Cys Lys Val Ser Asn Lys Ala Leu Pro Ala Pro Ile Glu
                 325                 330                 335
Lys Thr Ile Ser Lys Ala Lys Gly Gln Pro Arg Glu Pro Gln Val Tyr
             340                 345                 350
Thr Leu Pro Pro Ser Arg Glu Glu Met Thr Lys Asn Gln Val Ser Leu
         355                 360                 365
Thr Cys Leu Val Lys Gly Phe Tyr Pro Ser Asp Ile Ala Val Glu Trp
370                 375                 380
Glu Ser Asn Gly Gln Pro Glu Asn Asn Tyr Lys Thr Thr Pro Pro Val
385                 390                 395                 400
Leu Asp Ser Asp Gly Ser Phe Phe Leu Tyr Ser Lys Leu Thr Val Asp
                 405                 410                 415
Lys Ser Arg Trp Gln Gln Gly Asn Val Phe Ser Cys Ser Val Met His
             420                 425                 430
Glu Ala Leu His Asn His Tyr Thr Gln Lys Ser Leu Ser Leu Ser Pro
         435                 440                 445
Gly
```

```
<210> SEQ ID NO 78
<211> LENGTH: 450
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: VARIANT
<222> LOCATION: (1)..(1)
<223> OTHER INFORMATION: /replace="Pyroglutamate"
<220> FEATURE:
<221> NAME/KEY: MISC_FEATURE
<222> LOCATION: (1)..(450)
<223> OTHER INFORMATION: /note="Variant residues given in the sequence
      have no preference with respect to those in the annotations
      for variant positions"

<400> SEQUENCE: 78
```

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Asn Phe Ser Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Ile Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Glu Pro Gly Tyr Tyr Gly Ser Gly Leu Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Arg Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

```
Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
            325                 330                 335

Lys Thr Ile Ser Lys Ala Lys Gly Gln Pro Arg Glu Pro Gln Val Tyr
                340                 345                 350

Thr Leu Pro Pro Ser Arg Glu Glu Met Thr Lys Asn Gln Val Ser Leu
            355                 360                 365

Thr Cys Leu Val Lys Gly Phe Tyr Pro Ser Asp Ile Ala Val Glu Trp
        370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 79
<211> LENGTH: 215
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 79

Ser Tyr Val Leu Thr Gln Pro Pro Ser Val Ser Val Ala Pro Gly Glu
1               5                   10                  15

Thr Ala Arg Ile Thr Cys Gly Gly Asp Asp Ile Gly Asp Lys Arg Val
            20                  25                  30

His Trp Tyr Gln Lys Lys Pro Asp Gln Ala Pro Val Leu Val Val Tyr
        35                  40                  45

Glu Asp Arg Tyr Arg Pro Ser Gly Ile Pro Glu Arg Ile Ser Gly Ser
50                  55                  60

Asn Ser Gly Asn Thr Ala Thr Leu Thr Leu Ser Arg Val Glu Ala Gly
65                  70                  75                  80

Asp Glu Ala Asp Tyr Tyr Cys Gln Val Trp Asn Ser Ser Ser Asp His
            85                  90                  95

Pro Gly Val Phe Gly Gly Gly Thr Gln Leu Ile Ile Leu Gly Gln Pro
            100                 105                 110

Lys Ala Ala Pro Ser Val Thr Leu Phe Pro Pro Ser Ser Glu Glu Leu
        115                 120                 125

Gln Ala Asn Lys Ala Thr Leu Val Cys Leu Ile Ser Asp Phe Tyr Pro
    130                 135                 140

Gly Ala Val Thr Val Ala Trp Lys Ala Asp Ser Ser Pro Val Lys Ala
145                 150                 155                 160

Gly Val Glu Thr Thr Thr Pro Ser Lys Gln Ser Asn Asn Lys Tyr Ala
            165                 170                 175

Ala Ser Ser Tyr Leu Ser Leu Thr Pro Glu Gln Trp Lys Ser His Arg
        180                 185                 190
```

```
Ser Tyr Ser Cys Gln Val Thr His Glu Gly Ser Thr Val Glu Lys Thr
        195                 200                 205

Val Ala Pro Thr Glu Cys Ser
    210                 215

<210> SEQ ID NO 80
<211> LENGTH: 215
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 80

Ser Tyr Val Leu Thr Gln Pro Pro Ser Val Ser Val Ala Pro Gly Glu
1               5                   10                  15

Thr Ala Arg Ile Thr Cys Gly Gly Asp Asp Ile Gly Asp Lys Arg Val
            20                  25                  30

His Trp Tyr Gln Lys Lys Pro Asp Gln Ala Pro Val Leu Val Val Tyr
        35                  40                  45

Glu Asp Arg Tyr Arg Pro Ser Gly Ile Pro Glu Arg Ile Ser Gly Ser
    50                  55                  60

Asn Ser Gly Asn Thr Ala Thr Leu Thr Leu Ser Arg Val Glu Ala Gly
65                  70                  75                  80

Asp Glu Ala Asp Tyr Tyr Cys Gln Val Trp Asp Ser Ser Ser Asp Tyr
                85                  90                  95

Pro Gly Val Phe Gly Gly Gly Thr Gln Leu Ile Ile Leu Gly Gln Pro
            100                 105                 110

Lys Ala Ala Pro Ser Val Thr Leu Phe Pro Pro Ser Ser Glu Glu Leu
        115                 120                 125

Gln Ala Asn Lys Ala Thr Leu Val Cys Leu Ile Ser Asp Phe Tyr Pro
    130                 135                 140

Gly Ala Val Thr Val Ala Trp Lys Ala Asp Ser Ser Pro Val Lys Ala
145                 150                 155                 160

Gly Val Glu Thr Thr Thr Pro Ser Lys Gln Ser Asn Asn Lys Tyr Ala
                165                 170                 175

Ala Ser Ser Tyr Leu Ser Leu Thr Pro Glu Gln Trp Lys Ser His Arg
            180                 185                 190

Ser Tyr Ser Cys Gln Val Thr His Glu Gly Ser Thr Val Glu Lys Thr
        195                 200                 205

Val Ala Pro Thr Glu Cys Ser
    210                 215

<210> SEQ ID NO 81
<211> LENGTH: 215
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 81

Ser Tyr Val Leu Thr Gln Pro Pro Ser Val Ser Val Ala Pro Gly Glu
1               5                   10                  15

Thr Ala Arg Ile Thr Cys Gly Gly Asp Asp Ile Gly Asp Lys Arg Val
            20                  25                  30

His Trp Tyr Gln Lys Lys Pro Asp Gln Ala Pro Val Leu Val Val Tyr
```

```
                35                  40                  45
Glu Asp Arg Tyr Arg Pro Ser Gly Ile Pro Glu Arg Ile Ser Gly Ser
 50                  55                  60

Asn Ser Gly Asn Thr Ala Thr Leu Thr Leu Ser Arg Val Glu Ala Gly
 65                  70                  75                  80

Asp Glu Ala Asp Tyr Tyr Cys Gln Val Trp Tyr Ser Ser Pro Asp His
                 85                  90                  95

Pro Gly Val Phe Gly Gly Gly Thr Gln Leu Ile Ile Leu Gly Gln Pro
                100                 105                 110

Lys Ala Ala Pro Ser Val Thr Leu Phe Pro Pro Ser Ser Glu Glu Leu
                115                 120                 125

Gln Ala Asn Lys Ala Thr Leu Val Cys Leu Ile Ser Asp Phe Tyr Pro
                130                 135                 140

Gly Ala Val Thr Val Ala Trp Lys Ala Asp Ser Ser Pro Val Lys Ala
145                 150                 155                 160

Gly Val Glu Thr Thr Thr Pro Ser Lys Gln Ser Asn Asn Lys Tyr Ala
                165                 170                 175

Ala Ser Ser Tyr Leu Ser Leu Thr Pro Glu Gln Trp Lys Ser His Arg
                180                 185                 190

Ser Tyr Ser Cys Gln Val Thr His Glu Gly Ser Thr Val Glu Lys Thr
                195                 200                 205

Val Ala Pro Thr Glu Cys Ser
                210                 215
```

<210> SEQ ID NO 82
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"
<220> FEATURE:
<221> NAME/KEY: VARIANT
<222> LOCATION: (1)..(1)
<223> OTHER INFORMATION: /replace="Ala" or "Asp" or "Glu" or "Leu" or "Asn" or "Gln" or "Arg" or "Ser" or "Trp"
<220> FEATURE:
<221> NAME/KEY: VARIANT
<222> LOCATION: (2)..(2)
<223> OTHER INFORMATION: /replace="Phe" or "His" or "Asn" or "Arg" or "Ser"
<220> FEATURE:
<221> NAME/KEY: VARIANT
<222> LOCATION: (3)..(3)
<223> OTHER INFORMATION: /replace="His"
<220> FEATURE:
<221> NAME/KEY: VARIANT
<222> LOCATION: (4)..(4)
<223> OTHER INFORMATION: /replace="Ile" or "Thr" or "Val"
<220> FEATURE:
<221> NAME/KEY: MISC_FEATURE
<222> LOCATION: (1)..(5)
<223> OTHER INFORMATION: /note="Variant residues given in the sequence have no preference with respect to those in the annotations for variant positions"

<400> SEQUENCE: 82

```
Gly Tyr Tyr Met His
 1               5
```

<210> SEQ ID NO 83
<211> LENGTH: 11
<212> TYPE: PRT
<213> ORGANISM: Artificial Sequence

```
<220> FEATURE:
<221> NAME/KEY: source
<223> OTHER INFORMATION: /note="Description of Artificial Sequence:
      Synthetic peptide"
<220> FEATURE:
<221> NAME/KEY: VARIANT
<222> LOCATION: (1)..(1)
<223> OTHER INFORMATION: /replace="Gly"
<220> FEATURE:
<221> NAME/KEY: VARIANT
<222> LOCATION: (3)..(3)
<223> OTHER INFORMATION: /replace="Ala" or "Arg" or "Ser"
<220> FEATURE:
<221> NAME/KEY: VARIANT
<222> LOCATION: (5)..(5)
<223> OTHER INFORMATION: /replace="Phe" or "His" or "Ser"
<220> FEATURE:
<221> NAME/KEY: VARIANT
<222> LOCATION: (7)..(7)
<223> OTHER INFORMATION: /replace="Ala" or "Thr"
<220> FEATURE:
<221> NAME/KEY: VARIANT
<222> LOCATION: (10)..(10)
<223> OTHER INFORMATION: /replace="Gly"
<220> FEATURE:
<221> NAME/KEY: VARIANT
<222> LOCATION: (11)..(11)
<223> OTHER INFORMATION: /replace="His"
<220> FEATURE:
<221> NAME/KEY: MISC_FEATURE
<222> LOCATION: (1)..(11)
<223> OTHER INFORMATION: /note="Variant residues given in the sequence
      have no preference with respect to those in the annotations
      for variant positions"

<400> SEQUENCE: 83

Glu Pro Gly Tyr Tyr Gly Ser Gly Leu Asp Tyr
1               5                   10

<210> SEQ ID NO 84
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: VARIANT
<222> LOCATION: (2)..(2)
<223> OTHER INFORMATION: /replace="Ile"
<220> FEATURE:
<221> NAME/KEY: VARIANT
<222> LOCATION: (4)..(4)
<223> OTHER INFORMATION: /replace="Ala" or "Glu" or "Gly" or "His" or
      "Asn" or "Tyr"
<220> FEATURE:
<221> NAME/KEY: VARIANT
<222> LOCATION: (5)..(5)
<223> OTHER INFORMATION: /replace="Ala" or "Glu" or "Phe" or "Leu" or
      "Pro" or "Arg" or "Thr" or "Trp" or "Tyr"
<220> FEATURE:
<221> NAME/KEY: VARIANT
<222> LOCATION: (6)..(6)
<223> OTHER INFORMATION: /replace="Ala" or "Leu" or "Met" or "Arg"
<220> FEATURE:
<221> NAME/KEY: VARIANT
<222> LOCATION: (7)..(7)
<223> OTHER INFORMATION: /replace="Ala" or "Phe" or "Gly" or "Leu" or
      "Pro" or "Gln" or "Arg" or "Thr"
<220> FEATURE:
<221> NAME/KEY: VARIANT
<222> LOCATION: (8)..(8)
<223> OTHER INFORMATION: /replace="Glu" or "His" or "Val" or "Tyr"
<220> FEATURE:
<221> NAME/KEY: VARIANT
<222> LOCATION: (9)..(9)
```

```
<223> OTHER INFORMATION: /replace="Tyr"
<220> FEATURE:
<221> NAME/KEY: MISC_FEATURE
<222> LOCATION: (1)..(12)
<223> OTHER INFORMATION: /note="Variant residues given in the sequence
      have no preference with respect to those in the annotations
      for variant positions"

<400> SEQUENCE: 84

Gln Val Trp Asp Ser Ser Ser Asp His Pro Gly Val
1               5                   10

<210> SEQ ID NO 85
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: VARIANT
<222> LOCATION: (1)..(1)
<223> OTHER INFORMATION: /replace="Ala" or "Asp" or "Leu" or "Arg" or
      "Ser" or "Trp"
<220> FEATURE:
<221> NAME/KEY: VARIANT
<222> LOCATION: (2)..(2)
<223> OTHER INFORMATION: /replace="Phe" or "His" or "Asn"
<220> FEATURE:
<221> NAME/KEY: VARIANT
<222> LOCATION: (4)..(4)
<223> OTHER INFORMATION: /replace="Val"
<220> FEATURE:
<221> NAME/KEY: MISC_FEATURE
<222> LOCATION: (1)..(5)
<223> OTHER INFORMATION: /note="Variant residues given in the sequence
      have no preference with respect to those in the annotations
      for variant positions"

<400> SEQUENCE: 85

Gly Tyr Tyr Met His
1               5

<210> SEQ ID NO 86
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: VARIANT
<222> LOCATION: (5)..(5)
<223> OTHER INFORMATION: /replace="Phe"
<220> FEATURE:
<221> NAME/KEY: VARIANT
<222> LOCATION: (7)..(7)
<223> OTHER INFORMATION: /replace="Thr"
<220> FEATURE:
<221> NAME/KEY: VARIANT
<222> LOCATION: (11)..(11)
<223> OTHER INFORMATION: /replace="His"
<220> FEATURE:
<221> NAME/KEY: MISC_FEATURE
<222> LOCATION: (1)..(11)
<223> OTHER INFORMATION: /note="Variant residues given in the sequence
      have no preference with respect to those in the annotations
      for variant positions"

<400> SEQUENCE: 86

Glu Pro Gly Tyr Tyr Gly Ser Gly Leu Asp Tyr
1               5                   10
```

```
<210> SEQ ID NO 87
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: VARIANT
<222> LOCATION: (4)..(4)
<223> OTHER INFORMATION: /replace="Ala" or "Glu" or "His" or "Asn" or
      "Tyr"
<220> FEATURE:
<221> NAME/KEY: VARIANT
<222> LOCATION: (5)..(5)
<223> OTHER INFORMATION: /replace="Ala" or "Glu" or "Leu" or "Arg" or
      "Thr"
<220> FEATURE:
<221> NAME/KEY: VARIANT
<222> LOCATION: (6)..(6)
<223> OTHER INFORMATION: /replace="Ala" or "Leu" or "Arg"
<220> FEATURE:
<221> NAME/KEY: VARIANT
<222> LOCATION: (7)..(7)
<223> OTHER INFORMATION: /replace="Ala" or "Phe" or "Gly" or "Leu" or
      "Pro" or "Gln" or "Arg"
<220> FEATURE:
<221> NAME/KEY: VARIANT
<222> LOCATION: (8)..(8)
<223> OTHER INFORMATION: /replace="Glu" or "Val"
<220> FEATURE:
<221> NAME/KEY: VARIANT
<222> LOCATION: (9)..(9)
<223> OTHER INFORMATION: /replace="Tyr"
<220> FEATURE:
<221> NAME/KEY: MISC_FEATURE
<222> LOCATION: (1)..(12)
<223> OTHER INFORMATION: /note="Variant residues given in the sequence
      have no preference with respect to those in the annotations
      for variant positions"

<400> SEQUENCE: 87

Gln Val Trp Asp Ser Ser Ser Asp His Pro Gly Val
1               5                   10

<210> SEQ ID NO 88
<211> LENGTH: 254
<212> TYPE: PRT
<213> ORGANISM: Macaca fascicularis

<400> SEQUENCE: 88

Met Gly Asn Ser Cys Tyr Asn Ile Val Ala Thr Leu Leu Leu Val Leu
1               5                   10                  15

Asn Phe Glu Arg Thr Arg Ser Leu Gln Asp Leu Cys Ser Asn Cys Pro
            20                  25                  30

Ala Gly Thr Phe Cys Asp Asn Asn Arg Ser Gln Ile Cys Ser Pro Cys
        35                  40                  45

Pro Pro Asn Ser Phe Ser Ser Ala Gly Gly Gln Arg Thr Cys Asp Ile
    50                  55                  60

Cys Arg Gln Cys Lys Gly Val Phe Lys Thr Arg Lys Glu Cys Ser Ser
65                  70                  75                  80

Thr Ser Asn Ala Glu Cys Asp Cys Ile Ser Gly Tyr His Cys Leu Gly
                85                  90                  95

Ala Glu Cys Ser Met Cys Glu Gln Asp Cys Lys Gln Gly Gln Glu Leu
            100                 105                 110

Thr Lys Lys Gly Cys Lys Asp Cys Cys Phe Gly Thr Phe Asn Asp Gln
```

```
            115                 120                 125
Lys Arg Gly Ile Cys Arg Pro Trp Thr Asn Cys Ser Leu Asp Gly Lys
    130                 135                 140

Ser Val Leu Val Asn Gly Thr Lys Glu Arg Asp Val Val Cys Gly Pro
145                 150                 155                 160

Ser Pro Ala Asp Leu Ser Pro Gly Ala Ser Ala Thr Pro Pro Ala
                165                 170                 175

Pro Ala Arg Glu Pro Gly His Ser Pro Gln Ile Ile Phe Phe Leu Ala
            180                 185                 190

Leu Thr Ser Thr Val Val Leu Phe Leu Leu Phe Phe Leu Val Leu Arg
                195                 200                 205

Phe Ser Val Val Lys Arg Ser Arg Lys Lys Leu Leu Tyr Ile Phe Lys
210                 215                 220

Gln Pro Phe Met Arg Pro Val Gln Thr Thr Gln Glu Glu Asp Gly Cys
225                 230                 235                 240

Ser Cys Arg Phe Pro Glu Glu Glu Gly Gly Cys Glu Leu
                245                 250

<210> SEQ ID NO 89
<211> LENGTH: 256
<212> TYPE: PRT
<213> ORGANISM: Mus Musculus

<400> SEQUENCE: 89

Met Gly Asn Asn Cys Tyr Asn Val Val Ile Val Leu Leu Leu Val
1               5                   10                  15

Gly Cys Glu Lys Val Gly Ala Val Gln Asn Ser Cys Asp Asn Cys Gln
                20                  25                  30

Pro Gly Thr Phe Cys Arg Lys Tyr Asn Pro Val Cys Lys Ser Cys Pro
            35                  40                  45

Pro Ser Thr Phe Ser Ser Ile Gly Gly Gln Pro Asn Cys Asn Ile Cys
    50                  55                  60

Arg Val Cys Ala Gly Tyr Phe Arg Phe Lys Lys Phe Cys Ser Ser Thr
65                  70                  75                  80

His Asn Ala Glu Cys Glu Cys Ile Glu Gly Phe His Cys Leu Gly Pro
                85                  90                  95

Gln Cys Thr Arg Cys Glu Lys Asp Cys Arg Pro Gly Gln Glu Leu Thr
            100                 105                 110

Lys Gln Gly Cys Lys Thr Cys Ser Leu Gly Thr Phe Asn Asp Gln Asn
    115                 120                 125

Gly Thr Gly Val Cys Arg Pro Trp Thr Asn Cys Ser Leu Asp Gly Arg
            130                 135                 140

Ser Val Leu Lys Thr Gly Thr Thr Glu Lys Asp Val Val Cys Gly Pro
145                 150                 155                 160

Pro Val Val Ser Phe Ser Pro Ser Thr Thr Ile Ser Val Thr Pro Glu
                165                 170                 175

Gly Gly Pro Gly Gly His Ser Leu Gln Val Leu Thr Leu Phe Leu Ala
            180                 185                 190

Leu Thr Ser Ala Leu Leu Leu Ala Leu Ile Phe Ile Thr Leu Leu Phe
    195                 200                 205

Ser Val Leu Lys Trp Ile Arg Lys Lys Phe Pro His Ile Phe Lys Gln
210                 215                 220
```

-continued

```
Pro Phe Lys Lys Thr Thr Gly Ala Ala Gln Glu Glu Asp Ala Cys Ser
225                 230                 235                 240

Cys Arg Cys Pro Gln Glu Glu Gly Gly Gly Gly Gly Tyr Glu Leu
            245                 250                 255
```

ANTI-CD137 ANTIBODIES AND METHODS OF USE THEREOF

RELATED APPLICATIONS

This application claims the benefit of U.S. Provisional Application No. 62/485,365, filed Apr. 13, 2017, which is incorporated by reference herein in its entirety.

1. FIELD

The instant disclosure relates to antibodies that specifically bind to CD137 (e.g., human CD137) and methods of using the same.

2. BACKGROUND

CD137, also known as TNFRSF9 or 4-1BB, is a transmembrane protein in the Tumor Necrosis Factor (TNF) receptor superfamily. It has an N-terminal extracellular domain containing cysteine-rich motifs, a transmembrane domain, and a short C-terminal cytoplasmic domain containing potential phosphorylation sites. CD137 is expressed on activated $CD4^+$ T lymphocytes, activated $CD8^+$ T lymphocytes, activated natural killer (NK) cells, monocytes, dendritic cells, B cells, neutrophils, and mast cells (Vinay et al. (2011) Cellular & Molecular Immunology 8:281-84). CD137L, also known as TNFSF9 or 4-1BBL, is a ligand of CD137. Upon CD137L binding, CD137 transduces a co-stimulatory signal that promotes cell survival, proliferation, cytokine production, and activation of effector functions. CD137L binding to CD137 has also been shown to co-stimulate CD8+ T cells to a greater degree than CD4+ T cells.

Studies in animal models have shown that ligation of CD137, using either CD137L or agonistic antibodies, suppresses tumor growth by promoting T cell activity (Vinay et al. (2012) Mol. Cancer. Ther. 11:1062-70). CD137 has also been shown to enhance T cell immunity against human immunodeficiency virus (HIV) and hepatitis C virus (HCV) following vaccination (Munks et al. (2004) Immunology 112:559-66; Arribillaga et al. (2005) Vaccine 23:3493-99). Additionally, CD137 agonists have been shown to ameliorate autoimmunity in animal models of lupus, collagen-induced arthritis, and experimental autoimmune encephalomyelitis.

Given the apparent role of human CD137 in modulating immune responses, therapeutic agents designed to promote CD137 signaling hold great promise for the treatment of diseases that involve immune suppression.

3. SUMMARY

The instant disclosure provides antibodies that specifically bind to CD137 (e.g., human CD137 or cynomolgus CD137) and increase or promote CD137 function, e.g., CD137-mediated immune activation. Also provided are pharmaceutical compositions comprising these antibodies, nucleic acids encoding these antibodies, expression vectors and host cells for making these antibodies, and methods of treating a subject using these antibodies. The antibodies disclosed herein are particularly useful for increasing T cell activation against an antigen (e.g., a tumor antigen or an infectious disease antigen) and/or decreasing Treg-mediated immune suppression, and hence for treating cancer in a subject or treating or preventing an infectious disease in a subject.

Accordingly, in one aspect, the instant disclosure provides an antibody or isolated antibody comprising a heavy chain variable region (VH) comprising complementarity determining regions (CDRs) CDRH1, CDRH2 and CDRH3 and a light chain variable region (VL) comprising complementarity determining regions CDRL1, CDRL2 and CDRL3, wherein:
(a) CDRH1 comprises the amino acid sequence of $X_1X_2X_3X_4H$ (SEQ ID NO: 82), wherein
   $X_1$ is G, A, D, E, L, N, Q, R, S, or W;
   $X_2$ is Y, F, H, N, R, or S;
   $X_3$ is Y or H; and
   $X_4$ is M, I, T, or V;
(b) CDRH2 comprises the amino acid sequence of WINPNSGGTNYAQKFQG (SEQ ID NO: 2);
(c) CDRH3 comprises the amino acid sequence of $X_1PX_2YX_3GX_4GLX_5X_6$ (SEQ ID NO: 83), wherein
   $X_1$ is E or G;
   $X_2$ is G, A, R, or S;
   $X_3$ is Y, F, H, or S;
   $X_4$ is S, A, or T;
   $X_5$ is D or G; and
   $X_6$ is Y or H;
(d) CDRL1 comprises the amino acid sequence of GGDDIGDKRVH (SEQ ID NO: 4);
(e) CDRL2 comprises the amino acid sequence of EDRYRPS (SEQ ID NO: 5); and/or
(f) CDRL3 comprises the amino acid sequence of $QX_1WX_2X_3X_4X_5X_6X_7PGV$ (SEQ ID NO: 84), wherein
   $X_1$ is V or I;
   $X_2$ is D, A, E, G, H, N, or Y;
   $X_3$ is S, A, E, F, L, P, R, T, W, or Y;
   $X_4$ is S, A, L, M, or R;
   $X_5$ is S, A, F, G, L, P, Q, R, or T;
   $X_6$ is D, E, H, V, or Y; and
   $X_7$ is H or Y.
In certain embodiments,
(a) CDRH1 comprises the amino acid sequence of $X_1X_2YX_3H$ (SEQ ID NO: 85), wherein
   $X_1$ is G, A, D, L, R, S, or W;
   $X_2$ is Y, F, H, or N; and
   $X_3$ is M or V;
(b) CDRH3 comprises the amino acid sequence of $EPGYX_1GX_2GLDX_3$ (SEQ ID NO: 86), wherein
   $X_1$ is Y or F;
   $X_2$ is S or T; and
   $X_3$ is Y or H; and/or
(c) CDRL3 comprises the amino acid sequence of $QVWX_1X_2X_3X_4X_5X_6PGV$ (SEQ ID NO: 87), wherein
   $X_1$ is D, A, E, H, N, or Y;
   $X_2$ is S, A, E, L, R, or T;
   $X_3$ is S, A, L, or R;
   $X_4$ is S, A, F, G, L, P, Q, or R;
   $X_5$ is D, E, or V; and
   $X_6$ is H or Y.
In certain embodiments,
(a) CDRH1 comprises the amino acid sequence of GYYMH (SEQ ID NO: 1);
(b) CDRH3 comprises the amino acid sequence of EPGYYGSGLDY (SEQ ID NO: 3) or EPGYYGTGLDY (SEQ ID NO: 59); and/or
(c) CDRL3 comprises the amino acid sequence of QVWDSSSDHPGV (SEQ ID NO: 6), QVWNSSSDHPGV (SEQ ID NO: 60), QVWDSSSDYPGV (SEQ ID NO: 61), or QVWYSSPDHPGV (SEQ ID NO: 62).

In certain embodiments, the CDRH1, CDRH2, CDRH3, CDRL1, CDRL2, and CDRL3 comprise the amino acid sequences set forth in SEQ ID NOs: 1, 2, 3, 4, 5, and 6; 1, 2, 59, 4, 5, and 6; 1, 2, 3, 4, 5, and 60; 1, 2, 3, 4, 5, and 61; or 1, 2, 3, 4, 5, and 62, respectively.

In certain embodiments, the antibody comprises a VH comprising an amino acid sequence that is at least 75%, 80%, 85%, 90%, 95%, 99%, or 100% identical to the amino acid sequence of SEQ ID NO: 7. In certain embodiments, the VH comprises the amino acid sequence of SEQ ID NO: 7, 63, 64, or 65. In certain embodiments, the VH comprises the amino acid sequence of SEQ ID NO: 7. In certain embodiments, the amino acid sequence of the VH consists of the amino acid sequence of SEQ ID NO: 7, 63, 64, or 65. In certain embodiments, the amino acid sequence of the VH consists of the amino acid sequence of SEQ ID NO: 7. In certain embodiments, X is glutamine (Q). In certain embodiments, X is pyroglutamate (pE). In certain embodiments, the antibody comprises a VL comprising an amino acid sequence that is at least 75%, 80%, 85%, 90%, 95%, 99%, or 100% identical to the amino acid sequence of SEQ ID NO: 8. In certain embodiments, the VL comprises the amino acid sequence of SEQ ID NO: 8, 66, 67, or 68. In certain embodiments, the VL comprises the amino acid sequence of SEQ ID NO: 8. In certain embodiments, the amino acid sequence of the VL consists of the amino acid sequence of SEQ ID NO: 8, 66, 67, or 68. In certain embodiments, the amino acid sequence of the VL consists of the amino acid sequence of SEQ ID NO: 8.

In another aspect, the instant disclosure provides an isolated antibody that specifically binds to CD137 (e.g., human CD137 or cynomolgus CD137), the antibody comprising a VH comprising the amino acid sequence of SEQ ID NO: 7, 63, 64, or 65. In certain embodiments, the VH comprises the amino acid sequence of SEQ ID NO: 7. In certain embodiments, the amino acid sequence of the VH consists of the amino acid sequence of SEQ ID NO: 7, 63, 64, or 65. In certain embodiments, the amino acid sequence of the VH consists of the amino acid sequence of SEQ ID NO: 7. In certain embodiments, X is glutamine (Q). In certain embodiments, X is pyroglutamate (pE).

In another aspect, the instant disclosure provides an isolated antibody that specifically binds to CD137 (e.g., human CD137 or cynomolgus CD137), the antibody comprising a VL comprising the amino acid sequence of SEQ ID NO: 8, 66, 67, or 68. In certain embodiments, the VL comprises the amino acid sequence of SEQ ID NO: 8. In certain embodiments, the amino acid sequence of the VL consists of the amino acid sequence of SEQ ID NO: 8, 66, 67, or 68. In certain embodiments, the amino acid sequence of the VL consists of the amino acid sequence of SEQ ID NO: 8.

In another aspect, the instant disclosure provides an isolated antibody that specifically binds to CD137 (e.g., human CD137 or cynomolgus CD137), the antibody comprising a VH and a VL comprising the amino acid sequences of SEQ ID NO: 7 and 8; 63 and 8; 64 and 66; 7 and 67; or 65 and 68, respectively. In certain embodiments, the amino acid sequences of the VH and VL consist of the amino acid sequences of SEQ ID NO: 7 and 8; 63 and 8; 64 and 66; 7 and 67; or 65 and 68, respectively. In certain embodiments, X in SEQ ID NO: 7, 63, 64, or 65 is glutamine (Q). In certain embodiments, X in SEQ ID NO: 7, 63, 64, or 65 is pyroglutamate (pE).

In another aspect, the instant disclosure provides an isolated antibody that specifically binds to CD137 (e.g., human CD137 or cynomolgus CD137), the antibody comprising a VH having an amino acid sequence derived from a human IGHV1-2*02 germline sequence. In certain embodiments, the VH comprises the amino acid sequence set forth in SEQ ID NO: 3 or 59.

In another aspect, the instant disclosure provides an isolated antibody that specifically binds to CD137 (e.g., human CD137 or cynomolgus CD137), the antibody comprising a VL having an amino acid sequence derived from a human IGLV3-21*02 germline sequence. In certain embodiments, the VL comprises the amino acid sequence set forth in SEQ ID NO: 6, 60, 61, or 62.

In another aspect, the instant disclosure provides an isolated antibody that specifically binds to CD137 (e.g., human CD137 or cynomolgus CD137), the antibody comprising a VH having an amino acid sequence derived from a human IGHV1-2*02 germline sequence, and a VL having an amino acid sequence derived from a human IGLV3-21*02 germline sequence. In certain embodiments, the VH comprises the amino acid sequence set forth in SEQ ID NO: 3, and the VL comprises the amino acid sequence set forth in SEQ ID NO: 6, 60, 61, or 62.

In certain embodiments, the antibody comprises a heavy chain constant region selected from the group consisting of human IgG1, IgG2, IgG3, IgG4, IgA1, and IgA2.

In certain embodiments, the antibody comprises an IgG1 heavy chain constant region. In certain embodiments, the antibody comprises a heavy chain constant region comprising the amino acid sequence of SEQ ID NO: 15. In certain embodiments, the amino acid sequence of the IgG1 heavy chain constant region comprises an N297A mutation, numbered according to the EU numbering system. In certain embodiments, the antibody comprises a heavy chain constant region comprising the amino acid sequence of SEQ ID NO: 16. In certain embodiments, the amino acid sequence of the IgG1 heavy chain constant region comprises S267E and L328F mutations, numbered according to the EU numbering system. In certain embodiments, the antibody comprises a heavy chain constant region comprising the amino acid sequence of SEQ ID NO: 17.

In certain embodiments, the antibody comprises an IgG2 heavy chain constant region. In certain embodiments, the antibody comprises a heavy chain constant region comprising the amino acid sequence of SEQ ID NO: 18. In certain embodiments, the amino acid sequence of the IgG2 heavy chain constant region comprises an N297A mutation, numbered according to the EU numbering system. In certain embodiments, the antibody comprises a heavy chain constant region comprising the amino acid sequence of SEQ ID NO: 19.

In certain embodiments, the antibody comprises an IgG4 heavy chain constant region. In certain embodiments, the amino acid sequence of the IgG4 heavy chain constant region comprises an S228P mutation, numbered according to the EU numbering system. In certain embodiments, the antibody comprises a heavy chain constant region comprising the amino acid sequence of SEQ ID NO: 20.

In certain embodiments, the antibody comprises a heavy chain constant region that is a variant of a wild type heavy chain constant region, wherein the variant heavy chain constant region binds to an FcγR with higher affinity than the wild type heavy chain constant region binds to the FcγR. In certain embodiments, the FcγR is FcγRIIB.

In certain embodiments, the antibody comprises a light chain constant region comprising the amino acid sequence of SEQ ID NO: 22.

In another aspect, the instant disclosure provides an isolated antibody that specifically binds to CD137 (e.g., human CD137 or cynomolgus CD137), the antibody comprising: (a) a heavy chain comprising an amino acid sequence selected from the group consisting of SEQ ID NOs: 9-14, 49-54, and 73-78; and/or (b) a light chain comprising the amino acid sequence of SEQ ID NO: 21 and 79-81. In certain embodiments, the heavy chain and light chain comprise the amino acid sequences of SEQ ID NOs: 9 and 21; 10 and 21; 11 and 21; 12 and 21; 13 and 21; 14 and 21; 49 and 21; 50 and 21; 51 and 21; 52 and 21; 53 and 21; 54 and 21; 73 and 21; 74 and 21; 75 and 79; 76 and 79; 9 and 80; 49 and 80; 77 and 81; or 78 and 81, respectively. In certain embodiments, the heavy chain and light chain comprise the amino acid sequences of SEQ ID NOs: 9 and 21; or 49 and 21, respectively. In certain embodiments, the amino acid sequences of the heavy chain and light chain consist of the amino acid sequences of SEQ ID NOs: 9 and 21; 10 and 21; 11 and 21; 12 and 21; 13 and 21; 14 and 21; 49 and 21; 50 and 21; 51 and 21; 52 and 21; 53 and 21; 54 and 21; 73 and 21; 74 and 21; 75 and 79; 76 and 79; 9 and 80; 49 and 80; 77 and 81; or 78 and 81, respectively. In certain embodiments, the amino acid sequences of the heavy chain and light chain consist of the amino acid sequences of SEQ ID NOs: 9 and 21; or 49 and 21, respectively. In certain embodiments, X is glutamine (Q). In certain embodiments, X is pyroglutamate (pE).

In another aspect, the instant disclosure provides an isolated antibody that specifically binds to CD137 (e.g., human CD137 or cynomolgus CD137), wherein binding of the antibody to the CD137 increases the level of dimerization between the CD137 and a second human CD137 molecule relative to the level of the dimerization in the absence of the antibody. In certain embodiments, the binding of the antibody to the CD137 increases the level of pairwise binding between the PLAD domains of the two CD137 molecules relative to the level of pairwise binding between the PLAD domains of the two CD137 molecules in the absence of the antibody. In certain embodiments, the binding of the antibody to the CD137 increases the level of pairwise binding between a first region of the CD137 molecule and a second region of the second human CD137 molecule relative to the level of pairwise binding between the first region and the second region in the absence of the antibody, wherein the first region and/or the second region comprises the amino acid sequence of SEQ ID NO: 34.

In another aspect, the instant disclosure provides an isolated antibody that specifically binds to CD137 (e.g., human CD137 or cynomolgus CD137), wherein binding of the antibody to CD137 increases the level of CD137 multimerization (e.g., dimerization) relative to the level of CD137 multimerization (e.g., dimerization) in the absence of the antibody. In certain embodiments, the increase in the level of CD137 multimerization (e.g., dimerization) comprises an increase in the level of pairwise binding between the PLAD domains of two CD137 molecules. In certain embodiments, the increase in the level of CD137 multimerization (e.g., dimerization) comprises an increase in the level of pairwise binding between a first region of a first CD137 molecules and a second region of a second molecule, wherein the first and/or second region comprises the amino acid sequence of SEQ ID NO: 34.

In certain embodiments, the antibody is a multivalent antibody and is capable of binding to two or more molecules of CD137 simultaneously.

In certain embodiments, the antibody disclosed herein does not substantially inhibit human CD137 from binding to human CD137L.

In another aspect, the instant disclosure provides an isolated antibody that specifically binds to human CD137 and does not substantially inhibit human CD137 from binding to human CD137L.

In certain embodiments, the antibody does not substantially inhibit a soluble fragment of human CD137 from binding to a soluble fragment of human CD137L. In certain embodiments, the antibody does not substantially inhibit a CD137-expressing cell from binding to a soluble fragment of human CD137L. In certain embodiments, the antibody does not substantially inhibit a CD137-expressing cell from binding to a CD137L-expressing cell.

In certain embodiments, the antibody does not inhibit a soluble fragment of human CD137 from binding to a soluble fragment of human CD137L. In certain embodiments, the antibody does not inhibit a CD137-expressing cell from binding to a soluble fragment of human CD137L. In certain embodiments, the antibody does not inhibit a CD137-expressing cell from binding to a CD137L-expressing cell.

In certain embodiments, the antibody disclosed herein is agonistic to human CD137. In certain embodiments, the antibody increases or promotes an activity of human CD137. In certain embodiments, the ability of the antibody to increase or promote an activity of human CD137 is dependent on crosslinking of the antibody. In certain embodiments, the antibody does not substantially increase or promote an activity of human CD137 in the absence of crosslinking.

In another aspect, the instant disclosure provides an isolated antibody that specifically binds to CD137 (e.g., human CD137) and increases or promotes an activity of human CD137, wherein the ability of the antibody to increase or promote an activity of human CD137 is dependent on crosslinking of the antibody. In certain embodiments, the antibody does not substantially increase or promote an activity of human CD137 in the absence of crosslinking.

In certain embodiments, the ability of the antibody to increase or promote an activity of human CD137 is dependent on the presence of CD137L.

In another aspect, the instant disclosure provides an isolated antibody that specifically binds to CD137 (e.g., human CD137) and increases or promotes an activity of human CD137, wherein the ability of the antibody to increase or promote an activity of human CD137 is dependent on the presence of CD137L.

In certain embodiments, the ability of the antibody to increase or promote an activity of human CD137 positively correlates with the concentration of CD137L. In certain embodiments, the ability of the antibody to increase or promote the activity of human CD137 is a substantially increasing function of the concentration of the CD137L. In certain embodiments, the antibody does not substantially increase or promote an activity of human CD137 in the absence of CD137L. In certain embodiments, the antibody does not increase or promote an activity of human CD137 in the absence of CD137L.

In certain embodiments, the activity of human CD137 comprises activating a T-cell expressing the human CD137. In certain embodiments, the activity of human CD137 comprises inducing IL-2 production by peripheral blood mononuclear cells (PBMCs) stimulated with staphylococcal enterotoxin A (SEA). In certain embodiments, the activity of human CD137 comprises activating a natural killer (NK) cell expressing the human CD137. In certain embodiments, the activity of human CD137 comprises activating an antigen-presenting cell (APC) expressing CD137L.

In certain embodiments, the antibody binds to the same epitope of human CD137 as an antibody comprising a VH comprising the amino acid sequence of SEQ ID NO: 7 and a VL comprising the amino acid sequence of SEQ ID NO: 8.

In another aspect, the instant disclosure provides an isolated antibody that specifically binds to human CD137, wherein the antibody binds to the same epitope of human CD137 as an antibody comprising a VH comprising the amino acid sequence of SEQ ID NO: 7 and a VL comprising the amino acid sequence of SEQ ID NO: 8. In certain embodiments, the antibody binds to an epitope located within a CRD4 domain of human CD137. In certain embodiments, the CRD4 domain of human CD137 comprises the amino acid sequence set forth in SEQ ID NO: 42.

In certain embodiments, the antibody disclosed herein binds to an epitope located within a region of human CD137 consisting of the amino acid sequence of any one of SEQ ID NOs: 26-31 and 43. In certain embodiments, the antibody binds to an epitope located within a region of human CD137 consisting of the amino acid sequence of SEQ ID NO: 43.

In another aspect, the instant disclosure provides an isolated antibody that specifically binds to human CD137, wherein the antibody binds to an epitope located within a region of human CD137 consisting of the amino acid sequence of any one of SEQ ID NOs: 26-31 and 43. In certain embodiments, the antibody binds to an epitope located within a region of human CD137 consisting of the amino acid sequence of SEQ ID NO: 43.

In certain embodiments, the antibody does not substantially bind to a protein comprising the amino acid sequence of SEQ ID NO: 45. In certain embodiments, the antibody specifically binds to a protein comprising the amino acid sequence of SEQ ID NO: 46. In certain embodiments, the antibody specifically binds to a protein comprising the amino acid sequence of SEQ ID NO: 46, and does not substantially bind to a protein comprising the amino acid sequence of SEQ ID NO: 45. In certain embodiments, the antibody does not substantially bind to a protein consisting of or consisting essentially of the amino acid sequence of SEQ ID NO: 45. In certain embodiments, the antibody specifically binds to a protein consisting of or consisting essentially of the amino acid sequence of SEQ ID NO: 46. In certain embodiments, the antibody specifically binds to a protein consisting of or consisting essentially of the amino acid sequence of SEQ ID NO: 46, and does not substantially bind to a protein consisting of or consisting essentially of the amino acid sequence of SEQ ID NO: 45.

In certain embodiments, the antibody comprises a VH and a VL, wherein: (a) an F(ab')2 comprising two of each of the VH and the VL binds to an epitope located within a region of human CD137 consisting of the amino acid sequence of SEQ ID NO: 27; and/or (b) a Fab comprising the VH and the VL binds to an epitope located within a region of human CD137 consisting of the amino acid sequence of SEQ ID NO: 26 and, optionally, an epitope located within a region of human CD137 consisting of the amino acid sequence of SEQ ID NO: 28 or 29.

In certain embodiments, the antibody comprises a VH and a VL, wherein: (a) if the antibody is formatted as a F(ab')$_2$ comprising two of each of the VH and the VL, the F(ab')$_2$ binds to an epitope located within a region of human CD137 consisting of the amino acid sequence of SEQ ID NO: 27; and/or (b) if the antibody is formatted as a Fab comprising the VH and the VL, the Fab binds to an epitope located within a region of human CD137 consisting of the amino acid sequence of SEQ ID NO: 26 and optionally an epitope located within a region of human CD137 consisting of the amino acid sequence of SEQ ID NO: 28 or 29.

In certain embodiments, the antibody comprises a VH and a VL, wherein: (a) an F(ab')$_2$ comprising two of each of the VH and the VL substantially reduces the exchange of hydrogen with deuterium in a region of CD137 consisting of the amino acid sequence of SEQ ID NO: 34 relative to the exchange of hydrogen with deuterium in the same region in the absence of the F(ab')$_2$, as measured by a hydrogen/deuterium exchange assay; and (b) a Fab comprising the VH and the VL does not substantially reduce the exchange of hydrogen with deuterium in a region of CD137 consisting of the amino acid sequence of SEQ ID NO: 34 relative to the exchange of hydrogen with deuterium in the same region in the absence of the Fab, as measured by a hydrogen/deuterium exchange assay.

In certain embodiments, the antibody comprises a VH and a VL, wherein: (a) if the antibody is formatted as a F(ab')$_2$ comprising two of each of the VH and the VL, the F(ab')$_2$ substantially reduces the exchange of hydrogen with deuterium in a region of CD137 consisting of the amino acid sequence of SEQ ID NO: 34 relative to the exchange of hydrogen with deuterium in the same region in the absence of the F(ab')$_2$, as measured by a hydrogen/deuterium exchange assay; and (b) if the antibody is formatted as a Fab comprising the VH and the VL, the Fab does not substantially reduces the exchange of hydrogen with deuterium in a region of CD137 consisting of the amino acid sequence of SEQ ID NO: 34 relative to the exchange of hydrogen with deuterium in the same region in the absence of the Fab, as measured by a hydrogen/deuterium exchange assay.

In certain embodiments, the antibody specifically binds to a protein comprising the amino acid sequence of SEQ ID NO: 37, the antibody does not specifically bind to a protein comprising the amino acid sequence of SEQ ID NO: 38.

In another aspect, the instant disclosure provides an isolated antibody that specifically binds to human CD137, wherein the antibody specifically binds to a protein comprising the amino acid sequence of SEQ ID NO: 37; and the antibody does not specifically bind to a protein comprising the amino acid sequence of SEQ ID NO: 38.

In certain embodiments, the antibody disclosed herein is a human antibody. In certain embodiments, the antibody disclosed herein is a multispecific antibody.

In certain embodiments, the antibody disclosed herein is conjugated to a cytotoxic agent, cytostatic agent, toxin, radionuclide, or detectable label. In certain embodiments, the antibody is conjugated to a second antibody.

In another aspect, the instant disclosure provides an isolated polynucleotide encoding a VH and/or a VL, or a heavy chain and/or a light chain of the antibody as disclosed herein. In another aspect, the instant disclosure provides a vector comprising the polynucleotide as disclosed herein. In another aspect, the instant disclosure provides a recombinant host cell comprising the polynucleotide or the vector as disclosed herein.

In another aspect, the instant disclosure provides a pharmaceutical composition comprising the antibody, polynucleotide, vector, or host cell as disclosed herein; and a pharmaceutically acceptable carrier or excipient.

In another aspect, the instant disclosure provides a method of producing an antibody that specifically binds to human CD137, the method comprising culturing the host cell as disclosed herein under suitable conditions so that the polynucleotide is expressed and the antibody is produced.

In another aspect, the instant disclosure provides a method of increasing an immune response in a subject, the method comprising administering to the subject an effective amount of the antibody, polynucleotide, vector, host cell, or pharmaceutical composition as disclosed herein.

In another aspect, the instant disclosure provides a method of increasing T cell activation and/or NK cell activation in response to an antigen in a subject, the method comprising administering to the subject an effective amount of the antibody, polynucleotide, vector, host cell, or pharmaceutical composition as disclosed herein.

In another aspect, the instant disclosure provides a method of treating cancer in a subject, the method comprising administering to the subject an effective amount of the antibody, polynucleotide, vector, host cell, or pharmaceutical composition as disclosed herein.

In certain embodiments, the antibody, polynucleotide, vector, host cell, or pharmaceutical composition is administered systemically. In certain embodiments, the antibody, polynucleotide, vector, host cell, or pharmaceutical composition is administered intravenously. In certain embodiments, the antibody, polynucleotide, vector, host cell, or pharmaceutical composition is administered subcutaneously, intratumorally, or is delivered to a tumor draining lymph node.

In certain embodiments, the method of increasing an immune response in a subject, the method of increasing T cell activation and/or NK cell activation in response to an antigen in a subject, or the method of treating cancer in a subject disclosed herein further comprises administering an additional therapeutic agent to the subject. In certain embodiments, the additional therapeutic agent is a chemotherapeutic agent. In certain embodiments, the additional therapeutic agent is a checkpoint targeting agent. In certain embodiments, the checkpoint targeting agent is selected from the group consisting of an antagonist anti-PD-1 antibody, an antagonist anti-PD-L1 antibody, an antagonist anti-PD-L2 antibody, an antagonist anti-CTLA-4 antibody, an antagonist anti-TIM-3 antibody, an antagonist anti-LAG-3 antibody, an antagonist anti-VISTA antibody, an antagonist anti-CD96 antibody, an antagonist anti-CEACAM1 antibody, an antagonist anti-TIGIT antibody, an agonist anti-GITR antibody, and an agonist anti-OX40 antibody. In certain embodiments, the additional therapeutic agent is an anti-PD-1 antibody, optionally wherein the anti-PD-1 antibody is pembrolizumab or nivolumab. In certain embodiments, the additional therapeutic agent is an inhibitor of indoleamine-2,3-dioxygenase (IDO). In certain embodiments, the inhibitor is selected from the group consisting of epacadostat, F001287, indoximod, and NLG919. In certain embodiments, the additional therapeutic agent is a vaccine. In certain embodiments, the vaccine comprises a heat shock protein peptide complex (HSPPC) comprising a heat shock protein complexed with an antigenic peptide. In certain embodiments, the heat shock protein is hsc70 and is complexed with a tumor-associated antigenic peptide. In certain embodiments, the heat shock protein is gp96 protein and is complexed with a tumor-associated antigenic peptide, wherein the HSPPC is derived from a tumor obtained from a subject.

In another aspect, the instant disclosure provides a method of treating an infectious disease in a subject, the method comprising administering to the subject an effective amount of the antibody, polynucleotide, vector, host cell, or pharmaceutical composition as disclosed herein.

4. BRIEF DESCRIPTION OF THE DRAWINGS

FIGS. 1A and 1B are a series of flow cytometry graphs showing the binding of anti-CD137 antibody BA001 or an IgG1 isotype control antibody to cells expressing human CD137 (FIG. 1A) or cynomolgus CD137 (FIG. 1B) on their cell surfaces. In FIG. 1A, binding to human CD137 was assessed for Jurkat cells engineered to express human CD137 on their surfaces (left panel), activated human CEM/C1 T cells expressing endogenous CD137 (middle panel), or activated human primary CD8+ T cells (right panel). In FIG. 1B, binding to cynomolgus CD137 was assessed for Jurkat cells engineered to express cynomolgus CD137 on their surfaces (left panel) or activated cynomolgus primary CD8+ T cells (right panel).

FIGS. 2A and 2B are surface plasmon resonance graphs showing binding of human CD137L to human CD137, in the context of a CD137/BA001-F(ab')$_2$ complex. In FIG. 2A, BA001-F(ab')$_2$ was bound to a flow cell, and then CD137 was run over the flow cell, thereby forming a CD137/BA001-F(ab')$_2$ complex. CD137L was then run over the flow cell and was shown to bind to the complex. In FIG. 2B, preformed CD137/BA001-F(ab')$_2$ complex was first bound to the flow cell. CD137L was then run over the flow cell and was shown to bind to the complex.

FIGS. 3A-3C are graphs showing that anti-human CD137 antibody BA001 does not block CD137L binding to CD137. FIG. 3A is a series of flow cytometry plots showing that BA001 does not block binding of cells expressing CD137L on their surfaces to cells expressing CD137 on their surfaces. The top row of plots shows side scatter (SSC) and forward scatter (FSC) signal for each antibody, while the bottom row of plots shows Jurkat-CD137 (PE) and Jurkat-CD137L (FITC) signal for each antibody. FIGS. 3B and 3C are graphs showing in a co-culture of anti-CD137L-expressing cells and CD137-expressing cells, the percentage of conjugated cells out of the total number of cells, wherein an anti-CD137 antibody or isotype control antibody was added prior to (FIG. 3B) or after (FIG. 3C) the two types of cells were combined in a mixed culture.

FIGS. 4A-4B are graphs showing crosslinking dependency of anti-CD137 antibody BA001. FIG. 4A illustrates the NFκB-luciferase reporter activities in Jurkat cells expressing human CD137 incubated with 2 μg/mL of crosslinked BA001, an isotype control, or reference anti-CD137 antibody #2 in the absence of 1 μg/mL CD137L. The reporter activities are represented by luminescence levels, and are plotted against the log molar ratio of the crosslinker (AffiniPure F(ab')$_2$ Fragment Goat Anti-Human IgG) to antibody. FIG. 4B shows the NFκB-luciferase reporter activities in Jurkat cells expressing human CD137 co-cultured with CD16-expressing CHO cells.

FIG. 5 is a graph showing the production of IL-2 induced by anti-CD137 antibodies (i.e., BA001 and two reference anti-CD137 antibodies) or corresponding isotype control antibodies (i.e., IgG1, IgG2, and IgG4 isotype control antibodies, respectively) in human peripheral blood mononuclear cells (PBMCs) upon Staphylococcal Enterotoxin A (SEA) stimulation.

FIGS. 6A-6C are graphs showing the production of IL-2 induced by anti-CD137 antibodies in purified human T cells stimulated with anti-CD3 antibody (FIGS. 6A and 6B). CD137L expression was assessed in the purified human T cells used in these experiments by flow cytometry. No detectable CD137L expression was observed on these cells (FIG. 6C).

FIG. 7A is a graph showing crosslinking- and ligand-dependency of anti-CD137 antibody BA001 in the Jurkat reporter cells measured in the presence or absence of 1 μg/mL CD137L. FIG. 7B is a histogram showing the expression (or lack thereof) of CD137 and CD137L on the surfaces of the Jurkat reporter cells. Expression was analyzed from freshly thawed cells ("0 h"), cells cultured for 4 hours post thawing ("4 h"), and cells cultured for 24 hours post thawing ("24 h").

FIGS. 8A-8D are graphs showing NFκB-luciferase reporter activity in Jurkat cells expressing either human CD137 (FIGS. 8A and 8B) or cynomolgus CD137 (FIGS. 8C and 8D) and incubated with serial dilutions of the anti-CD137 antibody BA001 or an isotype control antibody. In one set of samples, cells were also incubated in the presence (FIGS. 8B and 8D) or absence (FIGS. 8A and 8C) of human CD137L.

FIGS. 9A-9C are a series of graphs showing NFκB-luciferase reporter activity in Jurkat cells expressing human CD137 and incubated with (i) 2 μg/ml of anti-CD137 antibody (BA001 or one of two reference anti-CD137 antibodies) or an appropriate isotype control antibody, and (ii) serial dilutions of human CD137L (ligand). In a first set of samples, the anti-CD137 antibody or isotype control antibody was added before CD137L (FIG. 9A). In a second set of samples, the anti-CD137 antibody or isotype control antibody was added simultaneously with CD137L (FIG. 9B). In a third set of samples, CD137L was added before the anti-CD137 antibody or isotype control antibody (FIG. 9C).

Figure 12A:
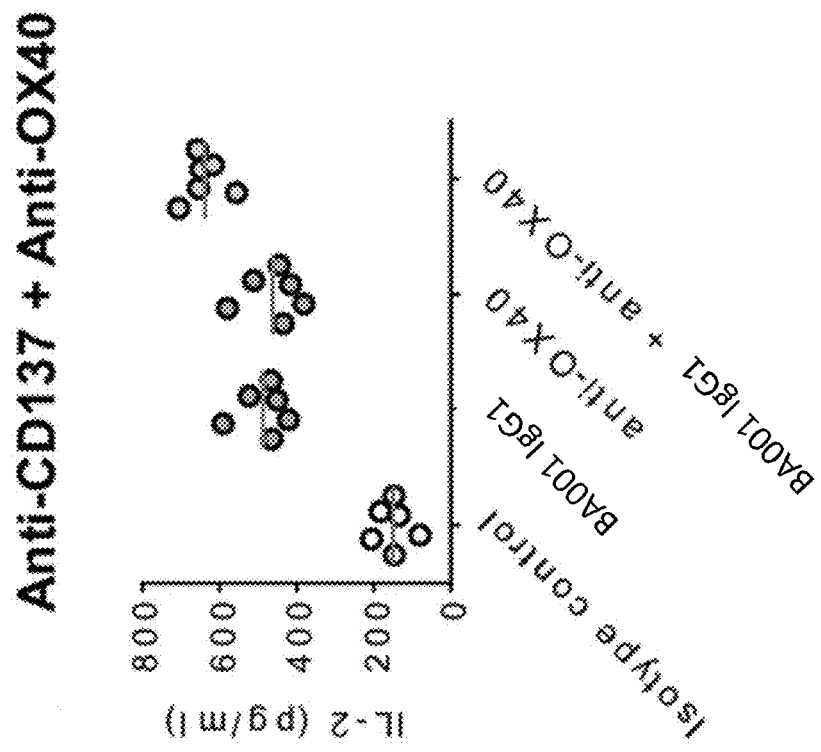
Figure 12B:
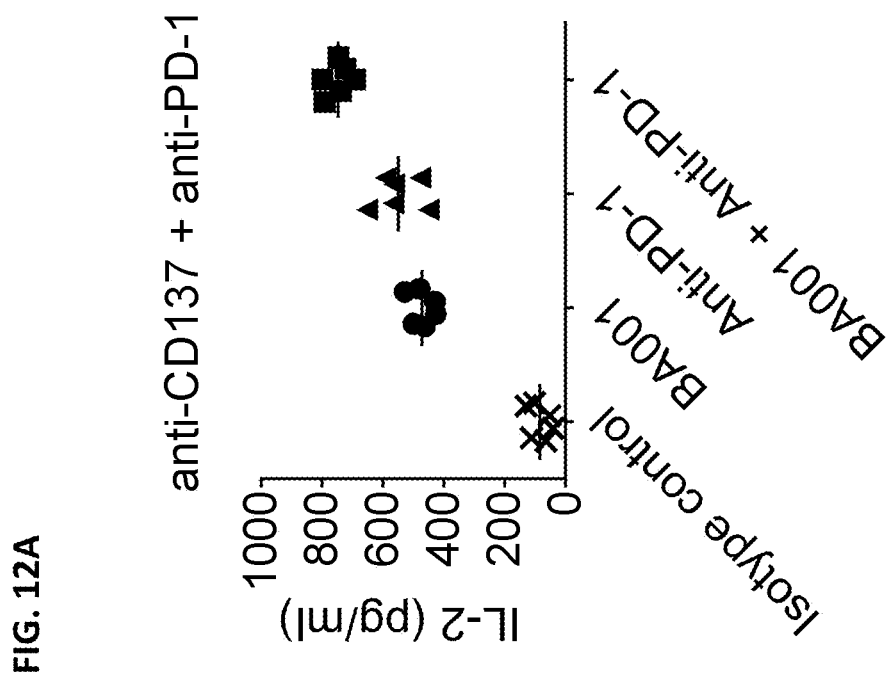

FIGS. 12A and 12B are graphs showing production of IL-2 induced by antibodies in human peripheral blood mononuclear cells (PBMCs) upon Staphylococcal Enterotoxin A (SEA) stimulation. Antibodies tested in FIG. 12A include anti-CD137 antibody BA001, isotype control antibody, an anti-PD-1 antibody, and a combination of BA001 and the anti-PD-1 antibody. Antibodies tested in FIG. 12B include anti-CD137 antibody BA001, isotype control antibody, an anti-OX40 antibody, and a combination of BA001 and the anti-OX40 antibody.

FIG. 13 is a sequence alignment for human CD137 and cynomolgus monkey CD137. An "*" (asterisk) indicates positions which have a single, fully conserved residue. A ":" (colon) indicates conservation between groups of strongly similar properties. A "." (period) indicates conservation between groups of weakly similar properties. The region boxed with dotted lines (DPCSNCPAGTFCDNNRNQICSPCPPNSFS-SAGGQRTCD, SEQ ID NO: 34) exhibited a mild decrease in deuterium uptake when human CD137 was bound to BA001-F(ab')$_2$, possibly owing to CD137 homodimerization at this region. The region boxed with solid lines (FNDQKRGICRPWTNCSL, SEQ ID NO: 26) exhibited a strong decrease in deuterium uptake when human CD137 was bound to BA001-Fab.

Figure 14A:
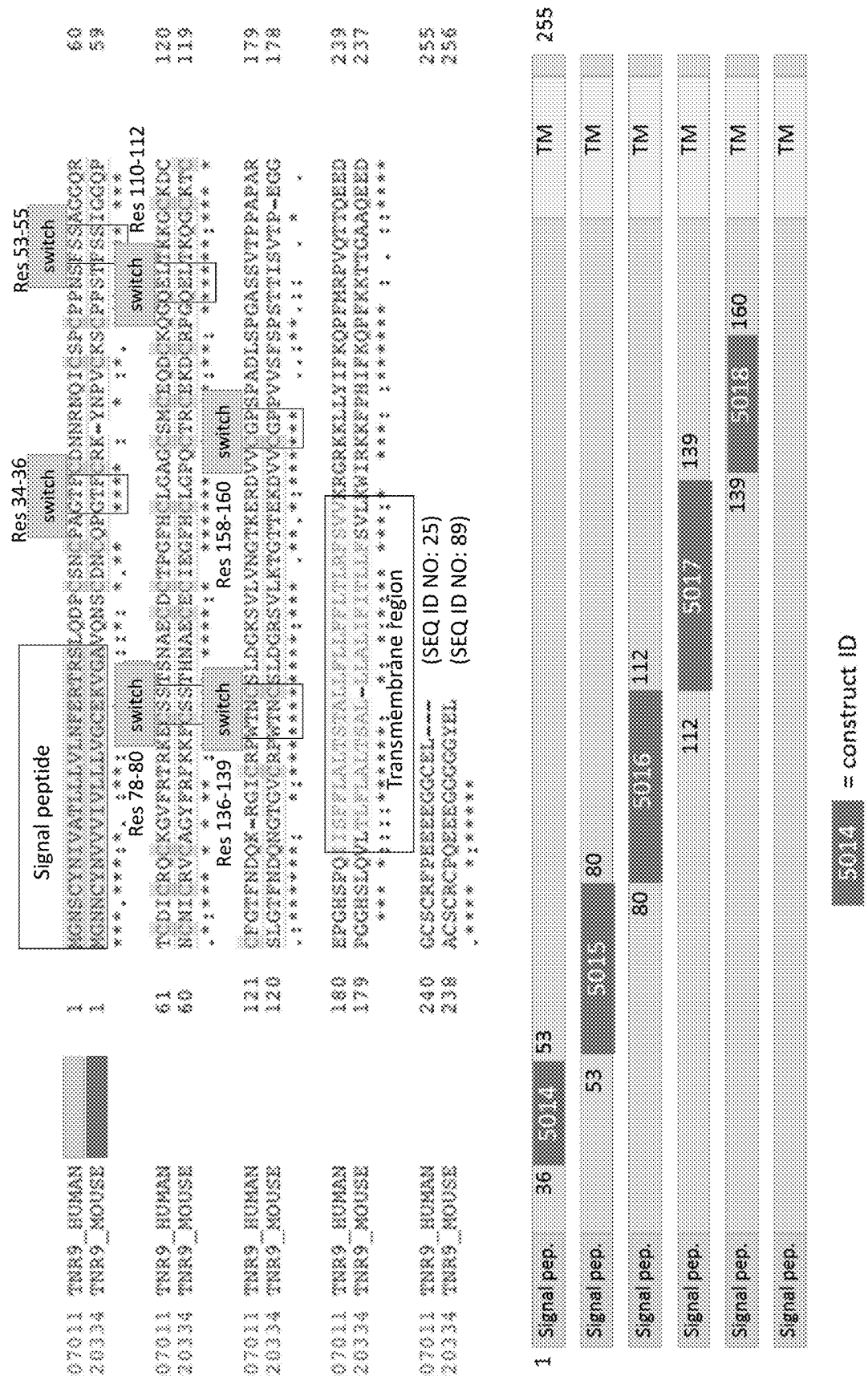
Figure 14B:
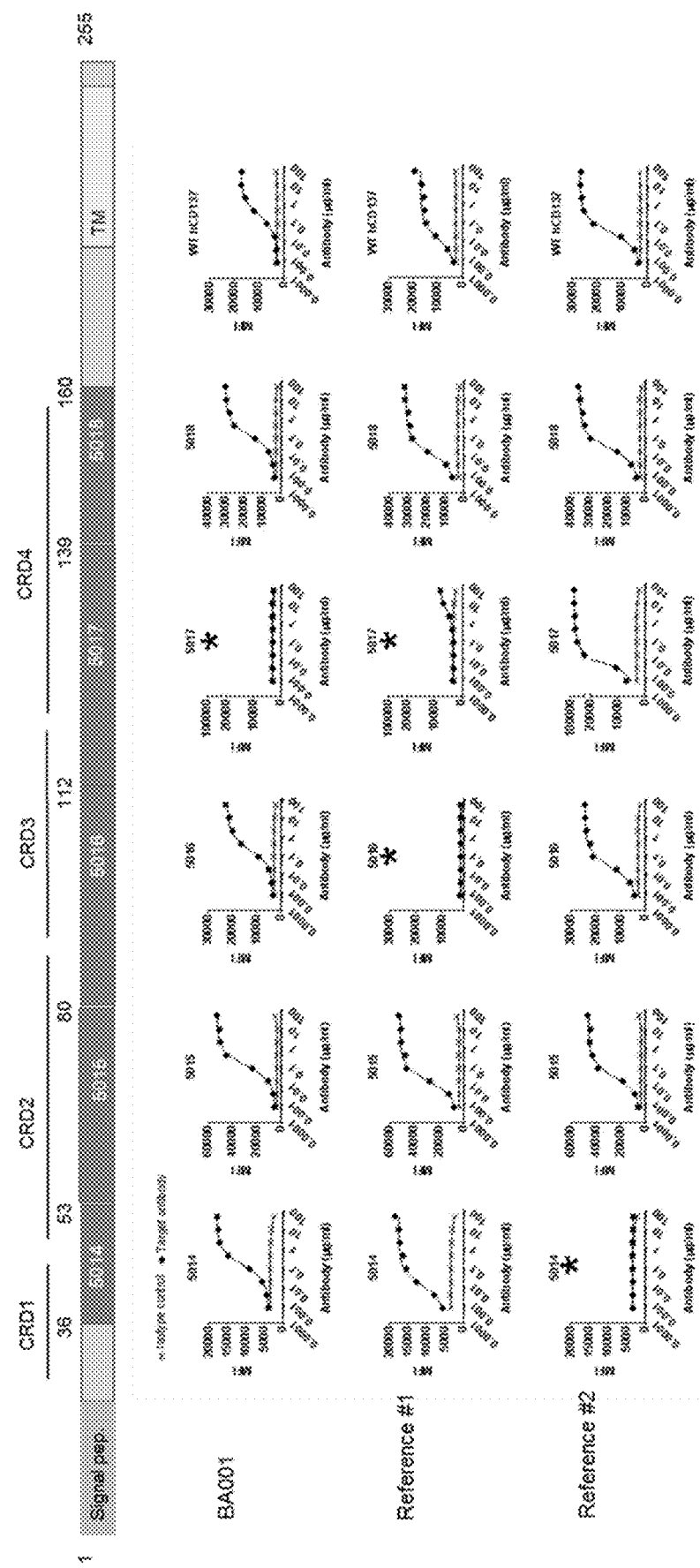

FIGS. 14A and 14B are a series of diagrams showing epitope mapping of BA001 by FACS. In FIG. 14A, a series of human-to-murine sequence switch mutants of CD137 were generated for each of the regions shown (i.e., 5014, 5015, 5016, 5017, and 5018, see Table 5 below). These mutant constructs were then transfected into Jurkat cells for analysis of anti-CD137 antibody binding by FACS. FIG. 14B shows cell binding data for BA001, reference anti-CD137 antibodies #1 and #2 ("Reference #1" and "Reference #2," respectively), and isotype control antibody to engineered Jurkat cells expressing each of the switch mutants described above.

Figure 15A:
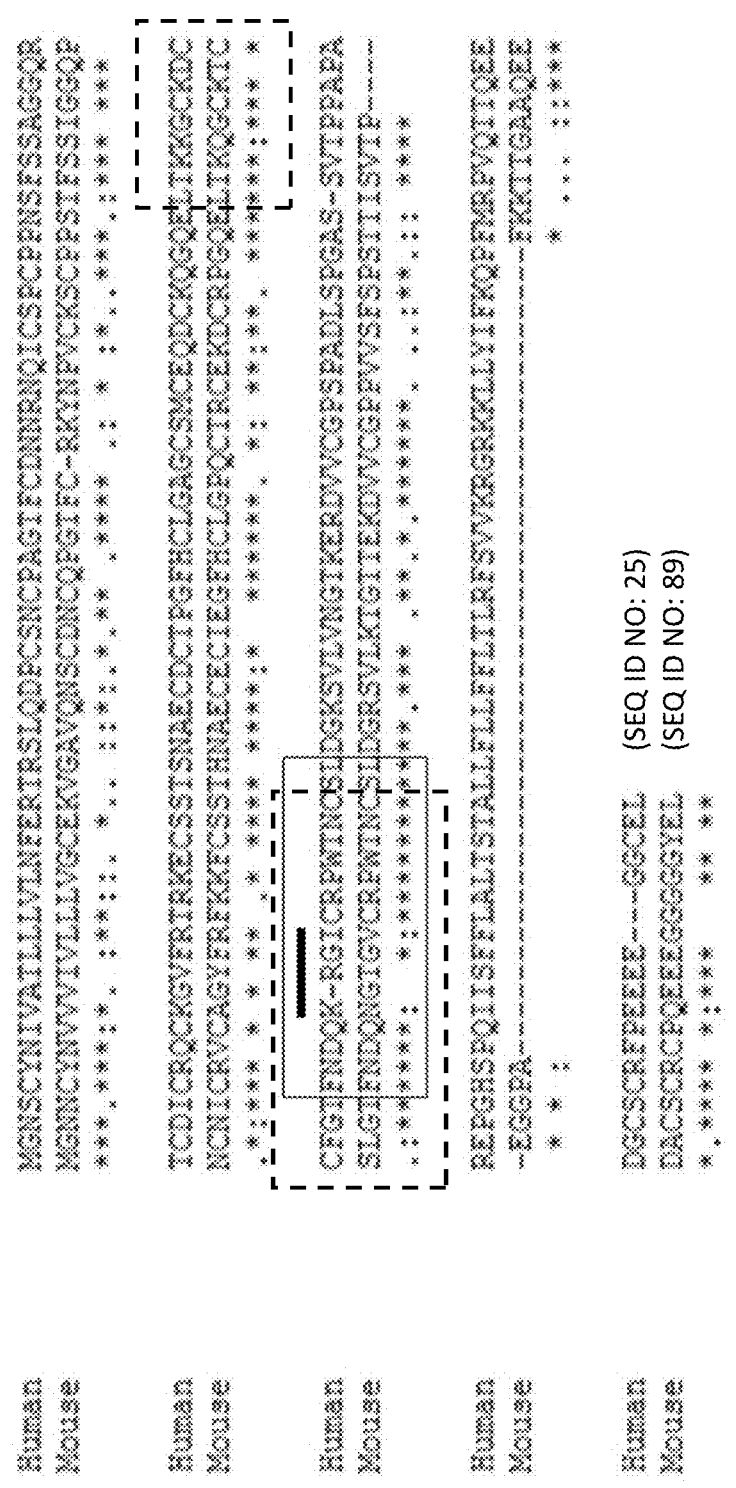
Figure 15B:
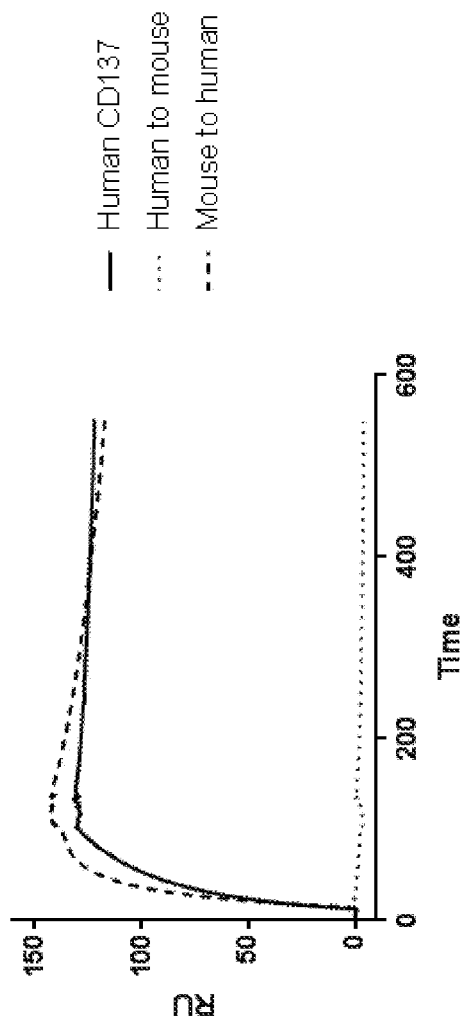
Figure 15C:
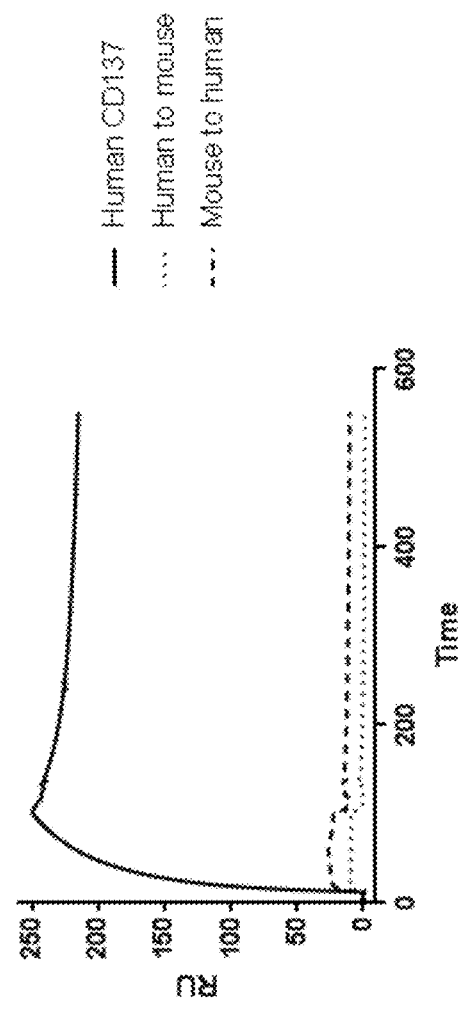

FIGS. 15A-15C show fine mapping of CD137 epitope by surface plasmon resonance (SPR) assay. FIG. 15A is a sequence alignment for human CD137 and murine CD137. An "*" (asterisk) indicates positions which have a single, fully conserved residue. A ":" (colon) indicates conservation between groups of strongly similar properties. A "." (period) indicates conservation between groups of weakly similar properties. The region boxed with solid lines (FNDQKR-GICRPWTNCSL, SEQ ID NO: 26) is an epitope region identified by the hydrogen/deuterium exchange assay as illustrated in FIG. 13. The region boxed with dotted lines (LTKKGCKDCCFGTFNDQKRGICRPWTNC, SEQ ID NO: 30) is the 5017 region identified from the binding assay using the human-mouse fusion constructs as illustrated in FIGS. 14A and 14B. The region highlighted by a solid line (KRGI, SEQ ID NO: 43) indicates the amino acid sequence that has been switched between the human and murine CD137 to generate chimeric proteins. FIG. 15B is a sensorgram showing the binding of BA001 to human CD137 and the chimeric proteins "human to mouse" and "mouse to human" by SPR assay. FIG. 15C is a sensorgram showing the binding of reference anti-CD137 antibody #1 ("Reference #1") to the same CD137 proteins in a similar SPR assay.

FIGS. 16A-16D are a series of graphs showing the binding of four BA001 variants, BA049, BA050, BA051, and BA052, to the extracellular domains of human CD137 (FIG. 16A), cynomolgus CD137 (FIG. 16B), mouse-human fusion construct 5017 ("mCD137-human112-139") (FIG. 16C), and mouse-human fusion construct 5015 ("mCD137-human53-80") (FIG. 16D), as measured by enzyme-linked immunosorbent assay (ELISA) using a fluorescent label as readout. The median fluorescence intensity levels were plotted against the concentrations of the anti-CD137 antibodies.

5. DETAILED DESCRIPTION

The instant disclosure provides antibodies that specifically bind to CD137 (e.g., human CD137 or cynomolgus CD137) and increase or promote CD137 function, e.g., CD137-mediated immune activation. Also provided are pharmaceutical compositions comprising these antibodies, nucleic acids encoding these antibodies, expression vectors and host cells for making these antibodies, and methods of treating a subject using these antibodies. The antibodies disclosed herein are particularly useful for increasing T cell activation in response to an antigen (e.g., a tumor antigen or an infectious disease antigen), and hence for treating cancer in a subject or treating or preventing an infectious disease in a subject. All instances of "isolated antibodies" described herein are additionally contemplated as antibodies that may be, but need not be, isolated. All instances of "isolated polynucleotides" described herein are additionally contemplated as polynucleotides that may be, but need not be, isolated. All instances of "antibodies" described herein are additionally contemplated as antibodies that may be, but need not be, isolated. All instances of "polynucleotides" described herein are additionally contemplated as polynucleotides that may be, but need not be, isolated.

5.1 Definitions

As used herein, the terms "about" and "approximately," when used to modify a numeric value or numeric range, indicate that deviations of 5% to 10% above (e.g., up to 5% to 10% above) and 5% to 10% below (e.g., up to 5% to 10% below) the value or range remain within the intended meaning of the recited value or range.

As used herein, the term "CD137" refers to TNF receptor superfamily member 9 (also known as 4-1BB) that in humans is encoded by the TNFRSF9 gene. As used herein, the term "human CD137" refers to a CD137 protein encoded by a wild-type human CD137 gene (e.g., GenBank™ accession number NM_001561.5) or an extracellular domain of such a protein. An exemplary amino acid sequence of an immature human CD137 protein is provided as SEQ ID NO: 25. An exemplary amino acid sequence of a mature human CD137 protein is provided as SEQ ID NO: 33. An exemplary amino acid sequence of an extracellular domain of a mature human CD137 protein is provided as SEQ ID NO: 24.

As used herein, the terms "antibody" and "antibodies" include full length antibodies, antigen-binding fragments of full length antibodies, and molecules comprising antibody CDRs, VH regions, and/or VL regions. Examples of antibodies include, without limitation, monoclonal antibodies, recombinantly produced antibodies, monospecific antibodies, multispecific antibodies (including bispecific antibodies), human antibodies, humanized antibodies, chimeric antibodies, immunoglobulins, synthetic antibodies, tetrameric antibodies comprising two heavy chain and two light chain molecules, an antibody light chain monomer, an antibody heavy chain monomer, an antibody light chain dimer, an antibody heavy chain dimer, an antibody light chain-antibody heavy chain pair, intrabodies, heteroconjugate antibodies, antibody-drug conjugates, single domain antibodies, monovalent antibodies, single chain antibodies or single-chain Fvs (scFv), camelized antibodies, affybodies, Fab fragments, F(ab')$_2$ fragments, disulfide-linked Fvs (sdFv), anti-idiotypic (anti-Id) antibodies (including, e.g., anti-anti-Id antibodies), and antigen-binding fragments of any of the above. In certain embodiments, antibodies described herein refer to polyclonal antibody populations. Antibodies can be of any type (e.g., IgG, IgE, IgM, IgD, IgA or IgY), any class (e.g., IgG$_1$, IgG$_2$, IgG$_3$, IgG$_4$, IgA$_1$ or IgA$_2$), or any subclass (e.g., IgG$_{2a}$ or IgG$_{2b}$) of immunoglobulin molecule. In certain embodiments, antibodies described herein are IgG antibodies, or a class (e.g., human IgG$_1$ or IgG$_4$) or subclass thereof. In a specific embodiment, the antibody is a humanized monoclonal antibody. In another specific embodiment, the antibody is a human monoclonal antibody.

As used herein, the terms "VH region" and "VL region" refer, respectively, to single antibody heavy and light chain variable regions, comprising FR (Framework Regions) 1, 2, 3 and 4 and CDR (Complementarity Determining Regions) 1, 2 and 3 (see Kabat et al., (1991) Sequences of Proteins of Immunological Interest (NIH Publication No. 91-3242, Bethesda), which is herein incorporated by reference in its entirety).

As used herein, the term "CDR" or "complementarity determining region" means the noncontiguous antigen combining sites found within the variable region of both heavy and light chain polypeptides. These particular regions have been described by Kabat et al., J. Biol. Chem. 252, 6609-6616 (1977) and Kabat et al., Sequences of protein of immunological interest. (1991), by Chothia et al., J. Mol. Biol. 196:901-917 (1987), and by MacCallum et al., J. Mol. Biol. 262:732-745 (1996), all of which are herein incorporated by reference in their entireties, where the definitions include overlapping or subsets of amino acid residues when compared against each other. In certain embodiments, the term "CDR" is a CDR as defined by MacCallum et al., J. Mol. Biol. 262:732-745 (1996) and Martin A. "Protein Sequence and Structure Analysis of Antibody Variable Domains," in *Antibody Engineering*, Kontermann and Dübel, eds., Chapter 31, pp. 422-439, Springer-Verlag, Berlin (2001). In certain embodiments, the term "CDR" is a CDR as defined by Kabat et al., J. Biol. Chem. 252, 6609-6616 (1977) and Kabat et al., Sequences of protein of immunological interest. (1991). In certain embodiments, heavy chain CDRs and light chain CDRs of an antibody are defined using different conventions. For example, in certain embodiments, the heavy chain CDRs are defined according to MacCallum (supra), and the light CDRs are defined according to Kabat (supra). CDRH1, CDRH2 and CDRH3 denote the heavy chain CDRs, and CDRL1, CDRL2 and CDRL3 denote the light chain CDRs.

As used herein, the term "framework (FR) amino acid residues" refers to those amino acids in the framework region of an immunoglobulin chain. The term "framework region" or "FR region" as used herein, includes the amino acid residues that are part of the variable region, but are not part of the CDRs (e.g., using the Kabat or MacCallum definition of CDRs).

As used herein, the terms "variable region" and "variable domain" are used interchangeably and are common in the art. The variable region typically refers to a portion of an antibody, generally, a portion of a light or heavy chain, typically about the amino-terminal 110 to 120 amino acids or 110 to 125 amino acids in the mature heavy chain and about 90 to 115 amino acids in the mature light chain, which differ extensively in sequence among antibodies and are used in the binding and specificity of a particular antibody for its particular antigen. The variability in sequence is concentrated in those regions called complementarity determining regions (CDRs) while the more highly conserved regions in the variable domain are called framework regions (FR). Without wishing to be bound by any particular mechanism or theory, it is believed that the CDRs of the light and heavy chains are primarily responsible for the interaction and specificity of the antibody with antigen. In certain embodiments, the variable region is a human variable region. In certain embodiments, the variable region comprises rodent or murine CDRs and human framework regions (FRs). In particular embodiments, the variable region is a primate (e.g., non-human primate) variable region. In certain embodiments, the variable region comprises rodent or murine CDRs and primate (e.g., non-human primate) framework regions (FRs).

The terms "VL" and "VL domain" are used interchangeably to refer to the light chain variable region of an antibody.

The terms "VH" and "VH domain" are used interchangeably to refer to the heavy chain variable region of an antibody.

As used herein, the terms "constant region" and "constant domain" are interchangeable and are common in the art. The constant region is an antibody portion, e.g., a carboxyl terminal portion of a light and/or heavy chain which is not directly involved in binding of an antibody to antigen but which can exhibit various effector functions, such as interaction with an Fc receptor (e.g., Fc gamma receptor). The constant region of an immunoglobulin molecule generally has a more conserved amino acid sequence relative to an immunoglobulin variable domain.

As used herein, the term "heavy chain" when used in reference to an antibody can refer to any distinct type, e.g., alpha (α), delta (δ), epsilon (ε), gamma (γ), and mu (μ), based on the amino acid sequence of the constant domain, which give rise to IgA, IgD, IgE, IgG, and IgM classes of antibodies, respectively, including subclasses of IgG, e.g., $IgG_1$, $IgG_2$, $IgG_3$, and $IgG_4$.

As used herein, the term "light chain" when used in reference to an antibody can refer to any distinct type, e.g., kappa (κ) or lambda (λ) based on the amino acid sequence of the constant domains. Light chain amino acid sequences are well known in the art. In specific embodiments, the light chain is a human light chain.

As used herein, the term "EU numbering system" refers to the EU numbering convention for the constant regions of an antibody, as described in Edelman, G. M. et al., Proc. Natl. Acad. USA, 63, 78-85 (1969) and Kabat et al, Sequences of Proteins of Immunological Interest, U.S. Dept. Health and Human Services, 5th edition, 1991, each of which is herein incorporated by reference in its entirety.

"Binding affinity" generally refers to the strength of the sum total of non-covalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the dissociation constant ($K_D$). Affinity can be measured and/or expressed in a number of ways known in the art, including, but not limited to, equilibrium dissociation constant ($K_D$), and equilibrium association constant ($K_A$). The $K_D$ is calculated from the quotient of $k_{off}/k_{on}$, whereas $K_A$ is calculated from the quotient of $k_{on}/k_{off}$. $k_{on}$ refers to the association rate constant of, e.g., an antibody to an antigen, and $k_{off}$ refers to the dissociation rate constant of, e.g., an antibody to an antigen. The $k_{on}$ and $k_{off}$ can be determined by techniques known to one of ordinary skill in the art, such as BIAcore® or KinExA. As used herein, a "lower affinity" refers to a larger $K_D$.

As used herein, the terms "specifically binds," "specifically recognizes," "immunospecifically binds," and "immunospecifically recognizes" are analogous terms in the context of antibodies and refer to molecules that bind to an antigen (e.g., epitope or immune complex) as such binding is understood by one skilled in the art. For example, a molecule that specifically binds to an antigen can bind to other peptides or polypeptides, generally with lower affinity as determined by, e.g., immunoassays, BIAcore®, KinExA 3000 instrument (Sapidyne Instruments, Boise, Id.), or other assays known in the art. In a specific embodiment, molecules that specifically bind to an antigen bind to the antigen with a $K_A$ that is at least 2 logs (e.g., factors of 10), 2.5 logs, 3 logs, 4 logs or greater than the $K_A$ when the molecules bind non-specifically to another antigen.

In another specific embodiment, molecules that specifically bind to an antigen do not cross react with other proteins under similar binding conditions. In another specific embodiment, molecules that specifically bind to CD137 do not cross react with other non-CD137 proteins. In a specific embodiment, provided herein is an antibody that binds to CD137 (e.g., human CD137 or cynomolgus CD137) with a higher affinity than to another unrelated antigen. In certain embodiments, provided herein is an antibody that binds to CD137 (e.g., human CD137 or cynomolgus CD137) with a 20%, 25%, 30%, 35%, 40%, 45%, 50%, 55%, 60%, 65%, 70%, 75%, 80%, 85%, 90%, 95% or higher affinity than to another, unrelated antigen as measured by, e.g., a radioimmunoassay, surface plasmon resonance, or kinetic exclusion assay. In a specific embodiment, the extent of binding of an anti-CD137 antibody described herein to an unrelated, non-CD137 protein is less than 10%, 15%, or 20% of the binding of the antibody to CD137 protein as measured by, e.g., a radioimmunoassay.

As used herein, A "does not substantially inhibit" B means that B is not reduced by more than 1%, 2%, 3%, 4%, 5%, 10%, 15%, 20%, 25%, or 30% in the presence of A relative to B in the absence of A.

As used herein, B is a "substantially increasing function" of A over a specified domain of A values if B substantially increases as A increases over the specified domain, e.g., in a given experiment, or using mean values from multiple experiments. This definition allows for a value of B corresponding to a specified value of A to be up to 1%, 2%, 3%, 4%, 5%, 10%, 15%), or 20%) lower relative to a value of B corresponding to any lower value of A.

As used herein, an "epitope" is a term in the art and refers to a localized region of an antigen to which an antibody can specifically bind. An epitope can be, for example, contiguous amino acids of a polypeptide (linear or contiguous epitope) or an epitope can, for example, come together from two or more non-contiguous regions of a polypeptide or polypeptides (conformational, non-linear, discontinuous, or non-contiguous epitope). In certain embodiments, the epitope to which an antibody binds can be determined by, e.g., NMR spectroscopy, X-ray diffraction crystallography studies, ELISA assays, hydrogen/deuterium exchange coupled with mass spectrometry (e.g., liquid chromatography electrospray mass spectrometry), array-based oligopeptide scanning assays (e.g., constraining peptides using CLIPS (Chemical Linkage of Peptides onto Scaffolds) to map discontinuous or conformational epitopes), and/or mutagenesis mapping (e.g., site-directed mutagenesis mapping). For X-ray crystallography, crystallization may be accomplished using any of the known methods in the art (e.g., Giegé R et al., (1994) Acta Crystallogr D Biol Crystallogr 50(Pt 4): 339-350; McPherson A (1990) Eur J Biochem 189: 1-23; Chayen N E (1997) Structure 5: 1269-1274; McPherson A (1976) J Biol Chem 251: 6300-6303, each of which is herein incorporated by reference in its entirety). Antibody:antigen crystals may be studied using well known X-ray diffraction techniques and may be refined using computer software such as X-PLOR (Yale University, 1992, distributed by Molecular Simulations, Inc.; see, e.g., Meth Enzymol (1985) volumes 114 & 115, eds Wyckoff H W et al.; U.S. 2004/0014194), and BUSTER (Bricogne G (1993) Acta Crystallogr D Biol Crystallogr 49(Pt 1): 37-60; Bricogne G (1997) Meth Enzymol 276A: 361-423, ed Carter C W; Roversi P et al., (2000) Acta Crystallogr D Biol Crystallogr 56(Pt 10): 1316-1323), each of which is herein incorporated by reference in its entirety. Mutagenesis mapping studies may be accomplished using any method known to one of skill in the art. See, e.g., Champe M et al., (1995) J Biol Chem 270: 1388-1394 and Cunningham B C & Wells J A (1989) Science 244: 1081-1085, each of which is herein incorporated by reference in its entirety, for a description of mutagenesis techniques, including alanine scanning mutagenesis techniques. CLIPS (Chemical Linkage of Peptides onto Scaffolds) is a technology to present one or more peptides in a structurally constrained configuration to behave as functional mimics of complex protein domains. See, e.g., U.S. Publication Nos. US 2008/0139407 A1 and US 2007/099240 A1, and U.S. Pat. No. 7,972,993, each of which is herein incorporated by reference in its entirety. In a specific embodiment, the epitope of an antibody is determined using alanine scanning mutagenesis studies. In a specific embodiment, the epitope of an antibody is determined using hydrogen/deuterium exchange coupled with mass spectrometry. In a specific embodiment, the epitope of an antibody is determined using CLIPS Epitope Mapping Technology from Pepscan Therapeutics. In a specific embodiment, the epitope of an antibody is determined by protein mutagenesis, e.g., by generating switch mutants of an antigen with portions of its ortholog from another species and then testing the switch mutants for loss of antibody binding (e.g., by a FACS-based cell binding assay, as described herein).

As used herein, the term "an epitope located within" a region of human CD137 refers to an epitope comprising one or more of the amino acid residues of the specified region. In certain embodiments, the epitope comprises each one of the amino acid residues located within the specified region. In certain embodiments, the epitope consists of each one of the amino acid residues located within the specified region. In certain embodiments, one or more additional amino acid residues of human CD137 outside the specified region bind to an antibody together with an epitope located within the specified region.

As used herein, the terms "T cell receptor" and "TCR" are used interchangeably and refer to full length heterodimeric αβ or γδ TCRs, antigen-binding fragments of full length TCRs, and molecules comprising TCR CDRs or variable regions. Examples of TCRs include, but are not limited to, full length TCRs, antigen-binding fragments of full length TCRs, soluble TCRs lacking transmembrane and cytoplasmic regions, single-chain TCRs containing variable regions of TCRs attached by a flexible linker, TCR chains linked by an engineered disulfide bond, monospecific TCRs, multi-specific TCRs (including bispecific TCRs), TCR fusions, human TCRs, humanized TCRs, chimeric TCRs, recombinantly produced TCRs, and synthetic TCRs. The term encompasses wild-type TCRs and genetically engineered TCRs (e.g., a chimeric TCR comprising a chimeric TCR chain which includes a first portion from a TCR of a first species and a second portion from a TCR of a second species).

As used herein, the term "level of CD137 multimerization" refers to the relative amount of multimeric (e.g., dimeric) CD137 compared to monomeric CD137 in a population of CD137 molecules (e.g., a population of CD137 molecules expressed on the surface of one or more cells).

As used herein, the terms "major histocompatibility complex" and "MHC" are used interchangeably and refer to an MHC class I molecule and/or an MHC class II molecule.

As used herein, the term "peptide-MHC complex" refers to an MHC molecule (MHC class I or MHC class II) with a peptide bound in the art-recognized peptide binding pocket of the MHC.

As used herein, the term "treat," "treating," and "treatment" refer to therapeutic or preventative measures described herein. The methods of "treatment" employ administration of an antibody to a subject having a disease or disorder, or predisposed to having such a disease or disorder, in order to prevent, cure, delay, reduce the severity of, or ameliorate one or more symptoms of the disease or disorder or recurring disease or disorder, or in order to prolong the survival of a subject beyond that expected in the absence of such treatment.

As used herein, the term "effective amount" in the context of the administration of a therapy to a subject refers to the amount of a therapy that achieves a desired prophylactic or therapeutic effect.

As used herein, the term "subject" includes any human or non-human animal. In one embodiment, the subject is a human or non-human mammal. In one embodiment, the subject is a human.

The determination of "percent identity" between two sequences (e.g., amino acid sequences or nucleic acid sequences) can be accomplished using a mathematical algorithm. A specific, non-limiting example of a mathematical algorithm utilized for the comparison of two sequences is the algorithm of Karlin S & Altschul S F (1990) PNAS 87: 2264-2268, modified as in Karlin S & Altschul S F (1993) PNAS 90: 5873-5877, each of which is herein incorporated by reference in its entirety. Such an algorithm is incorporated into the NBLAST and XBLAST programs of Altschul S F et al., (1990) J Mol Biol 215: 403, which is herein incorporated by reference in its entirety. BLAST nucleotide searches can be performed with the NBLAST nucleotide program parameters set, e.g., for score=100, wordlength=12 to obtain nucleotide sequences homologous to a nucleic acid molecules described herein. BLAST protein searches can be performed with the XBLAST program parameters set, e.g., to score 50, wordlength=3 to obtain amino acid sequences homologous to a protein molecule described herein. To obtain gapped alignments for comparison purposes, Gapped BLAST can be utilized as described in Altschul S F et al., (1997) Nuc Acids Res 25: 3389-3402, which is herein incorporated by reference in its entirety. Alternatively, PSI BLAST can be used to perform an iterated search which detects distant relationships between molecules (Id.). When utilizing BLAST, Gapped BLAST, and PSI Blast programs, the default parameters of the respective programs (e.g., of XBLAST and NBLAST) can be used (see, e.g., National Center for Biotechnology Information (NCBI) on the worldwide web, ncbi.nlm.nih.gov). Another specific, non-limiting example of a mathematical algorithm utilized for the comparison of sequences is the algorithm of Myers and Miller, 1988, CABIOS 4:11-17, which is herein incorporated by reference in its entirety. Such an algorithm is incorporated in the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used.

The percent identity between two sequences can be determined using techniques similar to those described above, with or without allowing gaps. In calculating percent identity, typically only exact matches are counted.

5.2 Anti-CD137 Antibodies

In one aspect the instant disclosure provides antibodies that specifically bind to CD137 (e.g., human CD137 or cynomolgus CD137) and increase or promote CD137 function. The amino acid sequences of exemplary antibodies are set forth in Table 1, herein.

TABLE 1

Amino acid sequences of exemplary anti-CD137 antibodies.

| Description | Amino Acid Sequence | SEQ ID NO: |
|---|---|---|
| CDRH1 consensus sequence 1 | $X_1X_2X_3X_4H$, wherein<br>$X_1$ is G, A, D, E, L, N, Q, R, S, or W;<br>$X_2$ is Y, F, H, N, R, or S;<br>$X_3$ is Y or H; and<br>$X_4$ is M, I, T, or V | 82 |
| CDRH3 consensus sequence 1 | $X_1PX_2YX_3GX_4GLX_5X_6$, wherein<br>$X_1$ is E or G;<br>$X_2$ is G, A, R, or S;<br>$X_3$ is Y, F, H, or S;<br>$X_4$ is S, A, or T;<br>$X_5$ is D or G; and<br>$X_6$ is Y or H | 83 |
| CDRL3 consensus sequence 1 | $QX_1WX_2X_3X_4X_5X_6X_7PGV$, wherein<br>$X_1$ is V or I;<br>$X_2$ is D, A, E, G, H, N, or Y;<br>$X_3$ is S, A, E, F, L, P, R, T, W, or Y;<br>$X_4$ is S, A, L, M, or R;<br>$X_5$ is S, A, F, G, L, P, Q, R, or T;<br>$X_6$ is D, E, H, V, or Y; and<br>$X_7$ is H or Y | 84 |
| CDRH1 consensus sequence 2 | $X_1X_2YX_3H$, wherein<br>$X_1$ is G, A, D, L, R, S, or W;<br>$X_2$ is Y, F, H, or N; and<br>$X_3$ is M or V | 85 |
| CDRH3 consensus sequence 2 | $EPGYX_1GX_2GLDX_3$, wherein<br>$X_1$ is Y or F;<br>$X_2$ is S or T; and<br>$X_3$ is Y or H | 86 |
| CDRL3 consensus sequence 2 | $QVWX_1X_2X_3X_4X_5X_6PGV$, wherein<br>$X_1$ is D, A, E, H, N, or Y;<br>$X_2$ is S, A, E, L, R, or T;<br>$X_3$ is S, A, L, or R;<br>$X_4$ is S, A, F, G, L, P, Q, or R;<br>$X_5$ is D, E, or V; and<br>$X_6$ is H or Y | 87 |
| BA001 CDRH1 | GYYMH | 1 |
| BA001 CDRH2 | WINPNSGGTNYAQKFQG | 2 |
| BA001 CDRH3 | EPGYYGSGLDY | 3 |
| BA001 CDRL1 | GGDDIGDKRVH | 4 |
| BA001 CDRL2 | EDRYRPS | 5 |
| BA001 CDRL3 | QVWDSSSDHPGV | 6 |
| BA001 VH | XVQLVQSGAEVKKPGASVKVSCKASGYTFTGYYMHW VRQAPGQGLEWMGWINPNSGGTNYAQKFQGRVTMT RDTSISTAYMELSRLRSDDTAVYYCAREPGYYGSGLD YWGQGTLVTVSS, wherein X = glutamine (Q) or pyroglutamate (pE) | 7 |
| BA001 VL | SYVLTQPPSVSVAPGETARITCGGDDIGDKRVHWYQK KPDQAPVLVVYEDRYRPSGIPERISGSNSGNTATLTLSR VEAGDEADYYCQVWDSSSDHPGVFGGGTQLIIL | 8 |
| BA001 full length heavy chain (IgG1) (without C-terminal lysine) | XVQLVQSGAEVKKPGASVKVSCKASGYTFTGYYMHW VRQAPGQGLEWMGWINPNSGGTNYAQKFQGRVTMT RDTSISTAYMELSRLRSDDTAVYYCAREPGYYGSGLD YWGQGTLVTVSSASTKGPSVFPLAPSSKSTSGGTAALG CLVKDYFPEPVTVSWNSGALTSGVHTFPAVLQSSGLYS LSSVVTVPSSSLGTQTYICNVNHKPSNTKVDKRVEPKS CDKTHTCPPCPAPELLGGPSVFLFPPKPKDTLMISRTPE VTCVVVDVSHEDPEVKFNWYVDGVEVHNAKTKPREE QYNSTYRVVSVLTVLHQDWLNGKEYKCKVSNKALPA PIEKTISKAKGQPREPQVYTLPPSREEMTKNQVSLTCLV KGFYPSDIAVEWESNGQPENNYKTTPPVLDSDGSFFLY | 9 |

TABLE 1-continued

Amino acid sequences of exemplary anti-CD137 antibodies.

| Description | Amino Acid Sequence | SEQ ID NO: |
|---|---|---|
| | SKLTVDKSRWQQGNVFSCSVMHEALHNHYTQKSLSLS PG, wherein X = glutamine (Q) or pyroglutamate (pE) | |
| BA001 full length heavy chain (IgG1) (with C-terminal lysine) | XVQLVQSGAEVKKPGASVKVSCKASGYTFTGYYMHW VRQAPGQGLEWMGWINPNSGGTNYAQKFQGRVTMT RDTSISTAYMELSRLRSDDTAVYYCAREPGYYGSLD YWGQGTLVTVSSASTKGPSVFPLAPSSKSTSGGTAALG CLVKDYFPEPVTVSWNSGALTSGVHTFPAVLQSSGLYS LSSVVTVPSSSLGTQTYICNVNHKPSNTKVDKRVEPKS CDKTHTCPPCPAPELLGGPSVFLFPPKPKDTLMISRTPE VTCVVVDVSHEDPEVKFNWYVDGVEVHNAKTKPREE QYNSTYRVVSVLTVLHQDWLNGKEYKCKVSNKALPA PIEKTISKAKGQPREPQVYTLPPSREEMTKNQVSLTCLV KGFYPSDIAVEWESNGQPENNYKTTPPVLDSDGSFFLY SKLTVDKSRWQQGNVFSCSVMHEALHNHYTQKSLSLS PGK, wherein X = glutamine (Q) or pyroglutamate (pE) | 49 |
| BA001 IgG1 N297A variant full length heavy chain (without C-terminal lysine) | XVQLVQSGAEVKKPGASVKVSCKASGYTFTGYYMHW VRQAPGQGLEWMGWINPNSGGTNYAQKFQGRVTMT RDTSISTAYMELSRLRSDDTAVYYCAREPGYYGSLD YWGQGTLVTVSSASTKGPSVFPLAPSSKSTSGGTAALG CLVKDYFPEPVTVSWNSGALTSGVHTFPAVLQSSGLYS LSSVVTVPSSSLGTQTYICNVNHKPSNTKVDKRVEPKS CDKTHTCPPCPAPELLGGPSVFLFPPKPKDTLMISRTPE VTCVVVDVSHEDPEVKFNWYVDGVEVHNAKTKPREE QYASTYRVVSVLTVLHQDWLNGKEYKCKVSNKALPA PIEKTISKAKGQPREPQVYTLPPSREEMTKNQVSLTCLV KGFYPSDIAVEWESNGQPENNYKTTPPVLDSDGSFFLY SKLTVDKSRWQQGNVFSCSVMHEALHNHYTQKSLSLS PG, wherein X = glutamine (Q) or pyroglutamate (pE) | 10 |
| BA001 IgG1 N297A variant full length heavy chain (with C-terminal lysine) | XVQLVQSGAEVKKPGASVKVSCKASGYTFTGYYMHW VRQAPGQGLEWMGWINPNSGGTNYAQKFQGRVTMT RDTSISTAYMELSRLRSDDTAVYYCAREPGYYGSLD YWGQGTLVTVSSASTKGPSVFPLAPSSKSTSGGTAALG CLVKDYFPEPVTVSWNSGALTSGVHTFPAVLQSSGLYS LSSVVTVPSSSLGTQTYICNVNHKPSNTKVDKRVEPKS CDKTHTCPPCPAPELLGGPSVFLFPPKPKDTLMISRTPE VTCVVVDVSHEDPEVKFNWYVDGVEVHNAKTKPREE QYASTYRVVSVLTVLHQDWLNGKEYKCKVSNKALPA PIEKTISKAKGQPREPQVYTLPPSREEMTKNQVSLTCLV KGFYPSDIAVEWESNGQPENNYKTTPPVLDSDGSFFLY SKLTVDKSRWQQGNVFSCSVMHEALHNHYTQKSLSLS PGK, wherein X = glutamine (Q) or pyroglutamate (pE) | 50 |
| BA001 IgG1 S267E L328F variant full length heavy chain (without C-terminal lysine) | XVQLVQSGAEVKKPGASVKVSCKASGYTFTGYYMHW VRQAPGQGLEWMGWINPNSGGTNYAQKFQGRVTMT RDTSISTAYMELSRLRSDDTAVYYCAREPGYYGSLD YWGQGTLVTVSSASTKGPSVFPLAPSSKSTSGGTAALG CLVKDYFPEPVTVSWNSGALTSGVHTFPAVLQSSGLYS LSSVVTVPSSSLGTQTYICNVNHKPSNTKVDKRVEPKS CDKTHTCPPCPAPELLGGPSVFLFPPKPKDTLMISRTPE VTCVVVDVEHEDPEVKFNWYVDGVEVHNAKTKPREE QYNSTYRVVSVLTVLHQDWLNGKEYKCKVSNKAFPA PIEKTISKAKGQPREPQVYTLPPSREEMTKNQVSLTCLV KGFYPSDIAVEWESNGQPENNYKTTPPVLDSDGSFFLY SKLTVDKSRWQQGNVFSCSVMHEALHNHYTQKSLSLS PG, wherein X = glutamine (Q) or pyroglutamate (pE) | 11 |
| BA001 IgG1 S267E L328F variant full length heavy chain (with C-terminal lysine) | XVQLVQSGAEVKKPGASVKVSCKASGYTFTGYYMHW VRQAPGQGLEWMGWINPNSGGTNYAQKFQGRVTMT RDTSISTAYMELSRLRSDDTAVYYCAREPGYYGSLD YWGQGTLVTVSSASTKGPSVFPLAPSSKSTSGGTAALG CLVKDYFPEPVTVSWNSGALTSGVHTFPAVLQSSGLYS LSSVVTVPSSSLGTQTYICNVNHKPSNTKVDKRVEPKS CDKTHTCPPCPAPELLGGPSVFLFPPKPKDTLMISRTPE VTCVVVDVEHEDPEVKFNWYVDGVEVHNAKTKPREE QYNSTYRVVSVLTVLHQDWLNGKEYKCKVSNKAFPA PIEKTISKAKGQPREPQVYTLPPSREEMTKNQVSLTCLV | 51 |

TABLE 1-continued

Amino acid sequences of exemplary anti-CD137 antibodies.

| Description | Amino Acid Sequence | SEQ ID NO: |
|---|---|---|
| | KGFYPSDIAVEWESNGQPENNYKTTPPVLDSDGSFFLY SKLTVDKSRWQQGNVFSCSVMHEALHNHYTQKSLSLS PGK, wherein X = glutamine (Q) or pyroglutamate (pE) | |
| BA001 IgG2 variant full length heavy chain (without C-terminal lysine) | XVQLVQSGAEVKKPGASVKVSCKASGYTFTGYYMHW VRQAPGQGLEWMGWINPNSGGTNYAQKFQGRVTMT RDTSISTAYMELSRLRSDDTAVYYCAREPGYYGSLD YWGQGTLVTVSSASTKGPSVFPLAPCSRSTSESTAALG CLVKDYFPEPVTVSWNSGALTSGVHTFPAVLQSSGLYS LSSVVTVPSSNFGTQTYTCNVDHKPSNTKVDKTVERK CCVECPPCPAPPVAGPSVFLFPPKPKDTLMISRTPEVTC VVVDVSHEDPEVQFNWYVDGVEVHNAKTKPREEQFN STFRVVSVLTVVHQDWLNGKEYKCKVSNKGLPAPIEK TISKTKGQPREPQVYTLPPSREEMTKNQVSLTCLVKGF YPSDIAVEWESNGQPENNYKTTPPMLDSDGSFFLYSKL TVDKSRWQQGNVFSCSVMHEALHNHYTQKSLSLSPG, wherein X = glutamine (Q) or pyroglutamate (pE) | 12 |
| BA001 IgG2 variant full length heavy chain (with C-terminal lysine) | XVQLVQSGAEVKKPGASVKVSCKASGYTFTGYYMHW VRQAPGQGLEWMGWINPNSGGTNYAQKFQGRVTMT RDTSISTAYMELSRLRSDDTAVYYCAREPGYYGSLD YWGQGTLVTVSSASTKGPSVFPLAPCSRSTSESTAALG CLVKDYFPEPVTVSWNSGALTSGVHTFPAVLQSSGLYS LSSVVTVPSSNFGTQTYTCNVDHKPSNTKVDKTVERK CCVECPPCPAPPVAGPSVFLFPPKPKDTLMISRTPEVTC VVVDVSHEDPEVQFNWYVDGVEVHNAKTKPREEQFN STFRVVSVLTVVHQDWLNGKEYKCKVSNKGLPAPIEK TISKTKGQPREPQVYTLPPSREEMTKNQVSLTCLVKGF YPSDIAVEWESNGQPENNYKTTPPMLDSDGSFFLYSKL TVDKSRWQQGNVFSCSVMHEALHNHYTQKSLSLSPG K, wherein X = glutamine (Q) or pyroglutamate (pE) | 52 |
| BA001 IgG2 N297A variant full length heavy chain (without C-terminal lysine) | XVQLVQSGAEVKKPGASVKVSCKASGYTFTGYYMHW VRQAPGQGLEWMGWINPNSGGTNYAQKFQGRVTMT RDTSISTAYMELSRLRSDDTAVYYCAREPGYYGSLD YWGQGTLVTVSSASTKGPSVFPLAPCSRSTSESTAALG CLVKDYFPEPVTVSWNSGALTSGVHTFPAVLQSSGLYS LSSVVTVPSSNFGTQTYTCNVDHKPSNTKVDKTVERK CCVECPPCPAPPVAGPSVFLFPPKPKDTLMISRTPEVTC VVVDVSHEDPEVQFNWYVDGVEVHNAKTKPREEQFA STFRVVSVLTVVHQDWLNGKEYKCKVSNKGLPAPIEK TISKTKGQPREPQVYTLPPSREEMTKNQVSLTCLVKGF YPSDINVEWESNGQPENNYKTTPPMLDSDGSFFLYSKL TVDKSRWQQGNVFSCSVMHEALHNHYTQKSLSLSPG, wherein X = glutamine (Q) or pyroglutamate (pE) | 13 |
| BA001 IgG2 N297A variant full length heavy chain (with C-terminal lysine) | XVQLVQSGAEVKKPGASVKVSCKASGYTFTGYYMHW VRQAPGQGLEWMGWINPNSGGTNYAQKFQGRVTMT RDTSISTAYMELSRLRSDDTAVYYCAREPGYYGSLD YWGQGTLVTVSSASTKGPSVFPLAPCSRSTSESTAALG CLVKDYFPEPVTVSWNSGALTSGVHTFPAVLQSSGLYS LSSVVTVPSSNFGTQTYTCNVDHKPSNTKVDKTVERK CCVECPPCPAPPVAGPSVFLFPPKPKDTLMISRTPEVTC VVVDVSHEDPEVQFNWYVDGVEVHNAKTKPREEQFA STFRVVSVLTVVHQDWLNGKEYKCKVSNKGLPAPIEK TISKTKGQPREPQVYTLPPSREEMTKNQVSLTCLVKGF YPSDINVEWESNGQPENNYKTTPPMLDSDGSFFLYSKL TVDKSRWQQGNVFSCSVMHEALHNHYTQKSLSLSPG K, wherein X = glutamine (Q) or pyroglutamate (pE) | 53 |
| BA001 IgG4 S228P variant full length heavy chain (without C-terminal lysine) | XVQLVQSGAEVKKPGASVKVSCKASGYTFTGYYMHW VRQAPGQGLEWMGWINPNSGGTNYAQKFQGRVTMT RDTSISTAYMELSRLRSDDTAVYYCAREPGYYGSLD YWGQGTLVTVSSASTKGPSVFPLAPCSRSTSESTAALG CLVKDYFPEPVTVSWNSGALTSGVHTFPAVLQSSGLYS LSSVVTVPSSSLGTKTYTCNVDHKPSNTKVDKRVESKY GPPCPPCPAPEFLGGPSVFLFPPKPKDTLMISRTPEVTCV VVDVSQEDPEVQFNWYVDGVEVHNAKTKPREEQFNS TYRVVSVLTVLHQDWLNGKEYKCKVSNKGLPSSIEKTI | 14 |

TABLE 1-continued

Amino acid sequences of exemplary anti-CD137 antibodies.

| Description | Amino Acid Sequence | SEQ ID NO: |
|---|---|---|
| | SKAKGQPREPQVYTLPPSQEEMTKNQVSLTCLVKGFY PSDIAVEWESNGQPENNYKTTPPVLDSDGSFFLYSRLT VDKSRWQEGNVFSCSVMHEALHNHYTQKSLSLSLG, wherein X = glutamine (Q) or pyroglutamate (pE) | |
| BA001 IgG4 S228P variant full length heavy chain (with C-terminal lysine) | XVQLVQSGAEVKKPGASVKVSCKASGYTFTGYYMHW VRQAPGQGLEWMGWINPNSGGTNYAQKFQGRVTMT RDTSISTAYMELSRLRSDDTAVYYCAREPGYYGSGLD YWGQGTLVTVSSASTKGPSVFPLAPCSRSTSESTAALG CLVKDYFPEPVTVSWNSGALTSGVHTFPAVLQSSGLYS LSSVVTVPSSSLGTKTYTCNVDHKPSNTKVDKRVESKY GPPCPPCPAPEFLGGPSVFLFPPKPKDTLMISRTPEVTCV VVDVSQEDPEVQFNWYVDGVEVHNAKTKPREEQFNS TYRVVSVLTVLHQDWLNGKEYKCKVSNKGLPSSIEKTI SKAKGQPREPQVYTLPPSQEEMTKNQVSLTCLVKGFY PSDIAVEWESNGQPENNYKTTPPVLDSDGSFFLYSRLT VDKSRWQEGNVFSCSVMHEALHNHYTQKSLSLSLGK, wherein X = glutamine (Q) or pyroglutamate (pE) | 54 |
| BA001 constant region (IgG1) | ASTKGPSVFPLAPSSKSTSGGTAALGCLVKDYFPEPVT VSWNSGALTSGVHTFPAVLQSSGLYSLSSVVTVPSSSL GTQTYICNVNHKPSNTKVDKRVEPKSCDKTHTCPPCPA PELLGGPSVFLFPPKPKDTLMISRTPEVTCVVVDVSHED PEVKFNWYVDGVEVHNAKTKPREEQYNSTYRVVSVL TVLHQDWLNGKEYKCKVSNKALPAPIEKTISKAKGQP REPQVYTLPPSREEMTKNQVSLTCLVKGFYPSDIAVEW ESNGQPENNYKTTPPVLDSDGSFFLYSKLTVDKSRWQ QGNVFSCSVMHEALHNHYTQKSLSLSPG | 15 |
| BA001 IgG1 N297A variant constant region | ASTKGPSVFPLAPSSKSTSGGTAALGCLVKDYFPEPVT VSWNSGALTSGVHTFPAVLQSSGLYSLSSVVTVPSSSL GTQTYICNVNHKPSNTKVDKRVEPKSCDKTHTCPPCPA PELLGGPSVFLFPPKPKDTLMISRTPEVTCVVVDVSHED PEVKFNWYVDGVEVHNAKTKPREEQYASTYRVVSVL TVLHQDWLNGKEYKCKVSNKALPAPIEKTISKAKGQP REPQVYTLPPSREEMTKNQVSLTCLVKGFYPSDIAVEW ESNGQPENNYKTTPPVLDSDGSFFLYSKLTVDKSRWQ QGNVFSCSVMHEALHNHYTQKSLSLSPG | 16 |
| BA001 IgG1 S267E L328F variant constant region | ASTKGPSVFPLAPSSKSTSGGTAALGCLVKDYFPEPVT VSWNSGALTSGVHTFPAVLQSSGLYSLSSVVTVPSSSL GTQTYICNVNHKPSNTKVDKRVEPKSCDKTHTCPPCPA PELLGGPSVFLFPPKPKDTLMISRTPEVTCVVVDVEHED PEVKFNWYVDGVEVHNAKTKPREEQYNSTYRVVSVL TVLHQDWLNGKEYKCKVSNKAFPAPIEKTISKAKGQP REPQVYTLPPSREEMTKNQVSLTCLVKGFYPSDIAVEW ESNGQPENNYKTTPPVLDSDGSFFLYSKLTVDKSRWQ QGNVFSCSVMHEALHNHYTQKSLSLSPG | 17 |
| BA001 IgG2 variant constant region | ASTKGPSVFPLAPCSRSTSESTAALGCLVKDYFPEPVTV SWNSGALTSGVHTFPAVLQSSGLYSLSSVVTVPSSNFG TQTYTCNVDHKPSNTKVDKTVERKCCVECPPCPAPPV AGPSVFLFPPKPKDTLMISRTPEVTCVVVDVSHEDPEV QFNWYVDGVEVHNAKTKPREEQFNSTFRVVSVLTVV HQDWLNGKEYKCKVSNKGLPAPIEKTISKTKGQPREP QVYTLPPSREEMTKNQVSLTCLVKGFYPSDIAVEWESN GQPENNYKTTPPMLDSDGSFFLYSKLTVDKSRWQQGN VFSCSVMHEALHNHYTQKSLSLSPG | 18 |
| BA001 IgG2 N297A variant constant region | ASTKGPSVFPLAPCSRSTSESTAALGCLVKDYFPEPVTV SWNSGALTSGVHTFPAVLQSSGLYSLSSVVTVPSSNFG TQTYTCNVDHKPSNTKVDKTVERKCCVECPPCPAPPV AGPSVFLFPPKPKDTLMISRTPEVTCVVVDVSHEDPEV QFNWYVDGVEVHNAKTKPREEQFASTFRVVSVLTVV HQDWLNGKEYKCKVSNKGLPAPIEKTISKTKGQPREP QVYTLPPSREEMTKNQVSLTCLVKGFYPSDINVEWESN GQPENNYKTTPPMLDSDGSFFLYSKLTVDKSRWQQGN VFSCSVMHEALHNHYTQKSLSLSPG | 19 |
| BA001 IgG4 S228P variant constant region | ASTKGPSVFPLAPCSRSTSESTAALGCLVKDYFPEPVTV SWNSGALTSGVHTFPAVLQSSGLYSLSSVVTVPSSSLG TKTYTCNVDHKPSNTKVDKRVESKYGPPCPPCPAPEFL | 20 |

TABLE 1-continued

Amino acid sequences of exemplary anti-CD137 antibodies.

| Description | Amino Acid Sequence | SEQ ID NO: |
| --- | --- | --- |
| | GGPSVFLFPPKPKDTLMISRTPEVTCVVVDVSQEDPEV QFNWYVDGVEVHNAKTKPREEQFNSTYRVVSVLTVL HQDWLNGKEYKCKVSNKGLPSSIEKTISKAKGQPREPQ VYTLPPSQEEMTKNQVSLTCLVKGFYPSDIAVEWESNG QPENNYKTTPPVLDSDGSFFLYSRLTVDKSRWQEGNV FSCSVMHEALHNHYTQKSLSLSLG | |
| BA001 full length light chain | SYVLTQPPSVSVAPGETARITCGGDDIGDKRVHWYQK KPDQAPVLVVYEDRYRPSGIPERISGSNSGNTATLTLSR VEAGDEADYYCQVWDSSSDHPGVFGGGTQLIILGQPK AAPSVTLFPPSSEELQANKATLVCLISDFYPGAVTVAW KADSSPVKAGVETTTPSKQSNNKYAASSYLSLTPEQW KSHRSYSCQVTHEGSTVEKTVAPTECS | 21 |
| BA001 light chain constant region | GQPKAAPSVTLFPPSSEELQANKATLVCLISDFYPGAVT VAWKADSSPVKAGVETTTPSKQSNNKYAASSYLSLTP EQWKSHRSYSCQVTHEGSTVEKTVAPTECS | 22 |
| BA001 scFv | QVQLVQSGAEVKKPGASVKVSCKASGYTFTGYYMHW VRQAPGQGLEWMGWINPNSGGTNYAQKFQGRVTMT RDTSISTAYMELSRLRSDDTAVYYCAREPGYYGSGLD YWGQGTLVTVSSGGGGSGGGGSGGGGASSYVLTQPPS VSVAPGETARITCGGDDIGDKRVHWYQKKPDQAPVLV VYEDRYRPSGIPERISGSNSGNTATLTLSRVEAGDEAD YYCQVWDSSSDHPGVFGGGTQLIIL | 55 |
| BA001 CDRH1 (bold) plus N-terminal flanking residues | TFTGYYMH | 56 |
| BA050 CDRH1 (bold) plus N-terminal flanking residues | SFTGYYMH | 57 |
| BA052 CDRH1 (bold) plus N-terminal flanking residues | NFSGYYMH | 58 |
| BA049 CDRH3 | EPGYYGTGLDY | 59 |
| BA050 CDRL3 | QVWNSSSDHPGV | 60 |
| BA051 CDRL3 | QVWDSSSDYPGV | 61 |
| BA052 CDRL3 | QVWYSSPDHPGV | 62 |
| BA049 VH | XVQLVQSGAEVKKPGASVKVSCKASGYTFTGYYMHW VRQAPGQGLEWMGWINPNSGGTNYAQKFQGRVTMT RDTSISTAYMELSRLRSDDTAVYYCAREPGYYGTGLD YWGQGTLVTVSS, wherein X = glutamine (Q) or pyroglutamate (pE) | 63 |
| BA050 VH | XVQLVQSGAEVKKPGASVKVSCKASGYSFTGYYMHW VRQAPGQGLEWMGWINPNSGGTNYAQKFQGRVTMT RDTSISTAYMELSRLRSDDTAVYYCAREPGYYGSGLD YWGQGTLVTVSS, wherein X = glutamine (Q) or pyroglutamate (pE) | 64 |
| BA052 VH | XVQLVQSGAEVKKPGASVKVSCKASGYNFSGYYMHW VRQAPGQGLEWMGWINPNSGGTNYAQKFQGRVTITR DTSISTAYMELSRLRSDDTAVYYCAREPGYYGSGLDY WGQGTLVTVSS, wherein X = glutamine (Q) or pyroglutamate (pE) | 65 |
| BA050 VL | SYVLTQPPSVSVAPGETARITCGGDDIGDKRVHWYQK KPDQAPVLVVYEDRYRPSGIPERISGSNSGNTATLTLSR VEAGDEADYYCQVWNSSSDHPGVFGGGTQLIIL | 66 |
| BA051 VL | SYVLTQPPSVSVAPGETARITCGGDDIGDKRVHWYQK KPDQAPVLVVYEDRYRPSGIPERISGSNSGNTATLTLSR VEAGDEADYYCQVWDSSSDYPGVFGGGTQLIIL | 67 |

TABLE 1-continued

Amino acid sequences of exemplary anti-CD137 antibodies.

| Description | Amino Acid Sequence | SEQ ID NO: |
| --- | --- | --- |
| BA052 VL | SYVLTQPPSVSVAPGETARITCGGDDIGDKRVHWYQK KPDQAPVLVVYEDRYRPSGIPERISGSNSGNTATLTLSR VEAGDEADYYCQVWYSSPDHPGVFGGGTQLIIL | 68 |
| BA049 scFv | XVQLVQSGAEVKKPGASVKVSCKASGYTFTGYYMHW VRQAPGQGLEWMGWINPNSGGTNYAQKFQGRVTMT RDTSISTAYMELSRLRSDDTAVYYCAREPGYYGTGLD YWGQGTLVTVSSGGGGSGGGGSGGGGASSYVLTQPPS VSVAPGETARITCGGDDIGDKRVHWYQKKPDQAPVLV VYEDRYRPSGIPERISGSNSGNTATLTLSRVEAGDEAD YYCQVWDSSSDHPGVFGGGTQLIIL, wherein X = glutamine (Q) or pyroglutamate (pE) | 69 |
| BA050 scFv | XVQLVQSGAEVKKPGASVKVSCKASGYSFTGYYMHW VRQAPGQGLEWMGWINPNSGGTNYAQKFQGRVTMT RDTSISTAYMELSRLRSDDTAVYYCAREPGYYGSGLD YWGQGTLVTVSSGGGGSGGGGSGGGGASSYVLTQPPS VSVAPGETARITCGGDDIGDKRVHWYQKKPDQAPVLV VYEDRYRPSGIPERISGSNSGNTATLTLSRVEAGDEAD YYCQVWNSSSDHPGVFGGGTQLIIL, wherein X = glutamine (Q) or pyroglutamate (pE) | 70 |
| BA051 scFv | XVQLVQSGAEVKKPGASVKVSCKASGYTFTGYYMHW VRQAPGQGLEWMGWINPNSGGTNYAQKFQGRVTMT RDTSISTAYMELSRLRSDDTAVYYCAREPGYYGSGLD YWGQGTLVTVSSGGGGSGGGGSGGGGASSYVLTQPPS VSVAPGETARITCGGDDIGDKRVHWYQKKPDQAPVLV VYEDRYRPSGIPERISGSNSGNTATLTLSRVEAGDEAD YYCQVWDSSSDYPGVFGGGTQLIIL, wherein X = glutamine (Q) or pyroglutamate (pE) | 71 |
| BA052 scFv | XVQLVQSGAEVKKPGASVKVSCKASGYNFSGYYMHW VRQAPGQGLEWMGWINPNSGGTNYAQKFQGRVTITR DTSISTAYMELSRLRSDDTAVYYCAREPGYYGSGLDY WGQGTLVTVSSGGGGSGGGGSGGGGASSYVLTQPPSV SVAPGETARITCGGDDIGDKRVHWYQKKPDQAPVLVV YEDRYRPSGIPERISGSNSGNTATLTLSRVEAGDEADY YCQVWYSSPDHPGVFGGGTQLIIL, wherein X = glutamine (Q) or pyroglutamate (pE) | 72 |
| BA049 full-length heavy chain (without C-terminal lysine) | XVQLVQSGAEVKKPGASVKVSCKASGYTFTGYYMHW VRQAPGQGLEWMGWINPNSGGTNYAQKFQGRVTMT RDTSISTAYMELSRLRSDDTAVYYCAREPGYYGTGLD YWGQGTLVTVSSASTKGPSVFPLAPSSKSTSGGTAALG CLVKDYFPEPVTVSWNSGALTSGVHTFPAVLQSSGLYS LSSVVTVPSSSLGTQTYICNVNHKPSNTKVDKRVEPKS CDKTHTCPPCPAPELLGGPSVFLFPPKPKDTLMISRTPE VTCVVVDVSHEDPEVKFNWYVDGVEVHNAKTKPREE QYNSTYRVVSVLTVLHQDWLNGKEYKCKVSNKALPA PIEKTISKAKGQPREPQVYTLPPSREEMTKNQVSLTCLV KGFYPSDIAVEWESNGQPENNYKTTPPVLDSDGSFFLY SKLTVDKSRWQQGNVFSCSVMHEALHNHYTQKSLSLS PG, wherein X = glutamine (Q) or pyroglutamate (pE) | 73 |
| BA049 full-length heavy chain (with C-terminal lysine) | XVQLVQSGAEVKKPGASVKVSCKASGYTFTGYYMHW VRQAPGQGLEWMGWINPNSGGTNYAQKFQGRVTMT RDTSISTAYMELSRLRSDDTAVYYCAREPGYYGTGLD YWGQGTLVTVSSASTKGPSVFPLAPSSKSTSGGTAALG CLVKDYFPEPVTVSWNSGALTSGVHTFPAVLQSSGLYS LSSVVTVPSSSLGTQTYICNVNHKPSNTKVDKRVEPKS CDKTHTCPPCPAPELLGGPSVFLFPPKPKDTLMISRTPE VTCVVVDVSHEDPEVKFNWYVDGVEVHNAKTKPREE QYNSTYRVVSVLTVLHQDWLNGKEYKCKVSNKALPA PIEKTISKAKGQPREPQVYTLPPSREEMTKNQVSLTCLV KGFYPSDIAVEWESNGQPENNYKTTPPVLDSDGSFFLY SKLTVDKSRWQQGNVFSCSVMHEALHNHYTQKSLSLS PGK, wherein X = glutamine (Q) or pyroglutamate (pE) | 74 |
| BA050 full-length heavy chain (without C- | XVQLVQSGAEVKKPGASVKVSCKASGYSFTGYYMHW VRQAPGQGLEWMGWINPNSGGTNYAQKFQGRVTMT RDTSISTAYMELSRLRSDDTAVYYCAREPGYYGSGLD | 75 |

TABLE 1-continued

Amino acid sequences of exemplary anti-CD137 antibodies.

| Description | Amino Acid Sequence | SEQ ID NO: |
|---|---|---|
| terminal lysine) | YWGQGTLVTVSSASTKGPSVFPLAPSSKSTSGGTAALG<br>CLVKDYFPEPVTVSWNSGALTSGVHTFPAVLQSSGLYS<br>LSSVVTVPSSSLGTQTYICNVNHKPSNTKVDKRVEPKS<br>CDKTHTCPPCPAPELLGGPSVFLFPPKPKDTLMISRTPE<br>VTCVVVDVSHEDPEVKFNWYVDGVEVHNAKTKPREE<br>QYNSTYRVVSVLTVLHQDWLNGKEYKCKVSNKALPA<br>PIEKTISKAKGQPREPQVYTLPPSREEMTKNQVSLTCLV<br>KGFYPSDIAVEWESNGQPENNYKTTPPVLDSDGSFFLY<br>SKLTVDKSRWQQGNVFSCSVMHEALHNHYTQKSLSLS<br>PG, wherein X = glutamine (Q) or pyroglutamate (pE) | |
| BA050 full-length heavy chain (with C-terminal lysine) | XVQLVQSGAEVKKPGASVKVSCKASGYSFTGYYMHW<br>VRQAPGQGLEWMGWINPNSGGTNYAQKFQGRVTMT<br>RDTSISTAYMELSRLRSDDTAVYYCAREPGYYGSGLD<br>YWGQGTLVTVSSASTKGPSVFPLAPSSKSTSGGTAALG<br>CLVKDYFPEPVTVSWNSGALTSGVHTFPAVLQSSGLYS<br>LSSVVTVPSSSLGTQTYICNVNHKPSNTKVDKRVEPKS<br>CDKTHTCPPCPAPELLGGPSVFLFPPKPKDTLMISRTPE<br>VTCVVVDVSHEDPEVKFNWYVDGVEVHNAKTKPREE<br>QYNSTYRVVSVLTVLHQDWLNGKEYKCKVSNKALPA<br>PIEKTISKAKGQPREPQVYTLPPSREEMTKNQVSLTCLV<br>KGFYPSDIAVEWESNGQPENNYKTTPPVLDSDGSFFLY<br>SKLTVDKSRWQQGNVFSCSVMHEALHNHYTQKSLSLS<br>PGK, wherein X = glutamine (Q) or pyroglutamate (pE) | 76 |
| BA052 full-length heavy chain (without C-terminal lysine) | XVQLVQSGAEVKKPGASVKVSCKASGYNFSGYYMHW<br>VRQAPGQGLEWMGWINPNSGGTNYAQKFQGRVTITR<br>DTSISTAYMELSRLRSDDTAVYYCAREPGYYGSGLDY<br>WGQGTLVTVSSASTKGPSVFPLAPSSKSTSGGTAALGC<br>LVKDYFPEPVTVSWNSGALTSGVHTFPAVLQSSGLYSL<br>SSVVTVPSSSLGTQTYICNVNHKPSNTKVDKRVEPKSC<br>DKTHTCPPCPAPELLGGPSVFLFPPKPKDTLMISRTPEV<br>TCVVVDVSHEDPEVKFNWYVDGVEVHNAKTKPREEQ<br>YNSTYRVVSVLTVLHQDWLNGKEYKCKVSNKALPAPI<br>EKTISKAKGQPREPQVYTLPPSREEMTKNQVSLTCLVK<br>GFYPSDIAVEWESNGQPENNYKTTPPVLDSDGSFFLYS<br>KLTVDKSRWQQGNVFSCSVMHEALHNHYTQKSLSLSP<br>G, wherein X = glutamine (Q) or pyroglutamate (pE) | 77 |
| BA052 full-length heavy chain (with C-terminal lysine) | XVQLVQSGAEVKKPGASVKVSCKASGYNFSGYYMHW<br>VRQAPGQGLEWMGWINPNSGGTNYAQKFQGRVTITR<br>DTSISTAYMELSRLRSDDTAVYYCAREPGYYGSGLDY<br>WGQGTLVTVSSASTKGPSVFPLAPSSKSTSGGTAALGC<br>LVKDYFPEPVTVSWNSGALTSGVHTFPAVLQSSGLYSL<br>SSVVTVPSSSLGTQTYICNVNHKPSNTKVDKRVEPKSC<br>DKTHTCPPCPAPELLGGPSVFLFPPKPKDTLMISRTPEV<br>TCVVVDVSHEDPEVKFNWYVDGVEVHNAKTKPREEQ<br>YNSTYRVVSVLTVLHQDWLNGKEYKCKVSNKALPAPI<br>EKTISKAKGQPREPQVYTLPPSREEMTKNQVSLTCLVK<br>GFYPSDIAVEWESNGQPENNYKTTPPVLDSDGSFFLYS<br>KLTVDKSRWQQGNVFSCSVMHEALHNHYTQKSLSLSP<br>GK, wherein X = glutamine (Q) or pyroglutamate (pE) | 78 |
| BA050 full-length light chain | SYVLTQPPSVSVAPGETARITCGGDDIGDKRVHWYQK<br>KPDQAPVLVVYEDRYRPSGIPERISGSNSGNTATLTLSR<br>VEAGDEADYYCQVWNSSSDHPGVFGGGTQLIILGQPK<br>AAPSVTLFPPSSEELQANKATLVCLISDFYPGAVTVAW<br>KADSSPVKAGVETTTPSKQSNNKYAASSYLSLTPEQW<br>KSHRSYSCQVTHEGSTVEKTVAPTECS | 79 |
| BA051 full-length light chain | SYVLTQPPSVSVAPGETARITCGGDDIGDKRVHWYQK<br>KPDQAPVLVVYEDRYRPSGIPERISGSNSGNTATLTLSR<br>VEAGDEADYYCQVWDSSSDYPGVFGGGTQLIILGQPK<br>AAPSVTLFPPSSEELQANKATLVCLISDFYPGAVTVAW<br>KADSSPVKAGVETTTPSKQSNNKYAASSYLSLTPEQW<br>KSHRSYSCQVTHEGSTVEKTVAPTECS | 80 |
| BA052 full-length light chain | SYVLTQPPSVSVAPGETARITCGGDDIGDKRVHWYQK<br>KPDQAPVLVVYEDRYRPSGIPERISGSNSGNTATLTLSR<br>VEAGDEADYYCQVWYSSPDHPGVFGGGTQLIILGQPK | 81 |

TABLE 1-continued

Amino acid sequences of exemplary anti-CD137 antibodies.

| Description | Amino Acid Sequence | SEQ ID NO: |
|---|---|---|
| | AAPSVTLFPPSSEELQANKATLVCLISDFYPGAVTVAW KADSSPVKAGVETTTPSKQSNNKYAASSYLSLTPEQW KSHRSYSCQVTHEGSTVEKTVAPTECS | |

TABLE 2

VH, VL, scFv, and full length heavy and light chain sequences of exemplary anti-CD137 antibodies.

| | SEQ ID NO | | | | |
|---|---|---|---|---|---|
| Antibody | VH | VL | scFv | Full-length heavy chain | Full-length light chain |
| BA001 | 7 | 8 | 55 | 9 | 21 |
| BA049 | 63 | 8 | 69 | 74 | 21 |
| BA050 | 64 | 66 | 70 | 76 | 79 |
| BA051 | 7 | 67 | 71 | 49 | 80 |
| BA052 | 65 | 68 | 72 | 78 | 81 |

TABLE 3

Closest germline genes to BA001.

| Closest germline gene | Amino Acid Sequence | SEQ ID NO: |
|---|---|---|
| IGHV1-2*02 heavy chain variable region | QVQLVQSGAEVKKPGASVKV SCKASGYTFTGYYMHWVRQA PGQGLEWMGWINPNSGGTNY AQKFQGRVTMTRDTSISTAY MELSRLRSDDTAVYYCAR | 40 |
| IGLV3-21*02 light chain variable region | SYVLTQPPSVSVAPGQTARI TCGGNNIGSKSVHWYQQKPG QAPVLVVYDDSDRPSGIPER FSGSNSGNTATLTISRVEAG DEADYYCQVWDSSSDH | 41 |

TABLE 4

Exemplary sequences of human CD137.

| Description | Amino Acid Sequence | SEQ ID NO: |
|---|---|---|
| CD137 signal peptide | MGNSCYNIVATLLLVLNFERTRS | 23 |
| Exemplary CD137 extracellular domain sequence | LQDPCSNCPAGTFCDNNRNQICS PCPPNSFSSAGGQRTCDICRQCK GVFRTRKECSSTSNAECDCTPGF HCLGAGCSMCEQDCKQGQELTKK GCKDCCFGTFNDQKRGICRPWTN CSLDGKSVLVNGTKERDVVCGPS PADLSPGASSVTPPAPAREPGHS PQ | 24 |
| Exemplary immature CD137 full length sequence | MGNSCYNIVATLLLVLNFERTRS LQDPCSNCPAGTFCDNNRNQICS PCPPNSFSSAGGQRTCDICRQCK GVFRTRKECSSTSNAECDCTPGF HCLGAGCSMCEQDCKQGQELTKK GCKDCCFGTFNDQKRGICRPWTN CSLDGKSVLVNGTKERDVVCGPS PADLSPGASSVTPPAPAREPGHS PQIISFFLALTSTALLFLLFFLT LRFSVVKRGRKKLLYIFKQPFMR PVQTTQEEDGCSCRFPEEEEGGC EL | 25 |
| CD137 extracellular epitope sequence #1 | FNDQKRGICRPWTNCSL | 26 |
| CD137 extracellular epitope sequence #2 | FNDQKRGICRPWTNCSLDGKSVL VNGTKERD | 27 |
| CD137 extracellular epitope sequence #3 | TPGFHCLGAG | 28 |
| CD137 extracellular epitope sequence #4 | KQGQEL | 29 |
| CD137 extracellular epitope sequence #5 | LTKKGCKDCCFGTFNDQKRGICR PWTNC | 30 |
| CD137 extracellular epitope sequence #6 | FNDQKRGICRPWTNC | 31 |
| Exemplary mature CD137 full length sequence | LQDPCSNCPAGTFCDNNRNQICS PCPPNSFSSAGGQRTCDICRQCK GVFRTRKECSSTSNAECDCTPGF HCLGAGCSMCEQDCKQGQELTKK GCKDCCFGTFNDQKRGICRPWTN CSLDGKSVLVNGTKERDVVCGPS PADLSPGASSVTPPAPAREPGHS PQIISFFLALTSTALLFLLFFLT LRFSVVKRGRKKLLYIFKQPFMR PVQTTQEEDGCSCRFPEEEEGGC EL | 33 |
| CD137 fragment | DPCSNCPAGTFCDNNRNQICSPC PPNSFSSAGGQRTCD | 34 |
| CD137 CRD4 sequence | CCFGTFNDQKRGICRPWTNCSLD GKSVLVNGTKERDVVC | 42 |
| CD137 fragment | KRGI | 43 |

In certain embodiments, the instant disclosure provides an isolated antibody that specifically binds to CD137 (e.g., human CD137 or cynomolgus CD137), the antibody comprising a VH domain comprising one, two, or all three of the CDRs of a VH domain set forth in Table 1 herein. In certain embodiments, the antibody comprises the CDRH1 of one of VH domains set forth in Table 1. In certain embodiments, the antibody comprises the CDRH2 of one of the VH domains set forth in Table 1. In certain embodiments, the antibody comprises the CDRH3 of one of the VH domains set forth in Table 1.

In certain embodiments, the instant disclosure provides an isolated antibody that specifically binds to CD137 (e.g., human CD137 or cynomolgus CD137), the antibody comprising a VL domain comprising one, two, or all three of the CDRs of a VL domain disclosed in Table 1 herein. In certain embodiments, the antibody comprises the CDRL1 of one of VL domains set forth in Table 1. In certain embodiments, the antibody comprises the CDRL2 of one of the VL domains set forth in Table 1. In certain embodiments, the antibody comprises the CDRL3 of one of the VL domains set forth in Table 1.

In certain embodiments, the CDRs of an antibody can be determined according to Kabat et al., J. Biol. Chem. 252, 6609-6616 (1977) and Kabat et al., Sequences of protein of immunological interest (1991), each of which is herein incorporated by reference in its entirety. In certain embodiments, the light chain CDRs of an antibody are determined according to Kabat and the heavy chain CDRs of an antibody are determined according to MacCallum (supra).

In certain embodiments, the CDRs of an antibody can be determined according to the Chothia numbering scheme, which refers to the location of immunoglobulin structural loops (see, e.g., Chothia C & Lesk A M, (1987), J Mol Biol 196: 901-917; Al-Lazikani B et al., (1997) J Mol Biol 273: 927-948; Chothia C et al., (1992) J Mol Biol 227: 799-817; Tramontano A et al., (1990) J Mol Biol 215(1): 175-82; and U.S. Pat. No. 7,709,226, all of which are herein incorporated by reference in their entireties). Typically, when using the Kabat numbering convention, the Chothia CDRH1 loop is present at heavy chain amino acids 26 to 32, 33, or 34, the Chothia CDRH2 loop is present at heavy chain amino acids 52 to 56, and the Chothia CDRH3 loop is present at heavy chain amino acids 95 to 102, while the Chothia CDRL1 loop is present at light chain amino acids 24 to 34, the Chothia CDRL2 loop is present at light chain amino acids 50 to 56, and the Chothia CDRL3 loop is present at light chain amino acids 89 to 97. The end of the Chothia CDRH1 loop when numbered using the Kabat numbering convention varies between H32 and H34 depending on the length of the loop (this is because the Kabat numbering scheme places the insertions at H35A and H35B; if neither 35A nor 35B is present, the loop ends at 32; if only 35A is present, the loop ends at 33; if both 35A and 35B are present, the loop ends at 34).

In certain embodiments, the instant disclosure provides an isolated antibody that specifically binds to CD137 (e.g., human CD137 or cynomolgus CD137), the antibody comprising the Chothia VH CDRs of a VH disclosed in Table 1 herein. In certain embodiments, the instant disclosure provides an isolated antibody that specifically binds to CD137 (e.g., human CD137 or cynomolgus CD137), the antibody comprising the Chothia VL CDRs of a VL disclosed in Table 1 herein. In certain embodiments, the instant disclosure provides an isolated antibody that specifically binds to CD137 (e.g., human CD137 or cynomolgus CD137), the antibody comprising the Chothia VH CDRs and Chothia VL CDRs of an antibody disclosed in Table 1 herein. In certain embodiments, antibodies that specifically bind to CD137 (e.g., human CD137 or cynomolgus CD137) comprise one or more CDRs, in which the Chothia and Kabat CDRs have the same amino acid sequence. In certain embodiments, the instant disclosure provides an isolated antibody that specifically binds to CD137 (e.g., human CD137 or cynomolgus CD137) and comprises combinations of Kabat CDRs and Chothia CDRs.

In certain embodiments, the CDRs of an antibody can be determined according to MacCallum R M et al., (1996) J Mol Biol 262: 732-745, herein incorporated by reference in its entirety. See also, e.g., Martin A. "Protein Sequence and Structure Analysis of Antibody Variable Domains," in *Antibody Engineering*, Kontermann and Dübel, eds., Chapter 31, pp. 422-439, Springer-Verlag, Berlin (2001), herein incorporated by reference in its entirety.

In certain embodiments, the CDRs of an antibody can be determined according to the IMGT numbering system as described in Lefranc M-P, (1999) The Immunologist 7: 132-136 and Lefranc M-P et al., (1999) Nucleic Acids Res 27: 209-212, each of which is herein incorporated by reference in its entirety. According to the IMGT numbering scheme, CDRH1 is at positions 26 to 35, CDRH2 is at positions 51 to 57, CDRH3 is at positions 93 to 102, CDRL1 is at positions 27 to 32, CDRL2 is at positions 50 to 52, and CDRL3 is at positions 89 to 97.

In certain embodiments, the instant disclosure provides antibodies that specifically bind to CD137 (e.g., human CD137 or cynomolgus CD137) and comprise CDRs of an antibody disclosed in Table 1 herein, as determined by the IMGT numbering system, for example, as described in Lefranc M-P (1999) supra and Lefranc M-P et al., (1999) supra.

In certain embodiments, the CDRs of an antibody can be determined according to the AbM numbering scheme, which refers to AbM hypervariable regions, which represent a compromise between the Kabat CDRs and Chothia structural loops, and are used by Oxford Molecular's AbM antibody modeling software (Oxford Molecular Group, Inc.), herein incorporated by reference in its entirety. In a particular embodiment, the instant disclosure provides antibodies that specifically bind to CD137 (e.g., human CD137 or cynomolgus CD137) and comprise CDRs of an antibody disclosed in Table 1 herein as determined by the AbM numbering scheme.

In certain embodiments, the instant disclosure provides an isolated antibody that specifically binds to CD137 (e.g., human CD137 or cynomolgus CD137), wherein the antibody comprises a heavy chain variable region comprising the CDRH1, CDRH2, and CDRH3 region amino acid sequences of a VH, and a light chain variable region comprising the CDRL1, CDRL2, and CDRL3 region amino acid sequences of a VL, wherein the amino acid sequences of the VH and the VL are set forth in SEQ ID NOs: 7 and 8; 63 and 8; 64 and 66; 7 and 67; or 65 and 68, respectively, and wherein each CDR is defined in accordance with the MacCallum definition, the Kabat definition, the Chothia definition, the combination of the Kabat definition and the Chothia definition, the IMGT numbering system, or the AbM definition of CDR. In certain embodiments, the instant disclosure provides an isolated antibody that specifically binds to CD137 (e.g., human CD137 or cynomolgus CD137), wherein the antibody comprises a heavy chain variable region comprising the CDRH1, CDRH2, and CDRH3 region amino acid sequences of a VH domain set forth in SEQ ID NO: 7, and a light chain variable region comprising the CDRL1, CDRL2, and CDRL3 region amino acid sequences of a VL domain set forth in SEQ ID NO: 8, wherein each CDR is defined in accordance with the MacCallum definition, the Kabat definition, the Chothia definition, the combination of the Kabat definition and the Chothia definition, the IMGT numbering system, or the AbM definition of CDR.

In another aspect, the instant disclosure provides an isolated antibody that specifically binds to CD137 (e.g., human CD137 or cynomolgus CD137), the antibody comprising a heavy chain variable region (VH) comprising complementarity determining regions (CDRs) CDRH1, CDRH2, and CDRH3, and a light chain variable region (VL) comprising CDRs CDRL1, CDRL2, and CDRL3, wherein:

(a) CDRH1 comprises the amino acid sequence of
  $X_1X_2X_3X_4H$ (SEQ ID NO: 82), wherein
  $X_1$ is G, A, D, E, L, N, Q, R, S, or W;
  $X_2$ is Y, F, H, N, R, or S;
  $X_3$ is Y or H; and
  $X_4$ is M, I, T, or V;
(b) CDRH2 comprises the amino acid sequence of
  WINPNSGGTNYAQKFQG (SEQ ID NO: 2);
(c) CDRH3 comprises the amino acid sequence of
  $X_1PX_2YX_3GX_4GLX_5X_6$ (SEQ ID NO: 83), wherein
  $X_1$ is E or G;
  $X_2$ is G, A, R, or S;
  $X_3$ is Y, F, H, or S;
  $X_4$ is S, A, or T;
  $X_5$ is D or G; and
  $X_6$ is Y or H;
(d) CDRL1 comprises the amino acid sequence of GGD-DIGDKRVH (SEQ ID NO: 4);
(e) CDRL2 comprises the amino acid sequence of
  EDRYRPS (SEQ ID NO: 5); and/or
(f) CDRL3 comprises the amino acid sequence of
  $QX_1WX_2X_3X_4X_5X_6X_7PGV$ (SEQ ID NO: 84), wherein
  $X_1$ is V or I;
  $X_2$ is D, A, E, G, H, N, or Y;
  $X_3$ is S, A, E, F, L, P, R, T, W, or Y;
  $X_4$ is S, A, L, M, or R;
  $X_5$ is S, A, F, G, L, P, Q, R, or T;
  $X_6$ is D, E, H, V, or Y; and
  $X_7$ is H or Y.

In certain embodiments, CDRH1 comprises the amino acid sequence of $X_1X_2X_3X_4H$ (SEQ ID NO: 82), wherein $X_1$ is G, A, D, E, L, N, Q, R, S, or W; $X_2$ is Y, F, H, N, R, or S; $X_3$ is Y or H; and $X_4$ is M, I, T, or V. In certain embodiments, CDRH3 comprises the amino acid sequence of $X_1PX_2YX_3GX_4GLX_5X_6$ (SEQ ID NO: 83), wherein $X_1$ is E or G; $X_2$ is G, A, R, or S; $X_3$ is Y, F, H, or S; $X_4$ is S, A, or T; $X_5$ is D or G; and $X_6$ is Y or H. In certain embodiments, CDRL3 comprises the amino acid sequence of $QX_1WX_2X_3X_4X_5X_6X_7PGV$ (SEQ ID NO: 84), wherein $X_1$ is V or I; $X_2$ is D, A, E, G, H, N, or Y; $X_3$ is S, A, E, F, L, P, R, T, W, or Y; $X_4$ is S, A, L, M, or R; $X_5$ is S, A, F, G, L, P, Q, R, or T; $X_6$ is D, E, H, V, or Y; and $X_7$ is H or Y. In certain embodiments, (a) CDRH1 comprises the amino acid sequence of
  $X_1X_2X_3X_4H$ (SEQ ID NO: 82), wherein
  $X_1$ is G, A, D, E, L, N, Q, R, S, or W;
  $X_2$ is Y, F, H, N, R, or S;
  $X_3$ is Y or H; and
  $X_4$ is M, I, T, or V;
(b) CDRH2 comprises the amino acid sequence of
  WINPNSGGTNYAQKFQG (SEQ ID NO: 2);
(c) CDRH3 comprises the amino acid sequence of
  $X_1PX_2YX_3GX_4GLX_5X_6$ (SEQ ID NO: 83), wherein
  $X_1$ is E or G;
  $X_2$ is G, A, R, or S;
  $X_3$ is Y, F, H, or S;
  $X_4$ is S, A, or T;
  $X_5$ is D or G; and
  $X_6$ is Y or H;
(d) CDRL1 comprises the amino acid sequence of GGD-DIGDKRVH (SEQ ID NO: 4);
(e) CDRL2 comprises the amino acid sequence of
  EDRYRPS (SEQ ID NO: 5); and
(f) CDRL3 comprises the amino acid sequence of
  $QX_1WX_2X_3X_4X_5X_6X_7PGV$ (SEQ ID NO: 84), wherein
  $X_1$ is V or I;
  $X_2$ is D, A, E, G, H, N, or Y;
  $X_3$ is S, A, E, F, L, P, R, T, W, or Y;
  $X_4$ is S, A, L, M, or R;
  $X_5$ is S, A, F, G, L, P, Q, R, or T;
  $X_6$ is D, E, H, V, or Y; and
  $X_7$ is H or Y.

In certain embodiments,
(a) CDRH1 comprises the amino acid sequence of
  $X_1X_2YX_3H$ (SEQ ID NO: 85), wherein
  $X_1$ is G, A, D, L, R, S, or W;
  $X_2$ is Y, F, H, or N; and
  $X_3$ is M or V;
(b) CDRH3 comprises the amino acid sequence of
  $EPGYX_1GX_2GLDX_3$ (SEQ ID NO: 86), wherein
  $X_1$ is Y or F;
  $X_2$ is S or T; and
  $X_3$ is Y or H; and/or
(c) CDRL3 comprises the amino acid sequence of
  $QVWX_1X_2X_3X_4X_5X_6PGV$ (SEQ ID NO: 87), wherein
  $X_1$ is D, A, E, H, N, or Y;
  $X_2$ is S, A, E, L, R, or T;
  $X_3$ is S, A, L, or R;
  $X_4$ is S, A, F, G, L, P, Q, or R;
  $X_5$ is D, E, or V; and
  $X_6$ is H or Y.

In certain embodiments, CDRH1 comprises the amino acid sequence of $X_1X_2YX_3H$ (SEQ ID NO: 85), wherein $X_1$ is G, A, D, L, R, S, or W; $X_2$ is Y, F, H, or N; and $X_3$ is M or V. In certain embodiments, CDRH3 comprises the amino acid sequence of $EPGYX_1GX_2GLDX_3$ (SEQ ID NO: 86), wherein $X_1$ is Y or F; $X_2$ is S or T; and $X_3$ is Y or H. In certain embodiments, CDRL3 comprises the amino acid sequence of $QVWX_1X_2X_3X_4X_5X_6PGV$ (SEQ ID NO: 87), wherein $X_1$ is D, A, E, H, N, or Y; $X_2$ is S, A, E, L, R, or T; $X_3$ is S, A, L, or R; $X_4$ is S, A, F, G, L, P, Q, or R; $X_5$ is D, E, or V; and $X_6$ is H or Y. In certain embodiments, (a) CDRH1 comprises the amino acid sequence of
  $X_1X_2YX_3H$ (SEQ ID NO: 85), wherein
  $X_1$ is G, A, D, L, R, S, or W;
  $X_2$ is Y, F, H, or N; and
  $X_3$ is M or V;
(b) CDRH3 comprises the amino acid sequence of
  $EPGYX_1GX_2GLDX_3$ (SEQ ID NO: 86), wherein
  $X_1$ is Y or F;
  $X_2$ is S or T; and
  $X_3$ is Y or H; and
(c) CDRL3 comprises the amino acid sequence of
  $QVWX_1X_2X_3X_4X_5X_6PGV$ (SEQ ID NO: 87), wherein
  $X_1$ is D, A, E, H, N, or Y;
  $X_2$ is S, A, E, L, R, or T;
  $X_3$ is S, A, L, or R;
  $X_4$ is S, A, F, G, L, P, Q, or R;
  $X_5$ is D, E, or V; and
  $X_6$ is H or Y.

In certain embodiments, the CDRH1 comprises the amino acid sequence of SEQ ID NO: 1. In certain embodiments, the CDRH3 comprises the amino acid sequence of SEQ ID NO: 3 or 59. In certain embodiments, the CDRL3 the amino acid sequence of SEQ ID NO: 6, 61, 62, or 63.

In certain embodiments, the instant disclosure provides an isolated antibody that specifically binds to CD137 (e.g., human CD137 or cynomolgus CD137), wherein the antibody comprises a VH domain comprising the CDRH1, CDRH2 and CDRH3 amino acid sequences set forth in SEQ ID NOs: 1, 2, and 3; or 1, 2, and 59, respectively. In certain embodiments, the instant disclosure provides an isolated antibody that specifically binds to CD137 (e.g., human CD137 or cynomolgus CD137), wherein the antibody comprises a VL domain comprising the CDRL1, CDRL2 and CDRL3 amino acid sequences set forth in SEQ ID NOs: 4, 5, and 6; 4, 5, and 60; 4, 5, and 61; or 4, 5, and 62, respectively. In certain embodiments, the instant disclosure provides an isolated antibody that specifically binds to CD137 (e.g., human CD137 or cynomolgus CD137), wherein the antibody comprises a heavy chain variable region comprising CDRH1, CDRH2, and CDRH3 regions, and a light chain variable region comprising CDRL1, CDRL2, and CDRL3 regions, wherein the CDRH1, CDRH2, CDRH3, CDRL1, CDRL2, and CDRL3 regions comprise the amino acid sequences set forth in SEQ ID NOs: 1, 2, 3, 4, 5, and 6; 1, 2, 59, 4, 5, and 6; 1, 2, 3, 4, 5, and 60; 1, 2, 3, 4, 5, and 61; or 1, 2, 3, 4, 5, and 62, respectively.

In certain embodiments, the instant disclosure provides an isolated antibody that specifically binds to CD137 (e.g., human CD137 or cynomolgus CD137), the antibody comprising:
(a) a CDRH1 comprises the amino acid sequence of GYYMH (SEQ ID NO: 1);
(b) a CDRH2 comprises the amino acid sequence of WINPNSGGTNYAQKFQG (SEQ ID NO: 2);
(c) a CDRH3 comprises the amino acid sequence of EPGYYGSGLDY (SEQ ID NO: 3);
(d) a CDRL1 comprises the amino acid sequence of GGD-DIGDKRVH (SEQ ID NO: 4);
(e) a CDRL2 comprises the amino acid sequence of EDRYRPS (SEQ ID NO: 5); and/or
(f) a CDRL3 comprises the amino acid sequence of QVWDSSSDHPGV (SEQ ID NO: 6).

In certain embodiments, the instant disclosure provides an isolated antibody that specifically binds to CD137 (e.g., human CD137 or cynomolgus CD137), wherein the antibody comprises a VH domain comprising the CDRH1, CDRH2 and CDRH3 amino acid sequences set forth in SEQ ID NOs: 1, 2, and 3, respectively. In certain embodiments, the instant disclosure provides an isolated antibody that specifically binds to CD137 (e.g., human CD137 or cynomolgus CD137), wherein the antibody comprises a VL domain comprising the CDRL1, CDRL2 and CDRL3 amino acid sequences set forth in SEQ ID NOs: 4, 5, and 6, respectively. In certain embodiments, the instant disclosure provides an isolated antibody that specifically binds to CD137 (e.g., human CD137 or cynomolgus CD137), wherein the antibody comprises a heavy chain variable region comprising CDRH1, CDRH2, and CDRH3 regions, and a light chain variable region comprising CDRL1, CDRL2, and CDRL3 regions, wherein the CDRH1, CDRH2, CDRH3, CDRL1, CDRL2, and CDRL3 regions comprise the amino acid sequences set forth in SEQ ID NOs: 1, 2, 3, 4, 5, and 6, respectively.

In certain embodiments, the instant disclosure provides an isolated antibody that specifically binds to CD137 (e.g., human CD137 or cynomolgus CD137), comprising a heavy chain variable region comprising an amino acid sequence of SEQ ID NO: 7. In certain embodiments, the instant disclosure provides an isolated antibody that specifically binds to CD137 (e.g., human CD137 or cynomolgus CD137), comprising a heavy chain variable region comprising an amino acid sequence that is at least 75%, 80%, 85%, 90%, 95%, or 100% (e.g., at least 86, 87, 88, 89, 90, 91, 92, 93, 94, 95, 96, 97, 98 or 99%) identical to the amino acid sequence set forth in SEQ ID NO: 7. In certain embodiments, the heavy chain variable region comprises the amino acid sequence of SEQ ID NO: 63, 64, or 65.

In certain embodiments, the instant disclosure provides an isolated antibody that specifically binds to CD137 (e.g., human CD137 or cynomolgus CD137), comprising a light chain variable region comprising an amino acid sequence of SEQ ID NO: 8. In certain embodiments, the instant disclosure provides an isolated antibody that specifically binds to CD137 (e.g., human CD137 or cynomolgus CD137), comprising a light chain variable region comprising an amino acid sequence that is at least 75%, 80%, 85%, 90%, 95%, or 100% (e.g., at least 86, 87, 88, 89, 90, 91, 92, 93, 94, 95, 96, 97, 98 or 99%) identical to the amino acid sequence set forth in SEQ ID NO: 8. In certain embodiments, the light chain variable region comprises the amino acid sequence of SEQ ID NO: 66, 67, or 68.

In certain embodiments, the instant disclosure provides an isolated antibody that specifically binds to CD137 (e.g., human CD137 or cynomolgus CD137), comprising a heavy chain variable region comprising an amino acid sequence of SEQ ID NO: 7, and a light chain variable region comprising an amino acid sequence of SEQ ID NO: 8. In certain embodiments, the instant disclosure provides an isolated antibody that specifically binds to CD137 (e.g., human CD137 or cynomolgus CD137), comprising a heavy chain variable region comprising an amino acid sequence that is at least 75%, 80%, 85%, 90%, 95%, or 100% (e.g., at least 86, 87, 88, 89, 90, 91, 92, 93, 94, 95, 96, 97, 98 or 99%) identical to the amino acid sequence set forth in SEQ ID NO: 7, and a light chain variable region comprising an amino acid sequence that is at least 75%, 80%, 85%, 90%, 95%, or 100% (e.g., at least 86, 87, 88, 89, 90, 91, 92, 93, 94, 95, 96, 97, 98 or 99%) identical to the amino acid sequence set forth in SEQ ID NO: 8. In certain embodiments, the heavy chain variable region and the light chain variable region comprise the amino acid sequences of SEQ ID NOs: 63 and 8; 64 and 66; 7 and 67; or 65 and 68, respectively.

In certain embodiments, the instant disclosure provides an isolated antibody that specifically binds to CD137 (e.g., human CD137 or cynomolgus CD137), comprising a heavy chain variable region having an amino acid sequence derived from a human IGHV1-2 germline sequence (e.g., IGHV1-2*02, e.g., having the amino acid sequence of SEQ ID NO: 40). One or more regions selected from framework 1, framework 2, framework 3, CDRH1, and CDRH2 (e.g., two, three, four or five of these regions) can be derived from a human IGHV1-2 germline sequence (e.g., IGHV1-2*02, e.g., having the amino acid sequence of SEQ ID NO: 40). In one embodiment, framework 1, framework 2, framework 3, CDRH1, and CDRH2 are all derived from a human IGHV1-2 germline sequence (e.g., IGHV1-2*02, e.g., having the amino acid sequence of SEQ ID NO: 40). In certain embodiments, the heavy chain variable region comprises the amino acid sequence set forth in SEQ ID NO: 3.

In certain embodiments, the instant disclosure provides an isolated antibody that specifically binds to CD137 (e.g., human CD137 or cynomolgus CD137), comprising a light chain variable region having an amino acid sequence derived from a human IGLV3-21 germline sequence (e.g., IGLV3-21*02, e.g., having the amino acid sequence of SEQ ID NO: 41, or IGLV3-21*03). One or more regions selected from framework 1, framework 2, framework 3, CDRL1, and CDRL2 (e.g., two, three, four or five of these regions) can be derived from a human IGLV3-21 germline sequence (e.g., IGLV3-21*02, e.g., having the amino acid sequence of SEQ ID NO: 41, or IGLV3-21*03). In one embodiment, framework 1, framework 2, framework 3, CDRL1, and CDRL2 are all derived from a human IGLV3-21 germline sequence (e.g., IGLV3-21*02, e.g., having the amino acid sequence of SEQ ID NO: 41, or IGLV3-21*03). In certain embodiments, the light chain variable region comprises the amino acid sequence set forth in SEQ ID NO: 6.

In certain embodiments, the instant disclosure provides an isolated antibody that specifically binds to CD137 (e.g., human CD137 or cynomolgus CD137), comprising a heavy chain variable region having an amino acid sequence derived from a human IGHV1-2 germline sequence (e.g., IGHV1-2*02, e.g., having the amino acid sequence of SEQ ID NO: 40), and a light chain variable region having an amino acid sequence derived from a human IGLV3-21 germline sequence (e.g., IGLV3-21*02, e.g., having the amino acid sequence of SEQ ID NO: 41, or IGLV3-21*03). In certain embodiments, the heavy chain variable region comprises the amino acid sequence set forth in SEQ ID NO: 3, and the light chain variable region comprises the amino acid sequence set forth in SEQ ID NO: 6.

In certain embodiments, the instant disclosure provides an isolated antibody that cross-competes for binding to CD137 (e.g., human CD137 or cynomolgus CD137) with an antibody comprising the heavy and light chain variable region amino acid sequences set forth in SEQ ID NOs: 7 and 8, respectively.

In certain embodiments, the instant disclosure provides an isolated antibody that binds to the same or an overlapping epitope of CD137 (e.g., an epitope of human CD137 or an epitope of cynomolgus CD137) as an antibody described herein, e.g., an antibody comprising the heavy and light chain variable region amino acid sequences set forth in SEQ ID NOs: 7 and 8, respectively. In certain embodiments, the epitope of an antibody can be determined by, e.g., NMR spectroscopy, surface plasmon resonance (BIAcore®), X-ray diffraction crystallography studies, ELISA assays, hydrogen/deuterium exchange coupled with mass spectrometry (e.g., liquid chromatography electrospray mass spectrometry), array-based oligo-peptide scanning assays, and/or mutagenesis mapping (e.g., site-directed mutagenesis mapping). For X-ray crystallography, crystallization may be accomplished using any of the known methods in the art (e.g., Giegé R et al., (1994) Acta Crystallogr D Biol Crystallogr 50(Pt 4): 339-350; McPherson A (1990) Eur J Biochem 189: 1-23; Chayen N E (1997) Structure 5: 1269-1274; McPherson A (1976) J Biol Chem 251: 6300-6303, all of which are herein incorporated by reference in their entireties). Antibody:antigen crystals may be studied using well known X-ray diffraction techniques and may be refined using computer software such as X-PLOR (Yale University, 1992, distributed by Molecular Simulations, Inc.; see, e.g., Meth Enzymol (1985) volumes 114 & 115, eds Wyckoff H W et al.; U.S. Patent Application No. 2004/0014194), and BUSTER (Bricogne G (1993) Acta Crystallogr D Biol Crystallogr 49(Pt 1): 37-60; Bricogne G (1997) Meth Enzymol 276A: 361-423, ed Carter C W; Roversi P et al., (2000) Acta Crystallogr D Biol Crystallogr 56(Pt 10): 1316-1323, all of which are herein incorporated by reference in their entireties). Mutagenesis mapping studies may be accomplished using any method known to one of skill in the art. See, e.g., Champe M et al., (1995) supra and Cunningham B C & Wells J A (1989) supra for a description of mutagenesis techniques, including alanine scanning mutagenesis techniques. In a specific embodiment, the epitope of an antibody is determined using alanine scanning mutagenesis studies. In addition, antibodies that recognize and bind to the same or overlapping epitopes of CD137 (e.g., human CD137 or cynomolgus CD137) can be identified using routine techniques such as an immunoassay, for example, by showing the ability of one antibody to block the binding of another antibody to a target antigen, i.e., a competitive binding assay. Competition binding assays also can be used to determine whether two antibodies have similar binding specificity for an epitope. Competitive binding can be determined in an assay in which the immunoglobulin under test inhibits specific binding of a reference antibody to a common antigen, such as CD137 (e.g., human CD137 or cynomolgus CD137). Numerous types of competitive binding assays are known, for example: solid phase direct or indirect radioimmunoassay (RIA), solid phase direct or indirect enzyme immunoassay (EIA), sandwich competition assay (see Stahli C et al., (1983) Methods Enzymol 9: 242-253); solid phase direct biotin-avidin EIA (see Kirkland T N et al., (1986) J Immunol 137: 3614-9); solid phase direct labeled assay, solid phase direct labeled sandwich assay (see Harlow E & Lane D, (1988) Antibodies: A Laboratory Manual, Cold Spring Harbor Press); solid phase direct label RIA using 1-125 label (see Morel G A et al., (1988) Mol Immunol 25(1): 7-15); solid phase direct biotin-avidin EIA (see Cheung R C et al., (1990) Virology 176: 546-52); and direct labeled RIA (see Moldenhauer G et al., (1990) Scand J Immunol 32: 77-82), all of which are herein incorporated by reference in their entireties. Typically, such an assay involves the use of purified antigen (e.g., CD137, such as human CD137 or cynomolgus CD137) bound to a solid surface or cells bearing either of these, an unlabeled test immunoglobulin and a labeled reference immunoglobulin. Competitive inhibition can be measured by determining the amount of label bound to the solid surface or cells in the presence of the test immunoglobulin. Usually the test immunoglobulin is present in excess. Usually, when a competing antibody is present in excess, it will inhibit specific binding of a reference antibody to a common antigen by at least 50-55%, 55-60%, 60-65%, 65-70%, 70-75% or more. A competition binding assay can be configured in a large number of different formats using either labeled antigen or labeled antibody. In a common version of this assay, the antigen is immobilized on a 96-well plate. The ability of unlabeled antibodies to block the binding of labeled antibodies to the antigen is then measured using radioactive or enzyme labels. For further details see, for example, Wagener C et al., (1983) J Immunol 130: 2308-2315; Wagener C et al., (1984) J Immunol Methods 68: 269-274; Kuroki M et al., (1990) Cancer Res 50: 4872-4879; Kuroki M et al., (1992) Immunol Invest 21: 523-538; Kuroki M et al., (1992) Hybridoma 11: 391-407 and Antibodies: A Laboratory Manual, Ed Harlow E & Lane D editors supra, pp. 386-389, all of which are herein incorporated by reference in their entireties.

In another aspect, the instant disclosure provides an antibody or isolated antibody that specifically binds to human CD137, wherein (a) the antibody specifically binds to a protein comprising the amino acid sequence of SEQ ID NO: 37 and (b) the antibody does not specifically bind to a protein comprising the amino acid sequence of SEQ ID NO: 38.

In another aspect, the instant disclosure provides an antibody or isolated antibody that specifically binds to human CD137, wherein the antibody specifically binds to a protein having the amino acid sequence of SEQ ID NO: 38 with a lower affinity than to a protein having the amino acid sequence of SEQ ID NO: 37.

In another aspect, the instant disclosure provides an antibody or isolated antibody that specifically binds to human CD137, wherein the antibody does not specifically bind to a protein having the amino acid sequence of SEQ ID NO: 38.

In another aspect, the instant disclosure provides an antibody or isolated antibody that specifically binds to human CD137, wherein the binding between the antibody and a protein having the amino acid sequence of SEQ ID NO: 38 is substantially weakened relative to the binding between the antibody and a protein having the amino acid sequence of SEQ ID NO: 37.

In another aspect, the instant disclosure provides an antibody or isolated antibody that specifically binds to human CD137, wherein the antibody exhibits, as compared to binding to a protein having the amino acid sequence of SEQ ID NO: 37, reduced or absent binding to a protein having the amino acid sequence of SEQ ID NO: 38.

In another aspect, the instant disclosure provides an antibody or isolated antibody that specifically binds to the same epitope of human CD137 as any antibody of the present invention. In certain embodiments, the antibody specifically binds to a protein having the amino acid sequence of SEQ ID NO: 38 with a lower affinity than to a protein having the amino acid sequence of SEQ ID NO: 37. In certain embodiments, the antibody does not specifically bind to a protein having the amino acid sequence of SEQ ID NO: 38. In certain embodiments, the binding between the antibody and a protein having the amino acid sequence of SEQ ID NO: 38 is substantially weakened relative to the binding between the antibody and a protein having the amino acid sequence of SEQ ID NO: 37. In one embodiment, the antibody exhibits, as compared to binding to a protein having the amino acid sequence of SEQ ID NO: 37, reduced or absent binding to a protein having the amino acid sequence of SEQ ID NO: 38.

In certain embodiments, the isolated antibody binds to an epitope located within a region of human CD137 comprising the amino acid sequence of any one of SEQ ID NOs: 26-31 and 43. In certain embodiments, the isolated antibody binds to an epitope located within a region of human CD137 consisting essentially of the amino acid sequence of any one of SEQ ID NOs: 26-31 and 43. In certain embodiments, the isolated antibody binds to an epitope located within a region of human CD137 consisting of the amino acid sequence of any one of SEQ ID NOs: 26-31 and 43. In certain embodiments, the isolated antibody binds to a discontinuous epitope located within a region of human CD137 comprising a plurality of amino acid sequences, each of the plurality of amino acid sequences consisting of, consisting essentially of, or comprising the amino acid sequence of any one of SEQ ID NOs: 26-31 and 43.

In certain embodiments, the isolated antibody binds to an epitope located within a region of human CD137 comprising, consisting essentially of, or consisting of the amino acid sequence set forth in SEQ ID NO: 26. In another aspect, the instant disclosure provides an antibody that, when bound to a human CD137 protein or fragment thereof, reduces hydrogen/deuterium exchange in a region consisting of the amino acid sequence set forth in SEQ ID NO: 26 relative to hydrogen/deuterium exchange in the region consisting of the amino acid sequence set forth in SEQ ID NO: 26 in the absence of the antibody, as determined by a hydrogen/deuterium exchange assay. In certain embodiments, the reduction in hydrogen/deuterium exchange is measured using hydrogen-deuterium exchange (HDX), for example as described herein in the examples.

In certain embodiments, the isolated antibody binds to an epitope located within a region of human CD137 comprising, consisting essentially of, or consisting of the amino acid sequence set forth in SEQ ID NO: 27. In another aspect, the instant disclosure provides an antibody that, when bound to a human CD137 protein or fragment thereof, reduces hydrogen/deuterium exchange in a region consisting of the amino acid sequence set forth in SEQ ID NO: 27 relative to hydrogen/deuterium exchange in the region consisting of the amino acid sequence set forth in SEQ ID NO: 27 in the absence of the antibody, as determined by a hydrogen/deuterium exchange assay. In certain embodiments, the reduction in hydrogen/deuterium exchange is measured using hydrogen-deuterium exchange (HDX), for example as described herein in the examples.

In certain embodiments, the isolated antibody binds to an epitope located within a region of human CD137 comprising, consisting essentially of, or consisting of the amino acid sequence set forth in SEQ ID NO: 28. In another aspect, the instant disclosure provides an antibody that, when bound to a human CD137 protein or fragment thereof, reduces hydrogen/deuterium exchange in a region consisting of the amino acid sequence set forth in SEQ ID NO: 28 relative to hydrogen/deuterium exchange in the region consisting of the amino acid sequence set forth in SEQ ID NO: 28 in the absence of the antibody, as determined by a hydrogen/deuterium exchange assay. In certain embodiments, the reduction in hydrogen/deuterium exchange is measured using hydrogen-deuterium exchange (HDX), for example as described herein in the examples.

In certain embodiments, the isolated antibody binds to an epitope located within a region of human CD137 comprising, consisting essentially of, or consisting of the amino acid sequence set forth in SEQ ID NO: 29. In another aspect, the instant disclosure provides an antibody that, when bound to a human CD137 protein or fragment thereof, reduces hydrogen/deuterium exchange in a region consisting of the amino acid sequence set forth in SEQ ID NO: 29 relative to hydrogen/deuterium exchange in the region consisting of the amino acid sequence set forth in SEQ ID NO: 29 in the absence of the antibody, as determined by a hydrogen/deuterium exchange assay. In certain embodiments, the reduction in hydrogen/deuterium exchange is measured using hydrogen-deuterium exchange (HDX), for example as described herein in the examples.

In certain embodiments, the isolated antibody binds to an epitope located within a region of human CD137 comprising, consisting essentially of, or consisting of the amino acid sequence set forth in SEQ ID NO: 30. In another aspect, the instant disclosure provides an antibody that, when bound to a human CD137 protein or fragment thereof, reduces hydrogen/deuterium exchange in a region consisting of the amino acid sequence set forth in SEQ ID NO: 30 relative to hydrogen/deuterium exchange in the region consisting of the amino acid sequence set forth in SEQ ID NO: 30 in the absence of the antibody, as determined by a hydrogen/deuterium exchange assay. In certain embodiments, the reduction in hydrogen/deuterium exchange is measured using hydrogen-deuterium exchange (HDX), for example as described herein in the examples.

In certain embodiments, the isolated antibody binds to an epitope located within a region of human CD137 comprising, consisting essentially of, or consisting of the amino acid sequence set forth in SEQ ID NO: 31. In another aspect, the instant disclosure provides an antibody that, when bound to a human CD137 protein or fragment thereof, reduces hydrogen/deuterium exchange in a region consisting of the amino acid sequence set forth in SEQ ID NO: 31 relative to hydrogen/deuterium exchange in the region consisting of the amino acid sequence set forth in SEQ ID NO: 31 in the absence of the antibody, as determined by a hydrogen/deuterium exchange assay. In certain embodiments, the reduction in hydrogen/deuterium exchange is measured using hydrogen-deuterium exchange (HDX), for example as described herein in the examples.

In certain embodiments, the isolated antibody binds to an epitope located within a region of human CD137 comprising, consisting essentially of, or consisting of the amino acid sequence of KRGI (SEQ ID NO: 43). In certain embodiments, the antibody binds to at least one, at least two, or at least three amino acid residues of KRGI. In certain embodiments, the antibody binds to all four amino acid residues of KRGI. In another aspect, the instant disclosure provides an antibody that, when bound to a human CD137 protein or fragment thereof, reduces hydrogen/deuterium exchange in a region consisting of the amino acid sequence set forth in SEQ ID NO: 43 relative to hydrogen/deuterium exchange in the region consisting of the amino acid sequence set forth in SEQ ID NO: 43 in the absence of the antibody, as determined by a hydrogen/deuterium exchange assay. In certain embodiments, the reduction in hydrogen/deuterium exchange is measured using hydrogen-deuterium exchange (HDX), for example as described herein in the examples. In another aspect, the instant disclosure provides an antibody that specifically binds to human CD137 and does not substantially bind to murine CD137. In certain embodiments, the antibody specifically binds to a protein comprising the amino acid sequence of SEQ ID NO: 46, and/or does not substantially bind to a protein comprising the amino acid sequence of SEQ ID NO: 45. In certain embodiments, the antibody specifically binds to a protein consisting of or consisting essentially of the amino acid sequence of SEQ ID NO: 46, and/or does not substantially bind to a protein consisting of or consisting essentially of the amino acid sequence of SEQ ID NO: 45. In certain embodiments, the antibody specifically binds to a protein consisting of or consisting essentially of the amino acid sequence of SEQ ID NO: 46, and does not substantially bind to a protein consisting of or consisting essentially of the amino acid sequence of SEQ ID NO: 45.

In another aspect, the instant disclosure provides an antibody or isolated antibody that binds, e.g., specifically binds, to the same epitope of human CD137 as an antibody of the present invention. In certain embodiments, the epitope is determined by hydrogen-deuterium exchange (HDX), for example as described in the examples, or by protein mutagenesis, for example as described in the examples.

In certain embodiments, the antibody comprises a VH and a VL, wherein if the antibody is formatted as a F(ab')$_2$ comprising two of each of the VH and the VL, the F(ab')$_2$ binds to an epitope located within a region of human CD137 consisting of the amino acid sequence of SEQ ID NO: 27. In certain embodiments, the antibody comprises a VH and a VL, wherein if the antibody is formatted as a F(ab')$_2$ comprising two of each of the VH and the VL, the F(ab')$_2$ substantially reduces (e.g., by at least 50%, 60%, 70%, 80%, 85%, 90%, 95%, 96%, 97%, 98%, or 99%) the exchange of hydrogen with deuterium in a region of CD137 consisting of the amino acid sequence of SEQ ID NO: 27 relative to the exchange of hydrogen with deuterium in the same region in the absence of the F(ab')$_2$, as measured by a hydrogen/deuterium exchange assay.

In certain embodiments, the antibody comprises a VH and a VL, wherein if the antibody is formatted as a Fab comprising the VH and the VL, the Fab binds to an epitope located within a region of human CD137 consisting of the amino acid sequence of SEQ ID NO: 26, and, optionally, an epitope located within a region of human CD137 consisting of the amino acid sequence of SEQ ID NOs: 28 and/or 29.

In certain embodiments, the antibody comprises a VH and a VL, wherein if the antibody is formatted as a Fab comprising the VH and the VL, the Fab substantially reduces (e.g., by at least 50%, 60%, 70%, 80%, 85%, 90%, 95%, 96%, 97%, 98%, or 99%) the exchange of hydrogen with deuterium in a region of CD137 consisting of the amino acid sequence of SEQ ID NO: 26 relative to the exchange of hydrogen with deuterium in the same region in the absence of the Fab, and, optionally, substantially reduces (e.g., by at least 50%, 60%, 70%, 80%, 85%, 90%, 95%, 96%, 97%, 98%, or 99%) the exchange of hydrogen with deuterium in a region of CD137 consisting of the amino acid sequence of SEQ ID NO: 28 and/or SEQ ID NO: 29 relative to the exchange of hydrogen with deuterium in the same regions in the absence of the Fab, as measured by a hydrogen/deuterium exchange assay.

In certain embodiments, the antibody comprises a VH and a VL, wherein if the antibody is formatted as a F(ab')$_2$ comprising two of chains, each chain comprising the VH and the VL, the F(ab')$_2$ substantially reduces (e.g., by at least 50%, 60%, 70%, 80%, 85%, 90%, 95%, 96%, 97%, 98%, or 99%) the exchange of hydrogen with deuterium in a region of CD137 consisting of the amino acid sequence of SEQ ID NO: 34 relative to the exchange of hydrogen with deuterium in the same region in the absence of the F(ab')$_2$, as measured by a hydrogen/deuterium exchange assay. In certain embodiments, the antibody comprises a VH and a VL, wherein if the antibody is formatted as a Fab comprising the VH and the VL, the Fab does not substantially reduce (e.g., no reduction by more than 1%, 2%, 3%, 4%, 5%, 10%, 15%, 20%, 25%, or 30%) the exchange of hydrogen with deuterium in a region of CD137 consisting of the amino acid sequence of SEQ ID NO: 34 relative to the exchange of hydrogen with deuterium in the same region in the absence of the Fab, as measured by a hydrogen/deuterium exchange assay.

In certain embodiments, the instant disclosure provides an isolated antibody that specifically binds to CD137 (e.g., human CD137 or cynomolgus CD137) and does not inhibit human CD137 from binding to human CD137L. In certain embodiments, the binding of human CD137 to human CD137L is not reduced by more than 1%, 2%, 3%, 4%, 5%, 10%, 15%, 20%, 25%, or 30% in the presence of the antibody relative to the binding of human CD137 to human CD137L in the absence of the antibody. In certain embodiments, the antibody does not inhibit a soluble fragment of human CD137 from binding to a soluble fragment of human CD137L. In certain embodiments, the binding of a soluble fragment of human CD137 to a soluble fragment of human CD137L is not reduced by more than 1%, 2%, 3%, 4%, 5%, 10%, 15%, 20%, 25%, or 30% in the presence of the antibody relative to the binding of a soluble fragment of human CD137 to a soluble fragment of human CD137L in the absence of the antibody. In certain embodiments, the antibody does not inhibit a CD137-expressing cell from binding to a soluble fragment of human CD137L. In certain embodiments, the binding of a CD137-expressing cell to a soluble fragment of human CD137L is not reduced by more than 1%, 2%, 3%, 4%, 5%, 10%, 15%, 20%, 25%, or 30% in the presence of the antibody relative to the binding of a CD137-expressing cell to a soluble fragment of human CD137L in the absence of the antibody. In certain embodiments, the antibody does not inhibit a CD137-expressing cell from binding to a CD137L-expressing cell. In certain embodiments, the binding of a CD137-expressing cell to a CD137L-expressing cell is not reduced by more than 1%, 2%, 3%, 4%, 5%, 10%, 15%, 20%, 25%, or 30% in the presence of the antibody relative to the binding of a CD137-expressing cell to a CD137L-expressing cell in the absence of the antibody.

In certain embodiments, the antibody disclosed herein increases the level of CD137 multimerization (e.g., dimerization or trimerization) relative to the level of CD137 multimerization in the absence of the antibody by at least about 1.1 fold, 1.2 fold, 1.3 fold, 1.4 fold, 1.5 fold, 2 fold, 2.5 fold, 3 fold, 3.5 fold, 4 fold, 4.5 fold, 5 fold, 6 fold, 7 fold, 8 fold, 9 fold, 10 fold, 15 fold, 20 fold, 30 fold, 40 fold, 50 fold, 60 fold, 70 fold, 80 fold, 90 fold, 100 fold, or more. In certain embodiments, the multimeric CD137 is present in a complex comprising CD137 and CD137L molecules (e.g., a complex comprising three CD137L molecules and two CD137 molecules, or a complex comprising three CD137L molecules and three CD137 molecules). In certain embodiments, the level of CD137 multimerization (e.g., dimerization or trimerization) is measured in an in vitro system comprising CD137 and CD137L molecules in equilibrium, optionally wherein the CD137 molecules are in a lipid bilayer membrane. In certain embodiments, the level of CD137 multimerization (e.g., dimerization or trimerization) is measured in a cell or on the plasma membrane of a cell. In certain embodiments, the level of CD137 multimerization (e.g., dimerization or trimerization) is measured using a soluble fragment of CD137.

In certain embodiments, the instant disclosure provides an isolated antibody that specifically binds to CD137 (e.g., human CD137 or cynomolgus CD137), the antibody comprising a heavy chain comprising the amino acid sequence set forth in SEQ ID NO: 9, 10, 11, 12, 13, 14, 49, 50, 51, 52, 53, 54, 73, 74, 75, 76, 77, or 78. In certain embodiments, the antibody comprises a heavy chain comprising the amino acid sequence set forth in SEQ ID NO: 9. In certain embodiments, the antibody comprises a heavy chain comprising the amino acid sequence set forth in SEQ ID NO: 10. In certain embodiments, the antibody comprises a heavy chain comprising the amino acid sequence set forth in SEQ ID NO: 11. In certain embodiments, the antibody comprises a heavy chain comprising the amino acid sequence set forth in SEQ ID NO: 12. In certain embodiments, the antibody comprises a heavy chain comprising the amino acid sequence set forth in SEQ ID NO: 13. In certain embodiments, the antibody comprises a heavy chain comprising the amino acid sequence set forth in SEQ ID NO: 14. In certain embodiments, the antibody comprises a heavy chain comprising the amino acid sequence set forth in SEQ ID NO: 49. In certain embodiments, the antibody comprises a heavy chain comprising the amino acid sequence set forth in SEQ ID NO: 50. In certain embodiments, the antibody comprises a heavy chain comprising the amino acid sequence set forth in SEQ ID NO: 51. In certain embodiments, the antibody comprises a heavy chain comprising the amino acid sequence set forth in SEQ ID NO: 52. In certain embodiments, the antibody comprises a heavy chain comprising the amino acid sequence set forth in SEQ ID NO: 53. In certain embodiments, the antibody comprises a heavy chain comprising the amino acid sequence set forth in SEQ ID NO: 54. In certain embodiments, the antibody comprises a heavy chain comprising the amino acid sequence set forth in SEQ ID NO: 73. In certain embodiments, the antibody comprises a heavy chain comprising the amino acid sequence set forth in SEQ ID NO: 74. In certain embodiments, the antibody comprises a heavy chain comprising the amino acid sequence set forth in SEQ ID NO: 75. In certain embodiments, the antibody comprises a heavy chain comprising the amino acid sequence set forth in SEQ ID NO: 76. In certain embodiments, the antibody comprises a heavy chain comprising the amino acid sequence set forth in SEQ ID NO: 77. In certain embodiments, the antibody comprises a heavy chain comprising the amino acid sequence set forth in SEQ ID NO: 78.

In certain embodiments, the instant disclosure provides an isolated antibody that specifically binds to CD137 (e.g., human CD137 or cynomolgus CD137), the antibody comprising a light chain comprising the amino acid sequence set forth in SEQ ID NO: 21, 79, 80, or 81. In certain embodiments, the antibody comprises a light chain comprising the amino acid sequence set forth in SEQ ID NO: 21. In certain embodiments, the antibody comprises a light chain comprising the amino acid sequence set forth in SEQ ID NO: 79. In certain embodiments, the antibody comprises a light chain comprising the amino acid sequence set forth in SEQ ID NO: 80. In certain embodiments, the antibody comprises a light chain comprising the amino acid sequence set forth in SEQ ID NO: 81.

In certain embodiments, the instant disclosure provides an isolated antibody that specifically binds to CD137 (e.g., human CD137 or cynomolgus CD137), the antibody comprising a heavy chain comprising the amino acid sequence of SEQ ID NO: 9, 10, 11, 12, 13, 14, 49, 50, 51, 52, 53, 54, 73, 74, 75, 76, 77, or 78; and a light chain comprising the amino acid sequence of SEQ ID NO: 21, 79, 80, or 81. In certain embodiments, the instant disclosure provides an isolated antibody that specifically binds to CD137 (e.g., human CD137 or cynomolgus CD137), the antibody comprising a heavy chain comprising the amino acid sequence of SEQ ID NO: 9; and a light chain comprising the amino acid sequence of SEQ ID NO: 21. In certain embodiments, the instant disclosure provides an isolated antibody that specifically binds to CD137 (e.g., human CD137 or cynomolgus CD137), the antibody comprising a heavy chain comprising the amino acid sequence of SEQ ID NO: 10; and a light chain comprising the amino acid sequence of SEQ ID NO: 21. In certain embodiments, the instant disclosure provides an isolated antibody that specifically binds to CD137 (e.g., human CD137 or cynomolgus CD137), the antibody comprising a heavy chain comprising the amino acid sequence of SEQ ID NO: 11; and a light chain comprising the amino acid sequence of SEQ ID NO: 21. In certain embodiments, the instant disclosure provides an isolated antibody that specifically binds to CD137 (e.g., human CD137 or cynomolgus CD137), the antibody comprising a heavy chain comprising the amino acid sequence of SEQ ID NO: 12; and a light chain comprising the amino acid sequence of SEQ ID NO: 21. In certain embodiments, the instant disclosure provides an isolated antibody that specifically binds to CD137 (e.g., human CD137 or cynomolgus CD137), the antibody comprising a heavy chain comprising the amino acid sequence of SEQ ID NO: 13; and a light chain comprising the amino acid sequence of SEQ ID NO: 21. In certain embodiments, the instant disclosure provides an isolated antibody that specifically binds to CD137 (e.g., human CD137 or cynomolgus CD137), the antibody comprising a heavy chain comprising the amino acid sequence of SEQ ID NO: 14; and a light chain comprising the amino acid sequence of SEQ ID NO: 21. In certain embodiments, the instant disclosure provides an isolated antibody that specifically binds to CD137 (e.g., human CD137 or cynomolgus CD137), the antibody comprising a heavy chain comprising the amino acid sequence of SEQ ID NO: 49; and a light chain comprising the amino acid sequence of SEQ ID NO: 21. In certain embodiments, the instant disclosure provides an isolated antibody that specifically binds to CD137 (e.g., human CD137 or cynomolgus CD137), the antibody comprising a heavy chain comprising the amino acid sequence of SEQ ID NO: 50; and a light chain comprising the amino acid sequence of SEQ ID NO: 21. In certain embodiments, the instant disclosure provides an isolated antibody that specifically binds to CD137 (e.g., human CD137 or cynomolgus CD137), the antibody comprising a heavy chain comprising the amino acid sequence of SEQ ID NO: 51; and a light chain comprising the amino acid sequence of SEQ ID NO: 21. In certain embodiments, the instant disclosure provides an isolated antibody that specifically binds to CD137 (e.g., human CD137 or cynomolgus CD137), the antibody comprising a heavy chain comprising the amino acid sequence of SEQ ID NO: 52; and a light chain comprising the amino acid sequence of SEQ ID NO: 21. In certain embodiments, the instant disclosure provides an isolated antibody that specifically binds to CD137 (e.g., human CD137 or cynomolgus CD137), the antibody comprising a heavy chain comprising the amino acid sequence of SEQ ID NO: 53; and a light chain comprising the amino acid sequence of SEQ ID NO: 21. In certain embodiments, the instant disclosure provides an isolated antibody that specifically binds to CD137 (e.g., human CD137 or cynomolgus CD137), the antibody comprising a heavy chain comprising the amino acid sequence of SEQ ID NO: 54; and a light chain comprising the amino acid sequence of SEQ ID NO: 21. In certain embodiments, the instant disclosure provides an isolated antibody that specifically binds to CD137 (e.g., human CD137 or cynomolgus CD137), the antibody comprising a heavy chain comprising the amino acid sequence of SEQ ID NO: 73; and a light chain comprising the amino acid sequence of SEQ ID NO: 21. In certain embodiments, the instant disclosure provides an isolated antibody that specifically binds to CD137 (e.g., human CD137 or cynomolgus CD137), the antibody comprising a heavy chain comprising the amino acid sequence of SEQ ID NO: 74; and a light chain comprising the amino acid sequence of SEQ ID NO: 21. In certain embodiments, the instant disclosure provides an isolated antibody that specifically binds to CD137 (e.g., human CD137 or cynomolgus CD137), the antibody comprising a heavy chain comprising the amino acid sequence of SEQ ID NO: 75; and a light chain comprising the amino acid sequence of SEQ ID NO: 79. In certain embodiments, the instant disclosure provides an isolated antibody that specifically binds to CD137 (e.g., human CD137 or cynomolgus CD137), the antibody comprising a heavy chain comprising the amino acid sequence of SEQ ID NO: 76; and a light chain comprising the amino acid sequence of SEQ ID NO: 79. In certain embodiments, the instant disclosure provides an isolated antibody that specifically binds to CD137 (e.g., human CD137 or cynomolgus CD137), the antibody comprising a heavy chain comprising the amino acid sequence of SEQ ID NO: 9; and a light chain comprising the amino acid sequence of SEQ ID NO: 80. In certain embodiments, the instant disclosure provides an isolated antibody that specifically binds to CD137 (e.g., human CD137 or cynomolgus CD137), the antibody comprising a heavy chain comprising the amino acid sequence of SEQ ID NO: 49; and a light chain comprising the amino acid sequence of SEQ ID NO: 80. In certain embodiments, the instant disclosure provides an isolated antibody that specifically binds to CD137 (e.g., human CD137 or cynomolgus CD137), the antibody comprising a heavy chain comprising the amino acid sequence of SEQ ID NO: 77; and a light chain comprising the amino acid sequence of SEQ ID NO: 81. In certain embodiments, the instant disclosure provides an isolated antibody that specifically binds to CD137 (e.g., human CD137 or cynomolgus CD137), the antibody comprising a heavy chain comprising the amino acid sequence of SEQ ID NO: 78; and a light chain comprising the amino acid sequence of SEQ ID NO: 81.

In certain embodiments, the antibody comprises a heavy chain consisting of the amino acid sequence of SEQ ID NO: 9, 10, 11, 12, 13, 14, 49, 50, 51, 52, 53, 54, 73, 74, 75, 76, 77, or 78; and a light chain consisting of the amino acid sequence of SEQ ID NO: 21, 79, 80, or 81. In certain embodiments, the antibody comprises a heavy chain consisting of the amino acid sequence of SEQ ID NO: 9; and a light chain consisting of the amino acid sequence of SEQ ID NO: 21. In certain embodiments, the antibody comprises a heavy chain consisting of the amino acid sequence of SEQ ID NO: 10; and a light chain consisting of the amino acid sequence of SEQ ID NO: 21. In certain embodiments, the antibody comprises a heavy chain consisting of the amino acid sequence of SEQ ID NO: 11; and a light chain consisting of the amino acid sequence of SEQ ID NO: 21. In certain embodiments, the antibody comprises a heavy chain consisting of the amino acid sequence of SEQ ID NO: 12; and a light chain consisting of the amino acid sequence of SEQ ID NO: 21. In certain embodiments, the antibody comprises a heavy chain consisting of the amino acid sequence of SEQ ID NO: 13; and a light chain consisting of the amino acid sequence of SEQ ID NO: 21. In certain embodiments, the antibody comprises a heavy chain consisting of the amino acid sequence of SEQ ID NO: 14; and a light chain consisting of the amino acid sequence of SEQ ID NO: 21. In certain embodiments, the antibody comprises a heavy chain consisting of the amino acid sequence of SEQ ID NO: 49; and a light chain consisting of the amino acid sequence of SEQ ID NO: 21. In certain embodiments, the antibody comprises a heavy chain consisting of the amino acid sequence of SEQ ID NO: 50; and a light chain consisting of the amino acid sequence of SEQ ID NO: 21. In certain embodiments, the antibody comprises a heavy chain consisting of the amino acid sequence of SEQ ID NO: 51; and a light chain consisting of the amino acid sequence of SEQ ID NO: 21. In certain embodiments, the antibody comprises a heavy chain consisting of the amino acid sequence of SEQ ID NO: 52; and a light chain consisting of the amino acid sequence of SEQ ID NO: 21. In certain embodiments, the antibody comprises a heavy chain consisting of the amino acid sequence of SEQ ID NO: 53; and a light chain consisting of the amino acid sequence of SEQ ID NO: 21. In certain embodiments, the antibody comprises a heavy chain consisting of the amino acid sequence of SEQ ID NO: 54; and a light chain consisting of the amino acid sequence of SEQ ID NO: 21. In certain embodiments, the antibody comprises a heavy chain consisting of the amino acid sequence of SEQ ID NO: 73; and a light chain consisting of the amino acid sequence of SEQ ID NO: 21. In certain embodiments, the antibody comprises a heavy chain consisting of the amino acid sequence of SEQ ID NO: 74; and a light chain consisting of the amino acid sequence of SEQ ID NO: 21. In certain embodiments, the antibody comprises a heavy chain consisting of the amino acid sequence of SEQ ID NO: 75; and a light chain consisting of the amino acid sequence of SEQ ID NO: 79. In certain embodiments, the antibody comprises a heavy chain consisting of the amino acid sequence of SEQ ID NO: 76; and a light chain consisting of the amino acid sequence of SEQ ID NO: 79. In certain embodiments, the antibody comprises a heavy chain consisting of the amino acid sequence of SEQ ID NO: 9; and a light chain consisting of the amino acid sequence of SEQ ID NO: 80. In certain embodiments, the antibody comprises a heavy chain consisting of the amino acid sequence of SEQ ID NO: 49; and a light chain consisting of the amino acid sequence of SEQ ID NO: 80. In certain embodiments, the antibody comprises a heavy chain consisting of the amino acid sequence of SEQ ID NO: 77; and a light chain consisting of the amino acid sequence of SEQ ID NO: 81. In certain embodiments, the antibody comprises a heavy chain consisting of the amino acid sequence of SEQ ID NO: 78; and a light chain consisting of the amino acid sequence of SEQ ID NO: 81.

Any antibody format can be used in the antibodies disclosed herein. In certain embodiments, the antibody is a single chain antibody or single-chain Fv (scFv). In certain embodiments, the antibody is a scFv fused with an Fc region (scFv-Fc). In certain embodiments, the antibody is a Fab fragment. In certain embodiments, the antibody is a F(ab')$_2$ fragment.

In certain embodiments, the antibody disclosed herein is a multispecific antibody (e.g., a bispecific antibody) which specifically binds to CD137 (e.g., human CD137 or cynomolgus CD137) and a second antigen.

In certain embodiments, the antibody disclosed herein is conjugated to a second antibody that specifically binds to a second antigen. In certain embodiments, the antibody disclosed herein is covalently conjugated to a second antibody. In certain embodiments, the antibody disclosed herein is non-covalently conjugated to a second antibody. In certain embodiments, the antibody disclosed herein is cross-linked to a second antibody. In certain embodiments, the second antigen is a tumor-associated antigen (e.g., a polypeptide overexpressed in a tumor, a polypeptide derived from an oncovirus, a polypeptide comprising a post-translational modification specific to a tumor, a polypeptide specifically mutated in a tumor). In certain embodiments, the tumor-associated antigen is EGFR (e.g., human EGFR), Her2 (e.g., human Her2), or CD20 (e.g., human CD20).

In certain embodiments, the antibody disclosed herein is conjugated to a cytotoxic agent, cytostatic agent, toxin, radionuclide, or detectable label. In certain embodiments, the cytotoxic agent is able to induce death or destruction of a cell in contact therewith. In certain embodiments, the cytostatic agent is able to prevent or substantially reduce proliferation and/or inhibits the activity or function of a cell in contact therewith. In certain embodiments, the cytotoxic agent or cytostatic agent is a chemotherapeutic agent. In certain embodiments, the radionuclide is selected from the group consisting of the isotopes $^3$H, $^{14}$C, $^{32}$P, $^{35}$S, $^{36}$Cl, $^{51}$Cr, $^{57}$Co, $^{58}$Co, $^{59}$Fe, $^{67}$Cu, $^{90}$Y, 99Tc, $^{111}$In, $^{117}$Lu, $^{121}$I, $^{124}$I, $^{125}$I, $^{131}$I, $^{198}$Au, $^{211}$At, $^{213}$Bi, $^{225}$Ac and $^{186}$Re. In certain embodiments, the detectable label comprises a fluorescent moiety or a click chemistry handle.

Any immunoglobulin (Ig) constant region can be used in the antibodies disclosed herein. In certain embodiments, the Ig region is a human IgG, IgE, IgM, IgD, IgA, or IgY immunoglobulin molecule, any class (e.g., IgG$_1$, IgG$_2$, IgG$_3$, IgG$_4$, IgA$_1$, and IgA$_2$), or any subclass (e.g., IgG$_{2a}$ and IgG$_{2b}$) of immunoglobulin molecule.

In certain embodiments, the instant disclosure provides an isolated antibody that specifically binds to CD137 (e.g., human CD137 or cynomolgus CD137), the antibody comprising a heavy chain constant region comprising the amino acid sequence of SEQ ID NO: 15, 16, 17, 18, 19, or 20. In certain embodiments, the instant disclosure provides an isolated antibody that specifically binds to CD137 (e.g., human CD137 or cynomolgus CD137), the antibody comprising a light chain constant region comprising the amino acid sequence of SEQ ID NO: 22.

In certain embodiments, one, two, or more mutations (e.g., amino acid substitutions) are introduced into the Fc region of an antibody described herein (e.g., CH2 domain (residues 231-340 of human IgG$_1$) and/or CH3 domain (residues 341-447 of human IgG$_1$) and/or the hinge region, numbered according to the EU numbering system, to alter one or more functional properties of the antibody, such as serum half-life, complement fixation, Fc receptor binding and/or antigen-dependent cellular cytotoxicity.

In certain embodiments, one, two, or more mutations (e.g., amino acid substitutions) are introduced into the hinge region of the Fc region (CH1 domain) such that the number of cysteine residues in the hinge region are altered (e.g., increased or decreased) as described in, e.g., U.S. Pat. No. 5,677,425, herein incorporated by reference in its entirety. The number of cysteine residues in the hinge region of the CH1 domain may be altered to, e.g., facilitate assembly of the light and heavy chains, or to alter (e.g., increase or decrease) the stability of the antibody.

In a specific embodiment, one, two, or more amino acid mutations (e.g., substitutions, insertions or deletions) are introduced into an IgG constant domain, or FcRn-binding fragment thereof (preferably an Fc or hinge-Fc domain fragment) to alter (e.g., decrease or increase) half-life of the antibody in vivo. See, e.g., International Publication Nos. WO 02/060919; WO 98/23289; and WO 97/34631; and U.S. Pat. Nos. 5,869,046, 6,121,022, 6,277,375 and 6,165,745, all of which are herein incorporated by reference in their entireties, for examples of mutations that will alter (e.g., decrease or increase) the half-life of an antibody in vivo. In certain embodiments, one, two or more amino acid mutations (e.g., substitutions, insertions, or deletions) are introduced into an IgG constant domain, or FcRn-binding fragment thereof (preferably an Fc or hinge-Fc domain fragment) to decrease the half-life of the antibody in vivo. In other embodiments, one, two or more amino acid mutations (e.g., substitutions, insertions or deletions) are introduced into an IgG constant domain, or FcRn-binding fragment thereof (preferably an Fc or hinge-Fc domain fragment) to increase the half-life of the antibody in vivo. In a specific embodiment, the antibodies may have one or more amino acid mutations (e.g., substitutions) in the second constant (CH2) domain (residues 231-340 of human IgG$_1$) and/or the third constant (CH3) domain (residues 341-447 of human IgG$_1$), numbered according to the EU numbering system. In a specific embodiment, the constant region of the IgG$_1$ of an antibody described herein comprises a methionine (M) to tyrosine (Y) substitution in position 252, a serine (S) to threonine (T) substitution in position 254, and a threonine (T) to glutamic acid (E) substitution in position 256, numbered according to the EU numbering system. See U.S. Pat. No. 7,658,921, which is herein incorporated by reference in its entirety. This type of mutant IgG, referred to as "YTE mutant" has been shown to display fourfold increased half-life as compared to wild-type versions of the same antibody (see Dall'Acqua W F et al., (2006) J Biol Chem 281: 23514-24, which is herein incorporated by reference in its entirety). In certain embodiments, an antibody comprises an IgG constant domain comprising one, two, three or more amino acid substitutions of amino acid residues at positions 251-257, 285-290, 308-314, 385-389, and 428-436, numbered according to the EU numbering system.

In certain embodiments, one, two, or more mutations (e.g., amino acid substitutions) are introduced into the Fc region of an antibody described herein (e.g., CH2 domain (residues 231-340 of human IgG$_1$) and/or CH3 domain (residues 341-447 of human IgG$_1$) and/or the hinge region, numbered according to the EU numbering system, to increase or decrease the affinity of the antibody for an Fc receptor (e.g., an activated Fc receptor) on the surface of an effector cell. Mutations in the Fc region of an antibody that decrease or increase the affinity of an antibody for an Fc receptor and techniques for introducing such mutations into the Fc receptor or fragment thereof are known to one of skill in the art. Examples of mutations in the Fc receptor of an antibody that can be made to alter the affinity of the antibody for an Fc receptor are described in, e.g., Smith P et al., (2012) PNAS 109: 6181-6186, U.S. Pat. No. 6,737,056, and International Publication Nos. WO 02/060919; WO 98/23289; and WO 97/34631, all of which are herein incorporated by reference in their entireties.

In certain embodiments, the antibody comprises a heavy chain constant region that is a variant of a wild type heavy chain constant region, wherein the variant heavy chain constant region binds to FcγRIIB with higher affinity than the wild type heavy chain constant region binds to FcγRIIB. In certain embodiments, the variant heavy chain constant region is a variant human heavy chain constant region, e.g., a variant human IgG1, a variant human IgG2, or a variant human IgG4 heavy chain constant region. In certain embodiments, the variant human IgG heavy chain constant region comprises one or more of the following amino acid mutations, according to the EU numbering system: G236D, P238D, S239D, S267E, L328F, and L328E. In certain embodiments, the variant human IgG heavy chain constant region comprises a set of amino acid mutations selected from the group consisting of: S267E and L328F; P238D and L328E; P238D and one or more substitutions selected from the group consisting of E233D, G237D, H268D, P271G, and A330R; P238D, E233D, G237D, H268D, P271G, and A330R; G236D and S267E; S239D and S267E; V262E, S267E, and L328F; and V264E, S267E, and L328F, according to the EU numbering system. In certain embodiments, the FcγRIIB is expressed on a cell selected from the group consisting of macrophages, monocytes, B cells, dendritic cells, endothelial cells, and activated T cells.

In a further embodiment, one, two, or more amino acid substitutions are introduced into an IgG constant domain Fc region to alter the effector function(s) of the antibody. For example, one or more amino acids selected from amino acid residues 234, 235, 236, 237, 297, 318, 320 and 322, numbered according to the EU numbering system, can be replaced with a different amino acid residue such that the antibody has an altered affinity for an effector ligand but retains the antigen-binding ability of the parent antibody. The effector ligand to which affinity is altered can be, for example, an Fc receptor or the C1 component of complement. This approach is described in further detail in U.S. Pat. Nos. 5,624,821 and 5,648,260, each of which is herein incorporated by reference in its entirety. In certain embodiments, the deletion or inactivation (through point mutations or other means) of a constant region domain may reduce Fc receptor binding of the circulating antibody thereby increasing tumor localization. See, e.g., U.S. Pat. Nos. 5,585,097 and 8,591,886, each of which is herein incorporated by reference in its entirety, for a description of mutations that delete or inactivate the constant domain and thereby increase tumor localization. In certain embodiments, one or more amino acid substitutions may be introduced into the Fc region of an antibody described herein to remove potential glycosylation sites on the Fc region, which may reduce Fc receptor binding (see, e.g., Shields R L et al., (2001) J Biol Chem 276: 6591-604, which is herein incorporated by reference in its entirety). In various embodiments, one or more of the following mutations in the constant region of an antibody described herein may be made: an N297A substitution; an N297Q substitution; a L235A substitution and a L237A substitution; a L234A substitution and a L235A substitution; a E233P substitution; a L234V substitution; a L235A substitution; a C236 deletion; a P238A substitution; a D265A substitution; a S267E substitution and L328F substitution; a A327Q substitution; or a P329A substitution, numbered according to the EU numbering system. In certain embodiments, a mutation selected from the group consisting of D265A, P329A, and a combination thereof, numbered according to the EU numbering system, may be made in the constant region of an antibody described herein.

In a specific embodiment, an antibody described herein comprises the constant domain of an IgG$_1$ with an N297Q or N297A amino acid substitution, numbered according to the EU numbering system. In one embodiment, an antibody described herein comprises the constant domain of an IgG$_1$ with a mutation selected from the group consisting of D265A, P329A, and a combination thereof, numbered according to the EU numbering system. In another embodiment, an antibody described herein comprises the constant domain of an IgG$_1$ with a mutation selected from the group consisting of L234A, L235A, and a combination thereof, numbered according to the EU numbering system. In certain embodiments, amino acid residues in the constant region of an antibody described herein in the positions corresponding to positions L234, L235, and D265 in a human IgG$_1$ heavy chain, numbered according to the EU numbering system, are not L, L, and D, respectively. This approach is described in detail in International Publication No. WO 14/108483, which is herein incorporated by reference in its entirety. In a particular embodiment, the amino acids corresponding to positions L234, L235, and D265 in a human IgG$_1$ heavy chain are F, E, and A; or A, A, and A, respectively, numbered according to the EU numbering system.

In certain embodiments, one or more amino acids selected from amino acid residues 329, 331, and 322 in the constant region of an antibody described herein, numbered according to the EU numbering system, can be replaced with a different amino acid residue such that the antibody has altered C1q binding and/or reduced or abolished complement dependent cytotoxicity (CDC). This approach is described in further detail in U.S. Pat. No. 6,194,551 (Idusogie et al.), which is herein incorporated by reference in its entirety. In certain embodiments, one or more amino acid residues within amino acid positions 231 to 238 in the N-terminal region of the CH2 domain of an antibody described herein are altered to thereby alter the ability of the antibody to fix complement, numbered according to the EU numbering system. This approach is described further in International Publication No. WO 94/29351, which is herein incorporated by reference in its entirety. In certain embodiments, the Fc region of an antibody described herein is modified to increase the ability of the antibody to mediate antibody dependent cellular cytotoxicity (ADCC) and/or to increase the affinity of the antibody for an Fcγ receptor by mutating one or more amino acids (e.g., introducing amino acid substitutions) at the following positions: 238, 239, 248, 249, 252, 254, 255, 256, 258, 265, 267, 268, 269, 270, 272, 276, 278, 280, 283, 285, 286, 289, 290, 292, 293, 294, 295, 296, 298, 301, 303, 305, 307, 309, 312, 315, 320, 322, 324, 326, 327, 328, 329, 330, 331, 333, 334, 335, 337, 338, 340, 360, 373, 376, 378, 382, 388, 389, 398, 414, 416, 419, 430, 434, 435, 437, 438, or 439, numbered according to the EU numbering system. This approach is described further in International Publication No. WO 00/42072, which is herein incorporated by reference in its entirety.

In certain embodiments, an antibody described herein comprises the constant region of an IgG$_4$ antibody and the serine at amino acid residue 228 of the heavy chain, numbered according to the EU numbering system, is substituted for proline. In certain embodiments, the instant disclosure provides an isolated antibody that specifically binds to CD137 (e.g., human CD137 or cynomolgus CD137), the antibody comprising a heavy chain constant region comprising the amino acid sequence of SEQ ID NO: 20.

In certain embodiments, any of the constant region mutations or modifications described herein can be introduced into one or both heavy chain constant regions of an antibody described herein having two heavy chain constant regions.

In certain embodiments of any of the aspects disclosed herein reciting SEQ ID NO: 7, 9, 10, 11, 12, 13, 14, 49, 50, 51, 52, 53, 54, 63, 64, 65, 69, 70, 71, 72, 73, 74, 75, 76, 77, or 78, X in SEQ ID NO: 7, 9, 10, 11, 12, 13, 14, 49, 50, 51, 52, 53, 54, 63, 64, 65, 69, 70, 71, 72, 73, 74, 75, 76, 77, or 78 is glutamine (Q). In certain embodiments of any of the aspects disclosed herein reciting SEQ ID NO: 7, 9, 10, 11, 12, 13, 14, 49, 50, 51, 52, 53, 54, 63, 64, 65, 69, 70, 71, 72, 73, 74, 75, 76, 77, or 78, X in SEQ ID NO: 7, 9, 10, 11, 12, 13, 14, 49, 50, 51, 52, 53, 54, 63, 64, 65, 69, 70, 71, 72, 73, 74, 75, 76, 77, or 78 is pyroglutamate (pE).

In certain embodiments, the instant disclosure provides an isolated antibody that specifically binds to CD137 (e.g., human CD137 or cynomolgus CD137) and functions as an agonist.

In certain embodiments, the instant disclosure provides an isolated antibody that specifically binds to CD137 (e.g., human CD137 or cynomolgus CD137) and increases or promotes CD137 (e.g., human CD137 or cynomolgus CD137) activity by at least 5%, 10%, 15%, 20%, 25%, 30%, 35%, 40%, 45%, 50%, 55%, 60%, 65%, 70%, 75%, 80%, 85%, 90%, 95%, 98%, or 99%, as assessed by methods described herein and/or known to one of skill in the art, relative to CD137 (e.g., human CD137 or cynomolgus CD137) activity without any antibody or with an unrelated antibody (e.g., an antibody that does not specifically bind to CD137 (e.g., human CD137 or cynomolgus CD137)). In certain embodiments, the instant disclosure provides an isolated antibody that specifically binds to CD137 (e.g., human CD137 or cynomolgus CD137) and increases or promotes CD137 (e.g., human CD137 or cynomolgus CD137) activity by at least about 1.2 fold, 1.3 fold, 1.4 fold, 1.5 fold, 2 fold, 2.5 fold, 3 fold, 3.5 fold, 4 fold, 4.5 fold, 5 fold, 6 fold, 7 fold, 8 fold, 9 fold, 10 fold, 15 fold, 20 fold, 30 fold, 40 fold, 50 fold, 60 fold, 70 fold, 80 fold, 90 fold, 100 fold, or more, as assessed by methods described herein and/or known to one of skill in the art, relative to CD137 (e.g., human CD137 or cynomolgus CD137) activity without any antibody or with an unrelated antibody (e.g., an antibody that does not specifically bind to CD137 (e.g., human CD137)). Non-limiting examples of CD137 (e.g., human CD137 or cynomolgus CD137) activity can include CD137 (e.g., human CD137 or cynomolgus CD137) signaling, CD137 (e.g., human CD137 or cynomolgus CD137) binding to CD137 (e.g., human CD137 or cynomolgus CD137) ligand (e.g., CD137L (e.g., human CD137 or cynomolgus CD137) or a fragment and/or fusion protein thereof), activation of a T cell (e.g., a T cell expressing human CD137), increase of cytokine production (e.g., IL-2, IFN-γ and/or TNF-α), activation of a natural killer (NK) cell, increase of CD137L activity, and activation of an antigen-presenting cell (APC) expressing CD137L. In specific embodiments, an increase in a CD137 (e.g., human CD137 or cynomolgus CD137) activity is assessed as described in the Examples, infra. In certain embodiments, the antibody increases or promotes an activity of CD137 (e.g., human CD137 or cynomolgus CD137) in the presence of a ligand of CD137 (e.g., CD137L (e.g., human CD137 or cynomolgus CD137) or a fragment and/or fusion protein thereof).

In certain embodiments, the ability of the antibody to activate, increase, or promote an activity of CD137 (e.g., human CD137 or cynomolgus CD137) depends on the presence of crosslinking of the antibody. In certain embodiments, the antibody minimally increases or promotes an activity of CD137 (e.g., human CD137 or cynomolgus CD137) in the absence of crosslinking of the antibody. In certain embodiments, the antibody does not substantially increase or promote an activity of CD137 (e.g., human CD137 or cynomolgus CD137) in the absence of crosslinking of the antibody. In one embodiment, the antibody minimally induces NF-κB signaling in a NF-κB reporter cell line, e.g., as measured in the examples described herein, in the absence of crosslinking of the antibody. In one embodiment, the antibody minimally induces IL-2 and/or IFNγ production from purified T cells under anti-CD3 antibody stimulation, e.g., as measured in the examples described herein, in the absence of crosslinking of the antibody. Crosslinking of an antibody contemplated herein includes clustering of the antibody. Methods of crosslinking used herein are known in the art. In certain embodiments, the antibody is crosslinked by an agent that dimerizes the Fc region of the antibody, e.g., the anti-human IgG (Fab')$_2$ as used in the examples described herein. In certain embodiments, the antibody is crosslinked by contact with a cell that expresses an Fc receptor that binds to the Fc region of the antibody (e.g., FcγRIIIa, FcγRIIIb, FcγRIIa, FcγRIIb, or FcγRI). In certain embodiments, the Fc receptor is expressed in a cluster on the surface of the cell. In certain embodiments, a ligand of the antigen that the antibody binds to is also expressed on the cell. In certain embodiments, the cell is an antigen-presenting cell (e.g., a macrophage, monocyte, dendritic cell, or B lymphocyte).

In certain embodiments, the ability of the antibody to activate, increase, or promote an activity of CD137 (e.g., human CD137 or cynomolgus CD137) depends on the presence of a ligand of CD137 (e.g., CD137L (e.g., human CD137 or cynomolgus CD137) or a fragment and/or fusion protein thereof). In certain embodiments, the antibody minimally increases or promotes an activity of CD137 (e.g., human CD137 or cynomolgus CD137) in the absence of a ligand of CD137 (e.g., CD137L (e.g., human CD137 or cynomolgus CD137) or a fragment and/or fusion protein thereof). In certain embodiments, the antibody does not substantially increase or promote an activity of CD137 (e.g., human CD137 or cynomolgus CD137) in the absence of a ligand of CD137 (e.g., CD137L (e.g., human CD137 or cynomolgus CD137) or a fragment and/or fusion protein thereof). In one embodiment, the antibody minimally induces IL-2 and/or IFNγ production from purified T cells under anti-CD3 antibody stimulation, e.g., as measured in the examples described herein. In one embodiment, the antibody minimally induces NF-κB signaling in a NF-κB reporter cell line, e.g., as measured in the examples described herein. In certain embodiments, the ability of the antibody to activate, increase, or promote an activity of human CD137 positively correlates with the concentration of CD137L. In certain embodiments, the CD137L dependency is observed when the antibody is crosslinked, e.g., with an anti-human IgG (Fab')$_2$ at a crosslinker-to-antibody ratio of about 1:1 to 1:10 (e.g., about 1:1, 1:2, 1:3, 1:4, 1:5, or lower).

In specific embodiments, the instant disclosure provides an isolated antibody that specifically binds to CD137 (e.g., human CD137 or cynomolgus CD137) and activates a T cell (e.g., a T cell expressing human CD137). In certain embodiments, the activated T cell expresses an increased level (e.g., increased by at least about 1.1 fold, 1.2 fold, 1.3 fold, 1.4 fold, 1.5 fold, 2 fold, 2.5 fold, 3 fold, 3.5 fold, 4 fold, 4.5 fold, 5 fold, 6 fold, 7 fold, 8 fold, 9 fold, 10 fold, 15 fold, 20 fold, 30 fold, 40 fold, 50 fold, 60 fold, 70 fold, 80 fold, 90 fold, or 100 fold) of one or more markers (e.g., perforin, granzyme A, granzyme B, Bcl-$X_L$), optionally wherein the level of the markers can be measured by flow cytometry. In certain embodiments, the antibody activates a T cell (e.g., a T cell expressing human CD137) in the presence of a ligand of CD137 (e.g., CD137L (e.g., human CD137 or cynomolgus CD137) or a fragment and/or fusion protein thereof). In certain embodiments, the antibody does not activate a T cell (e.g., a T cell expressing human CD137) in the absence of a ligand of CD137 (e.g., CD137L (e.g., human CD137 or cynomolgus CD137) or a fragment and/or fusion protein thereof).

In specific embodiments, the instant disclosure provides an isolated antibody that specifically binds to CD137 (e.g., human CD137 or cynomolgus CD137) and increases cytokine production (e.g., IL-2, IFN-γ and/or TNF-α) by at least about 5%, 10%, 15%, 20%, 25%, 30%, 35%, 40%, 45%, 50%, 55%, 60%, 65%, 70%, 75%, 80%, 85%, 90%, 95%, 98%, or 99%, as assessed by methods described herein (see the Examples, infra) or known to one of skill in the art, relative to cytokine production without any antibody or with an unrelated antibody (e.g., an antibody that does not specifically bind to CD137 (e.g., human CD137 or cynomolgus CD137)). In specific embodiments, the instant disclosure provides an isolated antibody that specifically binds to CD137 (e.g., human CD137 or cynomolgus CD137) and increases cytokine production (e.g., IL-2, IFN-γ and/or TNF-α) by at least about 1.2 fold, 1.3 fold, 1.4 fold, 1.5 fold, 2 fold, 2.5 fold, 3 fold, 3.5 fold, 4 fold, 4.5 fold, 5 fold, 6 fold, 7 fold, 8 fold, 9 fold, 10 fold, 15 fold, 20 fold, 30 fold, 40 fold, 50 fold, 60 fold, 70 fold, 80 fold, 90 fold, or 100 fold, as assessed by methods described herein (see the Examples, infra) or known to one of skill in the art, relative to cytokine production without any antibody or with an unrelated antibody (e.g., an antibody that does not specifically bind to CD137 (e.g., human CD137 or cynomolgus CD137)). In certain embodiments, the antibody increases cytokine production (e.g., IL-2, IFN-γ and/or TNF-α) in the presence of a ligand of CD137 (e.g., CD137L (e.g., human CD137 or cynomolgus CD137) or a fragment and/or fusion protein thereof). In certain embodiments, in the absence of a ligand of CD137 (e.g., CD137L (e.g., human CD137 or cynomolgus CD137) or a fragment and/or fusion protein thereof), the antibody does not increase cytokine production (e.g., IL-2, IFN-γ and/or TNF-α) by more than 1%, 2%, 3%, 4%, 5%, 10%, 15%, 20%, 25%, or 30%, relative to cytokine production without any antibody or with an unrelated antibody (e.g., an antibody that does not specifically bind to CD137 (e.g., human CD137 or cynomolgus CD137)).

In specific embodiments, the instant disclosure provides an isolated antibody that specifically binds to CD137 (e.g., human CD137 or cynomolgus CD137) and which either alone or in combination with an anti-PD-1 antibody (e.g., pembrolizumab or nivolumab), increases IL-2 and/or IFNγ production in human peripheral blood mononuclear cells (PBMCs) in response to *Staphylococcus* Enterotoxin A (SEA) stimulation by at least about 1.2 fold, 1.3 fold, 1.4 fold, 1.5 fold, 2 fold, 2.5 fold, 3 fold, 3.5 fold, 4 fold, 4.5 fold, 5 fold, 6 fold, 7 fold, 8 fold, 9 fold, 10 fold, 15 fold, 20 fold, 30 fold, 40 fold, 50 fold, 60 fold, 70 fold, 80 fold, 90 fold, or 100 fold, as assessed by methods described herein (see the Examples, infra) or known to one of skill in the art, relative to IL-2 and/or IFNγ production without any antibody or with an unrelated antibody (e.g., an antibody that does not specifically bind to CD137 (e.g., human CD137 or cynomolgus CD137)). In certain embodiments, human peripheral blood mononuclear cells (PBMCs) stimulated with *Staphylococcus* Enterotoxin A (SEA) in the presence of an antibody described herein, which specifically binds to CD137 (e.g., human CD137 or cynomolgus CD137), have increased IL-2 and/or IFNγ production by at least about 1.2 fold, 1.3 fold, 1.4 fold, 1.5 fold, 2 fold, 2.5 fold, 3 fold, 3.5 fold, 4 fold, 4.5 fold, 5 fold, 6 fold, 7 fold, 8 fold, 9 fold, 10 fold, 15 fold, 20 fold, 30 fold, 40 fold, 50 fold, 60 fold, 70 fold, 80 fold, 90 fold, or 100 fold, relative to IL-2 and/or IFNγ production from PBMCs only stimulated with SEA without any antibody or with an unrelated antibody (e.g., an antibody that does not specifically bind to CD137 (e.g., human CD137 or cynomolgus CD137)), as assessed by methods described herein (see the Examples, infra) or known to one of skill in the art. In certain embodiments, the antibody increases IL-2 and/or IFNγ production in human PBMCs in response to SEA stimulation in the presence of a ligand of CD137 (e.g., CD137L (e.g., human CD137 or cynomolgus CD137) or a fragment and/or fusion protein thereof). In certain embodiments, in the absence of a ligand of CD137 (e.g., CD137L (e.g., human CD137 or cynomolgus CD137) or a fragment and/or fusion protein thereof), the antibody does not increase IL-2 and/or IFNγ production in human PBMCs in response to SEA stimulation by more than 1%, 2%, 3%, 4%, 5%, 10%, 15%, 20%, 25%, or 30%, relative to cytokine production without any antibody or with an unrelated antibody (e.g., an antibody that does not specifically bind to CD137 (e.g., human CD137 or cynomolgus CD137)).

5.3 Pharmaceutical Compositions

Provided herein are compositions comprising an anti-CD137 (e.g., human CD137 or cynomolgus CD137) antibody disclosed herein having the desired degree of purity in a physiologically acceptable carrier, excipient or stabilizer (see, e.g., Remington's Pharmaceutical Sciences (1990) Mack Publishing Co., Easton, Pa.). Acceptable carriers, excipients, or stabilizers are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/ or non-ionic surfactants such as TWEEN™, PLURONICS™ or polyethylene glycol (PEG).

In a specific embodiment, pharmaceutical compositions comprise an anti-CD137 (e.g., human CD137 or cynomolgus CD137) antibody disclosed herein, and optionally one or more additional prophylactic or therapeutic agents, in a pharmaceutically acceptable carrier. In a specific embodiment, pharmaceutical compositions comprise an effective amount of an antibody described herein, and optionally one or more additional prophylactic or therapeutic agents, in a pharmaceutically acceptable carrier. In certain embodiments, the antibody is the only active ingredient included in the pharmaceutical composition. Pharmaceutical compositions described herein can be useful in increasing or promoting CD137 (e.g., human CD137 or cynomolgus CD137) activity and treating a condition, such as cancer or an infectious disease. In one embodiment, the present invention relates to a pharmaceutical composition of the present invention comprising an anti-CD137 antibody of the present invention for use as a medicament. In another embodiment, the present invention relates to a pharmaceutical composition of the present invention for use in a method for the treatment of cancer or an infectious disease.

Pharmaceutically acceptable carriers used in parenteral preparations include aqueous vehicles, nonaqueous vehicles, antimicrobial agents, isotonic agents, buffers, antioxidants, local anesthetics, suspending and dispersing agents, emulsifying agents, sequestering or chelating agents and other pharmaceutically acceptable substances. Examples of aqueous vehicles include Sodium Chloride Injection, Ringers Injection, Isotonic Dextrose Injection, Sterile Water Injection, Dextrose and Lactated Ringers Injection. Nonaqueous parenteral vehicles include fixed oils of vegetable origin, cottonseed oil, corn oil, sesame oil and peanut oil. Antimicrobial agents in bacteriostatic or fungistatic concentrations can be added to parenteral preparations packaged in multiple-dose containers which include phenols or cresols, mercurials, benzyl alcohol, chlorobutanol, methyl and propyl p-hydroxybenzoic acid esters, thimerosal, benzalkonium chloride and benzethonium chloride. Isotonic agents include sodium chloride and dextrose. Buffers include phosphate and citrate. Antioxidants include sodium bisulfate. Local anesthetics include procaine hydrochloride. Suspending and dispersing agents include sodium carboxymethylcelluose, hydroxypropyl methylcellulose and polyvinylpyrrolidone. Emulsifying agents include Polysorbate 80 (TWEEN® 80). A sequestering or chelating agent of metal ions includes EDTA. Pharmaceutical carriers also include ethyl alcohol, polyethylene glycol and propylene glycol for water miscible vehicles; and sodium hydroxide, hydrochloric acid, citric acid or lactic acid for pH adjustment.

A pharmaceutical composition may be formulated for any route of administration to a subject. Specific examples of routes of administration include intranasal, oral, pulmonary, transdermal, intradermal, and parenteral. Parenteral administration, characterized by either subcutaneous, intramuscular or intravenous injection, is also contemplated herein. Injectables can be prepared in conventional forms, either as liquid solutions or suspensions, solid forms suitable for solution or suspension in liquid prior to injection, or as emulsions. The injectables, solutions and emulsions also contain one or more excipients. Suitable excipients are, for example, water, saline, dextrose, glycerol or ethanol. In addition, if desired, the pharmaceutical compositions to be administered can also contain minor amounts of non-toxic auxiliary substances such as wetting or emulsifying agents, pH buffering agents, stabilizers, solubility enhancers, and other such agents, such as for example, sodium acetate, sorbitan monolaurate, triethanolamine oleate and cyclodextrins.

Preparations for parenteral administration of an antibody include sterile solutions ready for injection, sterile dry soluble products, such as lyophilized powders, ready to be combined with a solvent just prior to use, including hypodermic tablets, sterile suspensions ready for injection, sterile dry insoluble products ready to be combined with a vehicle just prior to use and sterile emulsions. The solutions may be either aqueous or nonaqueous.

If administered intravenously, suitable carriers include physiological saline or phosphate buffered saline (PBS), and solutions containing thickening and solubilizing agents, such as glucose, polyethylene glycol, and polypropylene glycol and mixtures thereof.

Topical mixtures comprising an antibody are prepared as described for the local and systemic administration. The resulting mixture can be a solution, suspension, emulsions or the like and can be formulated as creams, gels, ointments, emulsions, solutions, elixirs, lotions, suspensions, tinctures, pastes, foams, aerosols, irrigations, sprays, suppositories, bandages, dermal patches or any other formulations suitable for topical administration.

An anti-CD137 (e.g., human CD137 or cynomolgus CD137) antibody disclosed herein can be formulated as an aerosol for topical application, such as by inhalation (see, e.g., U.S. Pat. Nos. 4,044,126, 4,414,209 and 4,364,923, which describe aerosols for delivery of a steroid useful for treatment of inflammatory diseases, particularly asthma and are herein incorporated by reference in their entireties). These formulations for administration to the respiratory tract can be in the form of an aerosol or solution for a nebulizer, or as a microfine powder for insufflations, alone or in combination with an inert carrier such as lactose. In such a case, the particles of the formulation will, in one embodiment, have diameters of less than 50 microns, in one embodiment less than 10 microns.

An anti-CD137 (e.g., human CD137 or cynomolgus CD137) antibody disclosed herein can be formulated for local or topical application, such as for topical application to the skin and mucous membranes, such as in the eye, in the form of gels, creams, and lotions and for application to the eye or for intracisternal or intraspinal application. Topical administration is contemplated for transdermal delivery and also for administration to the eyes or mucosa, or for inhalation therapies. Nasal solutions of the antibody alone or in combination with other pharmaceutically acceptable excipients can also be administered.

Transdermal patches, including iontophoretic and electrophoretic devices, are well known to those of skill in the art, and can be used to administer an antibody. For example, such patches are disclosed in U.S. Pat. Nos. 6,267,983, 6,261,595, 6,256,533, 6,167,301, 6,024,975, 6,010715, 5,985,317, 5,983,134, 5,948,433, and 5,860,957, all of which are herein incorporated by reference in their entireties.

In certain embodiments, a pharmaceutical composition comprising an antibody described herein is a lyophilized powder, which can be reconstituted for administration as solutions, emulsions and other mixtures. It may also be reconstituted and formulated as solids or gels. The lyophilized powder is prepared by dissolving an antibody described herein, or a pharmaceutically acceptable derivative thereof, in a suitable solvent. In certain embodiments, the lyophilized powder is sterile. The solvent may contain an excipient which improves the stability or other pharmacological component of the powder or reconstituted solution, prepared from the powder. Excipients that may be used include, but are not limited to, dextrose, sorbitol, fructose, corn syrup, xylitol, glycerin, glucose, sucrose or other suitable agent. The solvent may also contain a buffer, such as citrate, sodium or potassium phosphate or other such buffer known to those of skill in the art at, in one embodiment, about neutral pH. Subsequent sterile filtration of the solution followed by lyophilization under standard conditions known to those of skill in the art provides the desired formulation. In one embodiment, the resulting solution will be apportioned into vials for lyophilization. Each vial will contain a single dosage or multiple dosages of the compound. The lyophilized powder can be stored under appropriate conditions, such as at about 4° C. to room temperature. Reconstitution of this lyophilized powder with water for injection provides a formulation for use in parenteral administration. For reconstitution, the lyophilized powder is added to sterile water or other suitable carrier. The precise amount depends upon the selected compound. Such amount can be empirically determined.

The anti-CD137 (e.g., human CD137 or cynomolgus CD137) antibodies disclosed herein and other compositions provided herein can also be formulated to be targeted to a particular tissue, receptor, or other area of the body of the subject to be treated. Many such targeting methods are well known to those of skill in the art. All such targeting methods are contemplated herein for use in the instant compositions. For non-limiting examples of targeting methods, see, e.g., U.S. Pat. Nos. 6,316,652, 6,274,552, 6,271,359, 6,253,872, 6,139,865, 6,131,570, 6,120,751, 6,071,495, 6,060,082, 6,048,736, 6,039,975, 6,004,534, 5,985,307, 5,972,366, 5,900,252, 5,840,674, 5,759,542 and 5,709,874, all of which are herein incorporated by reference in their entireties. In a specific embodiment, an antibody described herein is targeted to a tumor.

The compositions to be used for in vivo administration can be sterile. This is readily accomplished by filtration through, e.g., sterile filtration membranes.

5.4 Methods of Use and Uses

In another aspect, the instant disclosure provides a method of treating a subject using the anti-CD137 (e.g., human CD137 or cynomolgus CD137) antibodies disclosed herein. Any disease or disorder in a subject that would benefit from increase of CD137 (e.g., human CD137 or cynomolgus CD137) function can be treated using the anti-CD137 (e.g., human CD137 or cynomolgus CD137) antibodies disclosed herein. The anti-CD137 (e.g., human CD137) antibodies disclosed herein are particularly useful for inhibiting immune system tolerance to tumors, and accordingly can be used as an immunotherapy for subjects with cancer. For example, in certain embodiments, the instant disclosure provides a method of increasing T cell activation in response to an antigen in a subject, the method comprising administering to the subject an effective amount of an anti-CD137 (e.g., human CD137 or cynomolgus CD137) antibody or pharmaceutical composition thereof, as disclosed herein. In certain embodiments, the instant disclosure provides a method of treating cancer in a subject, the method comprising administering to the subject an effective amount of the antibody or pharmaceutical composition, as disclosed herein.

Cancers that can be treated with the anti-CD137 (e.g., human CD137 or cynomolgus CD137) antibodies or pharmaceutical compositions disclosed herein include, without limitation, a solid tumor, a hematological cancer (e.g., leukemia, lymphoma, myeloma, e.g., multiple myeloma), and a metastatic lesion. In one embodiment, the cancer is a solid tumor. Examples of solid tumors include malignancies, e.g., sarcomas and carcinomas, e.g., adenocarcinomas of the various organ systems, such as those affecting the lung, breast, ovarian, lymphoid, gastrointestinal (e.g., colon), anal, genitals and genitourinary tract (e.g., renal, urothelial, bladder cells, prostate), pharynx, CNS (e.g., brain, neural or glial cells), head and neck, skin (e.g., melanoma), and pancreas, as well as adenocarcinomas which include malignancies such as colon cancers, rectal cancer, renal-cell carcinoma, liver cancer, lung cancer (e.g., non-small cell lung cancer or small cell lung cancer), cancer of the small intestine and cancer of the esophagus. The cancer may be at an early, intermediate, late stage or metastatic cancer.

In one embodiment, the cancer is chosen from lung cancer (e.g., lung adenocarcinoma or non-small cell lung cancer (NSCLC) (e.g., NSCLC with squamous and/or non-squamous histology, or NSCLC adenocarcinoma)), melanoma (e.g., an advanced melanoma), renal cancer (e.g., a renal cell carcinoma), liver cancer (e.g., hepatocellular carcinoma), myeloma (e.g., a multiple myeloma), a prostate cancer, a breast cancer (e.g., a breast cancer that does not express one, two or all of estrogen receptor, progesterone receptor, or Her2/neu, e.g., a triple negative breast cancer), an ovarian cancer, a colorectal cancer, a pancreatic cancer, a head and neck cancer (e.g., head and neck squamous cell carcinoma (HNSCC), anal cancer, gastro-esophageal cancer (e.g., esophageal squamous cell carcinoma), mesothelioma, nasopharyngeal cancer, thyroid cancer, cervical cancer, epithelial cancer, peritoneal cancer, or a lymphoproliferative disease (e.g., a post-transplant lymphoproliferative disease). In a specific embodiment, the cancer is a cervical cancer.

In one embodiment, the cancer is a hematological cancer, for example, a leukemia, a lymphoma, or a myeloma. In one embodiment, the cancer is a leukemia, for example, acute lymphoblastic leukemia (ALL), acute myelogenous leukemia (AML), acute myeloblastic leukemia (AML), chronic lymphocytic leukemia (CLL), chronic myelogenous leukemia (CML), chronic myeloid leukemia (CML), chronic myelomonocytic leukemia (CMML), chronic lymphocytic leukemia (CLL), or hairy cell leukemia. In one embodiment, the cancer is a lymphoma, for example, B cell lymphoma, diffuse large B-cell lymphoma (DLBCL), activated B-cell like (ABC) diffuse large B cell lymphoma, germinal center B cell (GCB) diffuse large B cell lymphoma, mantle cell lymphoma, Hodgkin lymphoma, non-Hodgkin lymphoma, relapsed non-Hodgkin lymphoma, refractory non-Hodgkin lymphoma, recurrent follicular non-Hodgkin lymphoma, Burkitt lymphoma, small lymphocytic lymphoma, follicular lymphoma, lymphoplasmacytic lymphoma, or extranodal marginal zone lymphoma. In one embodiment the cancer is a myeloma, for example, multiple myeloma.

In another embodiment, the cancer is chosen from a carcinoma (e.g., advanced or metastatic carcinoma), melanoma or a lung carcinoma, e.g., a non-small cell lung carcinoma.

In one embodiment, the cancer is a lung cancer, e.g., a lung adenocarcinoma, non-small cell lung cancer or small cell lung cancer.

In one embodiment, the cancer is a melanoma, e.g., an advanced melanoma. In one embodiment, the cancer is an advanced or unresectable melanoma that does not respond to other therapies. In other embodiments, the cancer is a melanoma with a BRAF mutation (e.g., a BRAF V600 mutation). In yet other embodiments, the anti-CD137 (e.g., human CD137 or cynomolgus CD137) antibody or pharmaceutical composition disclosed herein is administered after treatment with an anti-CTLA-4 antibody (e.g., ipilimumab) with or without a BRAF inhibitor (e.g., vemurafenib or dabrafenib).

In another embodiment, the cancer is a hepatocarcinoma, e.g., an advanced hepatocarcinoma, with or without a viral infection, e.g., a chronic viral hepatitis.

In another embodiment, the cancer is a prostate cancer, e.g., an advanced prostate cancer.

In yet another embodiment, the cancer is a myeloma, e.g., multiple myeloma.

In yet another embodiment, the cancer is a renal cancer, e.g., a renal cell carcinoma (RCC) (e.g., a metastatic RCC, clear cell renal cell carcinoma (CCRCC) or kidney papillary cell carcinoma).

In yet another embodiment, the cancer is chosen from a lung cancer, a melanoma, a renal cancer, a breast cancer, a colorectal cancer, a leukemia, or a metastatic lesion of the cancer.

In certain embodiments, the instant disclosure provides a method of preventing or treating an infectious disease in a subject, the method comprising administering to the subject an effective amount of an anti-CD137 (e.g., human CD137 or cynomolgus CD137) antibody or pharmaceutical composition thereof, as disclosed herein. In one embodiment, provided herein are methods for preventing and/or treating an infection (e.g., a viral infection, a bacterial infection, a fungal infection, a protozoal infection, or a parasitic infection). The infection prevented and/or treated in accordance with the methods can be caused by an infectious agent identified herein. In a specific embodiment, an anti-CD137 (e.g., human CD137 or cynomolgus CD137) antibody described herein or a composition thereof is the only active agent administered to a subject. In certain embodiments, an anti-CD137 (e.g., human CD137 or cynomolgus CD137) antibody described herein or a composition thereof is used in combination with anti-infective interventions (e.g., antivirals, antibacterials, antifungals, or anti-helminthics) for the treatment of infectious diseases. Therefore, in a one embodiment, the present invention relates to an antibody and/or pharmaceutical composition of the present invention for use in a method of preventing and/or treating an infectious disease, optionally wherein the antibody or pharmaceutical composition is the only active agent administered to a subject, or wherein the antibody or pharmaceutical composition is used in combination with anti-infective interventions.

Infectious diseases that can be treated and/or prevented by anti-CD137 (e.g., human CD137 or cynomolgus CD137) antibodies or pharmaceutical compositions disclosed herein are caused by infectious agents including but not limited to bacteria, parasites, fungi, protozae, and viruses. In a specific embodiment, the infectious disease treated and/or prevented by anti-CD137 (e.g., human CD137 or cynomolgus CD137) antibodies or pharmaceutical compositions disclosed herein is caused by a virus. Viral diseases or viral infections that can be prevented and/or treated in accordance with the methods described herein include, but are not limited to, those caused by hepatitis type A, hepatitis type B, hepatitis type C, influenza (e.g., influenza A or influenza B), varicella, adenovirus, herpes simplex type I (HSV-I), herpes simplex type II (HSV-II), rinderpest, rhinovirus, echovirus, rotavirus, respiratory syncytial virus, papilloma virus, papova virus, cytomegalovirus, echinovirus, arbovirus, huntavirus, coxsackie virus, mumps virus, measles virus, rubella virus, polio virus, small pox, Epstein Barr virus, human immunodeficiency virus type I (HIV-I), human immunodeficiency virus type II (HIV-II), and agents of viral diseases such as viral meningitis, encephalitis, dengue or small pox.

Bacterial infections that can be prevented and/or treated include infections caused by *Escherichia coli, Klebsiella pneumoniae, Staphylococcus aureus, Enterococcus faecalis, Proteus vulgaris, Staphylococcus viridans*, and *Pseudomonas aeruginosa*. Bacterial diseases caused by bacteria (e.g., *Escherichia coli, Klebsiella pneumoniae, Staphylococcus aureus, Enterococcus faecalis, Proteus vulgaris, Staphylococcus viridans*, and *Pseudomonas aeruginosa*) that can be prevented and/or treated in accordance with the methods described herein include, but are not limited to, *Mycobacteria rickettsia, Mycoplasma, Neisseria, S. pneumonia, Borrelia burgdorferi* (Lyme disease), *Bacillus antracis* (anthrax), tetanus, *Streptococcus, Staphylococcus, mycobacterium*, pertissus, cholera, plague, diptheria, *chlamydia, S. aureus* and *legionella*.

Protozoal diseases or protozoal infections caused by protozoa that can be prevented and/or treated in accordance with the methods described herein include, but are not limited to, *leishmania*, coccidiosis, *trypanosoma schistosoma* or malaria. Parasitic diseases or parasitic infections caused by parasites that can be prevented and/or treated in accordance with the methods described herein include, but are not limited to, *chlamydia* and *rickettsia*.

Fungal diseases or fungal infections that can be prevented and/or treated in accordance with the methods described herein include, but are not limited to, those caused by *Candida* infections, zygomycosis, *Candida* mastitis, progressive disseminated trichosporonosis with latent trichosporonemia, disseminated candidiasis, pulmonary paracoccidioidomycosis, pulmonary aspergillosis, *Pneumocystis carinii* pneumonia, cryptococcal meningitis, coccidioidal meningoencephalitis and cerebrospinal vasculitis, *Aspergillus niger* infection, *Fusarium* keratitis, paranasal sinus mycoses, *Aspergillus fumigatus* endocarditis, tibial dyschondroplasia, *Candida glabrata* vaginitis, oropharyngeal candidiasis, X-linked chronic granulomatous disease, tinea pedis, cutaneous candidiasis, mycotic placentitis, disseminated trichosporonosis, allergic bronchopulmonary aspergillosis, mycotic keratitis, *Cryptococcus neoformans* infection, fungal peritonitis, Curvularia *geniculata* infection, staphylococcal endophthalmitis, sporotrichosis, and dermatophytosis.

In certain embodiments, these methods further comprise administering an additional therapeutic agent to the subject. In certain embodiments, the additional therapeutic agent is a chemotherapeutic, a radiotherapeutic, or a checkpoint targeting agent. In certain embodiments, the chemotherapeutic agent is a hypomethylating agent (e.g., azacitidine). In certain embodiments, the checkpoint targeting agent is selected from the group consisting of an antagonist anti-CTLA-4 antibody, an antagonist anti-PD-L1 antibody, an antagonist anti-PD-L2 antibody, an antagonist anti-PD-1 antibody, an antagonist anti-TIM-3 antibody, an antagonist anti-LAG-3 antibody, an antagonist anti-VISTA antibody, an antagonist anti-CD96 antibody, an antagonist anti-CEACAM1 antibody, an antibody anti-TIGIT antibody, an agonist anti-GITR antibody, and an agonist anti-OX40 antibody.

In one embodiment, the present invention relates to an antibody and/or pharmaceutical composition of the present invention for use in a method of the present invention, wherein the method further comprises administering an additional therapeutic agent to the subject. In one embodiment, the present invention relates to (a) an antibody and/or pharmaceutical composition of the present invention and (b) an additional therapeutic agent for use as a medicament. In one embodiment, the present invention relates to (a) an antibody and/or pharmaceutical composition of the present invention, and (b) an additional therapeutic agent for use in a method for the treatment of cancer. In a further embodiment, the present invention relates to a pharmaceutical composition, kit or kit-of-parts comprising (a) an antibody and/or pharmaceutical composition of the present invention and (b) an additional therapeutic agent. In one embodiment, the additional therapeutic agent is a chemotherapeutic, a radiotherapeutic, or a checkpoint targeting agent.

In certain embodiments, an anti-PD-1 antibody is used in methods disclosed herein. In certain embodiments, the anti-PD-1 antibody is nivolumab, also known as BMS-936558 or MDX1106, developed by Bristol-Myers Squibb. In certain embodiments, the anti-PD-1 antibody is pembrolizumab, also known as lambrolizumab or MK-3475, developed by Merck & Co. In certain embodiments, the anti-PD-1 antibody is pidilizumab, also known as CT-011, developed by CureTech. In certain embodiments, the anti-PD-1 antibody is MEDI0680, also known as AMP-514, developed by Medimmune. In certain embodiments, the anti-PD-1 antibody is PDR001 developed by Novartis Pharmaceuticals. In certain embodiments, the anti-PD-1 antibody is REGN2810 developed by Regeneron Pharmaceuticals. In certain embodiments, the anti-PD-1 antibody is PF-06801591 developed by Pfizer. In certain embodiments, the anti-PD-1 antibody is BGB-A317 developed by BeiGene. In certain embodiments, the anti-PD-1 antibody is TSR-042 developed by AnaptysBio and Tesaro. In certain embodiments, the anti-PD-1 antibody is SHR-1210 developed by Hengrui.

Further non-limiting examples of anti-PD-1 antibodies that may be used in treatment methods disclosed herein are disclosed in the following patents and patent applications, all of which are herein incorporated by reference in their entireties for all purposes: U.S. Pat. Nos. 6,808,710; 7,332,582; 7,488,802; 8,008,449; 8,114,845; 8,168,757; 8,354,509; 8,686,119; 8,735,553; 8,747,847; 8,779,105; 8,927,697; 8,993,731; 9,102,727; 9,205,148; U.S. Publication No. US 2013/0202623 A1; U.S. Publication No. US 2013/0291136 A1; U.S. Publication No. US 2014/0044738 A1; U.S. Publication No. US 2014/0356363 A1; U.S. Publication No. US 2016/0075783 A1; and PCT Publication No. WO 2013/033091 A1; PCT Publication No. WO 2015/036394 A1; PCT Publication No. WO 2014/179664 A2; PCT Publication No. WO 2014/209804 A1; PCT Publication No. WO 2014/206107 A1; PCT Publication No. WO 2015/058573 A1; PCT Publication No. WO 2015/085847 A1; PCT Publication No. WO 2015/200119 A1; PCT Publication No. WO 2016/015685 A1; and PCT Publication No. WO 2016/020856 A1.

In certain embodiments, an anti-PD-L1 antibody is used in methods disclosed herein. In certain embodiments, the anti-PD-L1 antibody is atezolizumab developed by Genentech. In certain embodiments, the anti-PD-L1 antibody is durvalumab developed by AstraZeneca, Celgene and Medimmune. In certain embodiments, the anti-PD-L1 antibody is avelumab, also known as MSB0010718C, developed by Merck Serono and Pfizer. In certain embodiments, the anti-PD-L1 antibody is MDX-1105 developed by Bristol-Myers Squibb. In certain embodiments, the anti-PD-L1 antibody is AMP-224 developed by Amplimmune and GSK.

Non-limiting examples of anti-PD-L1 antibodies that may be used in treatment methods disclosed herein are disclosed in the following patents and patent applications, all of which are herein incorporated by reference in their entireties for all purposes: U.S. Pat. Nos. 7,943,743; 8,168,179; 8,217,149; 8,552,154; 8,779,108; 8,981,063; 9,175,082; U.S. Publication No. US 2010/0203056 A1; U.S. Publication No. US 2003/0232323 A1; U.S. Publication No. US 2013/0323249 A1; U.S. Publication No. US 2014/0341917 A1; U.S. Publication No. US 2014/0044738 A1; U.S. Publication No. US 2015/0203580 A1; U.S. Publication No. US 2015/0225483 A1; U.S. Publication No. US 2015/0346208 A1; U.S. Publication No. US 2015/0355184 A1; and PCT Publication No. WO 2014/100079 A1; PCT Publication No. WO 2014/022758 A1; PCT Publication No. WO 2014/055897 A2; PCT Publication No. WO 2015/061668 A1; PCT Publication No. WO 2015/109124 A1; PCT Publication No. WO 2015/195163 A1; PCT Publication No. WO 2016/000619 A1; and PCT Publication No. WO 2016/030350 A1.

In certain embodiments, an anti-CD137 (e.g., human CD137 or cynomolgus CD137) antibody disclosed herein is administered to a subject in combination with a compound that targets an immunomodulatory enzyme(s) such as IDO (indoleamine-(2,3)-dioxygenase) and/or TDO (tryptophan 2,3-dioxygenase). Therefore, in one embodiment, the additional therapeutic agent is a compound that targets an immunomodulatory enzyme(s), such as an inhibitor of indoleamine-(2,3)-dioxygenase (IDO). In certain embodiments, such compound is selected from the group consisting of epacadostat (Incyte Corp; see, e.g., WO 2010/005958 which is herein incorporated by reference in its entirety), F001287 (Flexus Biosciences/Bristol-Myers Squibb), indoximod (NewLink Genetics), and NLG919 (NewLink Genetics). In one embodiment, the compound is epacadostat. In another embodiment, the compound is F001287. In another embodiment, the compound is indoximod. In another embodiment, the compound is NLG919. In a specific embodiment, an anti-CD137 (e.g., human CD137) antibody disclosed herein is administered to a subject in combination with an IDO inhibitor for treating cancer. The IDO inhibitor as described herein for use in treating cancer is present in a solid dosage form of a pharmaceutical composition such as a tablet, a pill or a capsule, wherein the pharmaceutical composition includes an IDO inhibitor and a pharmaceutically acceptable excipient. As such, the antibody as described herein and the IDO inhibitor as described herein can be administered separately, sequentially or concurrently as separate dosage forms. In one embodiment, the antibody is administered parenterally, and the IDO inhibitor is administered orally. In particular embodiments, the inhibitor is selected from the group consisting of epacadostat (Incyte Corporation), F001287 (Flexus Biosciences/Bristol-Myers Squibb), indoximod (NewLink Genetics), and NLG919 (NewLink Genetics). Epacadostat has been described in PCT Publication No. WO 2010/005958, which is herein incorporated by reference in its entirety for all purposes. In one embodiment, the inhibitor is epacadostat. In another embodiment, the inhibitor is F001287. In another embodiment, the inhibitor is indoximod. In another embodiment, the inhibitor is NLG919.

In certain embodiments, an anti-CD137 (e.g., human CD137 or cynomolgus CD137) antibody disclosed herein is administered to a subject in combination with a vaccine. The vaccine can be, e.g., a peptide vaccine, a DNA vaccine, or an RNA vaccine. In certain embodiments, the vaccine is a heat shock protein based tumor vaccine or a heat shock protein based pathogen vaccine. In a specific embodiment, an anti-CD137 (e.g., human CD137 or cynomolgus CD137) antibody disclosed herein is administered to a subject in combination with a heat shock protein based tumor-vaccine. Heat shock proteins (HSPs) are a family of highly conserved proteins found ubiquitously across all species. Their expression can be powerfully induced to much higher levels as a result of heat shock or other forms of stress, including exposure to toxins, oxidative stress or glucose deprivation. Five families have been classified according to molecular weight: HSP-110, -90, -70, -60 and -28. HSPs deliver immunogenic peptides through the cross-presentation pathway in antigen presenting cells (APCs) such as macrophages and dendritic cells (DCs), leading to T cell activation. HSPs function as chaperone carriers of tumor-associated antigenic peptides forming complexes able to induce tumor-specific immunity. Upon release from dying tumor cells, the HSP-antigen complexes are taken up by antigen-presenting cells (APCs) wherein the antigens are processed into peptides that bind MHC class I and class II molecules leading to the activation of anti-tumor CD8+ and CD4+ T cells. The immunity elicited by HSP complexes derived from tumor preparations is specifically directed against the unique antigenic peptide repertoire expressed by the cancer of each subject. Therefore, in one embodiment, the present invention relates to (a) an antibody and/or pharmaceutical composition of the present invention and (b) a vaccine for use as a medicament, for example for use in a method for the treatment of cancer. In one embodiment, the present invention relates to a pharmaceutical composition, kit or kit-of-parts comprising (a) an antibody and/or pharmaceutical composition of the present invention and (b) a vaccine. In one embodiment, the vaccine is a heat shock protein based tumor vaccine. In one embodiment, the vaccine is a heat shock protein based pathogen vaccine. In certain embodiments, the vaccine is as described in WO 2016/183486, incorporated herein by reference in its entirety.

A heat shock protein peptide complex (HSPPC) is a protein peptide complex consisting of a heat shock protein non-covalently complexed with antigenic peptides. HSPPCs elicit both innate and adaptive immune responses. In a specific embodiment, the antigenic peptide(s) displays antigenicity for the cancer being treated. HSPPCs are efficiently seized by APCs via membrane receptors (mainly CD91) or by binding to Toll-like receptors. HSPPC internalization results in functional maturation of the APCs with chemokine and cytokine production leading to activation of natural killer cells (NK), monocytes and Th1 and Th-2-mediated immune responses. In certain embodiments, HSPPCs used in methods disclosed herein comprise one or more heat shock proteins from the hsp60, hsp70, or hsp90 family of stress proteins complexed with antigenic peptides. In certain embodiments, HSPPCs comprise hsc70, hsp70, hsp90, hsp110, grp170, gp96, calreticulin, or combinations of two or more thereof.

In a specific embodiment, the heat shock protein peptide complex (HSPPC) comprises recombinant heat shock proteins (e.g., hsp70 or hsc70) or a peptide-binding domain thereof complexed with recombinant antigenic peptides. Recombinant heat shock proteins can be produced by recombinant DNA technology, for example, using human hsc70 sequence as described in Dworniczak and Mirault, Nucleic Acids Res. 15:5181-5197 (1987) and GenBank accession no. P11142 and/or Y00371, each of which is incorporated herein by reference in its entirety. In certain embodiments, Hsp70 sequences are as described in Hunt and Morimoto Proc. Natl. Acad. Sci. U.S.A. 82 (19), 6455-6459 (1985) and GenBank accession no. P0DMV8 and/or M11717, each of which is incorporated herein by reference in its entirety. Antigenic peptides can also be prepared by recombinant DNA methods known in the art.

In certain embodiments, the antigenic peptides comprise a modified amino acid. In certain embodiments, the modified amino acid comprises a post-translational modification. In certain embodiments, the modified amino acid comprises a mimetic of a post-translational modification. In certain embodiments, the modified amino acid is a Tyr, Ser, Thr, Arg, Lys, or His that has been phosphorylated on a side chain hydroxyl or amine. In certain embodiments, the modified amino acid is a mimetic of a Tyr, Ser, Thr, Arg, Lys, or His amino acid that has been phosphorylated on a side chain hydroxyl or amine.

In a specific embodiment, an anti-CD137 (e.g., human CD137 or cynomolgus CD137) antibody disclosed herein is administered to a subject in combination with a heat shock protein peptide complex (HSPPC), e.g., heat shock protein peptide complex-96 (HSPPC-96), to treat cancer. HSPPC-96 comprises a 96 kDa heat shock protein (Hsp), gp96, complexed to antigenic peptides. HSPPC-96 is a cancer immunotherapy manufactured from a subject's tumor and contains the cancer's antigenic "fingerprint." In certain embodiments, this fingerprint contains unique antigens that are present only in that particular subject's specific cancer cells and injection of the vaccine is intended to stimulate the subject's immune system to recognize and attack any cells with the specific cancer fingerprint. Therefore, in one embodiment, the present invention relates to an antibody and/or pharmaceutical composition of the present invention in combination with a heat shock protein peptide complex (HSPPC) for use as a medicament and/or for use in a method for the treatment of cancer.

In certain embodiments, the HSPPC, e.g., HSPPC-96, is produced from the tumor tissue of a subject. In a specific embodiment, the HSPPC (e.g., HSPPC-96) is produced from a tumor of the type of cancer or metastasis thereof being treated. In another specific embodiment, the HSPPC (e.g., HSPPC-96) is autologous to the subject being treated. In certain embodiments, the tumor tissue is non-necrotic tumor tissue. In certain embodiments, at least 1 gram (e.g., at least 1, at least 2, at least 3, at least 4, at least 5, at least 6, at least 7, at least 8, at least 9, or at least 10 grams) of non-necrotic tumor tissue is used to produce a vaccine regimen. In certain embodiments, after surgical resection, non-necrotic tumor tissue is frozen prior to use in vaccine preparation. In certain embodiments, the HSPPC, e.g., HSPPC-96, is isolated from the tumor tissue by purification techniques, filtered and prepared for an injectable vaccine. In certain embodiments, a subject is administered 6-12 doses of the HSPPC, e.g., HSPCC-96. In such embodiments, the HSPPC, e.g., HSPPC-96, doses may be administered weekly for the first 4 doses and then biweekly for the 2-8 additional doses.

Further examples of HSPPCs that may be used in accordance with the methods described herein are disclosed in the following patents and patent applications, all of which are herein incorporated by reference in their entireties: U.S. Pat. Nos. 6,391,306, 6,383,492, 6,403,095, 6,410,026, 6,436,404, 6,447,780, 6,447,781 and 6,610,659.

In certain embodiments, an anti-CD137 (e.g., human CD137 or cynomolgus CD137) antibody disclosed herein is administered to a subject in combination with an adjuvant. Various adjuvants can be used depending on the treatment context. Non-limiting examples of appropriate adjuvants include, but not limited to, Complete Freund's Adjuvant (CFA), Incomplete Freund's Adjuvant (IFA), montanide ISA (incomplete Seppic adjuvant), the Ribi adjuvant system (RAS), Titer Max, muramyl peptides, Syntex Adjuvant Formulation (SAF), alum (aluminum hydroxide and/or aluminum phosphate), aluminum salt adjuvants, Gerbu® adjuvants, nitrocellulose absorbed antigen, encapsulated or entrapped antigen, 3 De-O-acylated monophosphoryl lipid A (3 D-MPL), immunostimulatory oligonucleotides, toll-like receptor (TLR) ligands, mannan-binding lectin (MBL) ligands, STING agonists, immuno-stimulating complexes such as saponins, Quil A, QS-21, QS-7, ISCOMATRIX, and others. Other adjuvants include CpG oligonucleotides and double stranded RNA molecules, such as poly(A) and poly (U). Combinations of the above adjuvants may also be used. See, e.g., U.S. Pat. Nos. 6,645,495; 7,029,678; and 7,858,589, all of which are incorporated herein by reference in their entireties. In one embodiment, the adjuvant used herein is QS-21 STIMULON.

In certain embodiments, an anti-CD137 (e.g., human CD137 or cynomolgus CD137) antibody disclosed herein is administered to a subject in combination with an additional therapeutic agent comprising a TCR. In certain embodiments, the additional therapeutic agent is a soluble TCR. In certain embodiments, the additional therapeutic agent is a cell expressing a TCR. Therefore, in one embodiment, the present invention relates to an antibody and/or pharmaceutical composition of the present invention in combination with an additional therapeutic agent comprising a TCR for use as a medicament and/or for use in a method for the treatment of cancer.

In certain embodiments, an anti-CD137 (e.g., human CD137 or cynomolgus CD137) antibody disclosed herein is administered to a subject in combination with a cell expressing a chimeric antigen receptor (CAR). In certain embodiments, the cell is a T cell.

In certain embodiments, an anti-CD137 (e.g., human CD137 or cynomolgus CD137) antibody disclosed herein is administered to a subject in combination with a TCR mimic antibody. In certain embodiments, the TCR mimic antibody is an antibody that specifically binds to a peptide-MHC complex. For non-limiting examples of TCR mimic antibodies, see, e.g., U.S. Pat. No. 9,074,000 and U.S. Publication Nos. US 2009/0304679 A1 and US 2014/0134191 A1, all of which are incorporated herein by reference in their entireties.

In certain embodiments, an anti-CD137 (e.g., human CD137 or cynomolgus CD137) antibody disclosed herein is administered to a subject in combination with a bispecific T-cell engager (BiTE) (e.g., as described in WO2005061547A2, which is incorporated by reference herein in its entirety) and/or a dual-affinity re-targeting antibody (DART) (e.g., as described in WO2012162067A2, which is incorporated by reference herein in its entirety). In certain embodiments, the BiTE and/or DART specifically binds to a tumor-associated antigen (e.g., a polypeptide overexpressed in a tumor, a polypeptide derived from an oncovirus, a polypeptide comprising a post-translational modification specific to a tumor, a polypeptide specifically mutated in a tumor) and a molecule on an effector cell (e.g., CD3 or CD16). In certain embodiments, the tumor-associated antigen is EGFR (e.g., human EGFR), Her2 (e.g., human Her2), or CD20 (e.g., human CD20).

The anti-CD137 (e.g., human CD137 or cynomolgus CD137) antibody and the additional therapeutic agent (e.g., chemotherapeutic, radiotherapeutic, checkpoint targeting agent, IDO inhibitor, vaccine, adjuvant, a soluble TCR, a cell expressing a TCR, a cell expressing a chimeric antigen receptor, and/or a TCR mimic antibody) can be administered separately, sequentially or concurrently as separate dosage forms. In one embodiment, an anti-CD137 (e.g., human CD137 or cynomolgus CD137) antibody is administered parenterally, and an IDO inhibitor is administered orally.

An antibody or pharmaceutical composition described herein may be delivered to a subject by a variety of routes. These include, but are not limited to, parenteral, intranasal, intratracheal, oral, intradermal, topical, intramuscular, intraperitoneal, transdermal, intravenous, intratumoral, conjunctival, intra-arterial, and subcutaneous routes. Pulmonary administration can also be employed, e.g., by use of an inhaler or nebulizer, and formulation with an aerosolizing agent for use as a spray. In certain embodiments, the antibody or pharmaceutical composition described herein is delivered subcutaneously or intravenously. In certain embodiments, the antibody or pharmaceutical composition described herein is delivered intra-arterially. In certain embodiments, the antibody or pharmaceutical composition described herein is delivered intratumorally. In certain embodiments, the antibody or pharmaceutical composition described herein is delivered into a tumor draining lymph node.

The amount of an antibody or composition which will be effective in the treatment and/or prevention of a condition will depend on the nature of the disease, and can be determined by standard clinical techniques.

The precise dose to be employed in a composition will also depend on the route of administration, and the seriousness of the infection or disease caused by it, and should be decided according to the judgment of the practitioner and each subject's circumstances. For example, effective doses may also vary depending upon means of administration, target site, physiological state of the patient (including age, body weight and health), whether the patient is human or an animal, other medications administered, or whether treatment is prophylactic or therapeutic. Usually, the patient is a human, but non-human mammals, including transgenic mammals, can also be treated. Treatment dosages are optimally titrated to optimize safety and efficacy.

An anti-CD137 (e.g., human CD137 or cynomolgus CD137) antibody described herein can also be used to assay CD137 (e.g., human CD137 or cynomolgus CD137) protein levels in a biological sample using classical immunohistological methods known to those of skill in the art, including immunoassays, such as the enzyme linked immunosorbent assay (ELISA), immunoprecipitation, or Western blotting. Suitable antibody assay labels are known in the art and include enzyme labels, such as, glucose oxidase; radioisotopes, such as iodine ($^{125}$I, $^{121}$I), carbon ($^{14}$C), sulfur ($^{35}$S), tritium ($^{3}$H), indium ($^{121}$In), and technetium ($^{99}$Tc); luminescent labels, such as luminol; and fluorescent labels, such as fluorescein and rhodamine, and biotin. Such labels can be used to label an antibody described herein. Alternatively, a second antibody that recognizes an anti-CD137 (e.g., human CD137 or cynomolgus CD137) antibody described herein can be labeled and used in combination with an anti-CD137 (e.g., human CD137 or cynomolgus CD137) antibody to detect CD137 (e.g., human CD137 or cynomolgus CD137) protein levels. Therefore, in one embodiment, the present invention relates to the use of an antibody of the present invention for in vitro detection of CD137 (e.g., human CD137 or cynomolgus CD137) protein in a biological sample. In a further embodiment, the present invention relates to the use of an anti-CD137 antibody of the invention, for assaying and/or detecting CD137 (e.g., human CD137 or cynomolgus CD137) protein levels in a biological sample in vitro, optionally wherein the anti-CD137 antibody is conjugated to a radionuclide or detectable label, and/or carries a label described herein, and/or wherein an immunohistological method is used.

Assaying for the expression level of CD137 (e.g., human CD137 or cynomolgus CD137) protein is intended to include qualitatively or quantitatively measuring or estimating the level of CD137 (e.g., human CD137 or cynomolgus CD137) protein in a first biological sample either directly (e.g., by determining or estimating absolute protein level) or relatively (e.g., by comparing to the disease associated protein level in a second biological sample). CD137 (e.g., human CD137 or cynomolgus CD137) polypeptide expression level in the first biological sample can be measured or estimated and compared to a standard CD137 (e.g., human CD137 or cynomolgus CD137) protein level, the standard being taken, for example, from a second biological sample obtained from an individual not having the disorder or being determined by averaging levels from a population of individuals not having the disorder. As will be appreciated in the art, once the "standard" CD137 (e.g., human CD137 or cynomolgus CD137) polypeptide level is known, it can be used repeatedly as a standard for comparison. Therefore, in a further embodiment, the present invention relates to an in vitro method for assaying and/or detecting CD137 protein levels, for example human CD137 protein levels, in a biological sample, comprising qualitatively or quantitatively measuring or estimating the level of CD137 protein, for example of human CD137 protein, in a biological sample, by an immunohistological method.

As used herein, the term "biological sample" refers to any biological sample obtained from a subject, cell line, tissue, or other source of cells potentially expressing CD137 (e.g., human CD137 or cynomolgus CD137). Methods for obtaining tissue biopsies and body fluids from animals (e.g., humans or cynomolgus monkeys) are well known in the art. Biological samples include peripheral mononuclear blood cells.

An anti-CD137 (e.g., human CD137 or cynomolgus CD137) antibody described herein can be used for prognostic, diagnostic, monitoring and screening applications, including in vitro and in vivo applications well known and standard to the skilled artisan and based on the present description. Prognostic, diagnostic, monitoring and screening assays and kits for in vitro assessment and evaluation of immune system status and/or immune response may be utilized to predict, diagnose and monitor to evaluate patient samples including those known to have or suspected of having an immune system-dysfunction or with regard to an anticipated or desired immune system response, antigen response or vaccine response. The assessment and evaluation of immune system status and/or immune response is also useful in determining the suitability of a patient for a clinical trial of a drug or for the administration of a particular chemotherapeutic agent, a radiotherapeutic agent, or an antibody, including combinations thereof, versus a different agent or antibody. This type of prognostic and diagnostic monitoring and assessment is already in practice utilizing antibodies against the HER2 protein in breast cancer (HercepTest™, Dako) where the assay is also used to evaluate patients for antibody therapy using Herceptin®. In vivo applications include directed cell therapy and immune system modulation and radio imaging of immune responses. Therefore, in one embodiment, the present invention relates to an anti-CD137 antibody and/or pharmaceutical composition of the present invention for use as a diagnostic. In one embodiment, the present invention relates to an anti-CD137 antibody and/or pharmaceutical composition of the present invention for use in a method for the prediction, diagnosis and/or monitoring of a subject having or suspected to have an immune system-dysfunction and/or with regard to an anticipated or desired immune system response, antigen response or vaccine response. In another embodiment, the present invention relates to the use of anti-CD137 antibody of the invention, for predicting, diagnosing and/or monitoring of a subject having or suspected to have an immune system-dysfunction and/or with regard to an anticipated or desired immune system response, antigen response or vaccine response by assaying and/or detecting human CD137 protein levels in a biological sample of the subject in vitro.

In one embodiment, an anti-CD137 (e.g., human CD137 or cynomolgus CD137) antibody can be used in immunohistochemistry of biopsy samples. In one embodiment, the method is an in vitro method. In another embodiment, an anti-CD137 (e.g., human CD137 or cynomolgus CD137) antibody can be used to detect levels of CD137 (e.g., human CD137 or cynomolgus CD137), or levels of cells which contain CD137 (e.g., human CD137 or cynomolgus CD137) on their membrane surface, the levels of which can then be linked to certain disease symptoms. Anti-CD137 (e.g., human CD137 or cynomolgus CD137) antibodies described herein may carry a detectable or functional label and/or may be conjugated to a radionuclide or detectable label. When fluorescence labels are used, currently available microscopy and fluorescence-activated cell sorter analysis (FACS) or combination of both methods procedures known in the art may be utilized to identify and to quantitate the specific binding members. Anti-CD137 (e.g., human CD137 or cynomolgus CD137) antibodies described herein may carry or may be conjugated to a fluorescence label. Exemplary fluorescence labels include, for example, reactive and conjugated probes, e.g., Aminocoumarin, Fluorescein and Texas red, Alexa Fluor dyes, Cy dyes and DyLight dyes. An anti-CD137 (e.g., human CD137 or cynomolgus CD137) antibody may carry or may be conjugated to a radioactive label or radionuclide, such as the isotopes $^{3}H$, $^{14}C$, $^{32}P$, $^{35}S$, $^{36}Cl$, $^{51}Cr$, $^{57}Co$, $^{58}Co$, $^{59}Fe$, $^{67}Cu$, $^{90}Y$, $^{99}Tc$, $^{111}In$, $^{117}Lu$, $^{121}I$, $^{124}I$, $^{125}I$, $^{131}I$, $^{198}Au$, $^{211}At$, $^{213}Bi$, $^{225}Ac$ and $^{186}Re$. When radioactive labels are used, currently available counting procedures known in the art may be utilized to identify and quantitate the specific binding of anti-CD137 (e.g., human CD137 or cynomolgus CD137) antibody to CD137 (e.g., human CD137 or cynomolgus CD137). In the instance where the label is an enzyme, detection may be accomplished by any of the presently utilized colorimetric, spectrophotometric, fluoro spectrophotometric, amperometric or gasometric techniques as known in the art. This can be achieved by contacting a sample or a control sample with an anti-CD137 (e.g., human CD137 or cynomolgus CD137) antibody under conditions that allow for the formation of a complex between the antibody and CD137 (e.g., human CD137 or cynomolgus CD137). Any complexes formed between the antibody and CD137 (e.g., human CD137 or cynomolgus CD137) are detected and compared in the sample and the control. In light of the specific binding of the antibodies described herein for CD137 (e.g., human CD137 or cynomolgus CD137), the antibodies can be used to specifically detect CD137 (e.g., human CD137 or cynomolgus CD137) expression on the surface of cells. The antibodies described herein can also be used to purify CD137 (e.g., human CD137 or cynomolgus CD137) via immunoaffinity purification. Also included herein is an assay system which may be prepared in the form of a test kit, kit, or kit-of-parts for the quantitative analysis of the extent of the presence of, for instance, CD137 (e.g., human CD137 or cynomolgus CD137) or CD137 (e.g., human CD137 or cynomolgus CD137)/CD137 (e.g., human CD137 or cynomolgus CD137) ligand complexes. The system, test kit, kit or kit-of-parts may comprise a labeled component, e.g., a labeled antibody, and one or more additional immunochemical reagents.

5.5 Polynucleotides, Vectors and Methods of Producing Anti-CD137 Antibodies

In another aspect, provided herein are polynucleotides comprising a nucleotide sequence encoding an antibody described herein or a fragment thereof (e.g., a light chain variable region and/or heavy chain variable region) that specifically binds to a CD137 (e.g., human CD137 or cynomolgus CD137) antigen, and vectors, e.g., vectors comprising such polynucleotides for recombinant expression in host cells (e.g., E. coli and mammalian cells). Provided herein are polynucleotides comprising nucleotide sequences encoding a heavy and/or light chain of any of the antibodies provided herein, as well as vectors comprising such polynucleotide sequences, e.g., expression vectors for their efficient expression in host cells, e.g., mammalian cells.

As used herein, an "isolated" polynucleotide or nucleic acid molecule is one which is separated from other nucleic acid molecules which are present in the natural source (e.g., in a mouse or a human) of the nucleic acid molecule. Moreover, an "isolated" nucleic acid molecule, such as a cDNA molecule, can be substantially free of other cellular material, or culture medium when produced by recombinant techniques, or substantially free of chemical precursors or other chemicals when chemically synthesized. For example, the language "substantially free" includes preparations of polynucleotide or nucleic acid molecule having less than about 15%, 10%, 5%, 2%, 1%, 0.5%, or 0.1% (in particular less than about 10%) of other material, e.g., cellular material, culture medium, other nucleic acid molecules, chemical precursors and/or other chemicals. In a specific embodiment, a nucleic acid molecule(s) encoding an antibody described herein is isolated or purified.

In particular aspects, provided herein are polynucleotides comprising nucleotide sequences encoding antibodies, which specifically bind to a CD137 (e.g., human CD137 or cynomolgus CD137) polypeptide and comprises an amino acid sequence as described herein, as well as antibodies which compete with such antibodies for binding to a CD137 (e.g., human CD137 or cynomolgus CD137) polypeptide (e.g., in a dose-dependent manner), or which binds to the same epitope as that of such antibodies.

In certain aspects, provided herein are polynucleotides comprising a nucleotide sequence encoding the light chain or heavy chain of an antibody described herein. The polynucleotides can comprise nucleotide sequences encoding a light chain comprising the VL FRs and CDRs of antibodies described herein (see, e.g., Table 1) or nucleotide sequences encoding a heavy chain comprising the VH FRs and CDRs of antibodies described herein (see, e.g., Table 1).

Also provided herein are polynucleotides encoding an anti-CD137 (e.g., human CD137 or cynomolgus CD137) antibody that are optimized, e.g., by codon/RNA optimization, replacement with heterologous signal sequences, and elimination of mRNA instability elements. Methods to generate optimized nucleic acids encoding an anti-CD137 (e.g., human CD137 or cynomolgus CD137) antibody or a fragment thereof (e.g., light chain, heavy chain, VH domain, or VL domain) for recombinant expression by introducing codon changes and/or eliminating inhibitory regions in the mRNA can be carried out by adapting the optimization methods described in, e.g., U.S. Pat. Nos. 5,965,726; 6,174,666; 6,291,664; 6,414,132; and 6,794,498, accordingly, all of which are herein incorporated by reference in their entireties. For example, potential splice sites and instability elements (e.g., A/T or A/U rich elements) within the RNA can be mutated without altering the amino acids encoded by the nucleic acid sequences to increase stability of the RNA for recombinant expression. The alterations utilize the degeneracy of the genetic code, e.g., using an alternative codon for an identical amino acid. In certain embodiments, it can be desirable to alter one or more codons to encode a conservative mutation, e.g., a similar amino acid with similar chemical structure and properties and/or function as the original amino acid. Such methods can increase expression of an anti-CD137 (e.g., human CD137 or cynomolgus CD137) antibody or fragment thereof by at least 1 fold, 2 fold, 3 fold, 4 fold, 5 fold, 10 fold, 20 fold, 30 fold, 40 fold, 50 fold, 60 fold, 70 fold, 80 fold, 90 fold, or 100 fold or more relative to the expression of an anti-CD137 (e.g., human CD137 or cynomolgus CD137) antibody encoded by polynucleotides that have not been optimized.

In certain embodiments, an optimized polynucleotide sequence encoding an anti-CD137 (e.g., human CD137 or cynomolgus CD137) antibody described herein or a fragment thereof (e.g., VL domain and/or VH domain) can hybridize to an antisense (e.g., complementary) polynucleotide of an unoptimized polynucleotide sequence encoding an anti-CD137 (e.g., human CD137 or cynomolgus CD137) antibody described herein or a fragment thereof (e.g., VL domain and/or VH domain). In specific embodiments, an optimized nucleotide sequence encoding an anti-CD137 (e.g., human CD137 or cynomolgus CD137) antibody described herein or a fragment hybridizes under high stringency conditions to antisense polynucleotide of an unoptimized polynucleotide sequence encoding an anti-CD137 (e.g., human CD137 or cynomolgus CD137) antibody described herein or a fragment thereof. In a specific embodiment, an optimized nucleotide sequence encoding an anti-CD137 (e.g., human CD137 or cynomolgus CD137) antibody described herein or a fragment thereof hybridizes under high stringency, intermediate or lower stringency hybridization conditions to an antisense polynucleotide of an unoptimized nucleotide sequence encoding an anti-CD137 (e.g., human CD137 or cynomolgus CD137) antibody described herein or a fragment thereof. Information regarding hybridization conditions has been described, see, e.g., U.S. Patent Application Publication No. US 2005/0048549 (e.g., paragraphs 72-73), which is herein incorporated by reference in its entirety.

The polynucleotides can be obtained, and the nucleotide sequence of the polynucleotides determined, by any method known in the art. Nucleotide sequences encoding antibodies described herein, e.g., antibodies described in Table 1, and modified versions of these antibodies can be determined using methods well known in the art, i.e., nucleotide codons known to encode particular amino acids are assembled in such a way to generate a nucleic acid that encodes the antibody. Such a polynucleotide encoding the antibody can be assembled from chemically synthesized oligonucleotides (e.g., as described in Kutmeier G et al., (1994), BioTechniques 17: 242-6, herein incorporated by reference in its entirety), which, briefly, involves the synthesis of overlapping oligonucleotides containing portions of the sequence encoding the antibody, annealing and ligating of those oligonucleotides, and then amplification of the ligated oligonucleotides by PCR.

Alternatively, a polynucleotide encoding an antibody described herein can be generated from nucleic acid from a suitable source (e.g., a hybridoma) using methods well known in the art (e.g., PCR and other molecular cloning methods). For example, PCR amplification using synthetic primers hybridizable to the 3' and 5' ends of a known sequence can be performed using genomic DNA obtained from hybridoma cells producing the antibody of interest. Such PCR amplification methods can be used to obtain nucleic acids comprising the sequence encoding the light chain and/or heavy chain of an antibody. Such PCR amplification methods can be used to obtain nucleic acids comprising the sequence encoding the variable light chain region and/or the variable heavy chain region of an antibody. The amplified nucleic acids can be cloned into vectors for expression in host cells and for further cloning, for example, to generate chimeric and humanized antibodies.

If a clone containing a nucleic acid encoding a particular antibody is not available, but the sequence of the antibody molecule is known, a nucleic acid encoding the immunoglobulin can be chemically synthesized or obtained from a suitable source (e.g., an antibody cDNA library or a cDNA library generated from, or nucleic acid, preferably poly A+RNA, isolated from, any tissue or cells expressing the antibody, such as hybridoma cells selected to express an antibody described herein) by PCR amplification using synthetic primers hybridizable to the 3' and 5' ends of the sequence or by cloning using an oligonucleotide probe specific for the particular gene sequence to identify, e.g., a cDNA clone from a cDNA library that encodes the antibody. Amplified nucleic acids generated by PCR can then be cloned into replicable cloning vectors using any method well known in the art.

DNA encoding anti-CD137 (e.g., human CD137 or cynomolgus CD137) antibodies described herein can be readily isolated and sequenced using conventional procedures (e.g., by using oligonucleotide probes that are capable of binding specifically to genes encoding the heavy and light chains of the anti-CD137 (e.g., human CD137 or cynomolgus CD137) antibodies). Hybridoma cells can serve as a source of such DNA. Once isolated, the DNA can be placed into expression vectors, which are then transfected into host cells such as E. coli cells, simian COS cells, Chinese hamster ovary (CHO) cells (e.g., CHO cells from the CHO GS System™ (Lonza)), or myeloma cells that do not otherwise produce immunoglobulin protein, to obtain the synthesis of anti-CD137 (e.g., human CD137 or cynomolgus CD137) antibodies in the recombinant host cells.

To generate whole antibodies, PCR primers including VH or VL nucleotide sequences, a restriction site, and a flanking sequence to protect the restriction site can be used to amplify the VH or VL sequences in scFv clones. Utilizing cloning techniques known to those of skill in the art, the PCR amplified VH domains can be cloned into vectors expressing a heavy chain constant region, e.g., the human gamma 4 constant region, and the PCR amplified VL domains can be cloned into vectors expressing a light chain constant region, e.g., human kappa or lambda constant regions. In certain embodiments, the vectors for expressing the VH or VL domains comprise an EF-1α promoter, a secretion signal, a cloning site for the variable region, constant domains, and a selection marker such as neomycin. The VH and VL domains can also be cloned into one vector expressing the necessary constant regions. The heavy chain conversion vectors and light chain conversion vectors are then co-transfected into cell lines to generate stable or transient cell lines that express full-length antibodies, e.g., IgG, using techniques known to those of skill in the art.

The DNA also can be modified, for example, by substituting the coding sequence for human heavy and light chain constant domains in place of the murine sequences, or by covalently joining to the immunoglobulin coding sequence all or part of the coding sequence for a non-immunoglobulin polypeptide.

Also provided are polynucleotides that hybridize under high stringency, intermediate or lower stringency hybridization conditions to polynucleotides that encode an antibody described herein. In specific embodiments, polynucleotides described herein hybridize under high stringency, intermediate or lower stringency hybridization conditions to polynucleotides encoding a VH domain and/or VL domain provided herein.

Hybridization conditions have been described in the art and are known to one of skill in the art. For example, hybridization under stringent conditions can involve hybridization to filter-bound DNA in 6× sodium chloride/sodium citrate (SSC) at about 45° C. followed by one or more washes in 0.2×SSC/0.1% SDS at about 50-65° C.; hybridization under highly stringent conditions can involve hybridization to filter-bound nucleic acid in 6×SSC at about 45° C. followed by one or more washes in 0.1×SSC/0.2% SDS at about 68° C. Hybridization under other stringent hybridization conditions are known to those of skill in the art and have been described, see, for example, Ausubel F M et al., eds., (1989) Current Protocols in Molecular Biology, Vol. I, Green Publishing Associates, Inc. and John Wiley & Sons, Inc., New York at pages 6.3.1-6.3.6 and 2.10.3, which is herein incorporated by reference in its entirety.

In certain aspects, provided herein are cells (e.g., host cells) expressing (e.g., recombinantly) antibodies described herein which specifically bind to CD137 (e.g., human CD137 or cynomolgus CD137) and related polynucleotides and expression vectors. Provided herein are vectors (e.g., expression vectors) comprising polynucleotides comprising nucleotide sequences encoding anti-CD137 (e.g., human CD137 or cynomolgus CD137) antibodies or a fragment for recombinant expression in host cells, preferably in mammalian cells (e.g., CHO cells). Also provided herein are host cells comprising such vectors for recombinantly expressing anti-CD137 (e.g., human CD137 or cynomolgus CD137) antibodies described herein (e.g., human or humanized antibody). In a particular aspect, provided herein are methods for producing an antibody described herein, comprising expressing such antibody from a host cell.

Recombinant expression of an antibody described herein (e.g., a full-length antibody, heavy and/or light chain of an antibody, or a single chain antibody described herein) that specifically binds to CD137 (e.g., human CD137 or cynomolgus CD137) generally involves construction of an expression vector containing a polynucleotide that encodes the antibody. Once a polynucleotide encoding an antibody molecule, heavy and/or light chain of an antibody, or a fragment thereof (e.g., heavy and/or light chain variable regions) described herein has been obtained, the vector for the production of the antibody molecule can be produced by recombinant DNA technology using techniques well known in the art. Thus, methods for preparing a protein by expressing a polynucleotide containing an antibody or antibody fragment (e.g., light chain or heavy chain) encoding nucleotide sequence are described herein. Methods which are well known to those skilled in the art can be used to construct expression vectors containing antibody or antibody fragment (e.g., light chain or heavy chain) coding sequences and appropriate transcriptional and translational control signals. These methods include, for example, in vitro recombinant DNA techniques, synthetic techniques, and in vivo genetic recombination. Also provided are replicable vectors comprising a nucleotide sequence encoding an antibody molecule described herein, a heavy or light chain of an antibody, a heavy or light chain variable region of an antibody or a fragment thereof, or a heavy or light chain CDR, operably linked to a promoter. Such vectors can, for example, include the nucleotide sequence encoding the constant region of the antibody molecule (see, e.g., International Publication Nos. WO 86/05807 and WO 89/01036; and U.S. Pat. No. 5,122, 464, which are herein incorporated by reference in their entireties) and variable regions of the antibody can be cloned into such a vector for expression of the entire heavy, the entire light chain, or both the entire heavy and light chains.

An expression vector can be transferred to a cell (e.g., host cell) by conventional techniques and the resulting cells can then be cultured by conventional techniques to produce an antibody described herein or a fragment thereof. Thus, provided herein are host cells containing a polynucleotide encoding an antibody described herein or fragments thereof, or a heavy or light chain thereof, or fragment thereof, or a single chain antibody described herein, operably linked to a promoter for expression of such sequences in the host cell. In certain embodiments, for the expression of double-chained antibodies, vectors encoding both the heavy and light chains, individually, can be co-expressed in the host cell for expression of the entire immunoglobulin molecule, as detailed below. In certain embodiments, a host cell contains a vector comprising a polynucleotide encoding both the heavy chain and light chain of an antibody described herein, or a fragment thereof. In specific embodiments, a host cell contains two different vectors, a first vector comprising a polynucleotide encoding a heavy chain or a heavy chain variable region of an antibody described herein, or a fragment thereof, and a second vector comprising a polynucleotide encoding a light chain or a light chain variable region of an antibody described herein, or a fragment thereof. In other embodiments, a first host cell comprises a first vector comprising a polynucleotide encoding a heavy chain or a heavy chain variable region of an antibody described herein, or a fragment thereof, and a second host cell comprises a second vector comprising a polynucleotide encoding a light chain or a light chain variable region of an antibody described herein. In specific embodiments, a heavy chain/heavy chain variable region expressed by a first cell associated with a light chain/light chain variable region of a second cell to form an anti-CD137 (e.g., human CD137 or cynomolgus CD137) antibody described herein. In certain embodiments, provided herein is a population of host cells comprising such first host cell and such second host cell.

In a particular embodiment, provided herein is a population of vectors comprising a first vector comprising a polynucleotide encoding a light chain/light chain variable region of an anti-CD137 (e.g., human CD137 or cynomolgus CD137) antibody described herein, and a second vector comprising a polynucleotide encoding a heavy chain/heavy chain variable region of an anti-CD137 (e.g., human CD137 or cynomolgus CD137) antibody described herein.

A variety of host-expression vector systems can be utilized to express antibody molecules described herein (see, e.g., U.S. Pat. No. 5,807,715, which is herein incorporated by reference in its entirety). Such host-expression systems represent vehicles by which the coding sequences of interest can be produced and subsequently purified, but also represent cells which can, when transformed or transfected with the appropriate nucleotide coding sequences, express an antibody molecule described herein in situ. These include but are not limited to microorganisms such as bacteria (e.g., *E. coli* and *B. subtilis*) transformed with recombinant bacteriophage DNA, plasmid DNA or cosmid DNA expression vectors containing antibody coding sequences; yeast (e.g., *Saccharomyces Pichia*) transformed with recombinant yeast expression vectors containing antibody coding sequences; insect cell systems infected with recombinant virus expression vectors (e.g., baculovirus) containing antibody coding sequences; plant cell systems (e.g., green algae such as *Chlamydomonas reinhardtii*) infected with recombinant virus expression vectors (e.g., cauliflower mosaic virus, CaMV; tobacco mosaic virus, TMV) or transformed with recombinant plasmid expression vectors (e.g., Ti plasmid) containing antibody coding sequences; or mammalian cell systems (e.g., COS (e.g., COS1 or COS), CHO, BHK, MDCK, HEK 293, NS0, PER.C6, VERO, CRL7O3O, HsS78Bst, HeLa, and NIH 3T3, HEK-293T, HepG2, SP210, R1.1, B-W, L-M, BSC1, BSC40, YB/20 and BMT10 cells) harboring recombinant expression constructs containing promoters derived from the genome of mammalian cells (e.g., metallothionein promoter) or from mammalian viruses (e.g., the adenovirus late promoter; the vaccinia virus 7.5K promoter). In a specific embodiment, cells for expressing antibodies described herein are Chinese hamster ovary (CHO) cells, for example CHO cells from the CHO GS System™ (Lonza). In certain embodiments, the heavy chain and/or light chain of an antibody produced by a CHO cell may have an N-terminal glutamine or glutamate residue replaced by pyroglutamate. In a particular embodiment, cells for expressing antibodies described herein are human cells, e.g., human cell lines. In a specific embodiment, a mammalian expression vector is pOptiVEC™ or pcDNA3.3. In a particular embodiment, bacterial cells such as *Escherichia coli*, or eukaryotic cells (e.g., mammalian cells), especially for the expression of whole recombinant antibody molecule, are used for the expression of a recombinant antibody molecule. For example, mammalian cells such as CHO cells, in conjunction with a vector such as the major intermediate early gene promoter element from human cytomegalovirus is an effective expression system for antibodies (Foecking M K & Hofstetter H (1986) Gene 45: 101-5; and Cockett M I et al., (1990) Biotechnology 8(7): 662-7, each of which is herein incorporated by reference in its entirety). In certain embodiments, antibodies described herein are produced by CHO cells or NS0 cells. In a specific embodiment, the expression of nucleotide sequences encoding antibodies described herein which specifically bind to CD137 (e.g., human CD137 or cynomolgus CD137) is regulated by a constitutive promoter, inducible promoter or tissue specific promoter.

In bacterial systems, a number of expression vectors can be advantageously selected depending upon the use intended for the antibody molecule being expressed. For example, when a large quantity of such an antibody is to be produced, for the generation of pharmaceutical compositions of an antibody molecule, vectors which direct the expression of high levels of fusion protein products that are readily purified can be desirable. Such vectors include, but are not limited to, the *E. coli* expression vector pUR278 (Ruether U & Mueller-Hill B (1983) EMBO J 2: 1791-1794), in which the antibody coding sequence can be ligated individually into the vector in frame with the lac Z coding region so that a fusion protein is produced; pIN vectors (Inouye S & Inouye M (1985) Nuc Acids Res 13: 3101-3109; Van Heeke G & Schuster S M (1989) J Biol Chem 24: 5503-5509); and the like, all of which are herein incorporated by reference in their entireties. For example, pGEX vectors can also be used to express foreign polypeptides as fusion proteins with glutathione 5-transferase (GST). In general, such fusion proteins are soluble and can easily be purified from lysed cells by adsorption and binding to matrix glutathione agarose beads followed by elution in the presence of free glutathione. The pGEX vectors are designed to include thrombin or factor Xa protease cleavage sites so that the cloned target gene product can be released from the GST moiety.

In an insect system, *Autographa californica* nuclear polyhedrosis virus (AcNPV), for example, can be used as a vector to express foreign genes. The virus grows in *Spodoptera frugiperda* cells. The antibody coding sequence can be cloned individually into non-essential regions (for example the polyhedrin gene) of the virus and placed under control of an AcNPV promoter (for example the polyhedrin promoter).

In mammalian host cells, a number of viral-based expression systems can be utilized. In cases where an adenovirus is used as an expression vector, the antibody coding sequence of interest can be ligated to an adenovirus transcription/translation control complex, e.g., the late promoter and tripartite leader sequence. This chimeric gene can then be inserted in the adenovirus genome by in vitro or in vivo recombination. Insertion in a non-essential region of the viral genome (e.g., region E1 or E3) will result in a recombinant virus that is viable and capable of expressing the antibody molecule in infected hosts (e.g., see Logan J & Shenk T (1984) PNAS 81(12): 3655-9, which is herein incorporated by reference in its entirety). Specific initiation signals can also be required for efficient translation of inserted antibody coding sequences. These signals include the ATG initiation codon and adjacent sequences. Furthermore, the initiation codon must be in phase with the reading frame of the desired coding sequence to ensure translation of the entire insert. These exogenous translational control signals and initiation codons can be of a variety of origins, both natural and synthetic. The efficiency of expression can be enhanced by the inclusion of appropriate transcription enhancer elements, transcription terminators, etc. (see, e.g., Bitter G et al., (1987) Methods Enzymol. 153: 516-544, which is herein incorporated by reference in its entirety).

In addition, a host cell strain can be chosen which modulates the expression of the inserted sequences, or modifies and processes the gene product in the specific fashion desired. Such modifications (e.g., glycosylation) and processing (e.g., cleavage) of protein products can be important for the function of the protein. Different host cells have characteristic and specific mechanisms for the post-translational processing and modification of proteins and gene products. Appropriate cell lines or host systems can be chosen to ensure the correct modification and processing of the foreign protein expressed. To this end, eukaryotic host cells which possess the cellular machinery for proper processing of the primary transcript, glycosylation, and phosphorylation of the gene product can be used. Such mammalian host cells include but are not limited to CHO, VERO, BHK, Hela, MDCK, HEK 293, NIH 3T3, W138, BT483, Hs578T, HTB2, BT2O and T47D, NS0 (a murine myeloma cell line that does not endogenously produce any immunoglobulin chains), CRL7O3O, COS (e.g., COS1 or COS), PER.C6, VERO, HsS78Bst, HEK-293T, HepG2, SP210, R1.1, B-W, L-M, BSC1, BSC40, YB/20, BMT10 and HsS78Bst cells. In certain embodiments, anti-CD137 (e.g., human CD137 or cynomolgus CD137) antibodies described herein are produced in mammalian cells, such as CHO cells.

In a specific embodiment, the antibodies described herein have reduced fucose content or no fucose content. Such antibodies can be produced using techniques known one skilled in the art. For example, the antibodies can be expressed in cells deficient or lacking the ability of to fucosylate. In a specific example, cell lines with a knockout of both alleles of α1,6-fucosyltransferase can be used to produce antibodies with reduced fucose content. The Potelligent® system (Lonza) is an example of such a system that can be used to produce antibodies with reduced fucose content.

For long-term, high-yield production of recombinant proteins, stable expression cells can be generated. For example, cell lines which stably express an anti-CD137 (e.g., human CD137 or cynomolgus CD137) antibody described herein can be engineered. In specific embodiments, a cell provided herein stably expresses a light chain/light chain variable region and a heavy chain/heavy chain variable region which associate to form an antibody described herein.

In certain aspects, rather than using expression vectors which contain viral origins of replication, host cells can be transformed with DNA controlled by appropriate expression control elements (e.g., promoter, enhancer, sequences, transcription terminators, polyadenylation sites, etc.), and a selectable marker. Following the introduction of the foreign DNA/polynucleotide, engineered cells can be allowed to grow for 1-2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines. This method can advantageously be used to engineer cell lines which express an anti-CD137 (e.g., human CD137 or cynomolgus CD137) antibody described herein or a fragment thereof. Such engineered cell lines can be particularly useful in screening and evaluation of compositions that interact directly or indirectly with the antibody molecule.

A number of selection systems can be used, including but not limited to the herpes simplex virus thymidine kinase (Wigler M et al., (1977) Cell 11(1): 223-32), hypoxanthineguanine phosphoribosyltransferase (Szybalska E H & Szybalski W (1962) PNAS 48(12): 2026-2034) and adenine phosphoribosyltransferase (Lowy I et al., (1980) Cell 22(3): 817-23) genes in tk-, hgprt- or aprt-cells, respectively, all of which are herein incorporated by reference in their entireties. Also, antimetabolite resistance can be used as the basis of selection for the following genes: dhfr, which confers resistance to methotrexate (Wigler M et al., (1980) PNAS 77(6): 3567-70; O'Hare K et al., (1981) PNAS 78: 1527-31); gpt, which confers resistance to mycophenolic acid (Mulligan R C & Berg P (1981) PNAS 78(4): 2072-6); neo, which confers resistance to the aminoglycoside G-418 (Wu G Y & Wu C H (1991) Biotherapy 3: 87-95; Tolstoshev P (1993) Ann Rev Pharmacol Toxicol 32: 573-596; Mulligan R C (1993) Science 260: 926-932; and Morgan R A & Anderson W F (1993) Ann Rev Biochem 62: 191-217; Nabel G J & Felgner P L (1993) Trends Biotechnol 11(5): 211-5); and hygro, which confers resistance to hygromycin (Santerre R F et al., (1984) Gene 30(1-3): 147-56), all of which are herein incorporated by reference in their entireties. Methods commonly known in the art of recombinant DNA technology can be routinely applied to select the desired recombinant clone and such methods are described, for example, in Ausubel F M et al., (eds.), Current Protocols in Molecular Biology, John Wiley & Sons, N Y (1993); Kriegler M, Gene Transfer and Expression, A Laboratory Manual, Stockton Press, N Y (1990); and in Chapters 12 and 13, Dracopoli N C et al., (eds.), Current Protocols in Human Genetics, John Wiley & Sons, N Y (1994); Colbère-Garapin F et al., (1981) J Mol Biol 150: 1-14, all of which are herein incorporated by reference in their entireties.

The expression levels of an antibody molecule can be increased by vector amplification (for a review, see Bebbington C R & Hentschel C C G, The use of vectors based on gene amplification for the expression of cloned genes in mammalian cells in DNA cloning, Vol. 3 (Academic Press, New York, 1987), which is herein incorporated by reference in its entirety). When a marker in the vector system expressing antibody is amplifiable, increase in the level of inhibitor present in culture of host cell will increase the number of copies of the marker gene. Since the amplified region is associated with the antibody gene, production of the antibody will also increase (Crouse G F et al., (1983) Mol Cell Biol 3: 257-66, which is herein incorporated by reference in its entirety).

The host cell can be co-transfected with two or more expression vectors described herein, the first vector encoding a heavy chain derived polypeptide and the second vector encoding a light chain derived polypeptide. The two vectors can contain identical selectable markers which enable equal expression of heavy and light chain polypeptides. The host cells can be co-transfected with different amounts of the two or more expression vectors. For example, host cells can be transfected with any one of the following ratios of a first expression vector and a second expression vector:about 1:1, 1:2, 1:3, 1:4, 1:5, 1:6, 1:7, 1:8, 1:9, 1:10, 1:12, 1:15, 1:20, 1:25, 1:30, 1:35, 1:40, 1:45, or 1:50.

Alternatively, a single vector can be used which encodes, and is capable of expressing, both heavy and light chain polypeptides. In such situations, the light chain should be placed before the heavy chain to avoid an excess of toxic free heavy chain (Proudfoot N J (1986) Nature 322: 562-565; and Köhler G (1980) PNAS 77: 2197-2199, each of which is herein incorporated by reference in its entirety). The coding sequences for the heavy and light chains can comprise cDNA or genomic DNA. The expression vector can be monocistronic or multicistronic. A multicistronic nucleic acid construct can encode 2, 3, 4, 5, 6, 7, 8, 9, 10 or more genes/nucleotide sequences, or in the range of 2-5, 5-10, or 10-20 genes/nucleotide sequences. For example, a bicistronic nucleic acid construct can comprise, in the following order, a promoter, a first gene (e.g., heavy chain of an antibody described herein), and a second gene and (e.g., light chain of an antibody described herein). In such an expression vector, the transcription of both genes can be driven by the promoter, whereas the translation of the mRNA from the first gene can be by a cap-dependent scanning mechanism and the translation of the mRNA from the second gene can be by a cap-independent mechanism, e.g., by an IRES.

Once an antibody molecule described herein has been produced by recombinant expression, it can be purified by any method known in the art for purification of an immunoglobulin molecule, for example, by chromatography (e.g., ion exchange, affinity, particularly by affinity for the specific antigen after Protein A, and sizing column chromatography), centrifugation, differential solubility, or by any other standard technique for the purification of proteins. Further, the antibodies described herein can be fused to heterologous polypeptide sequences described herein or otherwise known in the art to facilitate purification.

In specific embodiments, an antibody described herein is isolated or purified. Generally, an isolated antibody is one that is substantially free of other antibodies with different antigenic specificities than the isolated antibody. For example, in a particular embodiment, a preparation of an antibody described herein is substantially free of cellular material and/or chemical precursors. The language "substantially free of cellular material" includes preparations of an antibody in which the antibody is separated from cellular components of the cells from which it is isolated or recombinantly produced. Thus, an antibody that is substantially free of cellular material includes preparations of antibody having less than about 30%, 20%, 10%, 5%, 2%, 1%, 0.5%, or 0.1% (by dry weight) of heterologous protein (also referred to herein as a "contaminating protein") and/or variants of an antibody, for example, different post-translational modified forms of an antibody or other different versions of an antibody (e.g., antibody fragments). When the antibody is recombinantly produced, it is also generally substantially free of culture medium, i.e., culture medium represents less than about 20%, 10%, 2%, 1%, 0.5%, or 0.1% of the volume of the protein preparation. When the antibody is produced by chemical synthesis, it is generally substantially free of chemical precursors or other chemicals, i.e., it is separated from chemical precursors or other chemicals which are involved in the synthesis of the protein. Accordingly, such preparations of the antibody have less than about 30%, 20%, 10%, or 5% (by dry weight) of chemical precursors or compounds other than the antibody of interest. In a specific embodiment, antibodies described herein are isolated or purified.

Antibodies or fragments thereof that specifically bind to CD137 (e.g., human CD137 or cynomolgus CD137) can be produced by any method known in the art for the synthesis of antibodies, for example, by chemical synthesis or by recombinant expression techniques. The methods described herein employ, unless otherwise indicated, conventional techniques in molecular biology, microbiology, genetic analysis, recombinant DNA, organic chemistry, biochemistry, PCR, oligonucleotide synthesis and modification, nucleic acid hybridization, and related fields within the skill of the art. These techniques are described, for example, in the references cited herein and are fully explained in the literature. See, e.g., Maniatis T et al., (1982) Molecular Cloning: A Laboratory Manual, Cold Spring Harbor Laboratory Press; Sambrook J et al., (1989), Molecular Cloning: A Laboratory Manual, Second Edition, Cold Spring Harbor Laboratory Press; Sambrook J et al., (2001) Molecular Cloning: A Laboratory Manual, Cold Spring Harbor Laboratory Press, Cold Spring Harbor, N.Y.; Ausubel F M et al., Current Protocols in Molecular Biology, John Wiley & Sons (1987 and annual updates); Current Protocols in Immunology, John Wiley & Sons (1987 and annual updates) Gait (ed.) (1984) Oligonucleotide Synthesis: A Practical Approach, IRL Press; Eckstein (ed.) (1991) Oligonucleotides and Analogues: A Practical Approach, IRL Press; Birren B et al., (eds.) (1999) Genome Analysis: A Laboratory Manual, Cold Spring Harbor Laboratory Press, all of which are herein incorporated by reference in their entireties.

In a specific embodiment, an antibody described herein is an antibody (e.g., recombinant antibody) prepared, expressed, created or isolated by any means that involves creation, e.g., via synthesis, genetic engineering of DNA sequences. In certain embodiments, such an antibody comprises sequences (e.g., DNA sequences or amino acid sequences) that do not naturally exist within the antibody germline repertoire of an animal or mammal (e.g., human) in vivo.

In one aspect, provided herein is a method of making an antibody which specifically binds to CD137 (e.g., human CD137 or cynomolgus CD137) comprising culturing a cell or host cell described herein. In one embodiment, the method is performed in vitro. In a certain aspect, provided herein is a method of making an antibody which specifically binds to CD137 (e.g., human CD137 or cynomolgus CD137) comprising expressing (e.g., recombinantly expressing) the antibody using a cell or host cell described herein (e.g., a cell or a host cell comprising polynucleotides encoding an antibody described herein). In a particular embodiment, the cell is an isolated cell. In a particular embodiment, the exogenous polynucleotides have been introduced into the cell. In a particular embodiment, the method further comprises the step of purifying the antibody obtained from the cell or host cell.

Methods for producing polyclonal antibodies are known in the art (see, for example, Chapter 11 in: Short Protocols in Molecular Biology, (2002) 5th Ed., Ausubel F M et al., eds., John Wiley and Sons, New York, which is herein incorporated by reference in its entirety).

Monoclonal antibodies can be prepared using a wide variety of techniques known in the art including the use of hybridoma, recombinant, and phage display technologies, or a combination thereof. For example, monoclonal antibodies can be produced using hybridoma techniques including those known in the art and taught, for example, in Harlow E & Lane D, Antibodies: A Laboratory Manual, (Cold Spring Harbor Laboratory Press, 2nd ed. 1988); Hammerling G J et al., in: Monoclonal Antibodies and T-Cell Hybridomas 563 681 (Elsevier, N.Y., 1981), each of which is herein incorporated by reference in its entirety. The term "monoclonal antibody" as used herein is not limited to antibodies produced through hybridoma technology. For example, monoclonal antibodies can be produced recombinantly from host cells exogenously expressing an antibody described herein or a fragment thereof, for example, light chain and/or heavy chain of such antibody.

In specific embodiments, a "monoclonal antibody," as used herein, is an antibody produced by a single cell (e.g., hybridoma or host cell producing a recombinant antibody), wherein the antibody specifically binds to CD137 (e.g., human CD137 or cynomolgus CD137) as determined, e.g., by ELISA or other antigen-binding or competitive binding assay known in the art or in the examples provided herein. In particular embodiments, a monoclonal antibody can be a chimeric antibody or a humanized antibody. In certain embodiments, a monoclonal antibody is a monovalent antibody or multivalent (e.g., bivalent) antibody. In particular embodiments, a monoclonal antibody is a monospecific or multispecific antibody (e.g., bispecific antibody). Monoclonal antibodies described herein can, for example, be made by the hybridoma method as described in Kohler G & Milstein C (1975) Nature 256: 495, which is herein incorporated by reference in its entirety, or can, e.g., be isolated from phage libraries using the techniques as described herein, for example. Other methods for the preparation of clonal cell lines and of monoclonal antibodies expressed thereby are well known in the art (see, for example, Chapter 11 in: Short Protocols in Molecular Biology, (2002) 5th Ed., Ausubel F M et al., supra).

As used herein, an antibody binds to an antigen multivalently (e.g., bivalently) when the antibody comprises at least two (e.g., two or more) monovalent binding domains, each monovalent binding domain capable of binding to an epitope on the antigen. Each monovalent binding domain can bind to the same or different epitopes on the antigen.

Methods for producing and screening for specific antibodies using hybridoma technology are routine and well known in the art. For example, in the hybridoma method, a mouse or other appropriate host animal, such as a sheep, goat, rabbit, rat, hamster or macaque monkey, is immunized to elicit lymphocytes that produce or are capable of producing antibodies that will specifically bind to the protein (e.g., CD137 (e.g., human CD137 or cynomolgus CD137)) used for immunization. Alternatively, lymphocytes may be immunized in vitro. Lymphocytes then are fused with myeloma cells using a suitable fusing agent, such as polyethylene glycol, to form a hybridoma cell (Goding J W (Ed), Monoclonal Antibodies: Principles and Practice, pp. 59-103 (Academic Press, 1986), herein incorporated by reference in its entirety). Additionally, a RIMMS (repetitive immunization multiple sites) technique can be used to immunize an animal (Kilpatrick K E et al., (1997) Hybridoma 16:381-9, herein incorporated by reference in its entirety).

In certain embodiments, mice (or other animals, such as rats, monkeys, donkeys, pigs, sheep, hamster, or dogs) can be immunized with an antigen (e.g., CD137 (e.g., human CD137 or cynomolgus CD137)) and once an immune response is detected, e.g., antibodies specific for the antigen are detected in the mouse serum, the mouse spleen is harvested and splenocytes isolated. The splenocytes are then fused by well-known techniques to any suitable myeloma cells, for example, cells from cell line SP20 available from the American Type Culture Collection (ATCC®) (Manassas, Va.), to form hybridomas. Hybridomas are selected and cloned by limited dilution. In certain embodiments, lymph nodes of the immunized mice are harvested and fused with NS0 myeloma cells.

The hybridoma cells thus prepared are seeded and grown in a suitable culture medium that preferably contains one or more substances that inhibit the growth or survival of the unfused, parental myeloma cells. For example, if the parental myeloma cells lack the enzyme hypoxanthine guanine phosphoribosyl transferase (HGPRT or HPRT), the culture medium for the hybridomas typically will include hypoxanthine, aminopterin, and thymidine (HAT medium), which substances prevent the growth of HGPRT-deficient cells.

Specific embodiments employ myeloma cells that fuse efficiently, support stable high-level production of antibody by the selected antibody-producing cells, and are sensitive to a medium such as HAT medium. Among these myeloma cell lines are murine myeloma lines, such as the NS0 cell line or those derived from MOPC-21 and MPC-11 mouse tumors available from the Salk Institute Cell Distribution Center, San Diego, Calif., USA, and SP-2 or X63-Ag8.653 cells available from the American Type Culture Collection, Rockville, Md., USA. Human myeloma and mouse-human heteromyeloma cell lines also have been described for the production of human monoclonal antibodies (Kozbor D (1984) J Immunol 133: 3001-5; Brodeur et al., Monoclonal Antibody Production Techniques and Applications, pp. 51-63 (Marcel Dekker, Inc., New York, 1987), each of which is herein incorporated by reference in its entirety).

Culture medium in which hybridoma cells are growing is assayed for production of monoclonal antibodies directed against CD137 (e.g., human CD137 or cynomolgus CD137). The binding specificity of monoclonal antibodies produced by hybridoma cells is determined by methods known in the art, for example, immunoprecipitation or by an in vitro binding assay, such as radioimmunoassay (RIA) or enzyme-linked immunoabsorbent assay (ELISA).

After hybridoma cells are identified that produce antibodies of the desired specificity, affinity, and/or activity, the clones may be subcloned by limiting dilution procedures and grown by standard methods (Goding J W (Ed), Monoclonal Antibodies: Principles and Practice, supra). Suitable culture media for this purpose include, for example, D-MEM or RPMI 1640 medium. In addition, the hybridoma cells may be grown in vivo as ascites tumors in an animal.

The monoclonal antibodies secreted by the subclones are suitably separated from the culture medium, ascites fluid, or serum by conventional immunoglobulin purification procedures such as, for example, protein A-Sepharose, hydroxylapatite chromatography, gel electrophoresis, dialysis, or affinity chromatography.

Antibodies described herein include, e.g., antibody fragments which recognize a specific CD137 (e.g., human CD137 or cynomolgus CD137), and which can be generated by any technique known to those of skill in the art. For example, Fab and F(ab')$_2$ fragments described herein can be produced by proteolytic cleavage of immunoglobulin molecules, using enzymes such as papain (to produce Fab fragments) or pepsin (to produce F(ab')$_2$ fragments). A Fab fragment corresponds to one of the two identical arms of an antibody molecule and contains the complete light chain paired with the VH and CH1 domains of the heavy chain. A F(ab')$_2$ fragment contains the two antigen-binding arms of an antibody molecule linked by disulfide bonds in the hinge region.

Further, the antibodies described herein can also be generated using various phage display methods known in the art. In phage display methods, functional antibody domains are displayed on the surface of phage particles which carry the polynucleotide sequences encoding them. In particular, DNA sequences encoding VH and VL domains are amplified from animal cDNA libraries (e.g., human or murine cDNA libraries of affected tissues). The DNA encoding the VH and VL domains are recombined together with a scFv linker by PCR and cloned into a phagemid vector. The vector is electroporated in E. coli and the E. coli is infected with helper phage. Phage used in these methods are typically filamentous phage including fd and M13, and the VH and VL domains are usually recombinantly fused to either the phage gene III or gene VIII. Phage expressing an antigen binding domain that binds to a particular antigen can be selected or identified with antigen, e.g., using labeled antigen or antigen bound or captured to a solid surface or bead. Examples of phage display methods that can be used to make the antibodies described herein include those disclosed in Brinkman U et al., (1995) J Immunol Methods 182: 41-50; Ames R S et al., (1995) J Immunol Methods 184: 177-186; Kettleborough C A et al., (1994) Eur J Immunol 24: 952-958; Persic L et al., (1997) Gene 187: 9-18; Burton D R & Barbas C F (1994) Advan Immunol 57: 191-280; PCT Application No. PCT/GB91/001134; International Publication Nos. WO 90/02809, WO 91/10737, WO 92/01047, WO 92/18619, WO 93/11236, WO 95/15982, WO 95/20401, and WO 97/13844; and U.S. Pat. Nos. 5,698,426, 5,223,409, 5,403,484, 5,580,717, 5,427,908, 5,750,753, 5,821,047, 5,571,698, 5,427,908, 5,516,637, 5,780,225, 5,658,727, 5,733,743 and 5,969,108, all of which are herein incorporated by reference in their entireties.

As described in the above references, after phage selection, the antibody coding regions from the phage can be isolated and used to generate whole antibodies, including human antibodies, or any other desired antigen binding fragment, and expressed in any desired host, including mammalian cells, insect cells, plant cells, yeast, and bacteria, e.g., as described below. Techniques to recombinantly produce antibody fragments such as Fab, Fab' and F(ab')$_2$ fragments can also be employed using methods known in the art such as those disclosed in PCT publication No. WO 92/22324; Mullinax R L et al., (1992) BioTechniques 12(6): 864-9; Sawai H et al., (1995) Am J Reprod Immunol 34: 26-34; and Better M et al., (1988) Science 240: 1041-1043, all of which are herein incorporated by reference in their entireties.

In certain embodiments, to generate whole antibodies, PCR primers including VH or VL nucleotide sequences, a restriction site, and a flanking sequence to protect the restriction site can be used to amplify the VH or VL sequences from a template, e.g., scFv clones. Utilizing cloning techniques known to those of skill in the art, the PCR amplified VH domains can be cloned into vectors expressing a VH constant region, and the PCR amplified VL domains can be cloned into vectors expressing a VL constant region, e.g., human kappa or lambda constant regions. The VH and VL domains can also be cloned into one vector expressing the necessary constant regions. The heavy chain conversion vectors and light chain conversion vectors are then co-transfected into cell lines to generate stable or transient cell lines that express full-length antibodies, e.g., IgG, using techniques known to those of skill in the art.

A chimeric antibody is a molecule in which different portions of the antibody are derived from different immunoglobulin molecules. For example, a chimeric antibody can contain a variable region of a mouse or rat monoclonal antibody fused to a constant region of a human antibody. Methods for producing chimeric antibodies are known in the art. See, e.g., Morrison S L (1985) Science 229: 1202-7; Oi V T & Morrison S L (1986) BioTechniques 4: 214-221; Gillies S D et al., (1989) J Immunol Methods 125: 191-202; and U.S. Pat. Nos. 5,807,715, 4,816,567, 4,816,397, and 6,331,415, all of which are herein incorporated by reference in their entireties.

A humanized antibody is capable of binding to a predetermined antigen and which comprises a framework region having substantially the amino acid sequence of a human immunoglobulin and CDRs having substantially the amino acid sequence of a non-human immunoglobulin (e.g., a murine immunoglobulin). In particular embodiments, a humanized antibody also comprises at least a portion of an immunoglobulin constant region (Fc), typically that of a human immunoglobulin. The antibody also can include the CH1, hinge, CH2, CH3, and CH4 regions of the heavy chain. A humanized antibody can be selected from any class of immunoglobulins, including IgM, IgG, IgD, IgA and IgE, and any isotype, including IgG$_1$, IgG$_2$, IgG$_3$ and IgG$_4$. Humanized antibodies can be produced using a variety of techniques known in the art, including but not limited to, CDR-grafting (European Patent No. EP 239400; International Publication No. WO 91/09967; and U.S. Pat. Nos. 5,225,539, 5,530,101, and 5,585,089), veneering or resurfacing (European Patent Nos. EP 592106 and EP 519596; Padlan E A (1991) Mol Immunol 28(4/5): 489-498; Studnicka G M et al., (1994) Prot Engineering 7(6): 805-814; and Roguska M A et al., (1994) PNAS 91: 969-973), chain shuffling (U.S. Pat. No. 5,565,332), and techniques disclosed in, e.g., U.S. Pat. Nos. 6,407,213, 5,766,886, International Publication No. WO 93/17105; Tan P et al., (2002) J Immunol 169: 1119-25; Caldas C et al., (2000) Protein Eng. 13(5): 353-60; Morea V et al., (2000) Methods 20(3): 267-79; Baca M et al., (1997) J Biol Chem 272(16): 10678-

84; Roguska M A et al., (1996) Protein Eng 9(10): 895 904; Couto J R et al., (1995) Cancer Res. 55 (23 Supp): 5973s-5977s; Couto J R et al., (1995) Cancer Res 55(8): 1717-22; Sandhu J S (1994) Gene 150(2): 409-10 and Pedersen J T et al., (1994) J Mol Biol 235(3): 959-73, all of which are herein incorporated by reference in their entireties. See also U.S. Application Publication No. US 2005/0042664 A1 (Feb. 24, 2005), which is herein incorporated by reference in its entirety.

Methods for making multispecific (e.g., bispecific antibodies) have been described, see, for example, U.S. Pat. Nos. 7,951,917; 7,183,076; 8,227,577; 5,837,242; 5,989,830; 5,869,620; 6,132,992 and 8,586,713, all of which are herein incorporated by reference in their entireties.

Single domain antibodies, for example, antibodies lacking the light chains, can be produced by methods well known in the art. See Riechmann L & Muyldermans S (1999) J Immunol 231: 25-38; Nuttall S D et al., (2000) Curr Pharm Biotechnol 1(3): 253-263; Muyldermans S, (2001) J Biotechnol 74(4): 277-302; U.S. Pat. No. 6,005,079; and International Publication Nos. WO 94/04678, WO 94/25591 and WO 01/44301, all of which are herein incorporated by reference in their entireties.

Further, antibodies that specifically bind to a CD137 (e.g., human CD137 or cynomolgus CD137) antigen can, in turn, be utilized to generate anti-idiotype antibodies that "mimic" an antigen using techniques well known to those skilled in the art. See, e.g., Greenspan N S & Bona C A (1989) FASEB J 7(5): 437-444; and Nissinoff A (1991) J Immunol 147(8): 2429-2438, each of which is herein incorporated by reference in its entirety.

In particular embodiments, an antibody described herein, which binds to the same epitope of CD137 (e.g., human CD137 or cynomolgus CD137) as an anti-CD137 (e.g., human CD137 or cynomolgus CD137) antibody described herein, is a human antibody. In particular embodiments, an antibody described herein, which competitively blocks (e.g., in a dose-dependent manner) any one of the antibodies described herein, from binding to CD137 (e.g., human CD137 or cynomolgus CD137), is a human antibody. Human antibodies can be produced using any method known in the art. For example, transgenic mice which are incapable of expressing functional endogenous immunoglobulins, but which can express human immunoglobulin genes, can be used. In particular, the human heavy and light chain immunoglobulin gene complexes can be introduced randomly or by homologous recombination into mouse embryonic stem cells. Alternatively, the human variable region, constant region, and diversity region can be introduced into mouse embryonic stem cells in addition to the human heavy and light chain genes. The mouse heavy and light chain immunoglobulin genes can be rendered non-functional separately or simultaneously with the introduction of human immunoglobulin loci by homologous recombination. In particular, homozygous deletion of the $J_H$ region prevents endogenous antibody production. The modified embryonic stem cells are expanded and microinjected into blastocysts to produce chimeric mice. The chimeric mice are then bred to produce homozygous offspring which express human antibodies. The transgenic mice are immunized in the normal fashion with a selected antigen, e.g., all or a portion of an antigen (e.g., CD137 (e.g., human CD137 or cynomolgus CD137)). Monoclonal antibodies directed against the antigen can be obtained from the immunized, transgenic mice using conventional hybridoma technology. The human immunoglobulin transgenes harbored by the transgenic mice rearrange during B cell differentiation, and subsequently undergo class switching and somatic mutation. Thus, using such a technique, it is possible to produce therapeutically useful IgG, IgA, IgM and IgE antibodies. For an overview of this technology for producing human antibodies, see Lonberg N & Huszar D (1995) Int Rev Immunol 13:65-93, herein incorporated by reference in its entirety. For a detailed discussion of this technology for producing human antibodies and human monoclonal antibodies and protocols for producing such antibodies, see, e.g., International Publication Nos. WO 98/24893, WO 96/34096 and WO 96/33735; and U.S. Pat. Nos. 5,413,923, 5,625,126, 5,633,425, 5,569,825, 5,661,016, 5,545,806, 5,814,318 and 5,939,598, all of which are herein incorporated by reference in their entireties. Examples of mice capable of producing human antibodies include the Xenomouse™ (Abgenix, Inc.; U.S. Pat. Nos. 6,075,181 and 6,150,184), the HuAb-Mouse™ (Mederex, Inc./Gen Pharm; U.S. Pat. Nos. 5,545,806 and 5,569,825), the Trans Chromo Mouse™ (Kirin) and the KM Mouse™ (Medarex/Kirin), all of which are herein incorporated by reference in their entireties.

Human antibodies that specifically bind to CD137 (e.g., human CD137 or cynomolgus CD137) can be made by a variety of methods known in the art including the phage display methods described above using antibody libraries derived from human immunoglobulin sequences. See also U.S. Pat. Nos. 4,444,887, 4,716,111, and 5,885,793; and International Publication Nos. WO 98/46645, WO 98/50433, WO 98/24893, WO 98/16654, WO 96/34096, WO 96/33735, and WO 91/10741, all of which are herein incorporated by reference in their entireties.

In certain embodiments, human antibodies can be produced using mouse-human hybridomas. For example, human peripheral blood lymphocytes transformed with Epstein-Barr virus (EBV) can be fused with mouse myeloma cells to produce mouse-human hybridomas secreting human monoclonal antibodies, and these mouse-human hybridomas can be screened to determine ones which secrete human monoclonal antibodies that specifically bind to a target antigen (e.g., CD137 (e.g., human CD137 or cynomolgus CD137)). Such methods are known and are described in the art, see, e.g., Shinmoto H et al., (2004) Cytotechnology 46: 19-23; Naganawa Y et al., (2005) Human Antibodies 14: 27-31, each of which is herein incorporated by reference in its entirety.

5.6 Kits

Also provided are kits comprising one or more antibodies described herein, or pharmaceutical compositions or conjugates thereof. In a specific embodiment, provided herein is a pharmaceutical pack or kit comprising one or more containers filled with one or more of the ingredients of the pharmaceutical compositions described herein, such as one or more antibodies provided herein. In certain embodiments, the kits contain a pharmaceutical composition described herein and any prophylactic or therapeutic agent, such as those described herein. In certain embodiments, the kits may contain a T cell mitogen, such as, e.g., phytohaemagglutinin (PHA) and/or phorbol myristate acetate (PMA), or a TCR complex stimulating antibody, such as an anti-CD3 antibody and anti-CD28 antibody. Optionally associated with such container(s) can be a notice in the form prescribed by a governmental agency regulating the manufacture, use or sale of pharmaceuticals or biological products, which notice reflects approval by the agency of manufacture, use or sale for human administration.

Also provided, are kits that can be used in the above methods. In one embodiment, a kit comprises an antibody described herein, preferably a purified antibody, in one or more containers. In a specific embodiment, kits described herein contain a substantially isolated CD137 (e.g., human CD137 or cynomolgus CD137) antigen as a control. In another specific embodiment, the kits described herein further comprise a control antibody which does not react with a CD137 (e.g., human CD137 or cynomolgus CD137) antigen. In another specific embodiment, kits described herein contain one or more elements for detecting the binding of an antibody to a CD137 (e.g., human CD137 or cynomolgus CD137) antigen (e.g., the antibody can be conjugated to a detectable substrate such as a fluorescent compound, an enzymatic substrate, a radioactive compound or a luminescent compound, or a second antibody which recognizes the first antibody can be conjugated to a detectable substrate). In specific embodiments, a kit provided herein can include a recombinantly produced or chemically synthesized CD137 (e.g., human CD137 or cynomolgus CD137) antigen. The CD137 (e.g., human CD137 or cynomolgus CD137) antigen provided in the kit can also be attached to a solid support. In a more specific embodiment, the detecting means of the above described kit includes a solid support to which a CD137 (e.g., human CD137 or cynomolgus CD137) antigen is attached. Such a kit can also include a non-attached reporter-labeled anti-human antibody or anti-mouse/rat antibody. In this embodiment, binding of the antibody to the CD137 (e.g., human CD137 or cynomolgus CD137) antigen can be detected by binding of the said reporter-labeled antibody. In one embodiment, the present invention relates to the use of a kit of the present invention for in vitro assaying and/or detecting CD137 antigen (e.g., human CD137 or cynomolgus CD137) in a biological sample.

6. EXAMPLES

The examples in this Section (i.e., Section 6) are offered by way of illustration, and not by way of limitation.

6.1 Example 1: Characterization of an Anti-CD137 Antibody

This example describes the characterization of antibodies that bind to human CD137. In particular, the BA001 antibody, which specifically binds to and stimulates the function of human CD137, was characterized. The sequence information of the variable regions of BA001 is provided in Table 1.

6.1.1 Anti-Human CD137 Antibody Binds to Cells Expressing CD137

The capacity of the human anti-CD137 IgG1 antibody BA001 to bind to cells expressing human CD137 or cynomolgus monkey CD137 was tested in a variety of cell types, as shown in FIGS. 1A and 1B.

Engineered Jurkat Cells

In one example, Jurkat cells were engineered to constitutively express either human CD137 or cynomolgus CD137 and used to analyze the binding of antibody BA001. Briefly, transfected Jurkat cells were plated in a 96-well round bottom plate at $5 \times 10^4$ cells/well, and incubated with serial dilutions of antibody (i.e., BA001 or isotype control, at the indicated concentrations) for 25 minutes at 4° C. (left panels of FIGS. 1A and 1B). The cells were washed twice and incubated with an anti-human lambda-PE secondary antibody (Life Technologies, Cat #MH10614). The cells were washed and suspended in 80 µl of 2% paraformaldehyde (Electron Microscopy Sciences) prepared in PBS. Data were collected with BD FACS Canto and analyzed using BD FACSDiva software.

As shown in FIGS. 1A and 1B (left panels), the BA001 antibody bound to Jurkat cells expressing either human CD137 or cynomolgus CD137.

Activated CEM/C1 T Cells

In a second example, the capacity of BA001 to bind to activated human CEM/C1 T cells expressing endogenous human CD137 was tested. Briefly, CEM/C1 cells were stimulated by incubation with 10 ng/ml Phorbol 12-myristate 13-acetate (PMA) and 1 µg/ml ionomycin at 37° C. for 18 hours. The stimulated cells were plated in a 96-well round bottom plate at $1 \times 10^5$ cells/well and incubated with serial dilutions of antibody (i.e., BA001 or isotype control, at concentrations shown in the middle panel of FIG. 1A) for 25 minutes at 4° C. The cells were washed twice and incubated with an anti-human lambda-PE secondary antibody (Life Technologies, Cat #MH10614). The cells were washed and suspended in 80 µl of 2% paraformaldehyde (Electron Microscopy Sciences) prepared in PBS. Data were collected with BD FACS Canto and analyzed using BD FACSDiva software.

As shown in the middle panel of FIG. 1A, the BA001 antibody bound to activated CEM/C1 cells expressing endogenous CD137.

Activated Primary CD8+ T Cells

In a third example, the capacity of BA001 to bind to activated human or cynomolgus CD8+ T cells was tested. Briefly, human or cynomolgus PBMCs were stimulated by incubation with 10 ng/ml PMA and 1 µg/ml ionomycin at 37° C. for 18 hours. The stimulated cells were plated in a 96-well round bottom plate at $1 \times 10^5$ cells/well and incubated with serial dilutions of antibody (i.e., BA001 or isotype control, at concentrations shown in the right panels of FIGS. 1A and 1B) and anti-human CD8-APC (Biolegend, Cat #311049) for 25 minutes at 4° C. The cells were washed twice and incubated with an F(ab')$_2$ goat anti-human IgG-PE secondary antibody (Jackson ImmunoResearch, Cat #109-116-098). The cells were washed and suspended in 80 µl of 2% paraformaldehyde (Electron Microscopy Sciences) prepared in PBS. Data were collected with BD FACS Canto, and then analyzed (gated on CD8+ T cells) using Flowjo V10.

As shown in the right panels of FIGS. 1A-1B, the BA001 antibody bound to activated human or cynomolgus CD8+ T cells expressing endogenous CD137.

6.1.2 Anti-CD137 Antibody does not Block CD137L Binding to CD137

Binding of CD137L to CD137/BA001-F(ab')$_2$ Complex

Surface plasmon resonance was used to evaluate the capacity of CD137L to bind to CD137 complexed to the F(ab')$_2$ fragment of BA001 (BA001-F(ab')$_2$). BA001-F(ab')$_2$ was generated using the FragIT™ kit, Genovis (Cat #A2-FR2-100). All interactions were analyzed at 25° C. using a BIAcore® T200 (GE Healthcare) and 1×HBS-P+ (GE Healthcare, BR-1006-71) as running buffer.

In one example, BA001-F(ab')$_2$ was immobilized on a chip and then bound to CD137, after which CD137L was permitted to bind to the CD137/BA001-F(ab')$_2$ complex. First, an anti-human Fab capture antibody (GE Healthcare, Fab Capture Kit, 28-9583-25) was immobilized on flow cell 2 of a CM5 series S sensor chip (GE Healthcare, 29-1496-03). BA001-F(ab')$_2$ was then diluted in 6.75 µg/ml in running buffer and immobilized to flow cell 1 at 10 µl/min for 120 seconds. As a control for measuring non-specific interaction of CD137 or CD137L, flow cell 1 of the chip was bound solely with the anti-human Fab capture antibody. After capture of BA001-F(ab')$_2$, 100 nM of CD137 (Acro Biosystem, 41B-H5227) was run at 30 µl/min for 90 seconds over both flow cells of the chip, followed by 400 seconds of dissociation. 200 nM of CD137L (R&D Systems, #2295-4L-025) was then run at 30 µl/min for 90 seconds over both flow cells, followed by a dissociation time of 400 seconds.

Figure 2A:
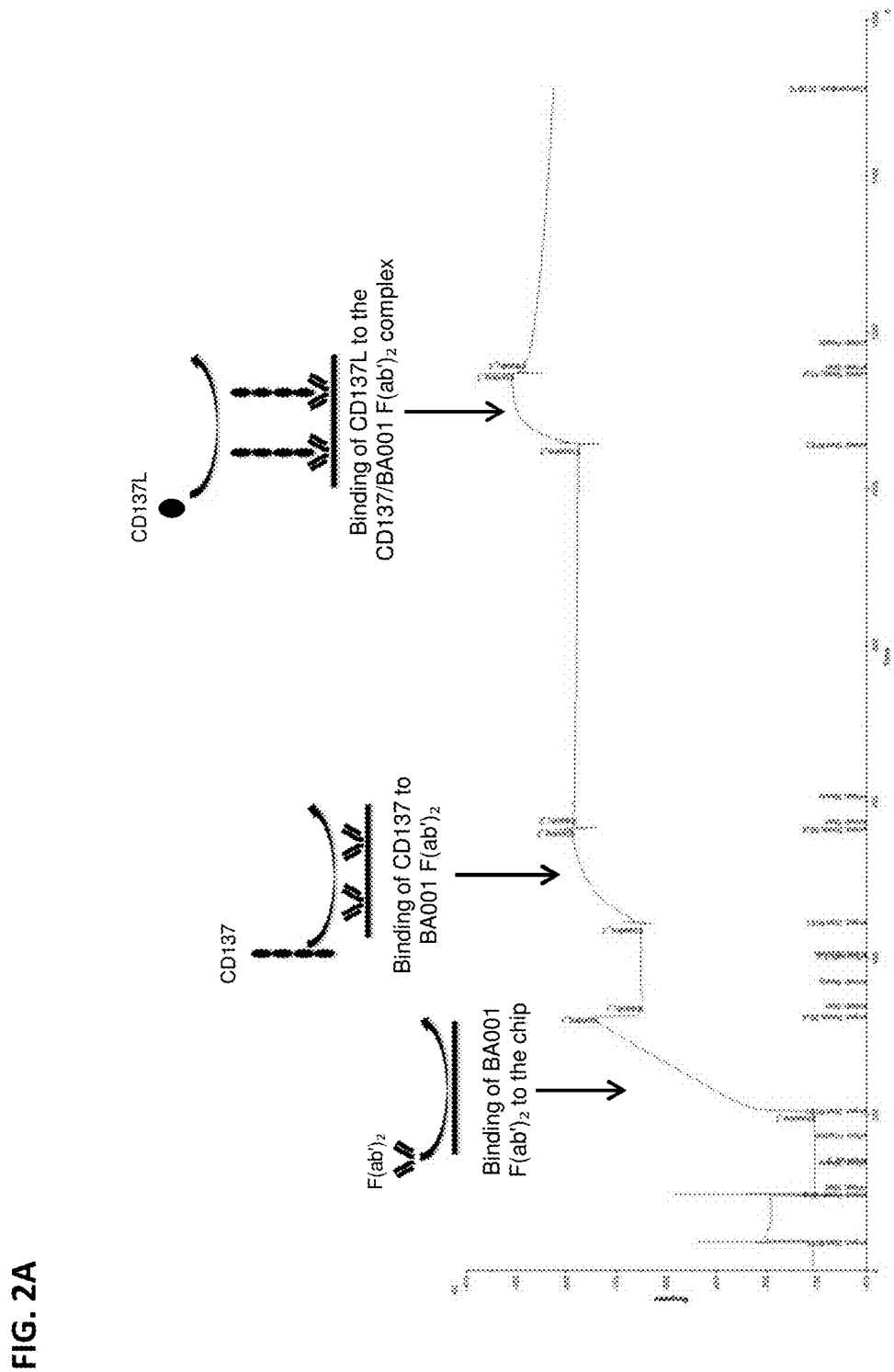

The response obtained for flow cell 2 minus the response obtained for flow cell 1 is shown in FIG. 2A. When CD137 was run over flow cell 2, an increase in the response signal was detected, showing the binding of CD137 to BA001-F (ab')$_2$. CD137 was seen to dissociate very slowly from BA001-F(ab')$_2$. CD137L was then run over flow cell 2 and an increase of the signal response was observed, showing the binding of CD137L to the CD137/BA001-F(ab')$_2$ complex. These results show that binding of BA001-F(ab')$_2$ to CD137 does not block the binding of CD137L to CD137.

In another example, an excess of CD137 (110 nM) was pre-mixed with BA001-F(ab')$_2$ (6 µg/ml, 54 nM) to form a CD137/BA001-F(ab')$_2$ complex. The complex was then immobilized on flow cell 3 of a CM5 series S sensor chip (GE Healthcare, 29-1496-03) at 10 µl/min for 180 seconds, followed by 60 seconds of dissociation. 60 nM of CD137L was then run at 50 µl/min for 90 seconds over all the flow cells followed by a dissociation time of 400 seconds. As a control for measuring non-specific interaction of CD137 or CD137L, flow cell 1 of the chip was bound solely with the anti-human Fab capture antibody.

Figure 2B:
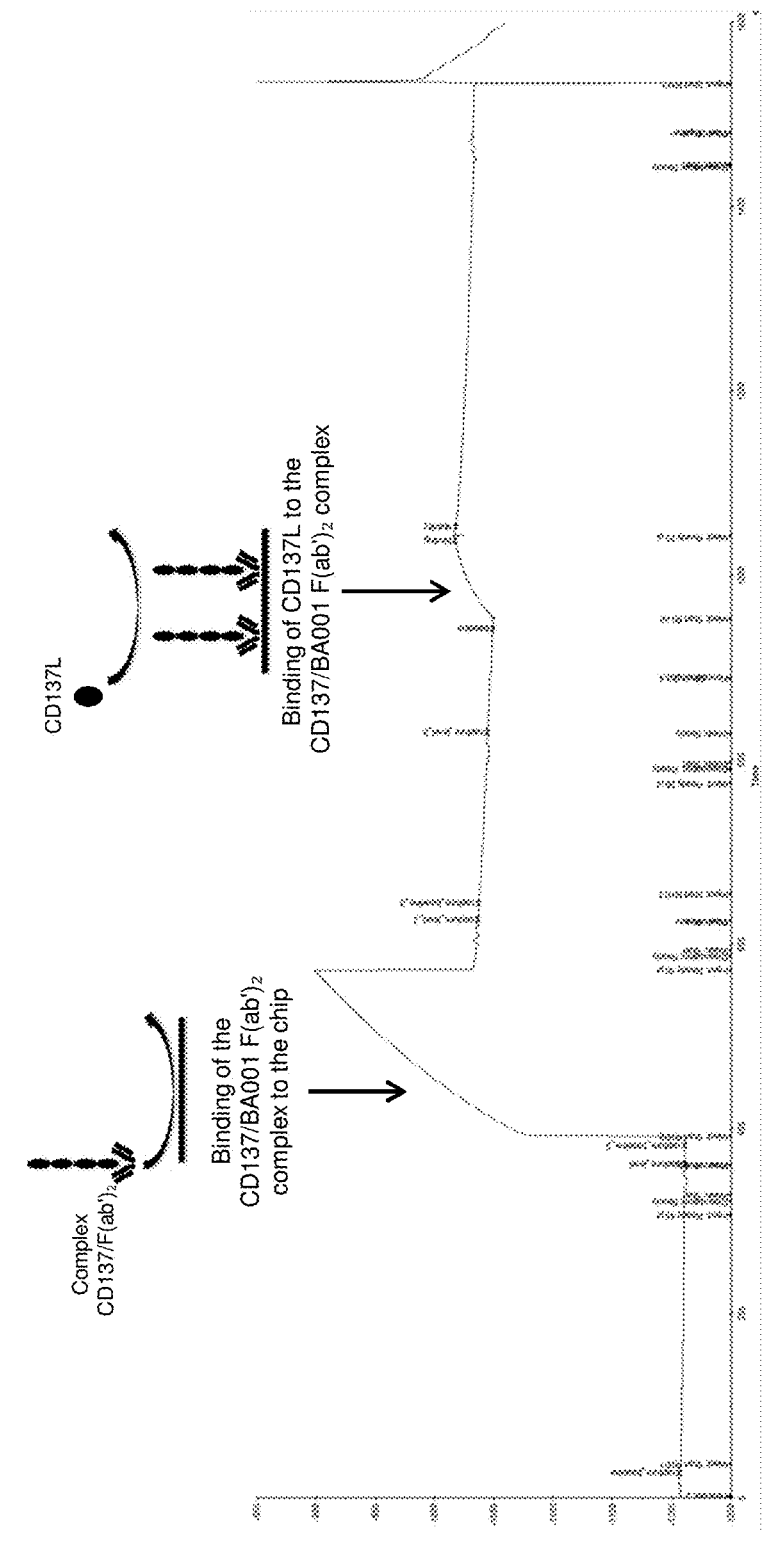

The response obtained for flow cell 3 minus the response obtained for flow cell 1 is shown in FIG. 2B. These data demonstrated that although BA001-F(ab')$_2$ bound to CD137 with high affinity, this interaction does not impair the binding of CD137L to CD137.

Similar results to those described in this example were also observed for BA001 and a Fab fragment derived from BA001 (BA001-Fab; data not shown). Thus, BA001 is a non-ligand blocking anti-CD137 antibody.
BA001 Did not Block Cell Surface CD137L Binding to Cell Surface CD137

To determine whether BA001 can block binding between CD137L and CD137 expressed on the surface of cells (i.e., in a more physiological setting), a cell conjugation assay was performed using the methodology described in Xiao et al. (JEM 211(5):943-959, 2014; incorporated herein by reference in its entirety). Briefly, one set of Jurkat cells was transfected with human CD137 (Jurkat-CD137) and another set of Jurkat cells was transfected with human CD137L (Jurkat-CD137L). CD137-expressing Jurkat cells were stained with the red dye PKH26 (Sigma Cat #PKH26GL-1KT) and CD137L-expressing Jurkat cells were stained with the green dye PKH67 (Sigma Cat #PKH67GL-1KT). Red dye-labeled Jurkat-CD137 cells (1×10$^5$/well) were incubated with 50 µg/ml of BA001, reference anti-CD137 antibody #1, reference anti-CD137 antibody #2, or isotype control in a round-bottom 96-well plate for 30 min at room temperature. Then green dye-labeled Jurkat-CD137L cells (1×10$^5$/well) were added and incubated for 45 min at 37° C. Cell to cell binding/conjugate formation was analyzed by flow cytometry using BD FACS Canto and BD FACSDiva software. The PE channel was used for the red dye and the FITC channel was used for the green dye. As such, binding between a CD137-expressing cell and a CD137L-expressing cell would result in a double-positive signal (i.e., red+green) that exhibits increased detected cell size. This effect would be reduced or abolished by a ligand blocking anti-CD137 antibody.

Figure 3A:
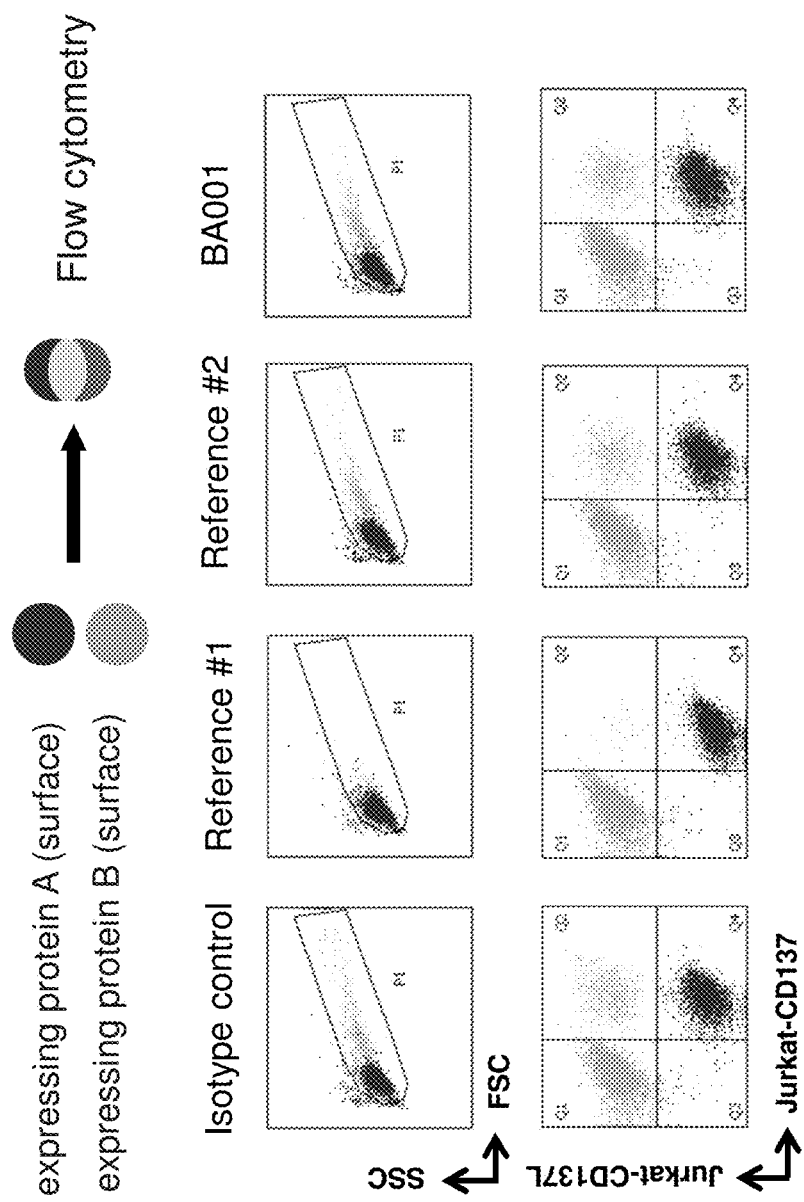

FIG. 3A shows that BA001 and reference anti-CD137 antibody #2 did not block CD137L on cells from binding to CD137 on cells. By contrast, reference anti-CD137 antibody #1 blocked ligand binding.

In a similar setting, CD137L-expressing and CD137-expressing cells were stained with the PKH26 red fluorescent cell linker or PKH67 green fluorescent cell linker, respectively, and suspended at a concentration of 4×10$^6$ cells/mL in Hanks' balanced salt solution (HBSS). A 3-fold serial dilution of BA001, reference anti-CD137 antibody #1, reference anti-CD137 antibody #2, or the respective isotype control antibody were prepared in HBSS at a 3× working concentration. In a U-bottom 96-well plate, 25 uL of Jurkat-CD137 cells were incubated at RT with 25 uL of an anti-CD137 antibody for 30 min, and CD137L-expressing cells were added. Alternatively, 25 uL of Jurkat-CD137 cells were incubated at RT with 25 uL of the CD137L-expressing cells for 30 min, and an anti-CD137 antibody was added. The plate was incubated for 45 minutes at 37 C and 5% CO2, and conjugates of CD137L-expressing cells and CD137-expressing cells were identified as PE and FITC double positivity by flow cytometry using the BD Fortessa cytometer.

Figure 3B:
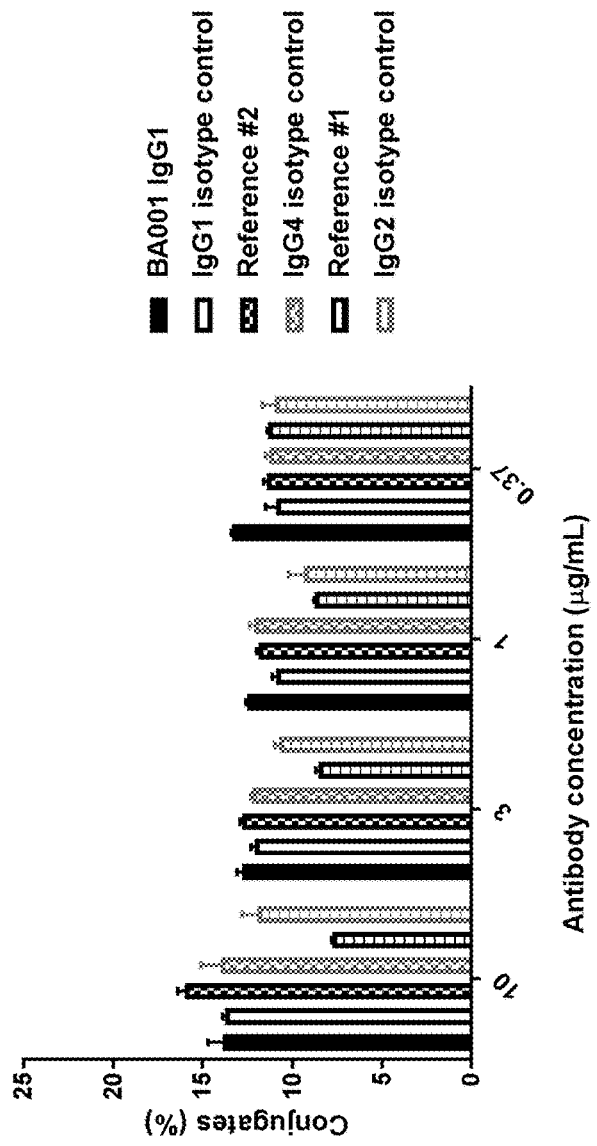
Figure 3C:
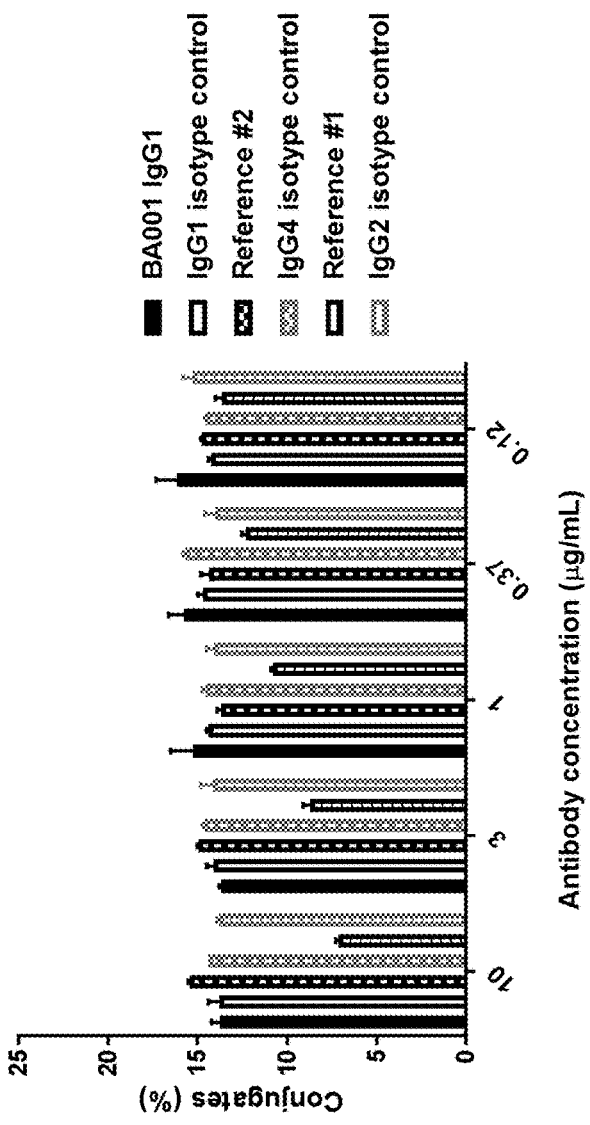

As shown in FIGS. 3B and 3C, BA001 and reference anti-CD137 antibody #2 did not affect the conjugation of CD137-expressing cells with the CD137L-expressing cells, when the anti-CD137 antibody was added prior to (FIG. 3B) or after (FIG. 3C) co-culture of the cells. By contrast, reference anti-CD137 antibody #1 inhibited the cell conjugation, indicating that this antibody blocked cell surface CD137L binding to cell surface CD137.

6.2 Example 2: The Agonistic Activity of Anti-CD137 Antibody is Crosslinking- and Ligand-Dependent

6.2.1 Anti-CD137 Antibody Induces NF-κB-Driven Gene Expression Only in the Presence of Antibody Crosslinking To characterize the ability of BA001 to activate CD137 signaling, Jurkat reporter cells were generated that incorporated (i) an NFκB-luciferase reporter construct, and (ii) an expression construct for either human or cynomolgus CD137. As such, activation of CD137 on the surface of the reporter cells induced downstream signaling that drives expression of luciferase under the control of the NFκB promoter.

It was discovered that the ability of BA001 to activate CD137 was dependent on BA001 crosslinking. Indeed, uncrosslinked BA001 was unable to stimulate reporter activity in Jurkat cells engineered to express CD137 and an NF-κB luciferase reporter construct (data not shown). To characterize the crosslinking dependency, BA001, an isotype control antibody, and reference anti-CD137 antibody #2 were incubated with a dose titration of crosslinker (AffiniPure F(ab')$_2$ Fragment Goat Anti-Human IgG, Fcγ Fragment Specific (Jackson ImmunoResearch, 109-006-098)). The Jurkat reporter cells were seeded at the density of 50,000 cells/well, and were incubated with 2 µg/mL BA001, an isotype control antibody, or reference anti-CD137 antibody #2 for 4 hours. The NF-kB activities were measured by Nano-Glo® Luciferase Assay System (Promega N1120).

Figure 4A:
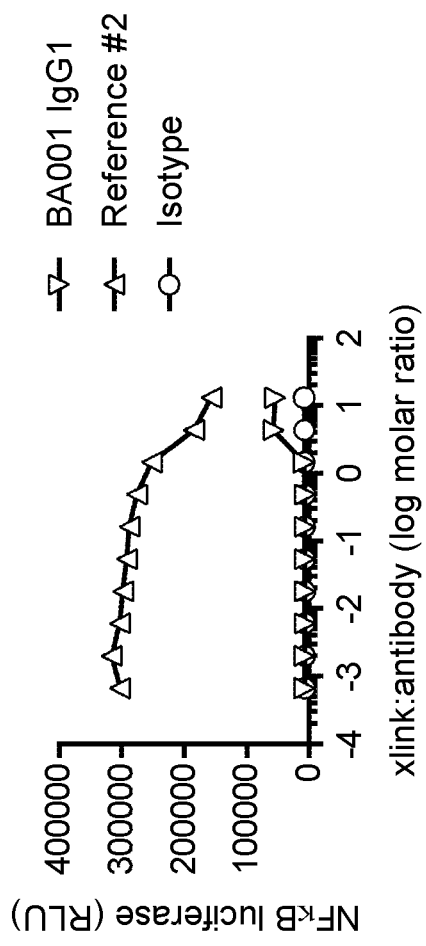

As shown in FIG. 4A, BA001 acquired activity in this assay when it was crosslinked at a crosslinker-to-antibody ratio above 1:1. By contrast, reference anti-CD137 antibody #2 was active without crosslinker, and gradually lost activity with an increasing amount of crosslinker.

It was further assessed whether BA001 was able to agonize CD137 upon antibody clustering in the absence of an artificial antibody crosslinker. Antibody clustering was induced by CHO cells engineered to express FcγRIIIa (CD16). Briefly, the Jurkat reporter cells at the density of 50,000 cells/well were co-cultured with a dose titration of CHO cells engineered to express CD16 or control CHO cells, in the presence of 2 μg/mL of BA001, an isotype control antibody, or a BA001 variant having an N297A mutation in the Fc region. The NF-kB activities were measured by Nano-Glo® Luciferase Assay System (Promega N1120) after 4 hours of incubation.

Figure 4B:
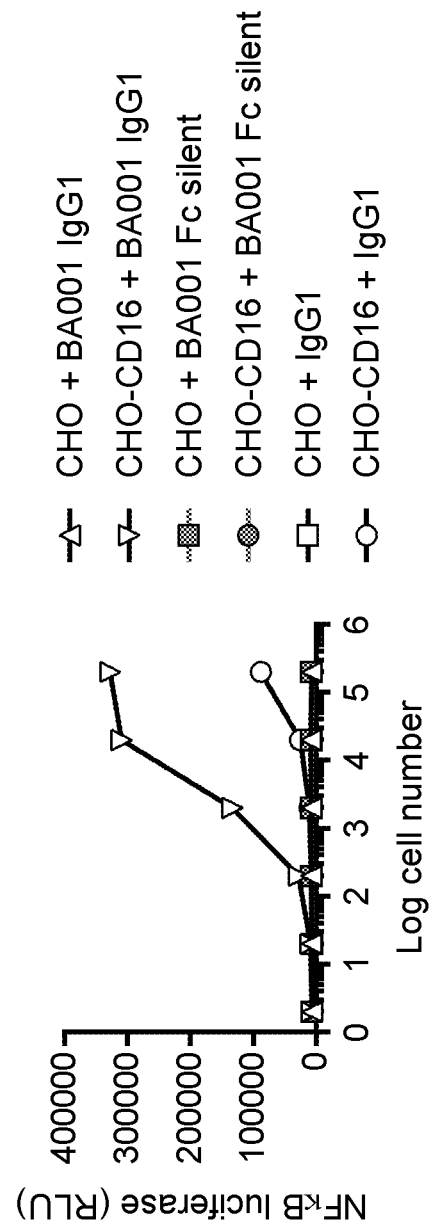

As shown in FIG. 4B, BA001 alone did not activate CD137 signaling, and CD16-expressing CHO cells alone had a limited effect. However, the combination of BA001 and CD16-expressing CHO cells synergistically activated the reporter cells. The N297A mutation abrogated the ability of BA001 to stimulate CD137 signaling, likely because the N297A Fc variant was not able to engage CD16 expressed on the CHO cells, and thus was not able to undergo antibody clustering. This result suggests that BA001 may be selectively active in a microenvironment wherein CD16-expressing cells (e.g., antigen-presenting cells or NK cells) are present.

6.2.2 Anti-CD137 Antibody Enhances T Cell Function with Whole PBMC but not with Purified T Cells BA001 Promoted IL-2 Secretion by Human T Cells in the Presence of CD137L The agonistic activity of BA001 on primary human PBMCs was assessed following Staphylococcal Enterotoxin A (SEA) stimulation. Briefly, cryopreserved PBMCs were stimulated with 200 ng/ml of the SEA superantigen (Toxin Technologies, Cat #AT101red) in the presence of serial dilutions of an antibody (i.e., BA001, reference anti-CD137 antibody #1 or #2, or an isotype control antibody, at the concentrations shown in FIG. 5) for 5 days at 37° C. IL-2 concentrations in the culture supernatant were analyzed by AlphaLISA (Perkin Elmer, Cat #AL221F). Each condition was tested with five replicates.

Figure 5:
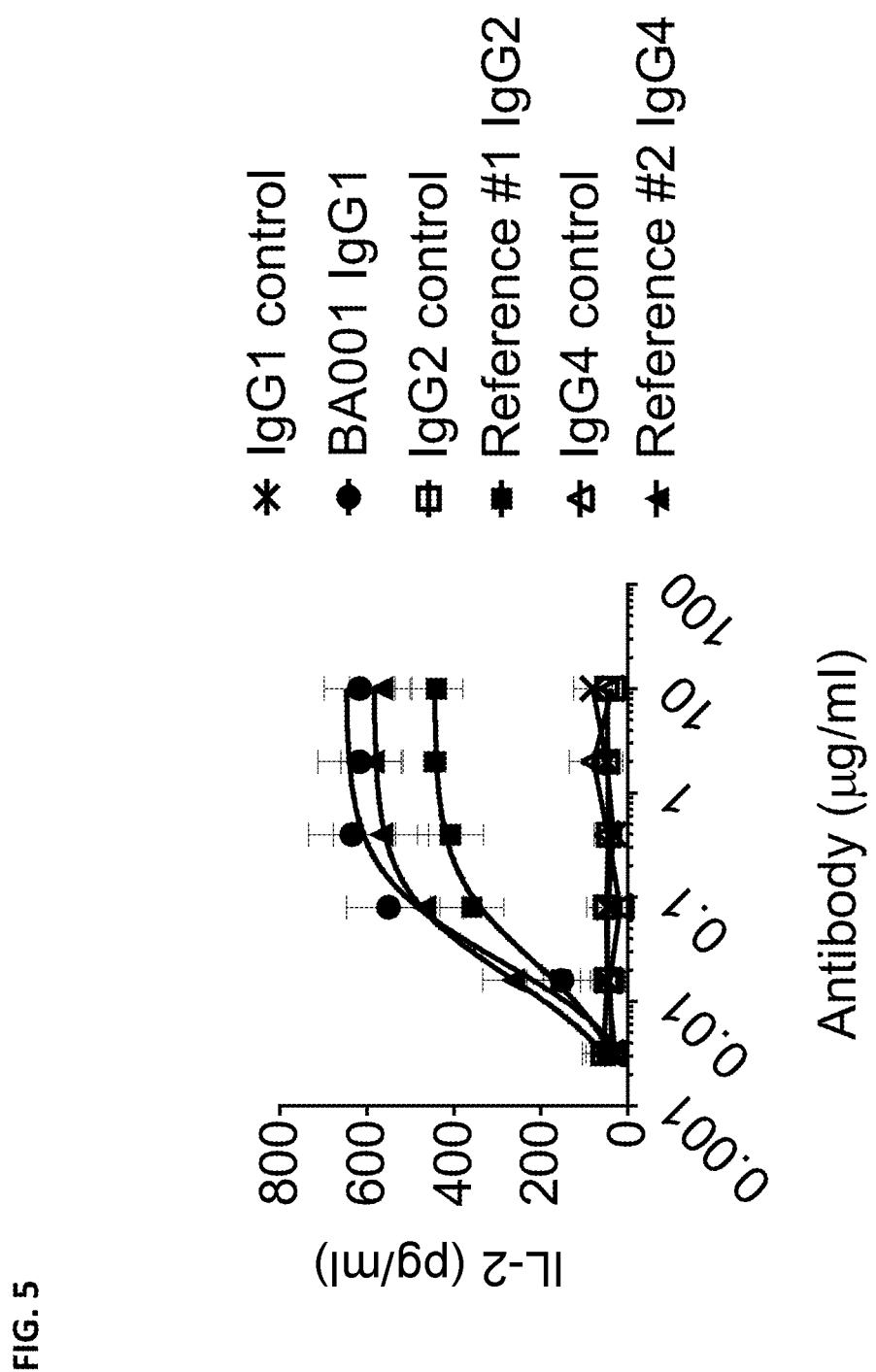

As shown in FIG. 5, the anti-CD137 antibody BA001 (IgG1) increased IL-2 production in human PBMCs in a dose-dependent manner, at levels comparable or greater than those of reference anti-CD137 antibodies.

BA001 Did not Promote IL-2 Secretion by Purified Human T Cells in the Absence of CD137L The agonistic activity of BA001 on purified, stimulated human T cells in the absence of antigen-presenting cells expressing CD137L was assessed. Briefly, T cells were purified from cryopreserved PBMCs using MACS Pan T Cell Isolation Kit (human) with autoMACS columns following the manufacturer instructions. The purified T cells were plated at $1\times10^6$ cells/well into 96-well culture plates pre-coated with low endotoxin, azide-free (LEAF) anti-CD3 antibody (Biolegend Cat #300432) at 2 μg/ml. Anti-CD137 antibody (BA001, reference anti-CD137 antibody #1, or reference anti-CD137 antibody #2) or isotype control at 5 μg/ml was cross-linked with F(ab')₂ fragment goat anti-human IgG (Jackson ImmunoResearch, Cat #109-006-098) and then added to the plate. Cells were incubated at 37° C. for three days. IL-2 concentrations in the culture supernatant were then analyzed by AlphaLISA (Perkin Elmer, Cat #AL221F). Each condition was tested with six replicates.

Figure 6C:
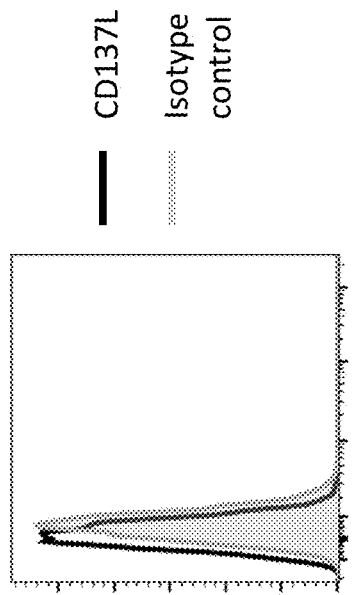
Figure 6B:
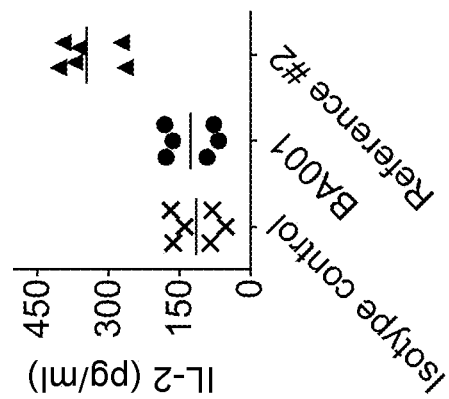
Figure 6A:
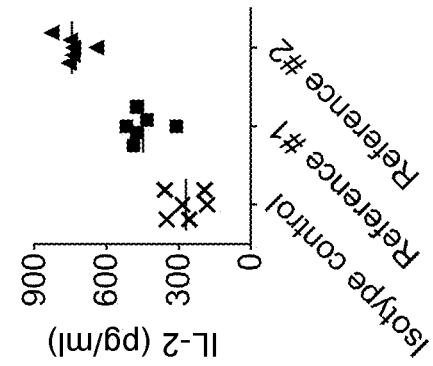

As shown in FIGS. 6A-6B, BA001 did not promote increased IL-2 secretion by purified T cells, relative to isotype control. By contrast, both reference anti-CD137 antibodies induced elevated IL-2 secretion by the purified T cells. FIG. 6C shows that the purified T cells did not express detectable levels of CD137L.

Taken together, the data in Section 6.2.2 show that the agonistic activity of BA001 was elevated in the presence of CD137L (e.g., produced by CD137L-expressing cells), as in whole PBMCs. It is contemplated that the agonistic activity of BA001 may require the presence of CD137L under the conditions used. Thus, these data demonstrated that the ability of BA001 to activate CD137-expressing cells might be ligand-dependent.

6.2.3 Anti-CD137 Antibody Only Induces NFκB-Driven Gene Expression in the Presence of CD137L Ligand Dependency of BA001 in NFκB-Luciferase Reporter Cells It was shown in section 6.2.1 that BA001 activity was dependent on crosslinking in the absence of CD137L. The effect of crosslinker in the presence of CD137L was further assessed. Briefly, 1 μg/mL CD137L (Recombinant Human 4-1BB Ligand/TNFSF9 (His-tag), R&D system, 2295-4L-025/CF) was optionally added to the culture system described above, and the NF-κB activity was measured similarly.

Figure 7A:
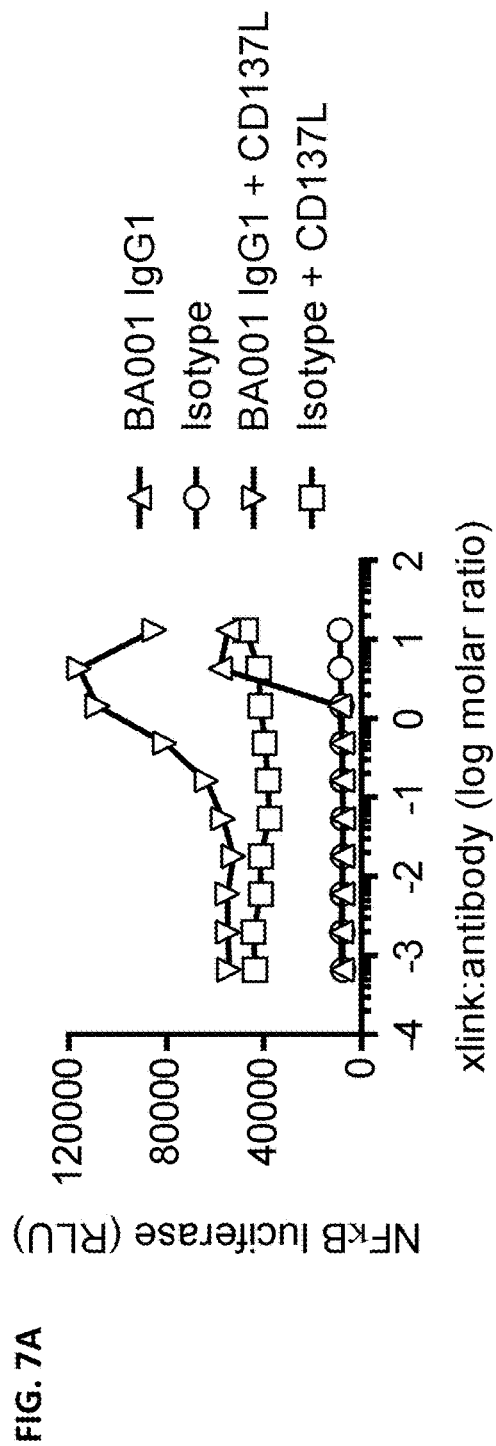

As shown in FIG. 7A, in the presence of CD137L, BA001 still required the crosslinker for activity in the reporter assay, and the effects of CD137L and crosslinking were additive. When the crosslinker-to-antibody ratio was about 1:10 to 1:1, BA001 showed activity only in the presence of CD137L.

To confirm that the exogenous CD137L was the sole source of CD137L in this experimental system, the Jurkat reporter cells were analyzed by flow cytometry. Briefly, CD137-expressing and CD137L-expressing Jurkat cells were thawed and cultured in RPMI medium supplemented with 10% fetal bovine serum and 1 μg/mL puromycin for 4 or 24 hours. For analysis by flow cytometry, $3\times10^4$ cells were plated in a 96 well U-bottom plate, washed twice with cold phosphate buffer saline supplement with 2% fetal bovine serum, and labeled with an anti-CD137 antibody conjugated with phycoerythrin (PE), an anti-CD137L antibody conjugated with allophycocyanin (APC), and a near-IR live/dead dye. In the staining control group, the cells were labeled with an irrelevant isotype control antibody conjugated with PE, an irrelevant isotype control antibody conjugated with APC, and the live/dead dye.

Figure 7B:
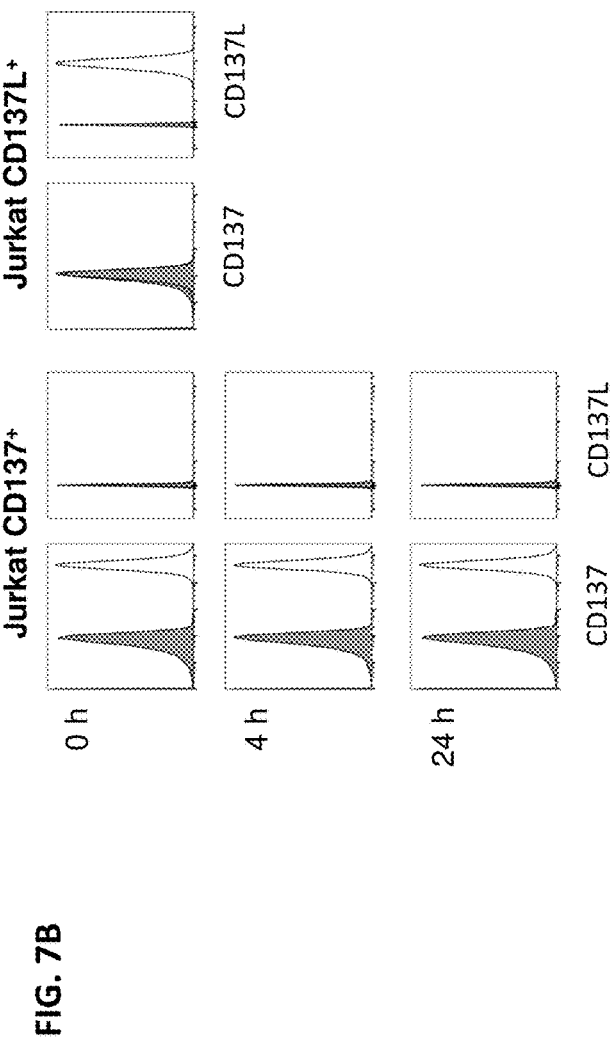

As shown in FIG. 7B, the CD137-expressing Jurkat reporter cells expressed high levels of CD137 but not CD137L. In comparison, the CD137L-expressing Jurkat cells expressed high levels of CD137L but not CD137.

In all the NF-κB activation assays below using Jurkat reporter cells, anti-CD137 antibodies and their isotype control antibodies were crosslinked at a ratio of 1:2.

Figure 8A:
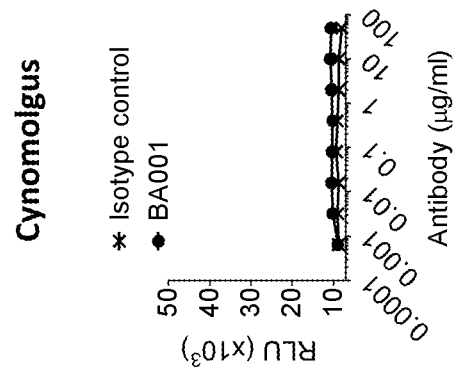
Figure 8B:
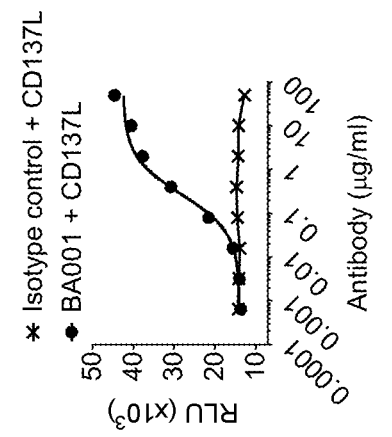

In one example, Jurkat NFκB-luciferase reporter cells expressing human CD137 (50,000 cells/well) were incubated with serial dilutions of BA001 or an isotype control, in the presence or absence of soluble human CD137L (125 ng/ml), for four hours at 37° C. Luciferase expression was detected using the Nano-Glo® Luciferase Assay System (Promega Cat #N1120) and an EnVision plate reader. As shown in FIG. 8A, BA001 did not induce NFκB-luciferase expression in the absence of CD137L. In the presence of CD137L, BA001 was able to induce NFκB-luciferase expression in a dose-dependent manner (FIG. 8B).

Figure 8C:
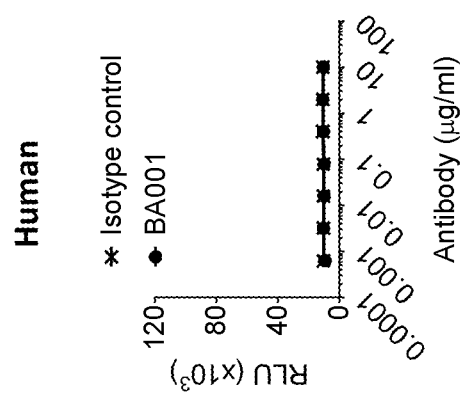
Figure 8D:
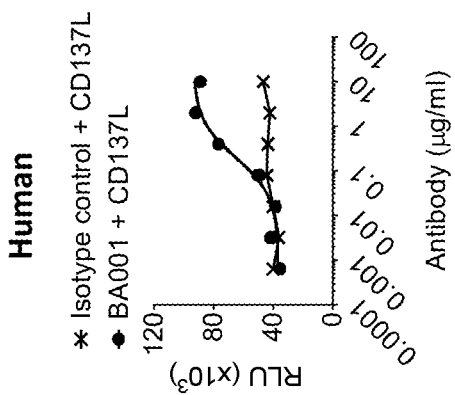

In another example, Jurkat NFκB-luciferase reporter cells expressing cynomolgus CD137 (50,000 cells/well) were incubated with serial dilutions of BA001 or an isotype control, in the presence or absence of soluble human CD137L (150 ng/ml), for four hours at 37° C. Luciferase expression was detected using the Nano-Glo® Luciferase Assay System (Promega Cat #N1120) and an EnVision plate reader. As shown in FIG. 8C, BA001 did not induce NFκB-luciferase expression in the absence of CD137L. In the presence of CD137L, BA001 was able to induce NFκB-luciferase expression in a dose-dependent manner (FIG. 8D).

Thus, these data show that BA001 induces human or cynomolgus CD137 signaling through NFκB only in the presence of the corresponding CD137L under the conditions used.

BA001 Cooperated with CD137L to Promote CD137 Signaling

Figure 9A:
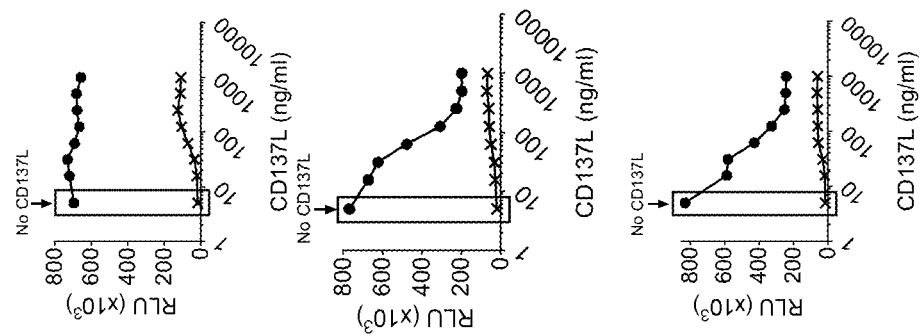
Figure 9B:
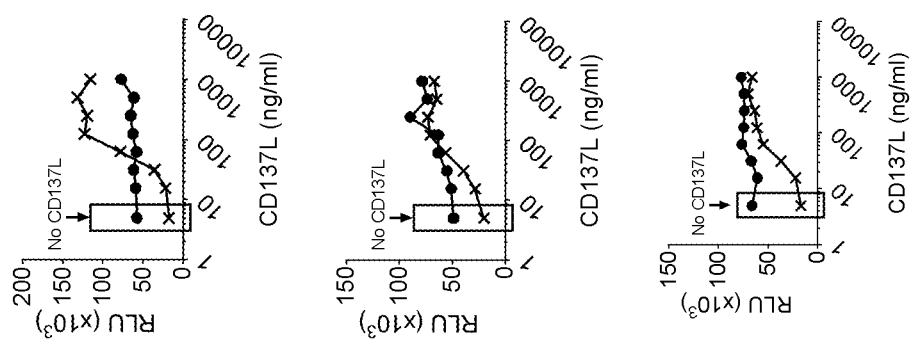
Figure 9C:
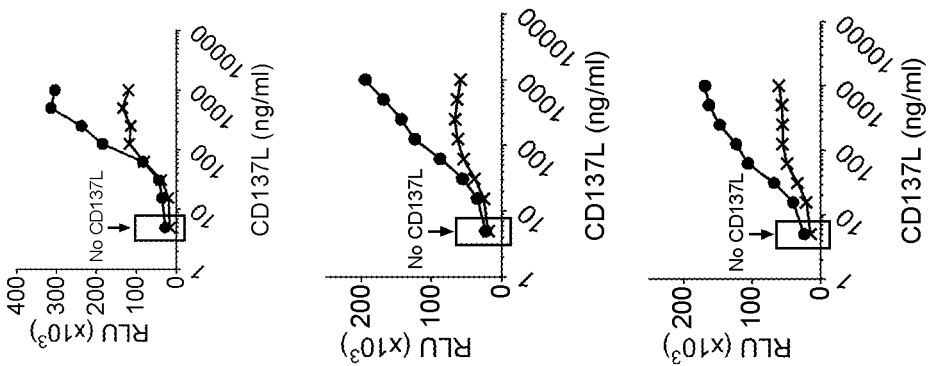

In a further example, Jurkat NFκB-luciferase reporter cells expressing human CD137 (50,000 cells/well) were incubated with 2 μg/ml of anti-CD137 antibody (BA001, reference anti-CD137 antibody #1, or reference anti-CD137 antibody #2) or an isotype control, in the presence of serial dilutions of soluble human CD137L (0-1000 ng/ml, as shown in FIGS. 9A-9C), for four hours at 37° C. In one set of samples, the anti-CD137 antibody was added before the CD137L (FIG. 9A). In a second set of samples, the anti-CD137 antibody and CD137L were added simultaneously (FIG. 9B). In a third set of samples, the CD137L was added before the anti-CD137 antibody (FIG. 9C). Luciferase expression was detected using the Nano-Glo® Luciferase Assay System (Promega Cat #N1120) and an EnVision plate reader.

As shown in FIGS. 9A-9C, CD137L induced NFκB-luciferase expression in a dose-dependent manner. BA001 induced NFκB-luciferase expression in a ligand-dependent manner, and substantially increased reporter expression beyond that detected for isotype control at higher ligand concentrations. This effect was observed regardless of the order in which antibody and ligand were added (FIGS. 9A-9C, left panels). By contrast, the ligand-blocking reference anti-CD137 antibody #1 drove approximately the same level of reporter expression regardless of the concentration of CD137L present (e.g., in the absence of CD137L) and regardless of the order in which antibody and ligand were added (FIGS. 9A-9C, middle panels). The partially/non-ligand blocking reference anti-CD137 antibody #2 also drove similar levels of reporter expression regardless of the concentration of CD137L present (e.g., in the absence of CD137L) when antibody was added before ligand (FIG. 9A, right panel), but showed substantial reduction of reporter expression at higher CD137L concentrations when antibody and ligand were added together (FIG. 9B, right panel) or when ligand was added before antibody (FIG. 9C, right panel).

6.3 Characterization of Anti-CD137 Antibody with Different Fc Regions

This example analyzes the impact of Fc/Fc receptor interaction on the functional activity of the anti-CD137 antibody BA001. In particular, the VH regions of BA001 were expressed with various Fc backbones, including IgG2 and IgG4, as well as IgG1 backbones in which the Fc region comprises the N297A or S267E/L328F (SELF) mutations, numbered according to the EU numbering system, and an IgG2 backbone in which the Fc region comprises the N297A mutation. As is known in the art, the IgG1 N297A and IgG2 N297A variants carry an Fc silent mutation that abolishes the engagement of FcγRs, and thus blocks ADCC/ADCP potential or cross-linking of antibodies via FcγRs. The IgG1 SELF Fc variant exhibits reduced FcγRIIIa binding and enhanced FcγRIIb binding, thus reducing ADCC/ADCP potential but enhancing cross-linking of antibodies via FcγRIIb. In some instances, the N-terminal residue of the heavy chain sequences of anti-CD137 antibodies described herein is glutamine. In some instances, the N-terminal residue of the heavy chain sequences of anti-CD137 antibodies described herein is pyroglutamate (e.g., due to post-translational processing).

The antibody BA001 (IgG1) comprises a heavy chain comprising the amino acid sequence of SEQ ID NO: 9 and a light chain comprising the amino acid sequence of SEQ ID NO: 21. The antibody BA001 IgG1 N297A (i.e., the IgG1 N297A variant of BA001) comprises a heavy chain comprising the amino acid sequence of SEQ ID NO: 10 and a light chain comprising the amino acid sequence of SEQ ID NO: 21. The antibody BA001 IgG1 SELF (i.e., the IgG1 S267E/L328F variant of BA001) comprises a heavy chain comprising the amino acid sequence of SEQ ID NO: 11 and a light chain comprising the amino acid sequence of SEQ ID NO: 21. The antibody BA001 IgG2 (i.e., the IgG2 variant of BA001) comprises a heavy chain comprising the amino acid sequence of SEQ ID NO: 12 and a light chain comprising the amino acid sequence of SEQ ID NO: 21. The antibody BA001 IgG2 N297A (i.e., the IgG2 N297A variant of BA001) comprises a heavy chain comprising the amino acid sequence of SEQ ID NO: 13 and a light chain comprising the amino acid sequence of SEQ ID NO: 21. The antibody BA001 IgG4 (i.e., the IgG4 variant of BA001) comprises a heavy chain comprising the amino acid sequence of SEQ ID NO: 14 and a light chain comprising the amino acid sequence of SEQ ID NO: 21. In some instances, an antibody including an IgG4 Fc region (e.g., antibody BA001 IgG4) includes an S228P mutation that may increase heavy chain stability. These Fc variants of BA001 were then tested in functional assays, as described below.

6.3.1 Fc Variant Functionality in Primary Human PBMCs

The functional activity of the BA001 Fc variants described above on primary human PBMCs was assessed following SEA stimulation. Briefly, cryopreserved PBMCs were stimulated with 200 ng/ml of the SEA superantigen (Toxin Technologies, Cat #AT101red) in the presence of serial dilutions of a BA001 Fc variant or the corresponding isotype control antibody for 5 days at 37° C. IL-2 concentrations in the culture supernatant were analyzed by AlphaLISA (Perkin Elmer, Cat #AL221F). Each condition was tested with five replicates.

Figure 10A:
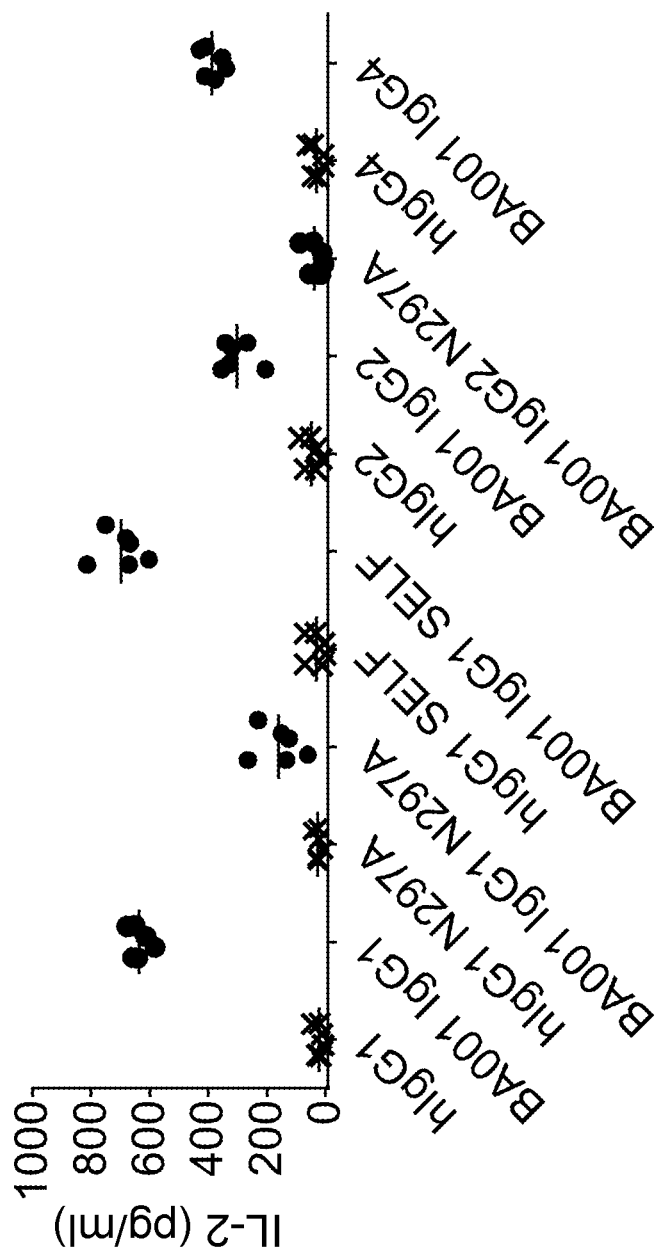
FIG. 10A is a graph showing the production of IL-2 induced by Fc variants of BA001 or corresponding isotype control antibodies in human peripheral blood mononuclear cells (PBMCs) upon Staphylococcal Enterotoxin A (SEA) stimulation.

As shown in FIG. 10A, BA001 IgG1 and BA001 IgG1 SELF each induced strong IL-2 expression in SEA-stimulated primary human PBMCs, which may be due to enhanced antibody cross-linking of these variants. By contrast, the BA001 IgG1 N297A and BA001 IgG2 N297A variants, which do not form antibody cross-linkages, exhibited little or no detectable function. These data indicated that antibody cross-linking enhanced the function of BA001 in agonizing CD137 on primary human T cells. BA001 IgG2 and BA001 IgG4 also induced a moderate level of IL-2 expression.

Figure 10B:
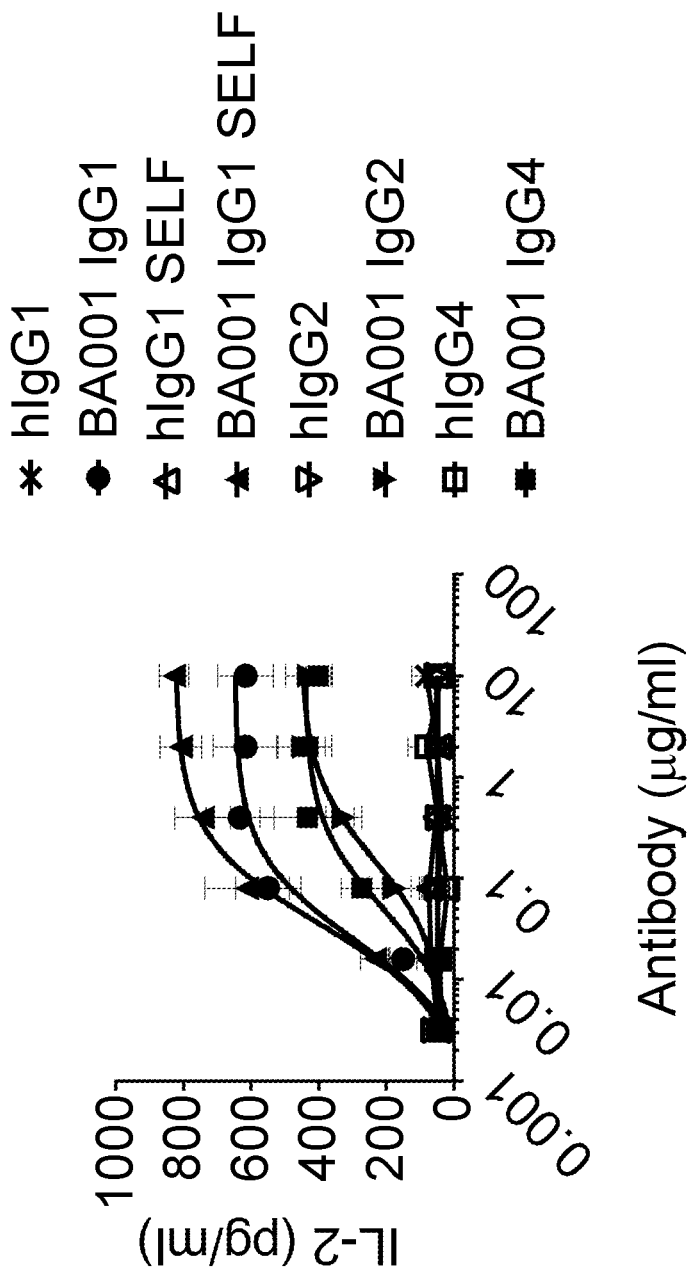
FIG. 10B is a graph showing production of IL-2 induced by serial dilutions of Fc variants of BA001 or corresponding isotype control antibodies in human peripheral blood mononuclear cells (PBMCs) upon Staphylococcal Enterotoxin A (SEA) stimulation.

FIG. 10B shows the dose-dependent activity of BA001 Fc variants, excluding the N297A mutants, in enhancing IL-2 expression by SEA-stimulated primary human T cells. BA001 IgG1 SELF and BA001 IgG1 induced the most robust effect, followed by BA001 IgG4 and BA001 IgG2.

6.3.2 Fc Variants Maintain Ligand Dependency

The ligand dependency of the BA001 Fc variants was examined using the NFκB-luciferase reporter system described in Section 2.2. Briefly, Jurkat NFκB-luciferase reporter cells expressing human CD137 (50,000 cells/well) were incubated with serial dilutions of a BA001 Fc variant or the corresponding isotype control crosslinked by the method described in Section 6.2.3, in the presence or absence of soluble human CD137L (125 ng/ml), for four hours at 37° C. Luciferase expression was detected using the Nano-Glo® Luciferase Assay System (Promega Cat #N1120) and an EnVision plate reader.

Figure 11:
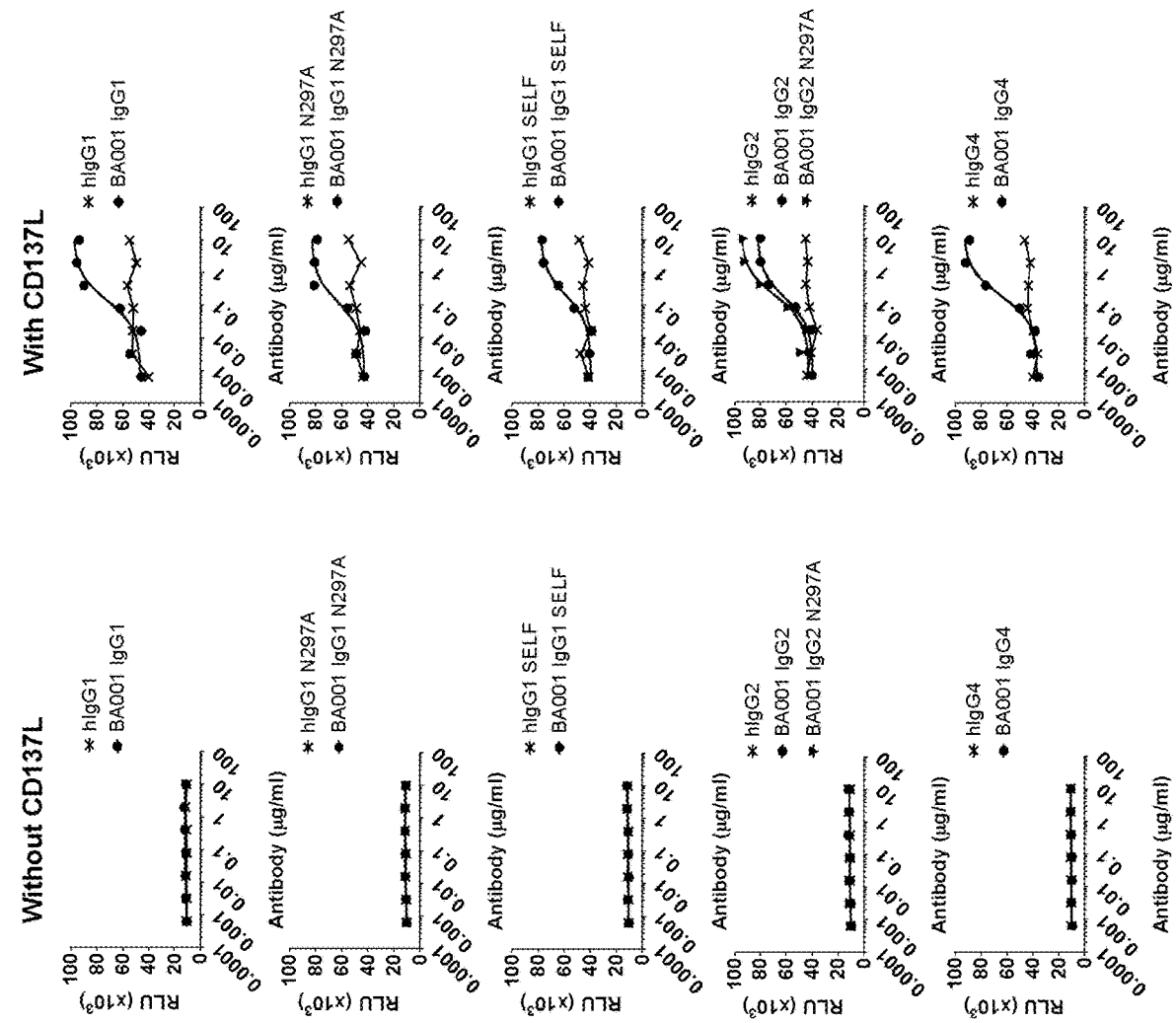
FIG. 11 is a series of NFκB-luciferase reporter activity in Jurkat cells expressing either human or cynomolgus CD137 and incubated with serial dilutions of an Fc variant of BA001 or an appropriate isotype control antibody. In one set of samples, cells were also incubated in the presence (right column) or absence (left column) of human CD137L.

As shown in FIG. 11, all of the BA001 Fc variants exhibited ligand-dependent CD137 agonism. In the absence of CD137L, no reporter activity was detected for any of the Fc variants tested (FIG. 11, left column), whereas in the presence of CD137L, the BA001 Fc variants all induced reporter expression in a dose-dependent manner (FIG. 11, right column). That the cross-linking deficient Fc variants were able to agonize CD137 in this context is likely due to the extremely high level of CD137 expressed by the reporter cells, in comparison to CD137 expression levels in primary T cells.

6.4 Combination Therapies

6.4.1 Combination with Anti-PD-1 Antibody

The anti-CD137 antibody BA001 was further assessed for its ability to stimulate cytokine production by activated T cells, alone or in combination with an anti-PD-1 antibody or an anti-OX40 antibody. In one example, cryopreserved primary human PBMCs were stimulated with SEA, as described above, in the presence of either BA001 (5 μg/ml) and isotype control (10 μg/ml), an anti-PD-1 antibody (10 μg/ml) and isotype control (5 μg/ml), a combination of BA001 (5 μg/ml) and the anti-PD-1 antibody (10 μg/ml), or isotype control alone (15 μg/ml). In another example, cryopreserved primary human PBMCs were stimulated with SEA, as described above, in the presence of either BA001 (5 μg/ml) and isotype control (10 μg/ml), an anti-OX40 antibody (10 μg/ml) and isotype control (5 μg/ml), a combination of BA001 (5 μg/ml) and the anti-OX40 antibody (10 μg/ml), or isotype control alone (15 μg/ml). IL-2 concentrations in the culture supernatant were analyzed by AlphaLISA (Perkin Elmer, Cat #AL221F). Each condition was tested with six replicates.

As shown in FIG. 12A, the combination of BA001 and the anti-PD-1 antibody resulted in greater IL-2 secretion than either antibody alone. Similarly, as shown in FIG. 12B, the combination of BA001 and the anti-OX40 antibody induced greater IL-2 secretion than either antibody alone.

6.5 Epitope Mapping

The interaction of human CD137 with the Fab fragment of BA001 (BA001-Fab) or the F(ab')$_2$ fragment of BA001 (BA001-F(ab')$_2$) was studied by HDX mass spectrometry. These data were used to identify the epitope regions bound by BA001-Fab and BA001-F(ab')$_2$ on the extracellular domain of human CD137.

6.5.1 Epitope Mapping of Anti-CD137 Antibody by Hydrogen-Deuterium Exchange (HDX)

The interaction of CD137 with anti-human CD137 F(ab')$_2$ and anti-human CD137 Fab were evaluated using the methods below.

(A) CD137 Interaction with Anti-Human CD137 F(ab')2

20 μL human CD137 (5.48 μg) or 20 μL human CD137 and BA001-F(ab')$_2$ mixture (5.48 μg: 22.36 μg) was incubated with 105 μL deuterium oxide labeling buffer (50 mM sodium phosphate, 100 mM sodium chloride at pD 7.4) for 0 sec, 60 sec, 300 sec, 1800 sec, 7200 sec and 14400 sec at 20° C. Hydrogen/deuterium exchange was quenched by adding 125 μL of 4 M guanidine hydrochloride, 0.85 M TCEP buffer (final pH is 2.5) and incubating the mixture for 5 min at 20° C. Subsequently, the quenched samples were subjected to on column pepsin/protease XIII digestion and LC-MS analysis, as described below. The mass spectra were recorded in MS only mode.

(B) CD137 Interaction with Anti-Human CD137 Fab

15 μL human CD137 (5.0 μg) or 15 μL human CD137 and BA001-Fab mixture (5.0 μg human CD137+15.0 μg Fab) was incubated with 110 μL deuterium oxide labeling buffer (50 mM sodium phosphate, 100 mM sodium chloride at pD 7.4) for 0 sec, 60 sec, 300 sec, and 1800 sec at 25° C. Hydrogen/deuterium exchange was quenched by adding 125 μL of 4 M guanidine hydrochloride, 0.85 M TCEP buffer (final pH is 2.5) and incubating the mixture for 3 min at 25° C. Subsequently, the quenched samples were subjected to on column pepsin/protease XIII digestion and LC-MS analysis, as described below. The mass spectra were recorded in MS only mode.

HDX Data Analysis

Raw MS data was processed using HDX WorkBench software for the analysis of H/D exchange MS data. The deuterium levels were calculated using the average mass difference between the deuterated peptide and its native form ($t_0$). For the calculation of deuterium incorporation, the mass spectra for a given peptide were combined across the extracted ion chromatogram peak and the weighted average m/z was calculated. The mass increase from the mass of the native peptide (0 minute) to the weighted averaged mass corresponds to the level of deuterium incorporation.

Pepsin/Protease XIII Digestion and LC-MS

His-tagged human CD137 (AcroBiosystems Inc.) was fragmented into peptides for use in HDX by pepsin/protease XII digestion. 5.48 μg of human CD137 in 125 μL control buffer (50 mM phosphate, 100 mM sodium chloride at pH 7.4) was denatured by adding 125 μL of 4 M guanidine hydrochloride, 0.85 M TCEP buffer (final pH is 2.5) and incubating the mixture for 5 min at 20° C. The mixture was subjected to on-column pepsin/protease XIII digestion using an in-house packed pepsin/protease XIII (w/w, 1:1) column and the resultant peptides were analyzed using an UPLC-MS system comprised of a Waters Acquity UPLC coupled to a Q Exactive™ Hybrid Quadrupole-Orbitrap Mass Spectrometer (Thermo). Peptide identification was performed by searching MS/MS data against the human CD137 sequence with Mascot. The mass tolerance for the precursor and product ions was 10 ppm and 0.05 Da, respectively.

Epitope Binding of Anti-Human CD137 F(ab')₂

Most of the CD137 peptides displayed identical or similar deuterium levels with and without BA001-F(ab')₂ present. Several peptide segments, however, were found to have significantly decreased deuterium incorporation upon F(ab')₂ binding. All the residues in this paragraph are numbered according to SEQ ID NO: 25. One region consisting of residues 125-155 (FNDQKRGI-CRPWTNCSLDGKSVLVNGTKERD, SEQ ID NO: 27), experienced strong deuterium protection when human CD137 was bound to BA001-F(ab')₂. Thus, this region corresponds to an epitope or portion thereof of BA001 on CD137. Inspection of the sequences of human and cynomolgus monkey CD137, to both of which BA001 binds strongly (FIGS. 1A and 1B), revealed complete sequence identity in the region described above (FIG. 11). By contrast, BA001 does not bind to any significant extent to murine CD137 (data not shown), which includes a number of amino acid substitutions and insertions relative to human CD137 in this region (FIG. 14A). Lastly, a fragment of CD137, residues 26-63 (DPCSNCPAGTFCDNNRNQICSPCPPNSFS-SAGGQRTCD, SEQ ID NO: 34), also showed deuterium protection. Without wishing to be bound by theory, it is contemplated that this signal reflects CD137 dimerization via a PLAD-PLAD interaction, which may be enhanced by each arm of BA001-F(ab')₂ binding to, e.g., one of two distinct CD137 molecules, thereby bringing the PLAD domains of the CD137 molecules into close enough proximity to permit PLAD-PLAD interaction.

Epitope Binding of Anti-Human CD137 Fab

Most of the CD137 peptides displayed identical or similar deuterium levels with and without BA001-Fab present. Several peptide segments, however, were found to have significantly decreased deuterium incorporation upon BA001-Fab binding. All the residues in this paragraph are numbered according to SEQ ID NO: 25. The region defined by residues 125-141 (FNDQKRGICRPWTNCSL, SEQ ID NO: 26) experienced strong deuterium protection when human CD137 was bound to BA001-Fab. This region thus corresponds to an epitope or portion thereof of BA001 on CD137. Two additional regions, consisting of residues 89-98 (TPGFHCLGAG, SEQ ID NO: 28), and residues 107-112 (KQGQEL, SEQ ID NO: 29), also exhibited substantial deuterium protection, and thus optionally correspond to additional epitopes, or portions thereof, of BA001 on CD137. Inspection of the sequences of human and cynomolgus monkey CD137, to both of which BA001 binds strongly (FIGS. 1A and 1B), revealed complete sequence identity in the regions corresponding to SEQ ID NO: 26 and 29, as described above (FIG. 13). BA001 does not bind to any significant extent to murine CD137 (data not shown), which differs substantially from human CD137 at these regions (FIG. 14A). Four amino acid substitutions were found in the region of the cynomolgus monkey sequence corresponding to SEQ ID NO: 28 (i.e., T82I, P83S, F85Y, and G91E). The region of CD137 consisting of residues 26-63 (SEQ ID NO: 34) did not exhibit any deuterium protection in this experiment. Without wishing to be bound by theory, it is contemplated that that binding of individual BA001-Fab fragments to single molecules of CD137 does not promote PLAD-PLAD dimerization.

6.5.2 Epitope Mapping of Anti-CD137 Antibody Using Human/Mouse Chimeric Proteins The epitope on human CD137 recognized by anti-CD137 antibody BA001 was further studied using a series of murine switch mutant constructs transfected into Jurkat cells, which could then be analyzed by FACS. Jurkat switch mutants were generated that each constitutively expressed a human CD137 containing a single mutated region within the extracellular domain, in which that portion of the human CD137 sequence was switched with the corresponding sequence from murine CD137 (i.e., mutants 5014-5018 shown in FIG. 14A; sequences provided in Table 5 below).

TABLE 5

Extracellular domain of human-mouse fusion construct sequences for CD137.

| Description | Amino Acid Sequence* | SEQ ID NO: |
|---|---|---|
| Extracellular domain of human-mouse fusion construct 5014 | LQDPCSNCPAGTFCRKYNPVC KSCPPSTFSSAGGQRTCDICR QCKGVFRTRKECSSTSNAECD CTPGFHCLGAGCSMCEQDCKQ GQELTKKGCKDCCFGTFNDQK RGICRPWTNCSLDGKSVLVNG TKERDVVCGPSPADLSPGASS VTPPAPARPGHSPQ | 35 |
| Extracellular domain of human-mouse fusion construct 5015 | LQDPCSNCPAGTFCDNNRNQI CSPCPPNSFSSIGGQPNCNIC RVCAGYFRFKKFCSSTSNAEC DCTPGFHCLGAGCSMCEQDCK QGQELTKKGCKDCCFGTFNDQ KRGICRPWTNCSLDGKSVLVN GTKERDVVCGPSPADLSPGAS SVTPPAPAREPGHSPQ | 36 |
| Extracellular domain of human-mouse fusion construct 5016 | LQDPCSNCPAGTFCDNNRNQI CSPCPPNSFSSAGGQRTCDIC RQCKGVFRTRKECSSTHNAEC ECIEGFHCLGPQCTRCEKDCR PGQELTKKGCKDCCFGTFNDQ KRGICRPWTNCSLDGKSVLVN GTKERDVVCGPSPADLSPGAS SVTPPAPAREPGHSPQ | 37 |
| Extracellular domain of human-mouse fusion construct 5017 | LQDPCSNCPAGTFCDNNRNQI CSPCPPNSFSSAGGQRTCDIC RQCKGVFRTRKECSSTSNAEC DCTPGFHCLGAGCSMCEQDCK QGQELTKQGCKTCSLGTFNDQ NGTGVCRPWTNCSLDGKSVLV NGTKERDVVCGPSPADLSPGA SSVTPPAPAREPGHSPQ | 38 |
| Extracellular domain of human-mouse fusion construct 5018 | LQDPCSNCPAGTFCDNNRNQI CSPCPPNSFSSAGGQRTCDIC RQCKGVFRTRKECSSTSNAEC DCTPGFHCLGAGCSMCEQDCK QGQELTKKGCKDCCFGTFNDQ KRGICRPWTNCSLDGRSVLKT GTTEKDVVCGPSPADLSPGAS SVTPPAPAREPGHSPQ | 39 |

*Human CD137 sequences are indicated in plain text. Murine CD137 sequences are bolded.

These engineered mutant cell lines were used to test whether anti-CD137 antibody can bind to particular switch mutants. Absence of binding would thereby indicate possible epitope locations. The cell binding assays were performed generally as described in Section 1.1. Briefly, transfected Jurkat cells were stained at 5×10⁴ cells/well using serial dilutions of anti-CD137 antibody (i.e., BA001, reference anti-CD137 antibody #1, or reference anti-CD137 antibody #2) in a 96-well plate for 25 minutes at 4° C. The cells were washed twice and incubated with F(ab')₂ goat anti-human IgG-PE secondary antibody (Jackson ImmunoResearch, Cat #109-116-098). The cells were then washed and suspended in 80 µl of 2% paraformaldehyde (Electron Microscopy Sciences) prepared in PBS. Data were collected with BD FACS Canto and analyzed using BD FACSDiva software.

As shown in FIG. 14B, antibody BA001 was able to bind to Jurkat cells expressing all of the murine switch mutants except mutant 5017, in which the sequence LTKKGCKDCCFGTFNDQKRGICRPWTNC (SEQ ID NO: 30) in human CD137 was replaced with a corresponding region in murine CD137. The binding pattern exhibited by BA001 is distinct from those exhibited by the reference anti-CD137 antibodies #1 and #2 (FIG. 14B). Reference anti-CD137 antibody #1 exhibited minimal binding to mutant 5017 at lower antibody concentrations, but binding was clearly detected at concentrations at or greater than 10 µg/ml. In addition, differing from BA001, reference anti-CD137 antibody #1 showed no binding to mutant 5016.

The BA001 epitope in human CD137 identified from the murine switch mutants substantially overlapped with the BA001 epitope identified in the HDX epitope mapping experiments described in Section 6.5.1. In the overlapping region, four continuous amino acid residues of human CD137, having the sequence of KRGI (SEQ ID NO: 43), were different from the sequence of NGTGV (SEQ ID NO: 44) found in the corresponding region of murine CD137 (FIG. 15A). This difference could account for the lack of substantial affinity of BA001 to murine CD137. To determine whether the sequence of KRGI (SEQ ID NO: 43) was an epitope recognized by BA001, two proteins comprising chimeric CD137 extracellular domains were generated: the "4-aa human to mouse" CD137 protein was a human CD137 extracellular domain having the KRGI sequence replaced with NGTGV; the "4-aa mouse to human" CD137 protein was a murine CD137 extracellular domain having the NGTGV sequence replaced with KRGI. These chimeric proteins further comprised a Gly-Ser linker and a 6xHis tag at the C-terminus. The sequences of the extracellular domains are provided in Table 6.

TABLE 6

Extracellular domain of chimeric CD137 proteins and fragments thereof

| Description | Amino Acid Sequence* | SEQ ID NO: |
|---|---|---|
| Murine CD137 fragment | NGTGV | 44 |
| Extracellular domain of "4-aa human to mouse" CD137 | LQDPCSNCPAGTFCDNNRNQICSP CPPNSFSSAGGQRTCDICRQCKGV FRTRKECSSTSNAECDCTPGFHCL GAGCSMCEQDCKQGQELTKKGCKD CCFGTFNDQNGTGVCRPWTNCSLD GKSVLVNGTKERDVVCGPSPADLS PGASSVTPPAPAREPGHSPQ | 45 |
| Extracellular domain of "4-aa mouse to human" CD137 | VQNSCDNCQPGTFCRKYNPVCKSC PPSTFSSIGGQPNCNICRVCAGYF RFKKFCSSTHNAECECIEGFHCLG PQCTRCEKDCRPGQELTKQGCKTC SLGTFNDQKRGICRPWTNCSLDGR SVLKTGTTEKDVVCGPPVVSFSPS TTISVTPEGGPGGHSLQVL | 46 |

The chimeric CD137 proteins described above were tested in a surface plasmon resonance (SPR) assay. Briefly, a CM5 sensor chip was first coated with an anti-human Fab antibody using the amine coupling kit. 6 µg/ml of BA001 and reference anti-CD137 antibody #1 was captured at a flow rate of 10 µl/min on flow-cells 2 and 3, respectively, keeping the flow-cell 1 as reference. A fully human CD137 protein, the "human to mouse" CD137 chimeric protein, and the "mouse to human" CD137 chimeric protein were then independently run at a concentration of 60 nM over the flow-cells at 30 µl/min for 90 seconds followed by a dissociation of 400 seconds. Sensorgrams were recorded during both the association and dissociation phases.

As shown in FIG. 15B, when the KRGI (SEQ ID NO: 43) sequence of human CD137 was replaced by the NGTGV (SEQ ID NO: 44) sequence of murine CD137, the chimeric protein lost its ability to bind BA001. Conversely, when the NGTGV (SEQ ID NO: 44) sequence of murine CD137 was replaced by the KRGI (SEQ ID NO: 43) sequence of human CD137, the chimeric protein gained the ability to bind BA001. These data suggested that the KRGI (SEQ ID NO: 43) sequence represented the critical epitope region of human CD137 involved in the binding to BA001.

In comparison, as shown in FIG. 15C, when the KRGI (SEQ ID NO: 43) sequence of human CD137 was replaced by the NGTGV (SEQ ID NO: 44) sequence of murine CD137, the chimeric protein lost its ability to bind reference anti-CD137 antibody #1. However, when the NGTGV (SEQ ID NO: 44) sequence of murine CD137 was replaced by the KRGI (SEQ ID NO: 43) sequence of human CD137, the chimeric protein did not gain the ability to bind reference anti-CD137 antibody #1. These data suggested that the KRGI (SEQ ID NO: 43) sequence, despite being necessary for the binding of reference anti-CD137 antibody #1, was not sufficient in the murine CD137 context.

6.6 Characterization of Anti-CD137 Antibody Variants

This example describes the characterization of anti-CD137 antibodies that are variants of the BA001 antibody. The sequence information of the variable regions of four of these antibodies is provided in Tables 1 and 2.

6.6.1 BA001 Variants Bind to Human and Cynomolgus CD137

Variants of BA001 were generated by screening scFv phage display libraries containing amino acid substitutions in CDRH1, CDRH3, and CDRL3 of BA001. Briefly, an scFv of BA001 comprising the amino acid sequence of SEQ ID NO: 55 was generated, mutagenesis of the scFv was conducted, and the positive clones were enriched by affinity-based selection. A total of 347 clones that bound to human CD137 were identified. Consensus CDRH1, CDRH3, and CDRL3 sequences constructed from analysis of the amino acid sequence of the 347 clones are set forth in SEQ ID NOs: 82, 83, and 84, respectively. Among the 347 clones, 233 had a dissociation rate of less than $1 \times 10^{-3}$ $s^{-1}$. Consensus CDRH1, CDRH3, and CDRL3 sequences constructed from these 233 clones are set forth in SEQ ID NOs: 85, 86, and 87, respectively.

The binding affinities of four of the BA001 variants to CD137 were further characterized. These four variants, named BA049, BA050, BA051, and BA052, comprised the scFv amino acid sequences set forth in SEQ ID NOs: 69, 70, 71, and 72, respectively, as provided in Table 1. The four variants were converted to an IgG1 format, and their heavy chain and light chain sequences are provided in Tables 1 and 2. To measure binding affinities, extracellular domains of human CD137, cynomolgus CD137, mouse-human fusion construct 5015 (murine CD137 with amino acid residues 53-81 replaced with the corresponding sequence of human CD137), and mouse-human fusion construct 5017 (murine CD137 with amino acid residues 112-140 replaced with the corresponding sequence of human CD137), each comprising a Gly-Ser linker followed by a 6×His tag, were used as antigens. The extracellular domain sequences of the two chimeric proteins (excluding the linker and 6×His tag) are provided in Table 7.

TABLE 7

Extracellular domain of chimeric CD137 proteins.

| Description | Amino Acid Sequence* | SEQ ID NO: |
| --- | --- | --- |
| Extracellular domain of mouse-human fusion construct 5015 | VQNSCDNCQPGTFCRKYNPVCKS CPPSTFSSAGGQRTCDICRQCKG VFRTRKECSSTHNAECECIEGFH CLGPQCTRCEKDCRPGQELTKQG CKTCSLGTFNDQNGTGVCRPWTN CSLDGRSVLKTGTTEKDVVCGPP VVSFSPSTTISVTPEGGPGGHSL QVL | 47 |
| Extracellular domain of mouse-human fusion construct 5017 | VQNSCDNCQPGTFCRKYNPVCKS CPPSTFSSIGGQPNCNICRVCAG YFRFKKFCSSTHNAECECIEGFH CLGPQCTRCEKDCRPGQELTKKG CKDCCFGTFNDQKRGICRPWTNC SLDGRSVLKTGTTEKDVVCGPPV VSFSPSTTISVTPEGGPGGHSLQ VL | 48 |

The affinities of the BA001 variants (in the IgG1 format) to the antigens were measured by ELISA. Specifically, 50 µl of 5 µg/ml of each antigen diluted in 1×PBS pH 7.4 (Gibco™, Cat no. 10010056) was added to each well in a Thermo Scientific™ Black 96-Well Immuno Plate (Thermofisher Scientific, Cat no. 437111) and incubated at 4° C. overnight. The plate was washed three times with PBS using the Biotek 405TS microplate washer with Biostack3 microplate stacker. The plate was blocked by incubating with 300 ul/well of 3% Milk Powder in PBS (Marvel dried skimmed milk powder) for 1 hour at room temperature, and were washed three times with 1×PBS. The antibodies titrated in 3% M-PBS (Milk Powder in 1×PBS) were added to the plate and incubated for 1 hour at room temperature. The plate was washed three times with 1×PBS with 0.1% Tween20 (Sigma Aldrich, Cat No. P1379) and three times with 1×PBS using the plate washer. 50 µl Biotin-SP (long spacer) AffiniPure Goat Anti-Human IgG, Fcγ Fragment Specific (Jackson Immuno Research, Code:109-065-098, Lot no. 123909) diluted at 1:2000 in 3% M-PBS was added to each well and incubated for 1 hour at room temperature. The plate was washed three times with 1×PBS with 0.1% Tween20 and three times with 1×PBS using the plate washer. For detection, 50 µl of DELFIA® Europium-labeled streptavidin (PerkinElmer, Part no. 1244-360, Lot no. 2195997) diluted in the DELFIA® Assay buffer (PerkinElmer, Part no. 4002-0010, Lot no. 646702) at 1:500 was added to each well and incubated for 1 hour at room temperature. The plate was washed three times with 1×PBS with 0.1% Tween20 and three times with PBS using the plate washer. 50 ul of DELFIA® enhancement solution (PerkinElmer, Part no. 4001-0010, Lot no. 650872) was added to each well, and incubated at room temperature for 5 mins with gentle shaking. Fluorescence was read at Excitation 340 nm and Emission 615 nm using Tecan Infinite M1000 Pro plate reader. The data was acquired with the Tecan iControl software version 1.11.1.0, and analyzed with Graphpad Prism version 7.02.

As shown in FIGS. 16A and 16B, the four BA001 variants showed binding to human and cynomolgus CD137. Additionally, they bound to mouse-human fusion construct 5017 ("mCD137-human112-139") (FIG. 16C) but not mouse-human fusion construct 5015 ("mCD137-human53-80") (FIG. 16D), indicating that they bound to an epitope of human CD137 in the region of amino acid residues 112-139. These data suggest that these four variants bound to the same or a similar epitope as BA001.

The invention is not to be limited in scope by the specific embodiments described herein. Indeed, various modifications of the invention in addition to those described will become apparent to those skilled in the art from the foregoing description and accompanying figures. Such modifications are intended to fall within the scope of the appended claims.

All references (e.g., publications or patents or patent applications) cited herein are incorporated herein by reference in their entireties and for all purposes to the same extent as if each individual reference (e.g., publication or patent or patent application) was specifically and individually indicated to be incorporated by reference in its entirety for all purposes.

Other embodiments are within the following claims.

What is claimed:

1. A polynucleotide encoding a VH, a VL, or a VH and a VL of an antibody that comprises: a VH comprising the CDRH1, CDRH2, and CDRH3 amino acid sequences of the VH amino acid sequence of SEQ ID NO: 7; and/or a VL comprising the CDRL1, CDRL2, and CDRL3 amino acid sequences of the VL amino acid sequence of SEQ ID NO: 8.

2. The polynucleotide of claim 1, wherein the antibody comprises the CDRH1, CDRH2, CDRH3, CDRL1, CDRL2, and CDRL3 amino acid sequences of SEQ ID NOs: 1, 2, 3, 4, 5, and 6, respectively.

3. The polynucleotide of claim 1, wherein the VH comprises the amino acid sequence of SEQ ID NO: 7, and the VL comprises the amino acid sequence of SEQ ID NO: 8.

4. The polynucleotide of claim 1, wherein the antibody comprises a heavy chain constant region selected from the group consisting of $IgG_1$, $IgG_2$, $IgG_3$, $IgG_4$, $IgA_1$, and $IgA_2$, optionally wherein:
   (a) the heavy chain constant region is human $IgG_1$ constant region comprising an N297A mutation;
   (b) the heavy chain constant region is human $IgG_1$ constant region comprising S267E and L328F mutations;
   (c) the heavy chain constant region is human $IgG_2$ constant region comprising a N297A mutation; or
   (d) the heavy chain constant region is human $IgG_4$ constant region comprising an S228P mutation.

5. The polynucleotide of claim 4, wherein the heavy chain constant region comprises an amino acid sequence selected from the group consisting of SEQ ID NOs: 15-20.

6. The polynucleotide of claim 1, wherein the antibody comprises a light chain constant region selected from the group consisting of a human kappa light chain constant region and a human lambda light chain constant region.

7. The polynucleotide of claim 6, wherein the light chain constant region comprises the amino acid sequence of SEQ ID NO: 22.

8. The polynucleotide of claim 1, wherein the antibody comprises a heavy chain comprising an amino acid sequence selected from the group consisting of SEQ ID NO: 9-14 and 49-54, and a light chain comprising the amino acid sequence of SEQ ID NO: 21.

9. The polynucleotide of claim 8, wherein the antibody comprises a heavy chain comprising the amino acid sequence of SEQ ID NO: 9, and a light chain comprising the amino acid sequence of SEQ ID NO: 21.

10. A vector comprising the polynucleotide of claim 1.

11. A vector comprising the polynucleotide of claim 3.

12. A vector comprising the polynucleotide of claim 9.

13. A recombinant host cell comprising:
   (a) a polynucleotide encoding a VH and a VL of an antibody; or
   (b) a first polynucleotide encoding a VH of an antibody and second polynucleotide encoding a VL of the antibody,
   wherein the antibody comprises: a VH comprising the CDRH1, CDRH2, and CDRH3 amino acid sequences of the VH amino acid sequence of SEQ ID NO: 7; and a VL comprising the CDRL1, CDRL2, and CDRL3 amino acid sequences of the VL amino acid sequence of SEQ ID NO: 8.

14. The recombinant host cell of claim 13, wherein the antibody comprises the CDRH1, CDRH2, CDRH3, CDRL1, CDRL2, and CDRL3 amino acid sequences of SEQ ID NOs: 1, 2, 3, 4, 5, and 6, respectively.

15. The recombinant host cell of claim 13, wherein the VH comprises the amino acid sequence of SEQ ID NO: 7, and the VL comprises the amino acid sequence of SEQ ID NO: 8.

16. The recombinant host cell of claim 13, wherein the antibody comprises a heavy chain constant region selected from the group consisting of $IgG_1$, $IgG_2$, $IgG_3$, $IgG_4$, $IgA_1$, and $IgA_2$, optionally wherein:
   (a) the heavy chain constant region is human $IgG_1$ constant region comprising an N297A mutation;
   (b) the heavy chain constant region is human $IgG_1$ constant region comprising S267E and L328F mutations;
   (c) the heavy chain constant region is human $IgG_2$ constant region comprising a N297A mutation; or
   (d) the heavy chain constant region is human $IgG_4$ constant region comprising an S228P mutation.

17. The recombinant host cell of claim 16, wherein the heavy chain constant region comprises an amino acid sequence selected from the group consisting of SEQ ID NOs: 15-20.

18. The recombinant host cell of claim 13, wherein the antibody comprises a light chain constant region selected from the group consisting of a human kappa light chain constant region and a human lambda light chain constant region.

19. The recombinant host cell of claim 18, wherein the light chain constant region comprises the amino acid sequence of SEQ ID NO: 22.

20. The recombinant host cell of claim 13, wherein the antibody comprises a heavy chain comprising an amino acid sequence selected from the group consisting of SEQ ID NO: 9-14 and 49-54, and a light chain comprising the amino acid sequence of SEQ ID NO: 21.

21. The recombinant host cell of claim 20, wherein the antibody comprises a heavy chain comprising the amino acid sequence of SEQ ID NO: 9, and a light chain comprising the amino acid sequence of SEQ ID NO: 21.

22. A method of producing an antibody that specifically binds to human CD137, the method comprising culturing the host cell of claim 13 under suitable conditions so that the polynucleotide is expressed and the antibody is produced.

23. A method of producing an antibody that specifically binds to human CD137, the method comprising culturing the host cell of claim 15 under suitable conditions so that the polynucleotide is expressed and the antibody is produced.

24. A method of producing an antibody that specifically binds to human CD137, the method comprising culturing the host cell of claim 21 under suitable conditions so that the polynucleotide is expressed and the antibody is produced.

* * * * *